United States Patent
Ushioda et al.

(10) Patent No.: US 11,434,207 B2
(45) Date of Patent: *Sep. 6, 2022

(54) P2X4 RECEPTOR ANTAGONIST

(71) Applicant: NIPPON CHEMIPHAR CO., LTD, Tokyo (JP)

(72) Inventors: Masatoshi Ushioda, Tokyo (JP); Kunio Kobayashi, Saitama (JP); Daisuke Saito, Tokyo (JP); Shogo Sakuma, Saitama (JP); Toshiyasu Imai, Tokyo (JP); Kazuhide Inoue, Fukuoka (JP)

(73) Assignee: NIPPON CHEMIPHAR CO., LTD, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/826,877

(22) Filed: Mar. 23, 2020

(65) Prior Publication Data
US 2020/0223806 A1    Jul. 16, 2020

Related U.S. Application Data

(62) Division of application No. 15/923,685, filed on Mar. 16, 2018, now Pat. No. 10,633,349, which is a division of application No. 15/176,857, filed on Jun. 8, 2016, now Pat. No. 9,969,700, which is a division of application No. 14/371,868, filed as application
(Continued)

(30) Foreign Application Priority Data

Jan. 13, 2012   (JP) ................... 2012-005343

(51) Int. Cl.
| | |
|---|---|
| *A61P 25/04* | (2006.01) |
| *A61P 29/00* | (2006.01) |
| *A61P 43/00* | (2006.01) |
| *C07D 243/10* | (2006.01) |
| *C07D 403/12* | (2006.01) |
| *C07D 401/12* | (2006.01) |
| *C07D 405/12* | (2006.01) |
| *C07D 243/12* | (2006.01) |
| *C07D 409/12* | (2006.01) |
| *C07D 401/04* | (2006.01) |
| *C07D 413/12* | (2006.01) |
| *C07D 471/04* | (2006.01) |

(52) U.S. Cl.
CPC ......... *C07D 243/10* (2013.01); *C07D 243/12* (2013.01); *C07D 401/04* (2013.01); *C07D 401/12* (2013.01); *C07D 403/12* (2013.01); *C07D 405/12* (2013.01); *C07D 409/12* (2013.01); *C07D 413/12* (2013.01); *C07D 471/04* (2013.01)

(58) Field of Classification Search
CPC ............ A61P 25/04; A61P 29/00; A61P 43/00
See application file for complete search history.

(56) References Cited

U.S. PATENT DOCUMENTS

| | | | |
|---|---|---|---|
| 7,375,101 B2 | 5/2008 | Leung et al. | |
| 8,962,613 B2 | 2/2015 | Sakuma | |
| 9,382,236 B2 | 7/2016 | Ushioda et al. | |
| 9,969,700 B2 | 5/2018 | Ushioda et al. | |
| 2005/0074819 A1 | 4/2005 | Inoue et al. | |
| 2005/0176699 A1 | 8/2005 | Leung et al. | |

(Continued)

FOREIGN PATENT DOCUMENTS

| | | |
|---|---|---|
| CA | 2 519 987 | 10/2004 |
| CA | 2 789 641 | 8/2010 |

(Continued)

OTHER PUBLICATIONS

Bo et al., "A P2X purinoceptor cDNA conferring a novel pharmacological profile," *FEBS Letters*, vol. 375, pp. 129-133, 1995.
Buell et al., "An antagonist-insensitive $P_{2x}$ receptor expressed in epithelia and brain," *The EMBO Journal*, vol. 15, No. 1 pp. 55-62, 1996.

(Continued)

*Primary Examiner* — Bruck Kifle
(74) *Attorney, Agent, or Firm* — Greenblum & Bernstein, P.L.C.

(57) ABSTRACT

The present invention relates to a diazepine derivative represented by the following general formula (I) (in the formula, $R^1$ and $R^2$ represent hydrogen atom and the like, or $R^1$ and $R^2$ bind together to form a naphthalene ring and the like together with the benzene ring to which they bind, $R^3$ and $R^4$ represent hydrogen atom and the like, $R^5$ represents hydrogen atom and the like, $R^6$ and $R^7$ represent hydrogen atom and the like, X represents C, CH or N, Y represents N, NH or C(=O), provided that when X is N, Y is not N or NH, and when X is C or CH, Y is not C(=O), Z represents oxygen atom or sulfur atom, A represents benzene ring and the like, B represents NHC(=O) and the like, D represents an atomic bond and the like, E represents an atomic bond and the like, G represents benzene which may be substituted and the like, and m represents an integer of 0 to 5) or a pharmacologically acceptable salt thereof, and a P2X4 receptor antagonist.

(I)

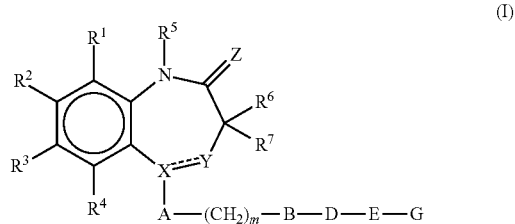

43 Claims, No Drawings

Related U.S. Application Data

No. PCT/JP2013/050320 on Jan. 10, 2013, now Pat. No. 9,382,236.

(56) References Cited

U.S. PATENT DOCUMENTS

| | | | |
|---|---|---|---|
| 2006/0128695 | A1 | 6/2006 | Bourguignon et al. |
| 2010/0256123 | A1 | 10/2010 | Sakuma et al. |
| 2018/0201587 | A1 | 7/2018 | Ushioda et al. |

FOREIGN PATENT DOCUMENTS

| | | |
|---|---|---|
| EP | 2058304 | 5/2009 |
| EP | 2397480 | 12/2011 |
| EP | 2716301 | 4/2014 |
| JP | 53-111093 | 9/1978 |
| JP | 02-304437 | 12/1990 |
| JP | 09-511223 | 11/1997 |
| JP | 09-511999 | 12/1997 |
| JP | 2005-516918 | 6/2005 |
| JP | 2006-509832 | 3/2006 |
| JP | 2006-521308 | 9/2006 |
| WO | 9528391 | 10/1995 |
| WO | 9528419 | 10/1995 |
| WO | 03/051274 | 6/2003 |
| WO | 2004/041258 | 5/2004 |
| WO | 2004/085440 | 10/2004 |
| WO | 2008/023847 | 2/2008 |
| WO | 2010/090300 | 8/2010 |
| WO | 2010/093061 | 8/2010 |
| WO | 2012/008478 | 1/2012 |
| WO | 2012/011549 | 1/2012 |
| WO | 2012/161301 | 11/2012 |

OTHER PUBLICATIONS

Coull et al., "BDNF from microglia causes the shift in neuronal anion gradient underlying neuropathic pain," *Nature*, Vo. 438, pp. 1017-1021, Dec. 2005.

Tsuda et al., "P2X$_4$ receptors induced in spinal microglia gate tactile allodynia after nerve injury," *Nature*, Vo. 424, pp. 778-783, Aug. 2003.

Nagata et al., "Inhibitory effects of antidepressants on P2X4 receptor: a novel mechanism in neuropathic pain relief", Lecture Abstract P3-N-114, from the 49th Convention of the Japanese Society for Neurochemistry (2006) Program.

Seguela et al., "A Novel Neuronal P$_{2x}$ ATP Receptor Ion Channel with Widespread Distribution in the Brain", *The Journal of Neuroscience*, vol. 16, No. 2, pp. 448-455, Jan. 1996.

Soto et al., "P2X$_4$: An ATP-activated ionotropic receptor cloned from rat brain", *Proc.Natl. Acad. Sci. USA*, vol. 93, pp. 3684-3688, Apr. 1996.

Wang et al., "Cloning and Pharmacological Characterization of a Fourth P2X Receptor Subtype Widely Expressed in Brain and Peripheral Tissues Including Various Endocrine Tissues", *Biochemical and Biophysical Research Communications*, vol. 220, pp. 196-202, 1996.

International Preliminary Report on Patentability for PCT/JP2013/050320, dated Jul. 15, 2014; with an English translation thereof.

International Search Report for PCT/JP2013/050320, dated Feb. 19, 2013; with an English translation thereof.

New Zealand Office action issued for application No. 627878, dated Apr. 20, 2015.

Extended European search report issued for application No. 13736295.0, dated May 4, 2015.

Chinese Office Action issued with respect to application No. 201380005473.4, dated Jun. 3, 2015.

Israeli Office issued with respect to application No. 233592, dated Nov. 23, 2015.

European Office Action issued with respect to application No. 13736295.0, dated Jan. 29, 2016.

Japanese Office Action from Patent Application No. 2013-553310 dated Nov. 1, 2016.

Japanese Office Action from Patent Application No. 2013-553310 dated Jun. 13, 2017.

Australian Office Action issued with respect to Application No. 2013208536, dated Sep. 9, 2016.

Chinese Office Action issued with respect to Application No. 201380005473.4, dated Oct. 10, 2016.

Rejection Decision issued with respect to Chinese patent application No. 201380005473.4, dated Mar. 26, 2018.

Examination report issued in the corresponding Indian patent application No. 6036/CHENP/2014, dated Aug. 29, 2018.

Korean Office Action, Korean Patent Office, Patent Application No. 2014-7022599, dated Apr. 11, 2019, with English Translation.

Office Action dated Feb. 11, 2020 issued in Indian Patent Application No. 6036/CHENP/2014.

Office Action issued in Chinese Patent Application No. 201810753396.5, dated Jan. 4, 2021, English translation.

Office Action issued in Chinese Patent Application No. 201910768337.X, dated Jul. 11, 2022, with English translation.

P2X4 RECEPTOR ANTAGONIST

The present application is a Divisional of U.S. application Ser. No. 15/923,685, filed Mar. 16, 2018, which is a Divisional of U.S. application Ser. No. 15/176,857, filed Jun. 8, 2016, which issued as U.S. Pat. No. 9,969,700, which is a Divisional of U.S. application Ser. No. 14/371,868, which issued as U.S. Pat. No. 9,382,236, which is a U.S. National stage of International Patent Application No. PCT/JP2013/050320, filed Jan. 10, 2013, which claims priority to Japanese Application No. 2012-005343, filed Jan. 13, 2012. The disclosures of each of the applications listed above are incorporated by reference herein in their entireties.

TECHNICAL FIELD

The present invention relates to a diazepine derivative having a P2X4 receptor antagonist activity.

BACKGROUND ART

The ATP receptors are roughly classified into the P2X family of the ion channel type receptors, and the P2Y family of the G protein coupling type receptors, and seven kinds (P2X1 to P2X7) and eight kinds (P2Y1, P2Y2, P2Y4, P2Y6, and P2Y11 to P2Y14) of subtypes have so far been reported, respectively.

The P2X4 receptor (Genebank No. X87763), a subtype of the P2X family, has been reported to be widely expressed in the central nervous system, and the like (Non-patent documents 1 to 5).

The onset mechanisms of intractable pains, including neuropathic pain, have not been precisely elucidated. If non-steroidal anti-inflammatory drugs (NSAIDs) and morphine are not effective, no therapy is available for that pain. Therefore, very heavy physical and mental burden is given to patients and surrounding people. Neuropathic pain is often caused by injury of a peripheral nerve or the central nerve, and it is caused by, for example, after-trouble of operation, cancer, spinal cord injury, herpes zoster, diabetic neuritis, trigeminal neuralgia, and the like.

Recently, Inoue et al. verified the involvement of the P2X receptor in neuropathic pain by using a spinal nerve-damaged animal model in which allodynia can be detected. The authors described that nerve-damaged type unusual pain (especially allodynia) is induced through the P2X4 receptor expressed in the microglia cells of the spinal cord (Non-patent documents 6 and 7, and Patent document 1).

Therefore, a substance that inhibits the activity of the P2X4 receptor is expected to be a prophylactic or therapeutic agent for pains of nociceptive pain, inflammatory pain, and neuropathic pain.

Patent document 2 reported that a benzofuro-1,4-diazepin-2-one derivative represented by the following general formula (A):

[Formula 1]

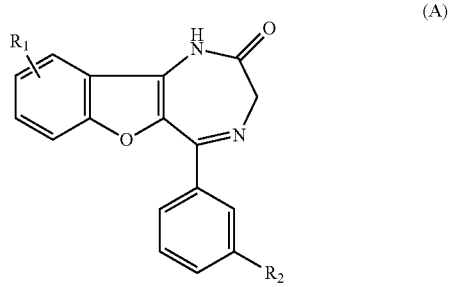

(A)

(in the formula, $R_1$ is a halogen, and $R_2$ is hydrogen, a halogen, nitro, cyano, C(O)—$OR_3$, C(O)—$NR_4R_5$, $SO_2$—$OR_3$, or $SO_2$—$NR_4R_5$, or alternatively, $R_1$ is hydrogen, and $R_2$ is a halogen, nitro, cyano, C(O)—$OR_3$, C(O)—$NR_4R_5$, $SO_2$—$OR_3$, or $SO_2$—$NR_4R_5$) has a P2X4 receptor antagonist activity.

It was also reported that paroxetine, which is an antidepressant, also has a P2X4 receptor antagonist activity (Non-patent document 8).

The inventors of the present invention also found that a naphtho[1,2-e]-1,4-diazepin-2-one derivative represented by the following formula (B):

[Formula 2]

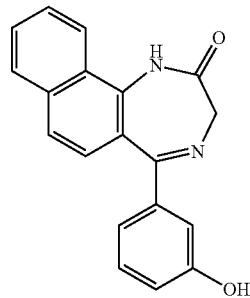

and related compounds thereof has a P2X4 receptor antagonist activity, and filed patent applications (Patent documents 3, 4 and 5).

The compounds of Patent documents 3 to 5 mentioned above and the compounds of the present invention represented by the general formula (I) mentioned later are distinguishable from each other in that, in the former compounds, the substituent of the phenyl group at the 5-position is hydroxy group, a halogen atom, an alkyl group having 1 to 8 carbon atoms, tetrazolyl group, or the like, whereas, in the latter compounds, the phenyl group or the heterocyclic ring represented by G is bound via NHC(=O), NHC(=O)NH, or NHS(O)$_2$ represented by B. In addition, although Patent documents 4 and 5 describe an acylamino group having 2 to 8 carbon atoms and an acylamino group having 2 to 8 carbon atoms and substituted with 1 to 3 halogen atoms as the substituent of the aforementioned phenyl group, they only refer to lower alkylcarbonylamino groups such as acetylamino and trifluoromethylcarbonylamino groups as specific examples thereof, and do not describe benzoylamino group wherein G is phenyl group, and B is NHC(=O) and the like of the compounds of the present invention represented by the general formula (I) mentioned later.

Further, Patent document 6 describes a naphtho[1,2-b]-1,4-diazepin-4-one derivative represented by the following formula (C):

[Formula 3]

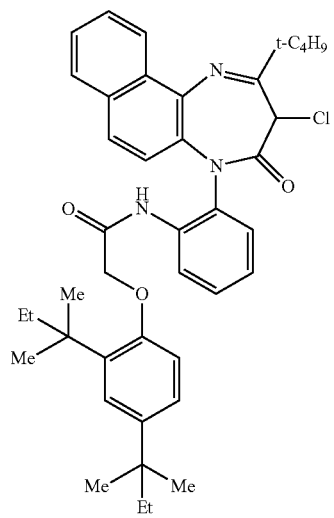

However, although Patent document 6 describes that the compound represented by the aforementioned formula (C) is used as a photographic coupler, there is no description suggesting relation between such a compound and P2X4 receptor antagonist activity.

Further, Patent document 7 describes a 1,4-benzodiazepine derivative having a phosphodiesterase 2 inhibitory activity, which is represented by the formula (D):

[Formula 4]

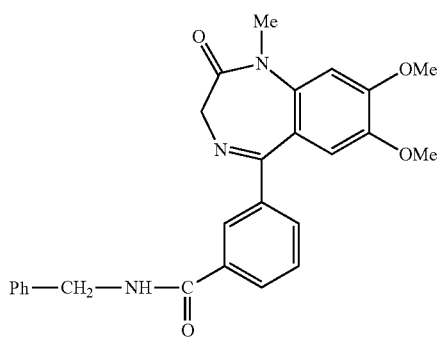

However, this patent document does not describe that the compound of the formula (D) has a P2X4 inhibitory activity.

PRIOR ART REFERENCES

Patent Documents

Patent document 1: Published U.S. Patent Application No. 20050074819
Patent document 2: WO2004/085440
Patent document 3: WO2008/023847
Patent document 4: WO2010/093061
Patent document 5: WO2010/090300
Patent document 6: Published Japanese Patent Application (Kokai) No. H2-304437
Patent document 7: WO2004/041258

Non-Patent Documents

Non-patent document 1: Buell et al. (1996) EMBO J., 15:55-62
Non-patent document 2: Seguela et al. (1996) J. Neurosci., 16:448-455
Non-patent document 3: Bo et al. (1995) FEBS Lett., 375:129-133
Non-patent document 4: Soto et al. (1996) Proc. Natl. Acad. Sci. USA, 93:3684-3688
Non-patent document 5: Wang et al. (1996) Biochem. Res. Commun., 220:196-202
Non-patent document 6: M. Tsuda et al. (2003) Nature, 424, 778-783
Non-patent document 7: Jeffrey A. M. Coull et al. (2005) Nature, 438, 1017-1021
Non-patent document 8: The 49th Convention of The Japanese Society for Neurochemistry (2006), Program Lecture Abstract P3-N-114

SUMMARY OF THE INVENTION

Problems to be Solved by the Invention

An object of the present invention is to provide a diazepine derivative represented by the following general formula (I) having a P2X4 receptor antagonist activity.

Means for Solving the Problem

The present invention thus relates to a compound represented by the following general formula (I), or a pharmacologically acceptable salt thereof:

[Formula 5]

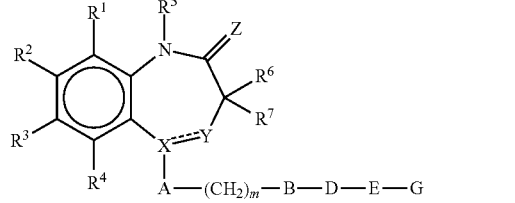

(wherein, $R^1$ and $R^2$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), a phenyl group which may be substituted, a pyridyl group which may be substituted, or an aralkyl group (the aryl moiety has 6 to 10 carbon atoms, and the alkylene moiety has 1 to 8 carbon atoms), or $R^1$ and $R^2$ may bind together to form a condensed ring selected from naphthalene ring, quinoline ring, isoquinoline ring, tetrahydronaphthalene ring, indane ring, tetrahydroquinoline ring, and tetrahydroisoquinoline ring together with the benzene ring to which they bind, and the ring constituted by $R^1$ and $R^2$, bound to each other, together with the carbon atoms to which $R^1$ and $R^2$ bind may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms), $R^3$ and $R^4$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), or an aralkyl group (the aryl moiety has 6 to 10 carbon atoms, and the alkylene moiety has 1 to 8 carbon atoms), $R^5$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety has 6 to 10 carbon atoms, and the alkylene moiety has 1 to 8 carbon atoms), $R^6$ and $R^7$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group, X represents C, CH or N, Y represents N, NH or C(=O), provided that when X is N, Y is not N, or NH, and when X is C or CH, Y is not C(=O), the double line consisting of the solid line and the broken line represents a single bond or a double bond, Z represents oxygen atom or sulfur atom, A represents benzene ring, pyridine ring, thiophene ring, pyrimidine ring, naphthalene ring, quinoline ring, or indole ring, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety has 6 to 10 carbon atoms, and the alkylene moiety has 1 to 8 carbon atoms), phenyl group, and pyridyl group, as a substituent, or represents an atomic bond, B represents $N(R^8)C(=O)$, NHCONH, $CCN(R^9)$, $NHC(=S)NH$, $N(R^{10})SO_2$, $SO_2N(R^{11})$, or $OSO_2$, wherein $R^8$, $R^9$, $R^{10}$ and $R^{11}$ represent hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety has 6 to 10 carbon atoms, and the alkylene moiety has 1 to 8 carbon atoms), D represents an alkylene chain having 1 to 6 carbon atoms, which may have 1 to 4 of the same or different substituents selected from an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, and an aralkyl group (the aryl moiety has 6 to 10 carbon atoms, and the alkylene moiety has 1 to 8 carbon atoms), as a substituent, and may further have a double bond, or represents an atomic bond, E represents O, S, $NR^{12}$, or an atomic bond, wherein $R^{12}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety has 6 to 10 carbon atoms, and the alkylene moiety has 1 to 8 carbon atoms), G represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, an alkylsulfonyl group having 1 to 6 carbon atoms, an aralkyl group (the aryl moiety has 6 to 10 carbon atoms, and the alkylene moiety has 1 to 8 carbon atoms), a phenyl group which may be substituted, a pyridyl group which may be substituted, an imidazolyl group which may be substituted, an oxazolyl group which may be substituted, and a thiazolyl group which may be substituted, as a substituent, and m represents an integer of 0 to 5, provided that when $R^1$ and $R^2$ do not bind together to form a ring, those compounds are excluded wherein, X is C, Y is N, the double line consisting of the solid line and the broken line is a double bond, Z is oxygen atom, A is benzene ring, m is 0, B is C(=O)NH, E is an atomic bond, and G is phenyl group).

The present invention also relates to:
a compound represented by the following general formula (II), or a pharmacologically acceptable salt thereof:

[Formula 6]

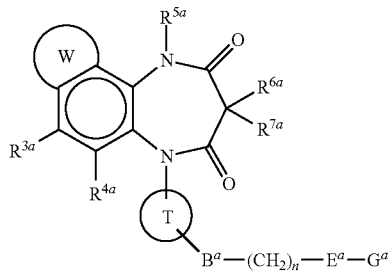

(II)

(wherein, in the formula,

[Formula 7]

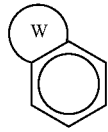

represents naphthalene ring, quinoline ring, isoquinoline ring, tetrahydronaphthalene ring, indane ring, tetrahydroquinoline ring, or tetrahydroisoquinoline ring, these rings may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms), $R^{3\,a}$ and $R^{4\,b}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), or an aralkyl group (the aryl moiety has 6 to 10 carbon atoms, and the alkylene moiety has 1 to 8 carbon atoms), $R^{5\,a}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety has 6 to 10 carbon atoms, and the alkylene moiety has 1 to 8 carbon atoms), $R^{6\,a}$ and $R^{7\,a}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group,

[Formula 8]

represents benzene ring, pyridine ring, thiophene ring, pyrimidine ring, naphthalene ring, quinoline ring, or indole ring, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety has 6 to 10 carbon atoms, and the alkylene moiety has 1 to 8 carbon atoms), phenyl group, and pyridyl group, as a substituent, $B^a$ represents $N(R^{8\,a})C(=O)$, NHCONH, $CON(R^{9\,a})$, NHC(=S)NH, $N(R^{10\,a})SO_2$, $SO_2N(R^{11\,a})$, or $OSO_2$, wherein $R^{8\,a}$, $R^{9a}$, $R^{10\,a}$ and $R^{11\,a}$ represent hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety has 6 to 10 carbon atoms, and the alkylene moiety has 1 to 8 carbon atoms), $E^a$ represents O, S, $NR^{12\,a}$, or an atomic bond, wherein $R^{12\,a}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety has 6 to 10 carbon atoms, and the alkylene moiety has 1 to 8 carbon atoms), $G^a$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, an alkylsulfonyl group having 1 to 6 carbon atoms, an aralkyl group (the aryl moiety has 6 to 10 carbon atoms, and the alkylene moiety has 1 to 8 carbon atoms), a phenyl group which may be substituted, a pyridyl group which may be substituted, an imidazolyl group which may be substituted, an oxazolyl group which may be substituted, and a thiazolyl group which may be substituted, as a substituent, and n represents an integer of 0 to 5).

The present invention also relates to a P2X4 receptor antagonist comprising the compound represented by the aforementioned general formula (I) or (II), or a pharmacologically acceptable salt thereof as an active ingredient.

The present invention further relates to a prophylactic or therapeutic agent for neuropathic pain comprising the compound represented by the aforementioned general formula (I) or (II), or a pharmacologically acceptable salt thereof as an active ingredient.

MODES FOR CARRYING OUT THE INVENTION

Hereafter, the present invention will be explained in detail.

In this specification, examples of the alkyl group having 1 to 8 carbon atoms include methyl group, ethyl group, propyl group, isopropyl group, butyl group, i-butyl group, t-butyl group, pentyl group, hexyl group, and the like.

Examples of the cycloalkyl group having 3 to 8 carbon atoms include cyclopropyl group, cyclohexyl group, and the like.

Examples of the alkenyl group having 2 to 8 carbon atoms include allyl group, and the like.

Examples of the alkoxy group having 1 to 8 carbon atoms include methoxy group, ethoxy group, propoxy group, isopropoxy group, butoxy group, i-butoxy group, t-butoxy group, pentyloxy group, hexyloxy group, and the like.

Examples of the alkyl group having 1 to 8 carbon atoms and substituted with 1 to 3 halogen atoms include methyl group, ethyl group, propyl group, isopropyl group, butyl group, t-butyl group, and the like, which are substituted with 1 to 3 of halogen atoms such as fluorine atom, chlorine atom, and bromine atom, and preferred examples include trifluoromethyl group, chloromethyl group, 2-chloroethyl group, 2-bromoethyl group, 2-fluoroethyl group, and the like.

Examples of the alkoxy group having 1 to 8 carbon atoms and substituted with 1 to 3 halogen atoms include methoxy group, ethoxy group, propoxy group, isopropoxy group, butoxy group, t-butoxy group, and the like, which are substituted with 1 to 3 of halogen atoms such as fluorine atom, chlorine atom, and bromine atom, and preferred examples include trifluoromethoxy group, chloromethoxy group, 2-chloroethoxy group, 2-bromoethoxy group, 2-fluoroethoxy group, and the like.

Examples of the halogen atom include fluorine atom, chlorine atom, bromine atom, and the like.

Examples of the alkylamino group having 1 to 8 carbon atoms include methylamino group, ethylamino group, and the like.

Examples of the dialkylamino group having 2 to 8 carbon atoms include dimethylamino group, diethylamino group, and the like.

Examples of the acylamino group having 2 to 8 carbon atoms include acetylamino group.

Examples of the acyl group having 2 to E carbon atoms include acetyl group, and the like.

Examples of the alkoxycarbonyl group (the alkoxy moiety has 1 to 8 carbon atoms) include methoxycarbonyl group, and the like.

Examples of the aralkyl group (the aryl moiety has 6 to 10 carbon atoms, and the alkylene moiety has 1 to 8 carbon atoms) include benzyl group, and the like.

Examples of the alkyl group having 1 to 8 carbon atoms and substituted with hydroxyl group include 2-hydroxyethyl group, and the like.

Examples of the alkylsulfinyl group having 1 to 6 carbon atoms include methanesulfinyl group, and the like.

Examples of the alkylthio group having 1 to 6 carbon atoms include methylthio group, and the like.

Examples of the alkylsulfonyl group having 1 to 6 carbon atoms include methanesulfonyl group, and the like.

Examples of the substituent of the phenyl group which may be substituted, the pyridyl group which may be substituted, the imidazolyl group which may be substituted, the oxazolyl group which may be substituted, and the thiazolyl group which may be substituted include a halogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, and the like.

As the compounds of the present invention represented by the aforementioned general formula (I), the following compounds are preferred.

(1) A compound represented by the aforementioned general formula (I), or a pharmacologically acceptable salt thereof, wherein $R^1$ and $R^2$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, a phenyl group which may be substituted, a pyridyl group which may be substituted, or an aralkyl group (the aryl moiety has 6 to 10 carbon atoms, and the alkylene moiety has 1 to 8 carbon atoms).

(2) The compound represented by the aforementioned general formula (I), or a pharmacologically acceptable salt thereof, wherein $R^1$ and $R^2$ bind together to form naphthalene ring, or tetrahydronaphthalene ring together with the benzene ring to which they bind, and the benzene ring or the cyclohexene ring constituted by $R^1$ and $R^2$, bound to each other, together with the carbon atoms to which $R^1$ and $R^2$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms).

(3) The compound represented by the aforementioned general formula (I), or a pharmacologically acceptable salt thereof, wherein $R^1$ and $R^2$ bind together to form naphthalene ring together with the benzene ring to which they bind, and the benzene ring constituted by $R^1$ and $R^2$, bound to each other, together with the carbon atoms to which $R^1$ and $R^2$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, and amino group.

(4) The compound represented by the aforementioned general formula (I) or the compound according to any one of (1) to (3) mentioned above, or a pharmacologically acceptable salt thereof, wherein $R^3$ and $R^4$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, or an aralkyl group (the aryl moiety has 6 to 10 carbon atoms, and the alkylene moiety has 1 to 8 carbon atoms).

(5) The compound represented by the aforementioned general formula (I) or the compound according to any one of (1) to (4) mentioned above, or a pharmacologically acceptable salt thereof, wherein $R^5$ is hydrogen atom, an alkyl group having 1 to 8 carbon atoms, or an aralkyl group (the aryl moiety has 6 to 10 carbon atoms, and the alkylene moiety has 1 to 8 carbon atoms).

(6) The compound represented by the aforementioned general formula (I) or the compound according to any one of (1) to (4) mentioned above, or a pharmacologically acceptable salt thereof, wherein $R^5$ is hydrogen atom.

(7) The compound represented by the aforementioned general formula (I) or the compound according to any one of (1) to (6) mentioned above, or a pharmacologically acceptable salt thereof, wherein $R^6$ and $R^7$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms.

(8) The compound represented by the aforementioned general formula (I) or the compound according to any one of (1) to (6) mentioned above, or a pharmacologically acceptable salt thereof, wherein both $R^6$ and $R^7$ are hydrogen atoms.

(9) The compound represented by the aforementioned general formula (I) or the compound according to any one of (1) to (8) mentioned above, or a pharmacologically acceptable salt thereof, wherein X is N, Y is C(=O), and the double line consisting of the solid line and the broken line is a single bond.

(10) The compound represented by the aforementioned general formula (I) or the compound according to any one of (1) to (8) mentioned above, or a pharmacologically acceptable salt thereof, wherein X is C, Y is N, and the double line consisting of the solid line and the broken line is a double bond.

(11) The compound represented by the aforementioned general formula (I) or the compound according to any one of (1) to (10) mentioned above, or a pharmacologically acceptable salt thereof, wherein Z is oxygen atom.

(12) The compound represented by the aforementioned general formula (I) or the compound according to any one of (1) to (11) mentioned above, or a pharmacologically acceptable salt thereof, wherein A is phenyl group, or pyridyl group, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety has 6 to 10 carbon atoms, and the alkylene moiety has 1 to 8 carbon atoms), phenyl group, and pyridyl group, as a substituent.

(13) The compound represented by the aforementioned general formula (I) or the compound according to any one of (1) to (11) mentioned above, or a pharmacologically acceptable salt thereof, wherein A is phenyl group, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, and amino group, as a substituent.

(14) The compound represented by the aforementioned general formula (I) or the compound according to any one of (1) to (11) mentioned above, or a pharmacologically acceptable salt thereof, wherein A is an atomic bond.

(15) The compound represented by the aforementioned general formula (I) or the compound according to any one of (1) to (14) mentioned above, or a pharmacologically acceptable salt thereof, wherein B is NHC(=O), NHCONH, CONH, NHC(=S)NH, NHSO$_2$, SO$_2$NH, or OSO$_2$.

(16) The compound represented by the aforementioned general formula (I) or the compound according to any one of (1) to (14) mentioned above, or a pharmacologically acceptable salt thereof, wherein B is NHC(=O), NHCONH, or NHSO$_2$.

(17) The compound represented by the aforementioned general formula (I) or the compound according to any one of (1) to (16) mentioned above, or a pharmacologically acceptable salt thereof, wherein D is an alkylene chain having 1 to 6 carbon atoms, which may have 1 to 4 of the same or different substituents selected from an alkyl group having 1 to 8 carbon atoms, and an alkyl group having 1 to 8 carbon atoms and substituted with 1 to 3 halogen atoms, as a substituent, and may further have a double bond.

(18) The compound represented by the aforementioned general formula (I) or the compound according to any one of (1) to (16) mentioned above, or a pharmacologically acceptable salt thereof, wherein D is an atomic bond.

(19) The compound represented by the aforementioned general formula (I) or the compound according to any one of (1) to (16) mentioned above, or a pharmacologically acceptable salt thereof, wherein E is an atomic bond.

(20) The compound represented by the aforementioned general formula (I) or the compound according to any one of (1) to (19) mentioned above, or a pharmacologically acceptable salt thereof, wherein G is piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine or pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms, as a substituent.

(21) The compound represented by the aforementioned general formula (I) or the compound according to any one of (1) to (19) mentioned above, or a pharmacologically acceptable salt thereof, wherein G is benzene, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms, as a substituent.

(22) The compound represented by the aforementioned general formula (I) or the compound according to any one of (1) to (21) mentioned above, or a pharmacologically acceptable salt thereof, wherein m is 0.

As the compounds of the present invention represented by the aforementioned general formula (II), the following compounds are preferred.

(23) The compound represented by the aforementioned general formula (II), or a pharmacologically acceptable salt thereof, wherein

[Formula 9]

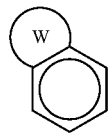

is naphthalene ring or tetrahydronaphthalene ring, which may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms), as a substituent.

(24) The compound represented by the aforementioned general formula (II), or a pharmacologically acceptable salt thereof, wherein

[Formula 10]

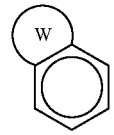

is naphthalene ring, which may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, and amino group, as a substituent.

(25) The compound represented by the aforementioned general formula (II) or the compound according to (23) or (24) mentioned above, or a pharmacologically acceptable salt thereof, wherein $R^{3\ a}$ and $R^{4\ a}$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, or an aralkyl group (the aryl moiety has 6 to 10 carbon atoms, and the alkylene moiety has 1 to 8 carbon atoms).

(26) The compound represented by the aforementioned general formula (II) or the compound according to any one of (23) to (25) mentioned above, or a pharmacologically acceptable salt thereof, wherein $R^{6\ a}$ is hydrogen atom, an alkyl group having 1 to 8 carbon atoms, or an aralkyl group (the aryl moiety has 6 to 10 carbon atoms, and the alkylene moiety has 1 to 8 carbon atoms).

(27) The compound represented by the aforementioned general formula (II) or the compound according to any one of (23) to (25) mentioned above, or a pharmacologically acceptable salt thereof, wherein $R^{6\ a}$ is hydrogen atom.

(28) The compound represented by the aforementioned general formula (II) or the compound according to any one of (23) to (27) mentioned above, or a pharmacologically acceptable salt thereof, wherein $R^{6\ a}$ and $R^{7\ a}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms.

(29) The compound represented by the aforementioned general formula (II) or the compound according to any one of (23) to (27) mentioned above, or a pharmacologically acceptable salt thereof, wherein both $R^{6\ a}$ and $R^{7\ a}$ are hydrogen atoms.

(30) The compound represented by the aforementioned general formula (II) or the compound according to any one of (23) to (29) mentioned above, or a pharmacologically acceptable salt thereof, wherein

[Formula 11]

is phenyl group, or pyridyl group, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety has 6 to 10 carbon atoms, and the alkylene moiety has 1 to 8 carbon atoms), phenyl group, and pyridyl group, as a substituent.

(31) The compound represented by the aforementioned general formula (II) or the compound according to any one of (23) to (29) mentioned above, or a pharmacologically acceptable salt thereof, wherein

[Formula 12]

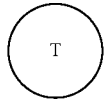

is phenyl group, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms: an alkoxy group having 1 to 8 carbon atoms and substituted with 1 to 3 halogen atoms: a halogen atom, hydroxyl group, nitro group, cyano group, and amino group, as a substituent.

(32) The compound represented by the aforementioned general formula (II) or the compound according to any one of (23) to (29) mentioned above, or a pharmacologically acceptable salt thereof, wherein

[Formula 13]

is an atomic bond.

(33) The compound represented by the aforementioned general formula (II) or the compound according to any one of (23) to (32) mentioned above, or a pharmacologically acceptable salt thereof, wherein $B^a$ is NHC(=O), NHCONH, CONH, NHC(=S)NH, NHSO$_2$, SO$_2$ NH, or OSO$_2$.

(34) The compound represented by the aforementioned general formula (II) or the compound according to any one of (23) to (32) mentioned above, or a pharmacologically acceptable salt thereof, wherein $B^a$ is NHC(=O), NHCONH, or NHSO$_2$.

(35) The compound represented by the aforementioned general formula (II) or the compound according to any one of (23) to (34) mentioned above, or a pharmacologically acceptable salt thereof, wherein $E^a$ is an atomic bond.

(36) The compound represented by the aforementioned general formula (II) or the compound according to any one of (23) to (35) mentioned above, or a pharmacologically acceptable salt thereof, wherein $G^a$ is piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms, as a substituent.

(37) The compound represented by the aforementioned general formula (II) or the compound according to any one of (23) to (35) mentioned above, or a pharmacologically acceptable salt thereof, wherein $G^a$ is benzene, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms, as a substituent.

(38) The compound represented by the aforementioned general formula (II) or the compound according to any one of (23) to (37) mentioned above, or a pharmacologically acceptable salt thereof, wherein n is 0.

Examples of the pharmacologically acceptable salts of the compounds represented by the aforementioned general formulas (I) and (II) include hydrochlorides, and alkali metal salts such as those of sodium, potassium, and lithium.

Further, there may be optical isomers of the compounds of the present invention such as cis- and trans-isomers, enantiomers, and racemates, and all of these substances fall within the scope of the present invention.

The synthetic schemes of the compounds of the present invention represented by the aforementioned general formula (I) or (II) are shown below.

The step from a compound represented by the general formula (i) to a compound represented by the general formula (m), which is a compound of the present invention, in the synthesis methods 1 and 2, the step from a compound represented by the general formula (u) to a compound represented by the general formula (w), which is a compound of the present invention, in the synthesis method 3, the step from a compound represented by the general formula (ab) to a compound represented by the general formula (ac), which is a compound of the present invention, in the synthesis method 4, the step from a compound represented by the general formula (ae) to a compound represented by the general formula (af), which is a compound of the present invention, in the synthesis method 5, and the amidation step from a compound represented by the general formula (am) to a compound represented by the general formula (an), which is a compound of the present invention, in the synthesis method 7 are performed by using a usual amidation reaction in which an amino compound is reacted with carboxylic acid, carboxylic acid halide, sulfonic acid halide or the like in the presence of pyridine, etc.

The step from a compound represented by the general formula (i) to a compound represented by the general formula (ai), which is a compound of the present invention, in the synthesis method 6 is performed by reacting an amino compound with an isocyanate compound or isothiocyanate.

The step from a compound represented by the general formula (au) to a compound represented by the general formula (av) or (aw), which is a compound of the present invention, in the synthesis method 8 is performed by oxidizing a compound represented by the general formula (au) with an oxidizing agent such as MCPBA.

Synthesis Method 1

[Formula 14]

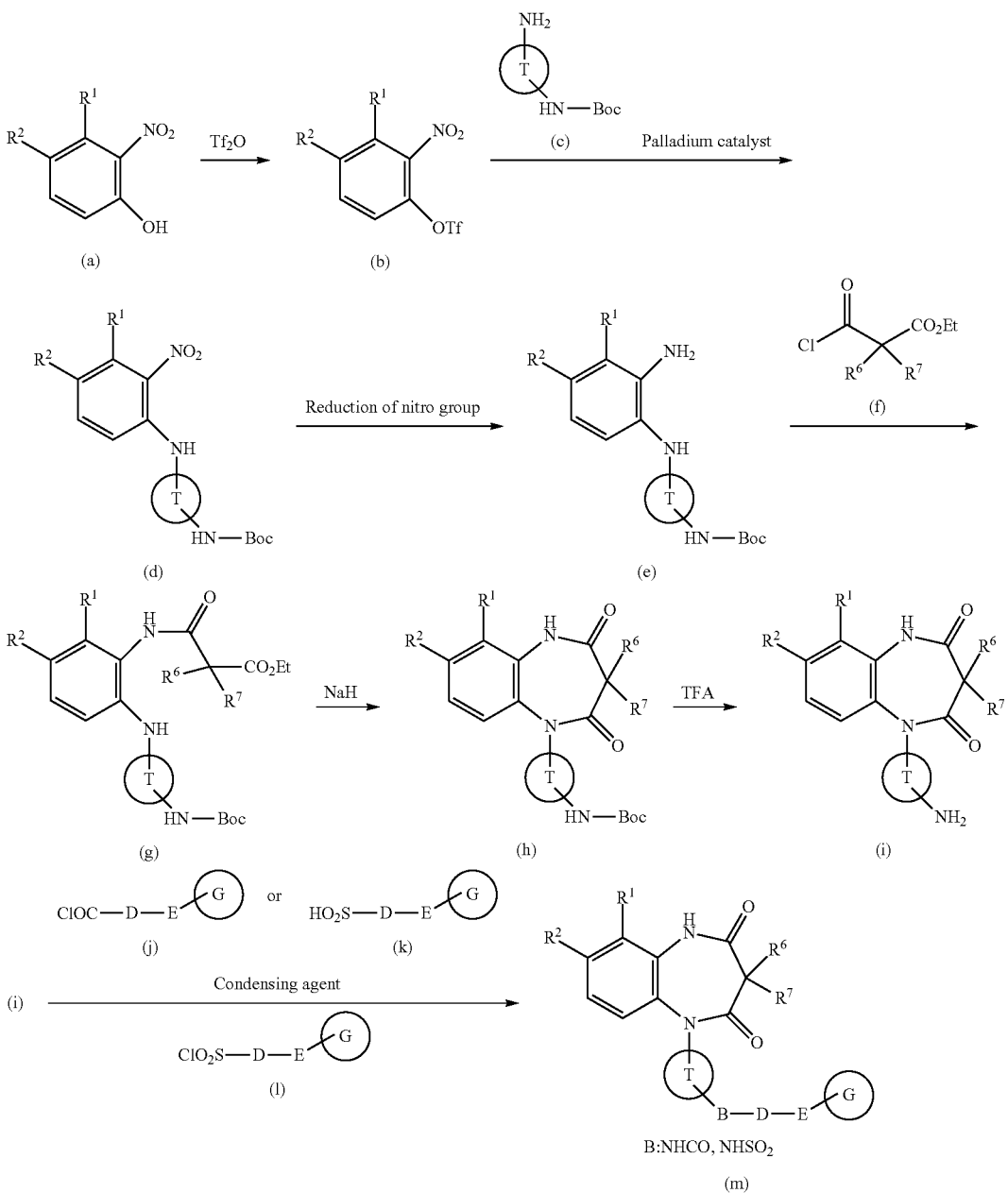

-continued
Synthesis Method 2
[Formula 15]
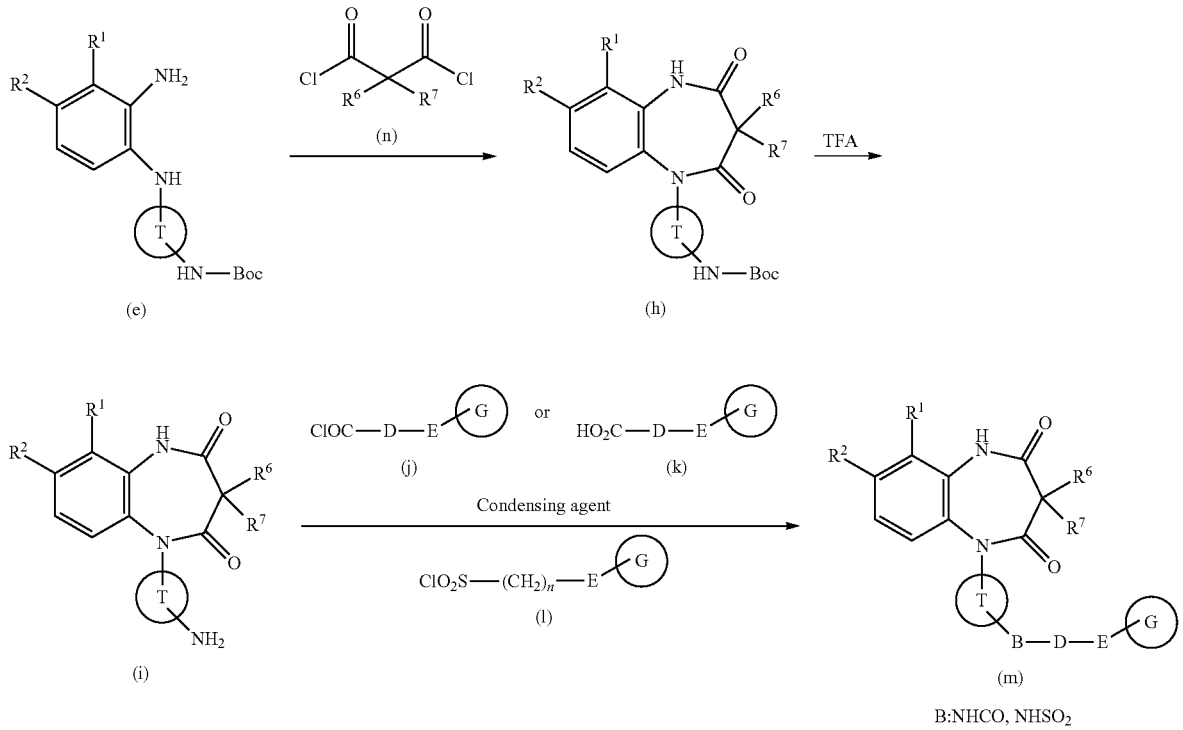
Synthesis Method 3
[Formula 16]
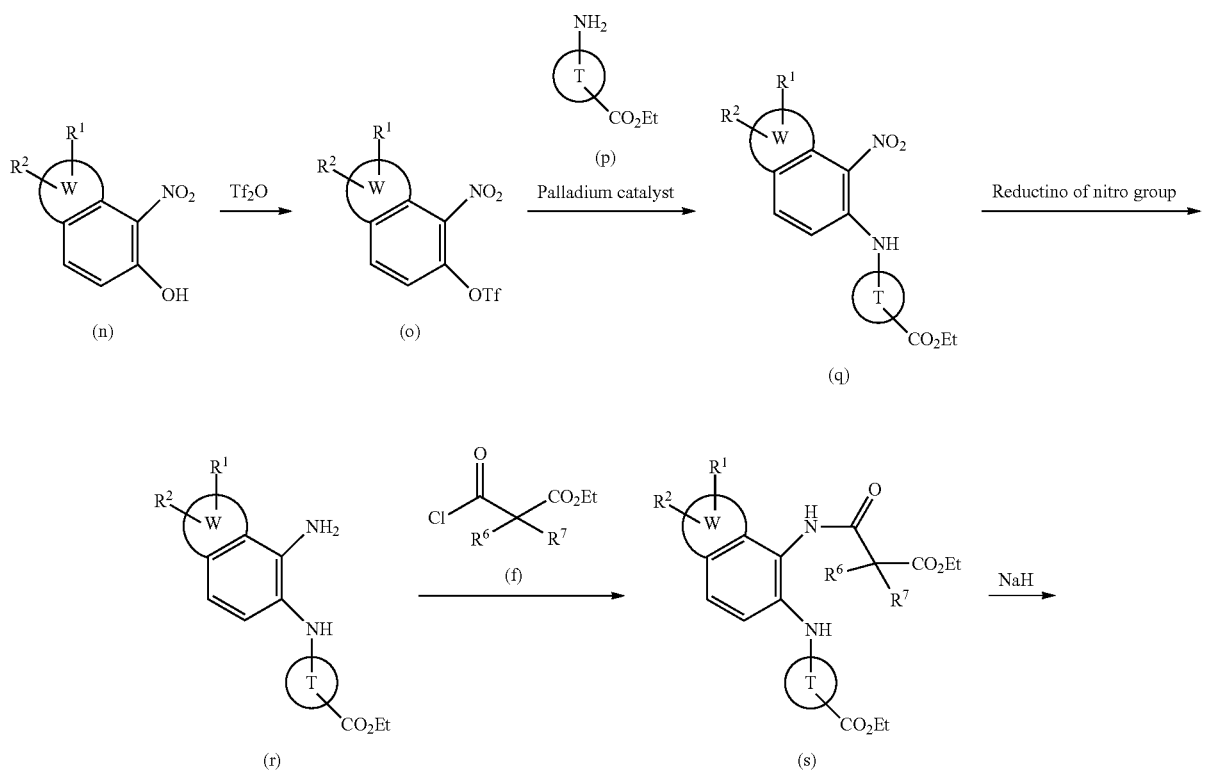

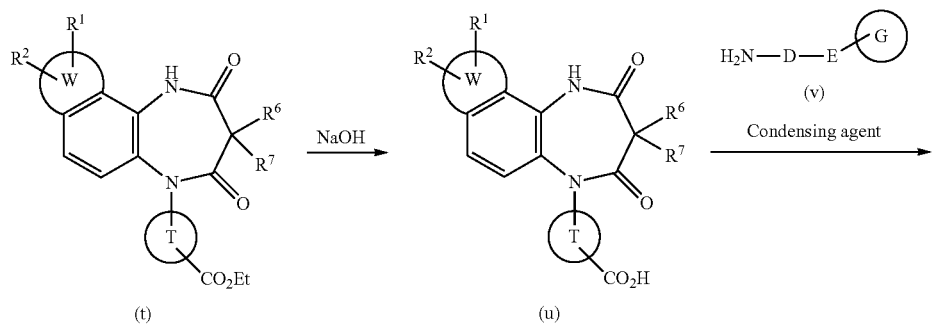
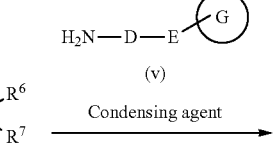
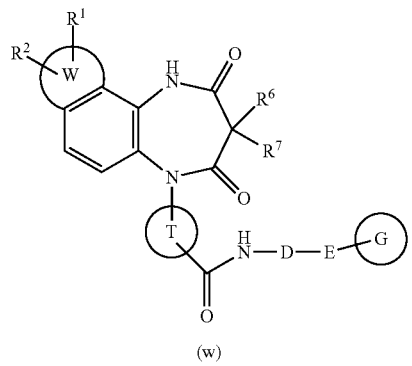
Synthesis Method 4
[Formula 17]
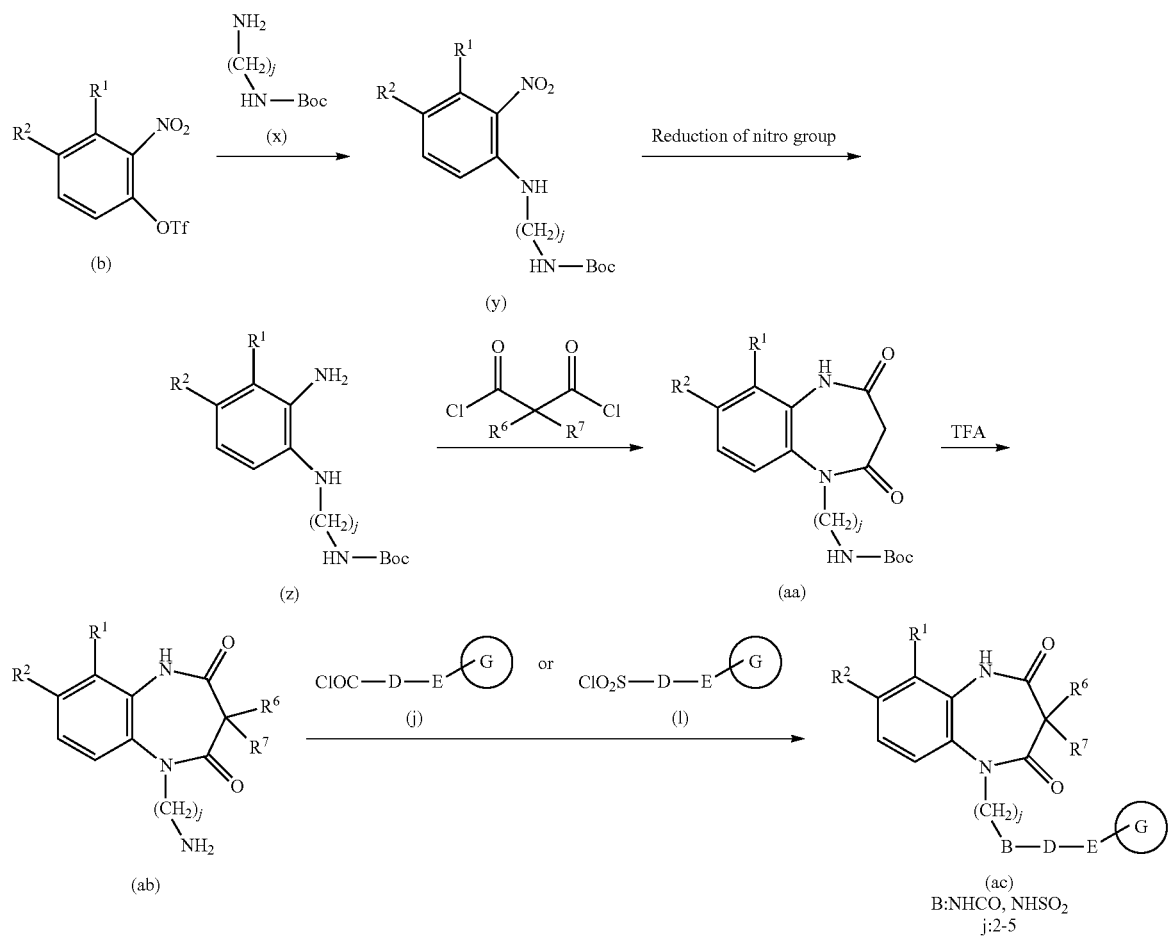

-continued
Synthesis Method 5
[Formula 18]
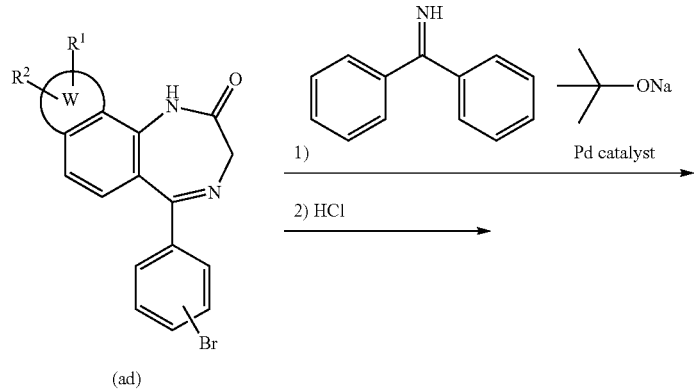
(ad)
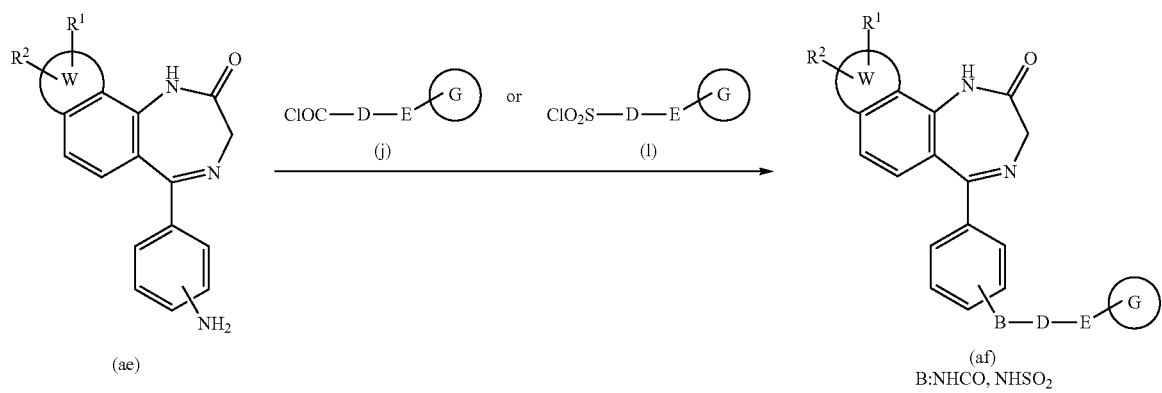
(ae) → (af)
B:NHCO, NHSO₂
Synthesis Method 6
[Formula 19]
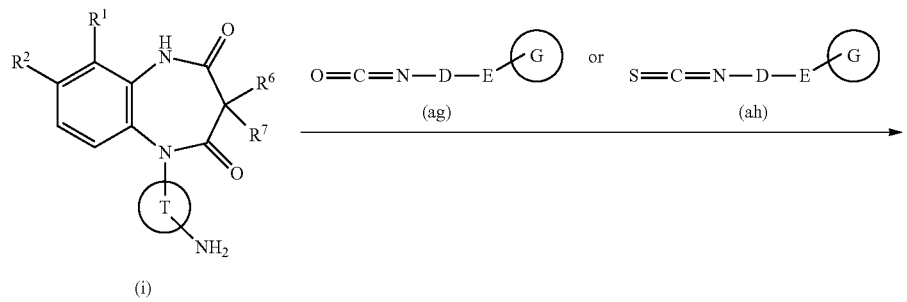
(i)
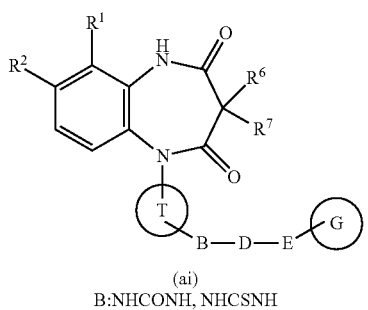
(ai)
B:NHCONH, NHCSNH -continued
Synthesis Method 7
[Formula 20]
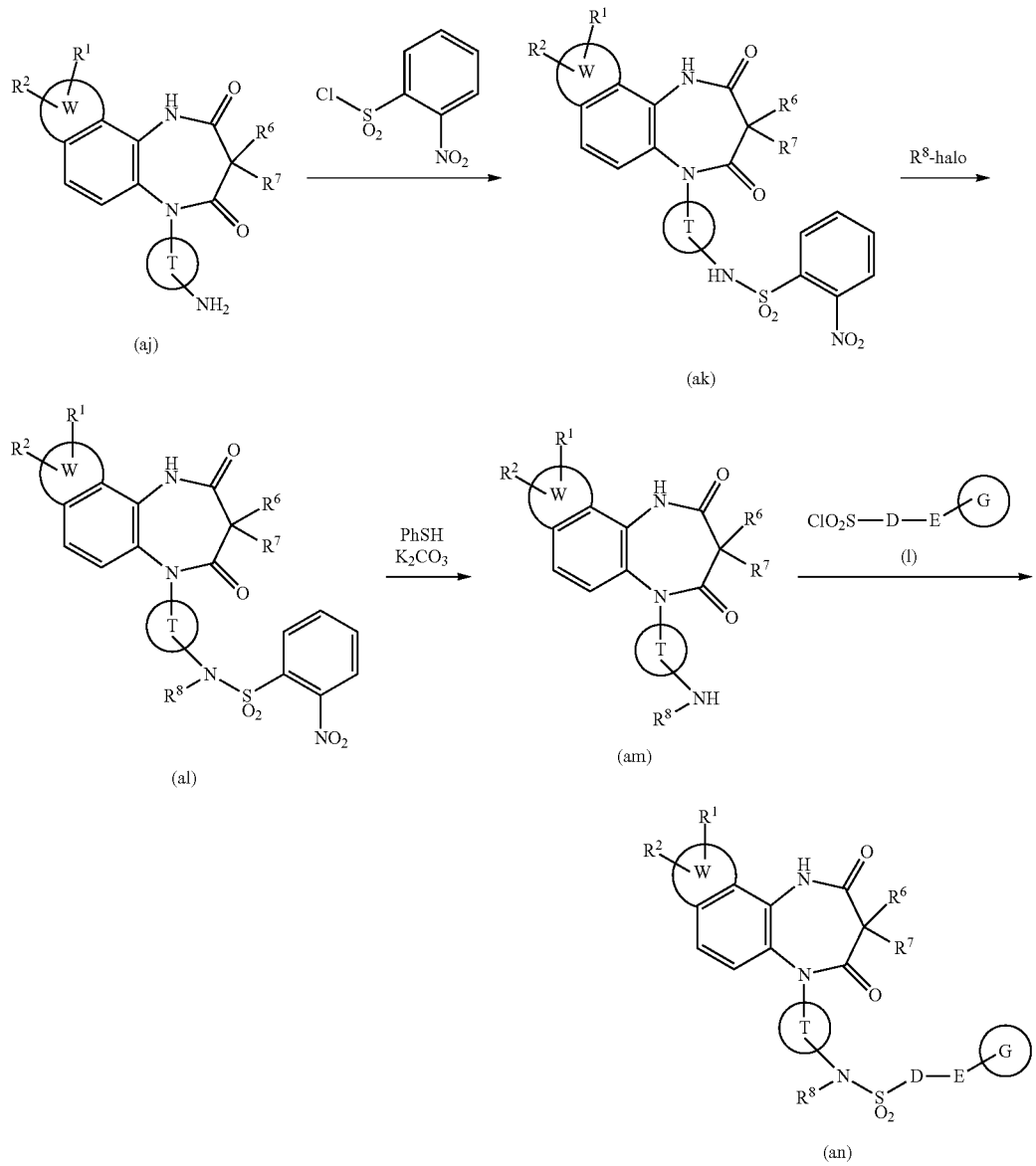
Synthesis Method 8
[Formula 21]
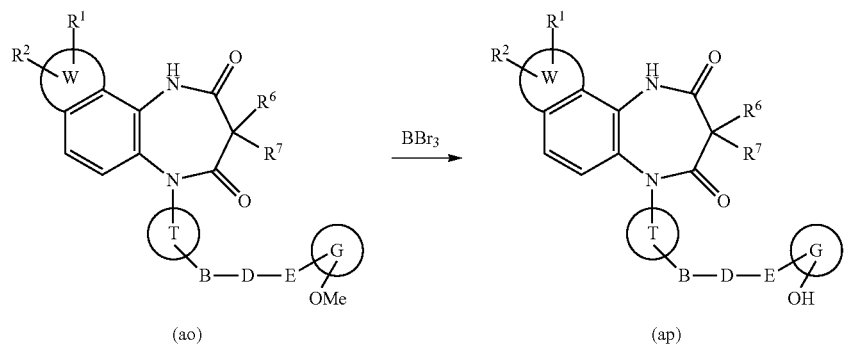

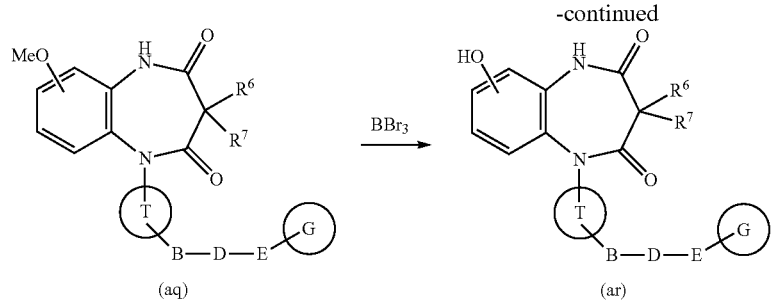
(aq) →BBr₃→ (ar)
-continued
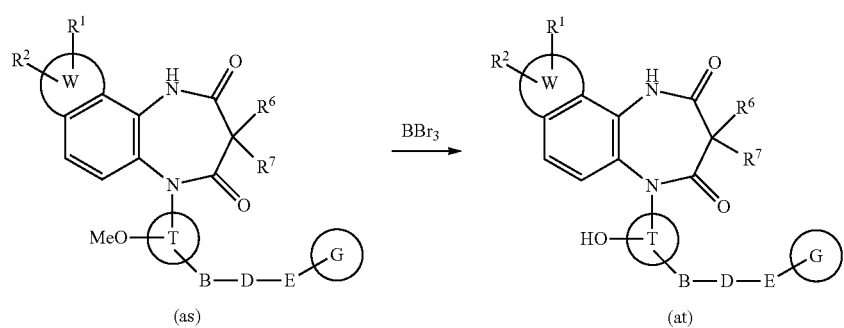
(as) →BBr₃→ (at)
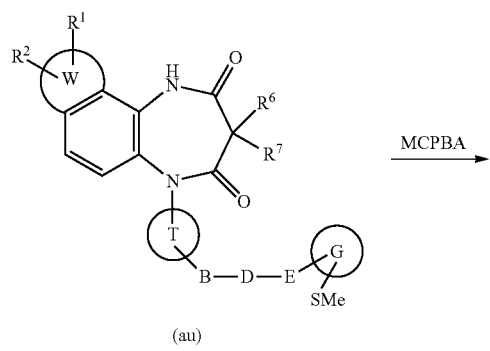
(au) →MCPBA→
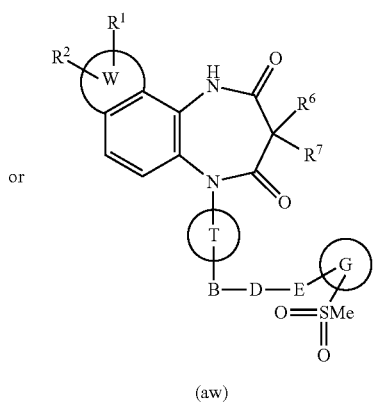
(av) or (aw)

The compounds of the present invention represented by the aforementioned general formulas (I) and (II) can be prepared by referring to the aforementioned synthesis methods and the examples mentioned later, as well as the aforementioned patent documents, prior art references, and the like.

Examples of typical compounds of the present invention obtained as described above are mentioned below.

Examples of Typical Compounds (1)

[Formula 22]

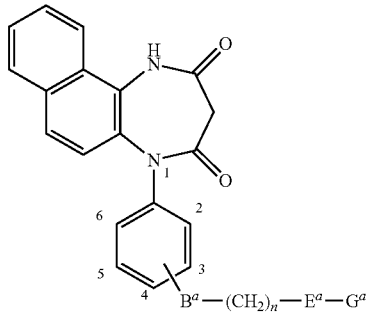

(In the formula, $B^a$ (substitution position), n, $E^a$, and $G^a$ are as shown in Tables 1 to 10)

TABLE 1

| $B^a$ (substitution position) | n | $E^a$ | $G^a$ |
|---|---|---|---|
| NHCO(4) | 0 | Atomic bond | Phenyl |
| NHCO(4) | 0 | Atomic bond | (2-CF$_3$)Phenyl |
| NHCO(4) | 0 | Atomic bond | (3-Br)Phenyl |
| NHCO(4) | 0 | Atomic bond | (4-CF$_3$)Phenyl |
| NHCO(4) | 0 | Atomic bond | (2-Me)Phenyl |
| NHCO(4) | 0 | Atomic bond | (2,6-Me)Phenyl |
| NHCO(4) | 0 | Atomic bond | (2,6-Cl)Phenyl |
| NHCO(4) | 0 | Atomic bond | (3-Cl)Phenyl |
| NHCO(4) | 1 | Atomic bond | Phenyl |
| NHC(=S)NH(4) | 0 | Atomic bond | Phenyl |
| NHCO(4) | 0 | Atomic bond | (2,3-OMe)Phenyl |
| NHCO(4) | 0 | Atomic bond | (2-OMe)Phenyl |
| NHCO(4) | 1 | Atomic bond | (2-Cl)Phenyl |
| NHCO(4) | 0 | Atomic bond | (2,3-Me)Phenyl |
| NHCO(4) | 0 | Atomic bond | (2,5-Me)Phenyl |
| NHCO(4) | 0 | Atomic bond | (2-Cl,5-Br)Phenyl |

TABLE 2

| $B^a$ (substitution position) | n | $E^a$ | $G^a$ |
|---|---|---|---|
| NHCO(4) | 0 | Atomic bond | (2,4-Cl)Phenyl |
| NHCO(4) | 0 | Atomic bond | (2-OH)Phenyl |
| NHCO(4) | 0 | Atomic bond | (2,3-OH)Phenyl |
| NHC(=O)NH(4) | 0 | Atomic bond | Phenyl |
| NHCO(4) | 1 | Atomic bond | (2,6-Cl)Phenyl |
| NHCO(4) | 1 | Atomic bond | (2-OMe)Phenyl |
| NHCO(4) | 1 | Atomic bond | (2-OH)Phenyl |
| NHC(=S)NH(4) | 0 | Atomic bond | (2-Cl)Phenyl |
| NHCO(4) | 0 | Atomic bond | (3-CF$_3$)Phenyl |
| NHCO(4) | 1 | Atomic bond | (2-CF$_3$)Phenyl |
| NHC(=O)NH(4) | 0 | Atomic bond | (2-Cl)Phenyl |
| NHCO(4) | 0 | Atomic bond | (2-Cl,3-OMe)Phenyl |
| NHCO(4) | 2 | Atomic bond | Phenyl |
| NHCO(4) | 0 | Atomic bond | 3-Indolyl |
| NHCO(4) | 0 | Atomic bond | (2-Cl,3-OH)Phenyl |
| NHCO(4) | 1 | O | Phenyl |

TABLE 3

| $B^a$ (substitution position) | n | $E^a$ | $G^a$ |
|---|---|---|---|
| NHCO(4) | 1 | Atomic bond | (2-Cl,4-OMe)Phenyl |
| NHCO(4) | 0 | Atomic bond | (1-Me)Imidazol-2-yl |
| NHCO(4) | 1 | Atomic bond | (2,4-Cl)Phenyl |
| NHCO(4) | 1 | Atomic bond | (2-Cl,4-OH)Phenyl |
| NHCO(4) | 1 | Atomic bond | Pyridin-3-yl |
| NHCO(4) | 0 | Atomic bond | Benzimidazol-2-yl |
| NHCO(4) | 0 | Atomic bond | (2-Cl)Phenyl |
| NHCO(4) | 0 | Atomic bond | (2-Br)Phenyl |
| NHCO(4) | 0 | Atomic bond | (2-I)Phenyl |
| NHCO(4) | 1 | Atomic bond | (2-Me)Phenyl |
| NHCO(4) | 0 | Atomic bond | Quinoxalin-2-yl |
| NHCO(4) | 0 | Atomic bond | (5-Me)Thiophen-2-yl |
| NHCO(3) | 1 | Atomic bond | (2-Cl)Phenyl |
| NHCO(4) | 0 | Atomic bond | (2,4,6-Me)Phenyl |
| NHCO(4) | 0 | Atomic bond | (2-Et)Phenyl |
| NHC(=S)NH(4) | 0 | Atomic bond | (2-Me)Phenyl |

TABLE 4

| $B^a$ (substitution position) | n | $E^a$ | $G^a$ |
|---|---|---|---|
| NHCO(4) | 0 | Atomic bond | (4-NMe$_2$)Phenyl |
| NHCO(4) | 1 | O | (2,4-Cl)Phenyl |
| NHCO(4) | 1 | O | (2-Me)Phenyl |
| NHCO(4) | 0 | Atomic bond | (2-Ac)Phenyl |
| NHCO(4) | 0 | Atomic bond | (2-tBu)Phenyl |
| NHCO(3) | 0 | Atomic bond | (2-I)Phenyl |
| NHCO(4) | 0 | Atomic bond | (1-Me)Piperidin-4-yl |
| NHCO(4) | 0 | Atomic bond | Benzofuran-2-yl |
| NHCO(4) | 0 | Atomic bond | (1-Me)Indol-3-yl |
| NHCO(4) | 0 | Atomic bond | (2-allyl)Phenyl |
| NHCO(4) | 0 | Atomic bond | (2-nPr)Phenyl |
| NHCO(4) | 0 | Atomic bond | (2-iPrO)Phenyl |
| NHCO(4) | 0 | Atomic bond | (3-Me)Thiophen-2-yl |
| NHCO(4) | 1 | O | (2-Me,3-Cl)Phenyl |
| NHCO(4) | 0 | Atomic bond | (2-CF$_3$,4-F)Phenyl |
| NHCO(4) | 0 | Atomic bond | (2-OMe,4-F)Phenyl |

TABLE 5

| $B^a$ (substitution position) | n | $E^a$ | $G^a$ |
|---|---|---|---|
| NHCO(4) | 0 | Atomic bond | (2-OH,4-F)Phenyl |
| NHCO(3) | 1 | Atomic bond | (2-I)Phenyl |
| NHCO(4) | 0 | Atomic bond | (3-NMe$_2$)Phenyl |
| NHCO(4) | 0 | Atomic bond | (2-OMe,4-I)Phenyl |
| NHCO(4) | 0 | Atomic bond | (2-OMe,6-F)Phenyl |
| NHCO(4) | 0 | Atomic bond | (2-OH,4-I)Phenyl |
| NHCO(4) | 0 | Atomic bond | (2-OH,6-F)Phenyl |
| NHCO(4) | 0 | Atomic bond | (2-F)Phenyl |
| NHCO(4) | 0 | Atomic bond | (2-NMe$_2$)Phenyl |
| NHCO(4) | 0 | Atomic bond | (2-OMe,6-Me)Phenyl |
| NHCO(4) | 0 | Atomic bond | (2-OH,6-Me)Phenyl |
| NHCO(4) | 2 | Atomic bond | (2-Me)Phenyl |
| CONH(4) | 0 | Atomic bond | Phenyl |

TABLE 5-continued

| $B^a$ (substitution position) | n | $E^a$ | $G^a$ |
|---|---|---|---|
| CONH(4) | 1 | Atomic bond | Phenyl |
| NHCO(4) | 2 | Atomic bond | (2-Cl)Phenyl |
| CONH(4) | 1 | Atomic bond | (2-Cl)Phenyl |

TABLE 6

| $B^a$ (substitution position) | n | $E^a$ | $G^a$ |
|---|---|---|---|
| CONH(4) | 0 | Atomic bond | (2-Cl)Phenyl |
| NHCO(4) | 0 | Atomic bond | (5-Br,2,3-methylenedioxy)Phenyl |
| NHCO(4) | 0 | Atomic bond | (2-OMe,6-Br)Phenyl |
| NHCO(4) | 0 | Atomic bond | (2-OH,6-Br)Phenyl |
| NHCO(4) | 0 | Atomic bond | (2-OMe,6-Cl)Phenyl |
| NHCO(4) | 0 | Atomic bond | (2-OH,6-Cl)Phenyl |
| NHCO(4) | 0 | Atomic bond | (2-OH,6-OMe)Phenyl |
| NHCO(4) | 0 | Atomic bond | (2-OMe,6-CF$_3$)Phenyl |
| NHCO(4) | 0 | Atomic bond | (2-OH,6-CF$_3$)Phenyl |
| NHCO(4) | 0 | Atomic bond | (2-Cl,5-SMe)Phenyl |
| NHCO(4) | 0 | Atomic bond | (2-SMe)Phenyl |
| NHCO(4) | 0 | Atomic bond | (3-SMe)Phenyl |
| NHCO(4) | 0 | Atomic bond | (2-OMe,6-Et)Phenyl |
| NHCO(4) | 0 | Atomic bond | (3-SO$_2$Me)Phenyl |
| NHCO(4) | 0 | Atomic bond | (2-OH,6-Et)Phenyl |
| NHCO(4) | 0 | Atomic bond | (3-S(=O)Me)Phenyl |

TABLE 7

| $B^a$ (substitution position) | n | $E^a$ | $G^a$ |
|---|---|---|---|
| NHCO(4) | 0 | Atomic bond | (2-Cl,5-S(=O)Me)Phenyl |
| NHCO(4) | 0 | Atomic bond | (2-S(=O)Me)Phenyl |
| NHCO(4) | 0 | Atomic bond | (3-Cl)Pyridin-2-yl |
| NHCO(4) | 0 | Atomic bond | (2-OMe,3-Cl)Phenyl |
| NHCO(4) | 0 | Atomic bond | (3-Me)Pyridin-2-yl |
| NHCO(4) | 0 | Atomic bond | (2-OH,3-Cl)Phenyl |
| NHCO(4) | 0 | Atomic bond | (3-OH)Pyridin-2-yl |
| NHCO(4) | 0 | Atomic bond | (3-Vinyl)Pyridin-2-yl |
| NHCO(4) | 0 | Atomic bond | (2-Et)Pyridin-2-yl |
| NHSO$_2$(4) | 0 | Atomic bond | (2-NO$_2$)Phenyl |
| NHSO$_2$(4) | 0 | Atomic bond | Phenyl |
| NHSO$_2$(4) | 0 | Atomic bond | (3-Br)Phenyl |
| NHSO$_2$(4) | 0 | Atomic bond | (3-OMe)Phenyl |
| NHSO$_2$(3) | 0 | Atomic bond | (2-NO$_2$)Phenyl |
| NMeSO$_2$(3) | 0 | Atomic bond | (2-NO$_2$)Phenyl |
| NHSO$_2$(3) | 0 | Atomic bond | Naphthalen-2-yl |

TABLE 8

| $B^a$ (substitution position) | n | $E^a$ | $G^a$ |
|---|---|---|---|
| NHSO$_2$(3) | 0 | Atomic bond | Naphthalen-1-yl |
| NHSO$_2$(4) | 0 | Atomic bond | Cyclohexyl |
| NHSO$_2$(4) | 0 | Atomic bond | Pyridin-3-yl |
| NHSO$_2$(4) | 0 | Atomic bond | (4-iPr)Phenyl |
| NHSO$_2$(4) | 1 | Atomic bond | Phenyl |
| NHSO$_2$(4) | 0 | Atomic bond | Thiophen-2-yl |
| NHSO$_2$(4) | 0 | Atomic bond | Naphthalen-2-yl |
| NBnSO$_2$(4) | 0 | Atomic bond | (2-NO$_2$)Phenyl |
| NMeSO$_2$(4) | 0 | Atomic bond | (3-Br)Phenyl |
| NMeSO$_2$(4) | 0 | Atomic bond | (2-NO$_2$)Phenyl |
| N(CH$_2$CH$_2$OH)SO$_2$(4) | 0 | Atomic bond | (2-NO$_2$)Phenyl |
| NHSO$_2$(4) | 1 | Atomic bond | (2-Cl)Phenyl |
| NHSO$_2$(4) | 1 | Atomic bond | (3-Br)Phenyl |
| NHSO$_2$(4) | 0 | Atomic bond | (2-CF$_3$)Phenyl |

TABLE 8-continued

| $B^a$ (substitution position) | n | $E^a$ | $G^a$ |
|---|---|---|---|
| NHSO$_2$(4) | 1 | Atomic bond | (2-Br)Phenyl |
| NHSO$_2$(4) | 1 | Atomic bond | (2-Me)Phenyl |

TABLE 9

| $B^a$ (substitution position) | n | $E^a$ | $G^a$ |
|---|---|---|---|
| NHSO$_2$(4) | 1 | Atomic bond | (2-NO$_2$)Phenyl |
| NHSO$_2$(4) | 2 | Atomic bond | Phenyl |
| NHSO$_2$(4) | 1 | Atomic bond | (4-Cl)Phenyl |
| NMeSO$_2$(4) | 1 | Atomic bond | (2-CF$_3$)Phenyl |
| NMeSO$_2$(4) | 1 | Atomic bond | (2-Et)Phenyl |
| NMeSO$_2$(4) | 1 | Atomic bond | (2,3-Me)Phenyl |
| NMeSO$_2$(4) | 2 | Atomic bond | (2-Cl)Phenyl |
| NMeSO$_2$(4) | 1 | Atomic bond | (2-NO$_2$)Phenyl |
| NMeSO$_2$(4) | 1 | Atomic bond | (2-NH$_2$)Phenyl |
| NMeSO$_2$(4) | 1 | Atomic bond | (2-NMe$_2$)Phenyl |

TABLE 10

| $B^a$ (substitution position) | n | $E^a$ | $G^a$ |
|---|---|---|---|
| NHCO(4) | 0 | Atomic bond | Pyridin-4-yl |
| NHCO(4) | 1 | O | Pyridin-3-yl |
| NHCO(4) | 0 | Atomic bond | Pyridin-3-yl |
| NHCO(4) | 0 | Atomic bond | (2-Me)Pyridin-3-yl |
| NHCO(4) | 0 | Atomic bond | (2-Cl)Pyridin-3-yl |
| NHCO(4) | 1 | O | Pyridin-2-yl |
| NHCO(4) | 0 | Atomic bond | (4-CF$_3$)Pyridin-3-yl |
| NHCO(4) | 0 | Atomic bond | (2-iPr)Phenyl |

Examples of Typical Compounds (2)

[Formula 23]

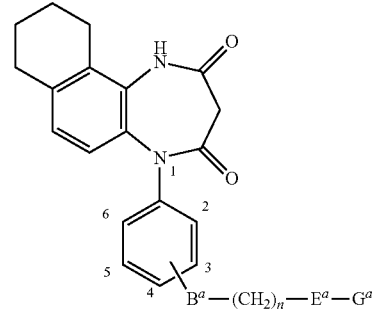

(In the formula, $B^a$ (substitution position), n, $E^a$, and $G^a$ are as shown in Tables 11 and 12)

TABLE 11

| $B^a$ (substitution position) | n | $E^a$ | $G^a$ |
|---|---|---|---|
| NHCO(4) | 0 | Atomic bond | Cyclohexyl |
| NHCO(4) | 0 | Atomic bond | (6-Me)Pyridin-2-yl |
| NHCO(4) | 0 | Atomic bond | (2-Me)Pyridin-3-yl |
| NHCO(4) | 0 | Atomic bond | (2-OMe,3-Me)Phenyl |
| NHCO(4) | 0 | Atomic bond | (2,3-Cl)Phenyl |
| NHCO(4) | 0 | Atomic bond | (2-OH,3-Me)Phenyl |
| NHCO(4) | 0 | Atomic bond | (2-I)Phenyl |
| NHCO(4) | 1 | Atomic bond | (1-Me)Pyrrol-2-yl |
| NHCO(4) | 1 | Atomic bond | (2-tBu)Phenyl |
| NHCO(4) | 0 | Atomic bond | (2-Isopropenyl)Phenyl |

TABLE 11-continued

| $B^a$ (substitution position) | n | $E^a$ | $G^a$ |
|---|---|---|---|
| NHCO(4) | 0 | Atomic bond | (2-iPr)Phenyl |
| NHCO(4) | 1 | Atomic bond | Morpholin-2-yl |
| NHCO(4) | 0 | Atomic band | (2-Cl)Pyridin-2-yl |

TABLE 12

| $B^a$ (substitution position) | n | $E^a$ | $G^a$ |
|---|---|---|---|
| NHSO$_2$(4) | 0 | Atomic bond | (2-NO$_2$)Phenyl |
| NMeSO$_2$(4) | 0 | Atomic bond | (2-NO$_2$)Phenyl |
| SO$_2$NH(4) | 0 | Atomic bond | Phenyl |
| OSO$_2$(4) | 0 | Atomic bond | (3-Br)Phenyl |
| NHSO$_2$(4) | 1 | Atomic bond | (2-Cl)Phenyl |
| NHSO$_2$(4) | 0 | Atomic bond | (3-Br)Phenyl |
| NHSO$_2$(4) | 0 | Atomic bond | (3-OMe)Phenyl |
| NHSO$_2$(4) | 1 | Atomic bond | (2,3-Cl)Phenyl |
| NHSO$_2$(4) | 1 | Atomic bond | (2,6-Cl)Phenyl |
| NHSO$_2$(4) | 1 | Atomic bond | (2-I)Phenyl |
| NMeSO$_2$(4) | 1 | Atomic bond | (2-Cl)Phenyl |

Examples of Typical Compounds (3)

[Formula 24]

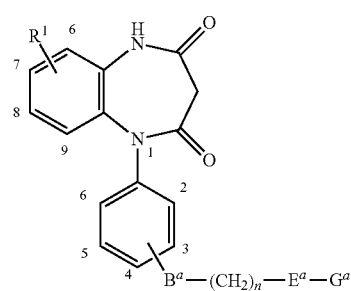

(In the formula, $R^1$, $B^a$ (substitution position), n, $E^a$, and $G^a$ are as shown in Table 13)

TABLE 13

| $R^1$ | $B^a$ (substitution position) | n | $E^a$ | $G^a$ |
|---|---|---|---|---|
| 7-OMe | NHCO(4) | 0 | Atomic bond | (2,3-Me)Phenyl |
| 7-OH | NHCO(4) | 0 | Atomic bond | (2,3-Me)Phenyl |
| 6-Me | NHCO(4) | 0 | Atomic bond | (2,3-Me)Phenyl |
| 6,7-Me | NHCO(4) | 0 | Atomic bond | (2-I)Phenyl |
| 6-Et | NHCO(4) | 0 | Atomic bond | (2-I)Phenyl |
| 7-Ph | NHCO(4) | 0 | Atomic bond | (2-Isopropyl)Phenyl |
| 7-(Pyridin-3yl) | NHCO(4) | 0 | Atomic bond | (2-Isopropyl)Phenyl |
| 7-(Pyridin-2yl) | NHCO(4) | 0 | Atomic bond | (2-Isopropyl)Phenyl |
| 7-Cl | NHSO$_2$(4) | 0 | Atomic bond | (2-Isopropyl)Phenyl |
| 7-Br | NHSO$_2$(4) | 0 | Atomic bond | (2-Isopropyl)Phenyl |
| 7-CF$_3$ | NHSO$_2$(4) | 0 | Atomic bond | (2-Isopropyl)Phenyl |
| H | NHSO$_2$(4) | 0 | Atomic bond | (2-Isopropyl)Phenyl |
| 6-Me,7-Br | NHSO$_2$(4) | 0 | Atomic bond | (2-Isopropyl)Phenyl |
| 7-OMe | NHSO$_2$(4) | 1 | Atomic bond | (2-Cl)Phenyl |
| 7-OH | NHSO$_2$(4) | 1 | Atomic bond | (2-Cl)Phenyl |
| 6-Me | NHSO$_2$(4) | 1 | Atomic bond | (2-Cl)Phenyl |

Examples of Typical Compounds (4)

[Formula 25]

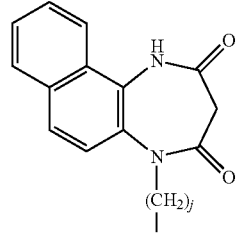

(In the formula, $B^a$ (substitution position), n, $E^a$, and $G^a$ are as shown in Table 14)

TABLE 14

| $B^a$ (substitution position) | n | $E^a$ | $G^a$ |
|---|---|---|---|
| NHCO | 0 | Atomic bond | (2-Cl,3-OMe)Phenyl |
| NHCO | 0 | Atomic bond | (2-I)Phenyl |
| NHSO$_2$ | 1 | Atomic bond | (2-Cl)Phenyl |
| NHSO$_2$ | 1 | Atomic bond | (2-Cl)Phenyl |

Examples of Typical Compounds (5)

[Formula 26]

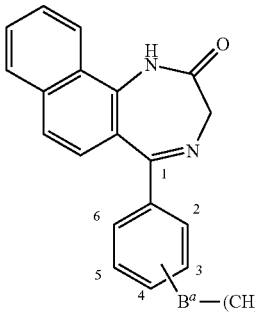

(In the formula, $B^a$ (substitution position), n, $E^a$, and $G^a$ are as shown in Table 15)

TABLE 15

| $B^a$ (substitution position) | n | $E^a$ | $G^a$ |
|---|---|---|---|
| NHCO(4) | 0 | Atomic bond | (2-Cl,3-OMe)Phenyl |
| NHCO(4) | 0 | Atomic bond | (2-Cl,3-OH)Phenyl |
| NHCO(4) | 0 | Atomic bond | (2-tBu)Phenyl |
| NHCO(4) | 0 | Atomic bond | (2-Cl,6-OMe)Phenyl |
| NHCO(4) | 0 | Atomic bond | (2-Cl,6-OH)Phenyl |
| NHSO$_2$(3) | 0 | Atomic bond | Phenyl |
| NHSO$_2$(4) | 1 | Atomic bond | (2-Cl)Phenyl |

Examples of Typical Compounds (6)

[Formula 27]

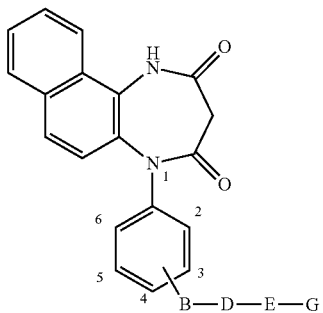

(In the formula, B (substitution position), D, E, and G are as shown in Table 16)

TABLE 16

| B (substitution position) | D | E | G |
|---|---|---|---|
| NHCO(4) | C(Me)H | Atomic bond | Phenyl |
| NHCO(4) | C(Me)$_2$ | Atomic bond | Phenyl |
| NHCO(4) | CH=CH | Atomic bond | Phenyl |
| NHCO(4) | C(Me)H | O | Phenyl |
| NHCO(4) | C(Me)$_2$ | O | Phenyl |
| NHCO(4) | CH=CH | Atomic bond | (2-Me)Phenyl |
| NHCO(4) | CH=CH | Atomic bond | (2-Cl)Phenyl |

Examples of Typical Compounds (7)

[Formula 28]

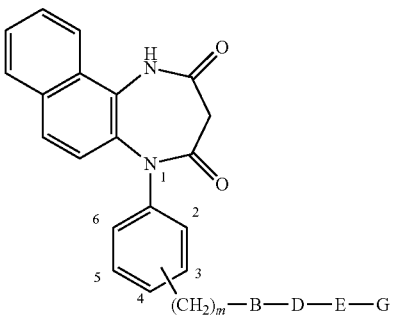

(In the formula, m (substitution position), B, D, E, and G are as shown in Table 17)

TABLE 17

| m (substitution position) | B | D | E | G |
|---|---|---|---|---|
| 1(4) | NHCO | Atomic bond | Atomic bond | Phenyl |
| 1(4) | NHCO | Atomic bond | Atomic bond | (2-Cl)Phenyl |
| 1(4) | NHSO$_2$ | CH$_2$ | Atomic bond | (2-Cl)Phenyl |

Examples of Typical Compounds (8)

[Formula 29]

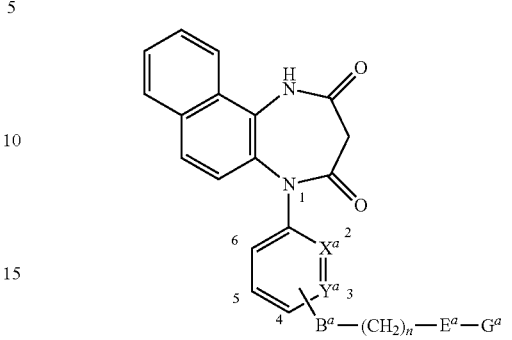

(In the formula, $X^a$, $Y^a$, $B^a$ (substitution position), n, $E^a$, and $G^a$ are as shown Table 18)

TABLE 18

| $X^a$ | $Y^a$ | $B^a$ (substitution position) | n | $E^a$ | $G^a$ |
|---|---|---|---|---|---|
| CH | C—F | NHCO(4) | 0 | Atomic bond | (2,3-Me)Phenyl |
| CH | C—OH | NHCO(4) | 0 | Atomic bond | (2,3-Me)Phenyl |
| CH | C—F | NHCO(4) | 0 | Atomic bond | (2-I)Phenyl |
| CH | N | NHCO(4) | 0 | Atomic bond | (2-I)Phenyl |
| CH | N | NHCO(4) | 0 | Atomic bond | Phenyl |
| N | CH | NHCO(4) | 0 | Atomic bond | (2-I)Phenyl |
| CH | N | NHCO(4) | 0 | Atomic bond | (2-Cl)Phenyl |
| CH | N | NHCO(4) | 0 | Atomic bond | (2-OH)Phenyl |
| CH | N | NHC(=O)NH(4) | 0 | Atomic bond | (2-OH)Phenyl |
| CH | N | NHCO(4) | 0 | Atomic bond | (2-OH,6-Me)Phenyl |
| CH | N | NHCO(4) | 0 | Atomic bond | (2-OH,6-Cl)Phenyl |
| CH | N | NHCO(3) | 0 | Atomic bond | (2-OH,6-Cl)Phenyl |
| CH | N | NHCO(4) | 0 | Atomic bond | (2-Cl)Pyridin-2-yl |
| CH | N | NHCO(4) | 1 | Atomic bond | (2-Cl)Pyridin-2-yl |
| CH | N | NHCO(4) | 0 | Atomic bond | (2-Me)Pyridin-2-yl |
| CH | C—OMe | NHSO$_2$(4) | 1 | Atomic bond | (2-Cl)Phenyl |
| CH | C—OH | NHSO$_2$(4) | 1 | Atomic bond | (2-Cl)Phenyl |

Examples of Typical Compounds (9)

[Formula 30]

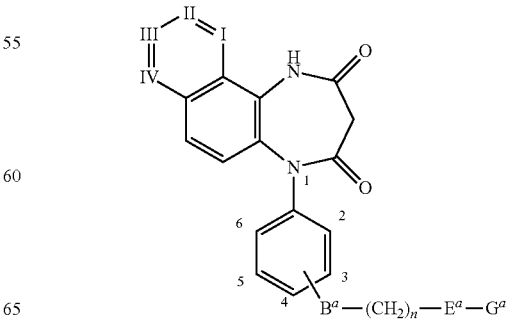

(In the formula, I=II-III=IV, $B^a$ (substitution position), n, $E^a$, and $G^a$ are as shown Table 19)

TABLE 19

| I=II—III=IV | $B^a$ (substitution position) | n | $E^a$ | $G^a$ |
|---|---|---|---|---|
| N=CH—CH=CH | NHCO(4) | 0 | Atomic bond | (2-I)Phenyl |
| CH=N—CH=CH | NHCO(4) | 0 | Atomic bond | (2-I)Phenyl |
| CH=CH—N=CH | NHCO(4) | 0 | Atomic bond | (2-I)Phenyl |
| CH=CH—CH=N | NHCO(4) | 0 | Atomic bond | (2-I)Phenyl |
| N=CH—CH=CH | NHCO(4) | 1 | O | Phenyl |
| N=CH—CH=CH | NHCO(3) | 0 | Atomic bond | (2-I)Phenyl |
| N=CH—CH=CH | NHCO(4) | 0 | Atomic bond | (2-Cl)Phenyl |
| N=CH—CH=CH | NHCO(4) | 0 | Atomic bond | (2-OH)Phenyl |
| N=CH—CH=CH | NHC(=O)NH(4) | 0 | Atomic bond | (2-OH)Phenyl |
| N=CH—CH=CH | NHCO(4) | 1 | O | (2-OH,6-Me)Phenyl |
| N=CH—CH=CH | NHCO(4) | 0 | Atomic bond | (2-OH,6-Cl)Phenyl |
| N=CH—CH=CH | NHCO(3) | 0 | Atomic bond | (2-OH,6-Cl)Phenyl |
| N=CH—CH=CH | NHCO(4) | 0 | Atomic bond | (2-Cl)Pyridin-2-yl |
| N=CH—CH=CH | NHCO(4) | 1 | Atomic bond | (2-Cl)Pyridin-2-yl |
| N=CH—CH=CH | NHCO(4) | 0 | Atomic bond | (2-Me)Pyridin-2-yl |
| CH=CH—N=CH | NHCO(4) | 0 | Atomic bond | (2-Cl)Pyridin-3-yl |

Examples of typical compounds (10)

[Formula 31]

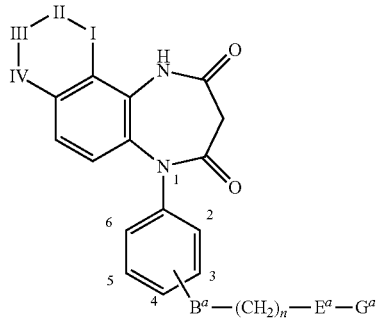

(In the formula, I=II-III=IV, $B^a$ (substitution position), n, $E^a$, and $G^a$ are as shown in Table 20)

TABLE 20

| I=II—III=IV | $B^a$ (substitution position) | n | $E^a$ | $G^a$ |
|---|---|---|---|---|
| NH—CH$_2$—CH$_2$—CH$_2$ | NHCO(4) | 0 | Atomic bond | (2-I)Phenyl |
| CH$_2$—NH—CH$_2$—CH$_2$ | NHCO(4) | 0 | Atomic bond | (2-I)Phenyl |
| CH$_2$—CH$_2$—NH—CH$_2$ | NHCO(4) | 0 | Atomic bond | (2-I)Phenyl |
| CH$_2$—CH$_2$—CH$_2$—NH | NHCO(4) | 0 | Atomic bond | (2-I)Phenyl |
| CH$_2$—CH$_2$—NH—CH$_2$ | NHCO(4) | 1 | O | Phenyl |
| CH$_2$—CH$_2$—NH—CH$_2$ | NHCO(3) | 0 | Atomic bond | (2-I)Phenyl |
| CH$_2$—CH$_2$—NH—CH$_2$ | NHCO(4) | 0 | Atomic bond | (2-Cl)Phenyl |
| CH$_2$—CH$_2$—NH—CH$_2$ | NHCO(4) | 0 | Atomic bond | (2-Cl)Pyridin-3-yl |
| CH$_2$—CH$_2$—NH—CH$_2$ | NHCO(4) | 0 | Atomic bond | (2-OH)Phenyl |
| CH$_2$—CH$_2$—NH—CH$_2$ | NHC(=O)NH(4) | 0 | Atomic bond | (2-OH)Phenyl |
| CH$_2$—CH$_2$—NH—CH$_2$ | NHCO(4) | 1 | O | (2-OH,6-Me)Phenyl |
| CH$_2$—CH$_2$—NH—CH$_2$ | NHCO(4) | 0 | Atomic bond | (2-OH,6-Cl)Phenyl |
| CH$_2$—CH$_2$—NH—CH$_2$ | NHCO(3) | 0 | Atomic bond | (2-OH,6-Cl)Phenyl |
| CH$_2$—CH$_2$—NH—CH$_2$ | NHCO(4) | 0 | Atomic bond | (2-Cl)Pyridin-2-yl |
| CH$_2$—CH$_2$—NH—CH$_2$ | NHCO(4) | 1 | Atomic bond | (2-Cl)Pyridin-2-yl |
| CH$_2$—CH$_2$—NH—CH$_2$ | NHCO(4) | 0 | Atomic bond | (2-Me)Pyridin-2-yl |
| CH$_2$—CH$_2$—NH—CH$_2$ | NHCO(4) | 0 | Atomic bond | (2-Cl)Pyridin-3-yl |

Examples of typical compounds (11)

[Formula 32]

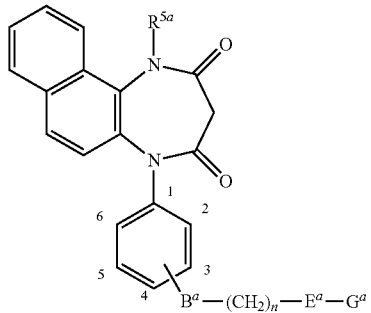

(In the formula, $R^{5a}$, $B^a$ (substitution position), n, $E^a$, and $G^a$ are as shown Table 21)

TABLE 21

| $R^{5a}$ | $B^a$ (substitution position) | n | $E^a$ | $G^a$ |
|---|---|---|---|---|
| Bn | NBnSO$_2$(4) | 0 | Atomic bond | (2-NO$_2$)Phenyl |
| Me | NBnSO$_2$(4) | 0 | Atomic bond | (2-NO$_2$)Phenyl |
| Et | NBnSO$_2$(4) | 0 | Atomic bond | (2-NO$_2$)Phenyl |

Hereafter, the pharmacological efficacies of the compounds of the present invention will be described.

The P2X4 receptor antagonist activity of the compounds of the present invention was measured as follows.

The ATP receptor (human P2X4) was introduced into the 1321N1 cells, and the cells were used as a stable ATP receptor expression system. The P2X4-expressing 1321N1 cells were inoculated on a 96-well plate, cultured under the conditions of 37° C. and 5% CO$_2$ for 24 hours, and used for calcium measurement. Fura-2 AM, which is a calcium fluorescent indicator, was dissolved in an extracellular fluid for calcium imaging, and the inoculated cells were treated with the solution, and left standing at room temperature for 45 minutes so that Fura-2 AM was incorporated into the cells. For the measurement, a microplate reader, FLUOstar Optima (BMG Labtech), was used. The light emitted from a xenon lamp was passed through 340 nm and 380 nm filters, respectively, and irradiated on the cells, fluorescences of 510 nm, F340 and F380, emitted from the cells were measured, and change of the ratio F340/F380 was used as an index of change of intracellular calcium level. The measurement was performed by adding ATP to each well at a final concentration of 1 μM, and observing the ATP-induced Ca$^{2+}$ response over time. In the measurement, a treatment with a test substance was performed 15 minutes before the addition of ATP, and the inhibition activity of the test substance was calculated by comparison of the result with the result obtained in the absence of the test substance.

As clearly seen from the results for the compounds of Examples 215 and 216, the compounds of the present invention showed superior P2X4 receptor antagonist activity (Tables 22 and 23).

As clearly seen from the result for the compound of Example 217, the compound of the present invention showed superior analgesic activity.

Therefore, the diazepine derivatives represented by the aforementioned general formula (I) and (II), and pharmacologically acceptable salts thereof have a P2X4 receptor antagonist activity, and accordingly, it is considered that they are useful as prophylactic or therapeutic agents for pains of nociceptive pain, inflammatory pain, and neuropathic pain. More specifically, they are useful as prophylactic and therapeutic agents for pains accompanying various cancers, pains accompanying diabetic nerve damage, pains accompanying viral diseases such as herpes, arthrosis deformans, and the like. The prophylactic or therapeutic agent of the present invention may be used together with other medicaments if needed, and may be used together with, for example, opioid analgesics (morphine, fentanyl), sodium channel blockers (Novocain, lidocaine), NSAIDs (aspirin, ibuprofen), and the like. Further, when it is used for cancerous pain, it may be used together with, for example, anticancer agents such as anticancer chemotherapeutic agents.

The compounds of the present invention can be administered to a human by an appropriate administration method, such as oral administration or parenteral administration.

For manufacturing pharmaceutical preparations containing the compounds of the present invention, dosage forms such as tablets, granules, powders, capsules, suspensions, injections, and suppositories can be prepared by the methods usually used in the field of pharmaceutical manufacturing.

For manufacturing such preparations, in the case of tablets, for example, usual excipients, disintegrating agents, binders, lubricants, dyes, and the like are used. Examples of excipient include lactose, D-mannitol, crystalline cellulose, glucose, and the like, examples of disintegrating agent include starch, carboxymethylcellulose calcium (CMC-Ca), and the like, examples of lubricant include magnesium stearate, talc, and the like, and examples of binder include hydroxypropylcellulose (HPC), gelatin, polyvinylpyrrolidone (PVP), and the like. For manufacturing injection, solvents, stabilizers, dissolving aids, suspending agents, emulsifiers, soothing agents, buffering agents, preservatives, and the like are used.

As for the administration dose, the compounds of the present invention as the active ingredient can usually be administered to an adult in a daily dose of about 0.01 to 100 mg in the case of injection, or a daily dose of 1 to 2000 mg in the case of oral administration, but the dose may be increased or decreased depending on age, symptoms, and the like.

Hereafter, the present invention will be explained in more detail with reference to examples. However, the present invention is not limited to these examples.

Example 1

5-(4-Benzoylaminophenyl)-1H-naphtho[1,2-b][1,4]diazepine-2,4(3H,5H)-dione (1) tert-Butyl 4-(1-nitro-2-naphthylamino)phenylcarbamate 1-Nitro-2-naphthyl trifluoromethanesulfonate (20.26 g, 63.07 mmol), tert-butyl 4-aminophenylcarbamate (13.13 g, 63.07 mmol), triphenylphosphine (1.65 g, 6.31 mmol), tetrakis(triphenylphosphine)palladium(0) (3.64 g, 3.15 mmol), potassium carbonate (8.72 g, 63.07 mmol), and dry toluene (600 mL) were mixed, and the mixture was refluxed by heating for 6 hours under a nitrogen atmosphere. After the reaction mixture was left to cool, the insoluble matter was separated by filtration, and washed off with ethyl acetate. The organic layer was washed with saturated aqueous sodium hydrogencarbonate, and dried over anhydrous sodium sulfate. The solvent was evaporated under reduced pressure, and the residue was purified by silica gel column chromatography (hexane/ethyl acetate=4/1), and then recrystallized from ethyl acetate/hexane to obtain the title compound (18.67 g, yield 78%) as yellow crystals.

$^1$H NMR (CDCl$_3$, 400 MHz) δ: 1.54 (9H, s), 6.53 (1H, s), 7.21 (2H, d, J=9 Hz), 7.21 (1H, d, J=9 Hz), 7.37 (1H, t, J=7 Hz), 7.44 (2-H, d, J=9 Hz), 7.62 (1H, dt, J=1 Hz, 9 Hz), 7.68 (1H, d, J=7 Hz), 7.70 (1H, d, J=9 Hz), 8.61 (1H, d, J=9 Hz), 9.67 (1H, s)

(2) tert-Butyl 4-(1-amino-2-naphthylamino)phenylcarbamate tert-Butyl 4-(1-nitro-2-naphthylamino)phenylcarbamate (18.67 g, 49.21 mmol) was dissolved in tetrahydrofuran (180 mL) and methanol (180 mL), the mixture was added with platinum oxide (360 mg), and the mixture was stirred at room temperature for 2 hours under a hydrogen atmosphere. The catalyst was separated by filtration, then the solvent was evaporated under reduced pressure, and the residue was washed with methanol to give the title compound (15.67 g, yield 91%) as off-white crystals.

$^1$H NMR (DMSO-d$_6$, 400 MHz) δ: 1.45 (9H, s), 5.23 (2H, br s), 6.62 (2H, d, J=9 Hz), 7.0-7.3 (5H, m), 7.3-7.4 (2H, m), 7.72 (1H, d, J=8 Hz), 8.06 (1H, d, J=8 Hz), 8.90 (1H, br s)

(3) 5-(4-Aminophenyl)-1H-naphtho[1,2-b][1,4]diazepine-2,4(3H,5H)-dione tert-Butyl 4-(1-amino-2-naphthylamino)phenylcarbamate (3.00 g, 8.58 mmol), and sodium hydrogencarbonate (2.16 g, 25.7 mmol) were suspended in chloroform (60 mL), and the suspension was added dropwise with ethyl malonyl chloride (1.22 mL, 9.5 mmol) over 1 minute with stirring under ice cooling. This reaction mixture was stirred for 1 hour under ice cooling, and then added with water, the mixture was stirred for 10 minutes, and the chloroform layer was dried over anhydrous sodium sulfate. The solvent was evaporated under reduced pressure to give a crude product of ethyl 3-[[2-[[4-[(tert-butoxycarbonyl)amino]phenyl]amino]-1-naphthyl]amino]-3-oxopropionate (4 g) as brown crystals.

This crude product (4 g) was dissolved in dry tetrahydrofuran (172 mL), the solution was added with 60% sodium hydride (1.72 g, 42.9 mmol) over 1 minute with stirring under ice cooling, and the mixture was stirred under ice cooling for 30 minutes, and then at room temperature for 3 hours. This reaction mixture was added with saturated aqueous ammonium chloride with stirring under ice cooling, and the organic layer was dried over anhydrous sodium sulfate. The solvent was evaporated under reduced pressure to obtain a crude product of 5-(4-tert-butoxycarbonylaminophenyl)-1H-naphtho[1,2-b][1,4]diazepine-2,4(3H,5H)-dione (4 g) as pale brown crystals.

This crude product (4 g) was suspended in dichloromethane (176 mL), the suspension was added dropwise with trifluoroacetic acid (13.1 mL, 176 mL) over 10 minutes with stirring under ice cooling, and then the mixture was stirred under ice cooling for 1 hour, and then at room temperature for 16 hours. The solvent was evaporated at room temperature, the residue was added with saturated aqueous sodium hydrogencarbonate and ethyl acetate, and the mixture was stirred at room temperature for 2 hours. The precipitated crystals were taken by filtration, and washed with water and then with ethyl acetate to give the title compound (1.23 g, yield 45%) as brown crystals.

$^1$H NMR (DMSO-$d_6$, 400 MHz) δ: 3.10 (1H, d, J=12 Hz), 3.61 (1H, d, J=12 Hz), 5.26 (2H, s), 6.58 (2H, d, J=9 Hz), 6.84 (2H, d, J=8 Hz), 7.04 (1H, d, J=9 Hz), 7.57 (1H, t, J=7 Hz), 7.6-7.7 (2H, m), 7.90 (1H, d, J=8 Hz), 8.22 (1H, d, J=8 Hz), 10.80 (1H, s)

(4) 5-(4-Benzoylaminophenyl)-1H-naphtho[1,2-b][1,4]diazepine-2,4(3H,5H)-dione 5-(4-Aminophenyl)-1H-naphtho[1,2-b][1,4]diazepine-2,4(3H,5H)-dione (30 mg, 0.095 mmol), dry pyridine (3 mL), and benzoyl chloride (35 μL, 0.3 mmol) were mixed, and the mixture was stirred at room temperature for 4 hours and 30 minutes. The reaction mixture was added with saturated aqueous sodium hydrogencarbonate, the mixture was extracted with chloroform, and the organic layer was washed with saturated brine, and dried over anhydrous sodium sulfate. The solvent was evaporated under reduced pressure, and the residue was purified by silica gel chromatography (methanol/chloroform=1/10) to give the title compound (36 mg, yield 91%) as white powder.

$^1$H NMR (DMSO-$d_6$, 400 MHz) δ: 3.15 (1H, d, J=12 Hz), 3.70 (1H, d, J=12 Hz), 7.02 (1H, d, J=9 Hz), 7.21 (2H, d, J=9 Hz), 7.5-7.7 (6H, m), 7.85 (2H, d, J=9 Hz), 7.9-8.0 (3H, m), 8.25 (1H, d, J=9 Hz), 10.38 (1H, s), 10.90 (1H, s).

Example 2

5-[4-[(2-(Trifluoromethyl)benzoyl]aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (16 mg, 0.050 mmol) obtained in Example 1, (3), and 2-(trifluoromethyl)benzoyl chloride (16 mg, 0.077 mmol), the title compound (20 mg, yield 81%) was obtained as off-white crystals in the same manner as that of Example 1, (4).

$^1$H NMR (CDCl$_3$, 400 MHz) δ: 3.57 (1H, d, J=11 Hz), 3.60 (1H, d, J=11 Hz), 7.06 (1H, d, J=9 Hz), 7.2-7.4 (2H, m), 7.5-7.8 (10H, m), 7.87 (1H, d, J=9 Hz), 8.08 (1H, d, J=8 Hz), 8.61 (1H, s).

Example 3

5-[4-(3-Bromobenzoyl)aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (16 mg, 0.050 mmol) obtained in Example 1, (3), and 3-bromobenzoyl chloride (17 mg, 0.077 mmol), the title compound (15 mg, yield 60%) was obtained as off-white crystals in the same manner as that of Example 1, (4).

$^1$H NMR (CDCl$_3$, 400 MHz) δ: 3.61 (2H, s), 7.04 (1H, d, J=8 Hz), 7.25 (2H, d, J=8 Hz), 7.38 (1H, t, J=8 Hz), 7.5-7.7 (6H, m), 7.79 (1H, d, J=8 Hz), 7.86 (1H, d, J=8 Hz), 7.93 (1H, s), 8.01 (1H, br t, J=1 Hz), 8.06 (1H, d, J=9 Hz), 8.30 (1H, br s).

Example 4

5-[4-[4-(Trifluoromethyl)benzoyl]aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (16 mg, 0.050 mmol) obtained in Example 1, (3), and 4-(trifluoromethyl)benzoyl chloride (16 mg, 0.077 mmol), the title compound (10 mg, yield 41%) was obtained as white crystals in the same manner as that of Example 1, (4).

$^1$H NMR (DMSO-$d_6$, 400 MHz) δ: 3.15 (1H, d, J=12 Hz), 3.71 (1H, d, J=12 Hz), 7.01 (1H, d, J=9 Hz), 7.24 (2H, d, J=9 Hz), 7.59 (1H, t, J=8 Hz), 7.67 (1H, d, J=8 Hz), 7.70 (1H, d, J=9 Hz), 7.85 (2H, d, J=9 Hz), 7.91 (2H, d, J=8 Hz), 8.15 (2H, d, J=9 Hz), 8.26 (1H, d, J=8 Hz), 10.58 (1H, s), 10.88 (1H, br s).

Example 5

5-[4-(2-Methylbenzoyl)aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (16 mg, 0.050 mmol) obtained in Example 1, (3), and 2-methylbenzoyl chloride (16 mg, 0.100 mmol), the title compound (13 mg, yield 59%) was obtained as off-white crystals in the same manner as that of Example 1, (4).

$^1$H NMR (CDCl$_3$, 400 MHz) δ: 2.94 (3H, s), 3.60 (2H, s), 7.06 (1H, d, J=9 Hz), 7.2-7.3 (3H, m), 7.36 (1H, t, J=7 Hz), 7.47 (1H, d, J=7 Hz), 7.6-7.8 (6H, m), 7.86 (1H, d, J=8 Hz), 8.09 (1H, d, J=8 Hz), 8.52 (1H, s).

Example 6

5-[4-(2,6-Dimethylbenzoylamino)phenyl]-1H-naphtho[1,2-b][1,4]diazepine-2,4(3H,5H)-dione By using 5-(4-aminophenyl)-1H-naphth[1,2-b][1,4]diazepine-2,4(3H,5H)-dione (30 mg, 0.095 mmol) obtained in Example 1, (3), and 2,6-dimethylbenzoyl chloride (0.143 mmol), the title compound (12 mg, yield 18%) was obtained in the same manner as that of Example 1, (4).

$^1$H NMR (CDCl$_3$, 400 MHz) δ: 2.34 (6H, s), 3.55 (1H, d, J=12 Hz), 3.59 (1H, d, J=12 Hz), 7.01 (2H, d, J=8 Hz), 7.07 (1H, d, J=9 Hz), 7.16 (1H, t, J=7 Hz), 7.2-7.3 (2H, m), 7.5-7.8 (6H, m), 7.85 (1H, d, J=8 Hz), 8.16 (1H, d, J=9 Hz), 9.23 (1H, s).

Example 7

5-[4-(2,6-Dichlorobenzoyl)aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (20 mg, 0.063 mmol) obtained in Example 1, (3), and 2,6-dichlorobenzoyl chloride (20 mg, 0.095 mmol), the title compound (20 mg, yield 64%) was obtained as pale yellow crystals in the same manner as that of Example 1, (4).

$^1$H NMR (CDCl$_3$, 400 MHz) δ: 3.56 (1H, d, J=12 Hz), 3.59 (1H, d, J=12 Hz), 5.9-6.1 (1H, br), 7.06 (1H, d, J=9 Hz), 7.2-7.4 (5H, m), 7.5-7.7 (5H, m), 7.86 (1H, d, J=8 Hz), 8.08 (1H, d, J=8 Hz), 8.57 (1H, s).

Example 8

5-[4-(3-Chlorobenzoyl)aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (20 mg, 0.063 mmol) obtained in Example 1, (3), and 3-chlorobenzoyl chloride (17 mg, 0.095 mmol), the title compound (15 mg, yield 52%) was obtained as pale yellow crystals in the same manner as that of Example 1, (4).

$^1$H NMR (DMSO-$d_6$, 400 MHz) δ: 3.15 (1H, d, J=12 Hz), 3.71 (1H, d, J=12 Hz), 7.01 (1H, d, J=9 Hz), 7.22 (2H, d, J=9 Hz), 7.56 (1H, d, J=8 Hz), 7.5-7.7 (4H, m), 7.84 (2H, d, J=8 Hz), 7.91 (2H, d, J=9 Hz), 8.00 (1H, s), 8.25 (1H, d, J=9 Hz), 10.46 (1H, s), 10.89 (1H, br s).

Example 9

5-[4-(2-Phenylacetylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and phenylacetyl chloride (40 μL, 0.303 mmol), the title compound (15 ng, yield 36%) was obtained in the same manner as that of Example 1.

$^1$H NMR (DMSO-$d_6$, 400 MHz) δ: 3.14 (1H, d, J=12 Hz), 3.65 (2H, s), 3.68 (1H, d, J=12 Hz), 6.97 (1H, d, J=9 Hz), 7.16 (2H, d, J=9 Hz), 7.2-7.4 (6H, m), 7.5-7.7 (4H, m), 7.91 (1H, d, J=8 Hz), 8.25 (1H, d, J=8 Hz), 10.31 (1H, s), 10.87 (1H, s).

Example 10

1-[4-(2,4-Dioxo-1,2,3,4-tetrahydronaphtho[1,2-b][1,4]diazepin-5-yl)phenyl]-3-phenylthiourea 5-(4-Aminophenyl)-1H-naphtho[1,2-b][1,4]diazepine-2,4(3H,5H)-dione (190 mg, 0.6 mmol) obtained in Example 1, (3), phenyl isothiocyanate (243 mg, 1.8 mmol), and tetrahydrofuran (76 mL) were mixed, and the mixture was refluxed by heating for 24 hours. After the mixture was left to cool to room temperature, the insoluble matter was removed by filtration, and the filtrate was concentrated under reduced pressure. The residue was purified by silica gel column chromatography (methanol/chloroform=1/50) to obtain the title compound (114 mg, yield 42%) as slightly yellow crystals.

$^1$H NMR (DMSO-$d_6$, 400 MHz) δ: 3.15 (1H, d, J=12 Hz), 3.78 (1H, d, J=12 Hz), 7.01 (1H, d, J=9 Hz), 7.1-7.2 (3H, m), 7.3-7.4 (2H, m), 7.4-7.5 (2H, m), 7.5-7.7 (5H, m), 7.92 (1H, d, J=8 Hz), 8.26 (1H, d, J=8 Hz), 9.89 (2H, s), 10.90 (1H, s).

Example 11

5-[4-(2,3-Dimethoxybenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (100 mg, 0.315 mmol) obtained in Example 1, (3), and 2,3-dimethoxybenzoyl chloride (0.473 mmol), the title compound (83 mg, yield 55%) was obtained in the same manner as that of Example 1, (4).

$^1$H NMR (CDCl$_3$, 400 MHz) δ: 3.62 (2H, s), 3.93 (3H, s), 3.99 (3H, s), 7.0-7.2 (2H, m), 7.21 (1H, t, J=8 Hz), 7.2-7.3 (2H, m), 7.5-7.6 (2H, m), 7.69 (1H, t, J=7 Hz), 7.7-7.8 (3H, m), 7.84 (1H, d, J=8 Hz), 8.15 (1H, d, J=8 Hz), 9.17 (1H, br s), 10.10 (1H, br s).

Example 12

5-[4-(2-Methoxybenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (100 mg, 0.315 mmol) obtained in Example 1, (3), and 2-methoxybenzoyl chloride (63 μL, 0.473 mmol), the title compound (65 mg, yield 46%) was obtained in the same manner as that of Example 1, (4).

$^1$H NMR (CDCl$_3$, 400 MHz) δ: 3.61 (2H, s), 4.05 (3H, s), 7.02 (1H, d, J=8 Hz), 7.05 (1H, d, J=9 Hz), 7.11 (1H, t, J=7 Hz), 7.24 (2H, d, J=9 Hz), 7.4-7.5 (1H, m), 7.5-7.6 (2H, m), 7.6-7.8 (3H, m), 7.84 (1H, d, J=8 Hz), 8.15 (1H, d, J=8 Hz), 8.24 (1H, dd, J=1 Hz, 8 Hz), 9.1-9.3 (1H, m), 9.85 (1H, br s).

Example 13

5-[4-[(2-Chlorophenylacetyl)amino]phenyl]-1H-naphtho[1,2-b][1,4]diazepine-2,4(3H,5H)-dione 2-Chlorophenylacetic acid (51 mg, 0.3 mmol) was dissolved in ethyl acetate (1.5 mL), the solution was added with thionyl chloride (26 μL, 0.36 mmol), and the mixture was refluxed by heating for 4 hours. The solvent was evaporated under reduced pressure to give 2-chlorophenylacetyl chloride. By using this compound and 5-(4-aminophenyl)-1H-naphtho[1,2-b][1,4]diazepine-2,4(3H,5H)-dione (190 mg, 0.6 mmol) obtained in Example 1, (3), the title compound (10 mg, yield 11%) was obtained as pale yellow crystals in the same manner as that of Example 1, (4).

$^1$H NMR (DMSO-$d_6$, 400 MHz) δ: 3.14 (1H, d, J=12 Hz), 3.69 (1H, d, J=12 Hz), 3.85 (2H, s), 7.00 (1H, d, J=9 Hz), 7.17 (2H, d, J=8 Hz), 7.3-7.4 (2H, m), 7.4-7.5 (2H, m), 7.5-7.7 (5H, m), 7.91 (1H, d, J=8 Hz), 8.25 (1H, d, J=9 Hz), 10.36 (1H, s), 10.88 (1H, s).

Example 14

5-[4-(2,3-Dimethylbenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 2,3-dimethylbenzoyl chloride (0.143 mmol), the title compound (4.5 mg, yield 11%) was obtained in the same manner as that of Example 1, (4).

$^1$H NMR (CDCl$_3$, 400 MHz) δ: 2.31 (3H, s), 2.37 (3H, s), 3.58 (2H, s), 7.06 (1H, d, J=9 Hz), 7.14 (1H, d, J=7 Hz), 7.2-7.3 (4H, m), 7.42 (1H, br s), 7.5-7.7 (5H, m), 7.84 (1H, d, J=8 Hz), 8.05 (1H, d, J=8 Hz), 8.23 (1H, br s).

Example 15

5-[4-(2,5-Dimethylbenzoylamino)phenyl]-1H-naphtho[1,2-b][1,4]diazepine-2,4(3H,5H)-dione By using 5-(4-aminophenyl)-1H-naphth[1,2-b][1,4]diazepine-2,4(3H,5H)-dione (30 mg, 0.095 mmol) obtained in Example 1, (3), and 2,5-dimethylbenzoyl chloride (0.143 mmol), the title compound (14 mg, yield 33%) was obtained in the same manner as that of Example 1, (4).

¹H NMR (CDCl₃, 400 MHz) δ: 2.33 (3H, s), 2.42 (3H, s), 3.59 (2H, s), 7.05 (1H, d, J=9 Hz), 7.12 (1H, d, J=8 Hz), 7.15 (1H, d, J=8 Hz), 7.2-7.3 (3H, m), 7.5-7.8 (6H, m), 7.85 (1H, d, J=8 Hz), 8.13 (1H, d, J=9 Hz), 9.00 (1H, br s).

Example 16

5-[4-(5-Bromo-2-chlorobenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (20 mg, 0.063 mmol) obtained in Example 1, (3), and 5-bromo-2-chlorobenzoyl chloride (0.0945 mmol), the title compound (8 mg, yield 24%) was obtained as pale yellow crystals in the same manner as that of Example 1, (4).
¹H NMR (CDCl₃, 400 MHz) δ: 3.61 (2H, s), 7.05 (1H, d, J=9 Hz), 7.28 (1H, d, J=9 Hz), 7.33 (1H, d, J=9 Hz), 7.55 (1H, dd, J=2 Hz, 9 Hz), 7.6-7.8 (6H, m), 7.8-7.9 (3H, m), 8.04 (1H, d, J=9 Hz), 8.11 (1H, s).

Example 17

5-[4-(2,4-Dichlorobenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (25 mg, 0.078 mmol) obtained in Example 1, (3), and 2,4-dichlorobenzoyl chloride (25 mg, 0.118 mmol), the title compound (20 mg, yield 52%) was obtained as white crystals in the same manner as that of Example 1, (4).
¹H NMR (CDCl₃, 400 MHz) δ: 3.60 (2H, s), 7.00 (1H, d, J=8 Hz), 7.26 (2H, d, J=8 Hz), 7.37 (1H, dd, J=2 Hz, 8 Hz), 7.48 (1H, d, J=2 Hz), 7.5-7.8 (6H, m), 7.87 (1H, d, J=8 Hz), 7.99 (1H, s), 8.06 (1H, d, J=8 Hz), 8.31 (1H, br s).

Example 18

5-[4-(2-Hydroxybenzoylamino)phenyl]-1H-naphtho[1,2-b][1,4]diazepine-2,4(3H,5H)-dione 5-[4-(2-Methoxybenzoylamino)phenyl]-1H-naphtho[1,2-b][1,4]diazepine-2,4(3H,5H)-dione (56 mg, 0.124 mmol) obtained in Example 12 was dissolved in dichloromethane (1.2 mL), the solution was added with a 1 M solution of boron tribromide in dichloromethane (0.37 mL, 0.37 mmol) on an ice bath, and the mixture was stirred at room temperature for 16 hours. After completion of the reaction, the reaction mixture was added with 25% aqueous ammonia, and the mixture was extracted with chloroform. Then, the organic layer was dried over sodium sulfate, and the solvent was evaporated under reduced pressure. The obtained residue was purified by silica gel column chromatography (chloroform/methanol=100/1) to give the title compound (39 mg, yield 72%).
¹H NMR (DMSO-d₆, 400 MHz) δ: 3.16 (1H, d, J=12 Hz), 3.70 (1H, d, J=12 Hz), 6.89 (1H, t, J=7 Hz), 6.94 (1H, d, J=8 Hz), 7.02 (1H, d, J=9 Hz), 7.22 (2H, d, J=9 Hz), 7.39 (1H, t, J=8 Hz), 7.59 (1H, t, J=8 Hz), 7.65 (1H, d, J=8 Hz), 7.70 (1H, d, J=9 Hz), 7.78 (2H, d, J=9 Hz), 7.92 (1H, d, J=8 Hz), 8.25 (1H, d, J=9 Hz), 10.89 (2H, br s).

Example 19

5-[4-(2,3-Dihydroxybenzoylamino)phenyl]-1H-naphtho[1,2-b][1,4]diazepine-2,4(3H,5H)-dione By using 5-[4-(2,3-dimethoxybenzoylamino)phenyl]-1H-naphtho[1,2-b][1,4]diazepine-2,4(3H,5H)-dione (71 mg, 0.147 mmol) obtained in Example 11, the title compound (4.9 mg, yield 7%) was obtained in the same manner as that of Example 18.
¹H NMR (DMSO-d₆, 400 MHz) δ: 3.15 (1H, d, J=12 Hz), 3.71 (1H, d, J=12 Hz), 6.6-6.8 (1H, m), 6.9-7.0 (1H, m), 7.01 (1H, d, J=9 Hz), 7.22 (2H, d, J=9 Hz), 7.39 (1H, d, J=9 Hz), 7.59 (1H, t, J=8 Hz), 7.65 (1H, d, J=8 Hz), 7.70 (1H, d, J=9 Hz), 7.76 (2H, d, J=9 Hz), 7.91 (1H, d, J=8 Hz), 8.25 (1H, d, J=8 Hz), 10.89 (1H, s).

Example 20

1-[4-(2,4-Dioxo-1,2,3,4-tetrahydronaphtho[1,2-b][1,4]diazepin-5-yl)phenyl]-3-phenylurea A suspension of 5-(4-aminophenyl)-1H-naphtho[1,2-b][1,4]diazepine-2,4(3H,5H)-dione (32 mg, 0.10 mmol) obtained in Example 1, (3) in anhydrous tetrahydrofuran (10 mL) was added with phenyl isocyanate (27 μL, 0.25 mmol), the mixture was refluxed by heating at 65° C. for 4 hours. The solvent was evaporated under reduced pressure, and the residue was purified by silica gel column chromatography (chloroform/methanol=50/1) to obtain the title compound (9 mg, yield 21%) as white powder.
¹H NMR (DMSO-d₆, 400 MHz) δ: 3.15 (1H, d, J=12 Hz), 3.69 (1H, d, J=12 Hz), 6.97 (1H, t, J=8 Hz), 7.02 (1H, d, J=9 Hz), 7.14 (2H, d, J=9 Hz), 7.28 (2H, t, J=8 Hz), 7.45 (2H, d, J=8 Hz), 7.52 (2H, d, J=9 Hz), 7.59 (1H, t, J=8 Hz), 7.6-7.7 (2H, m), 7.91 (1H, d, J=8 Hz), 8.25 (1H, d, J=8 Hz), 8.68 (1H, s), 8.81 (1H, s), 10.86 (1H, s).

Example 21

5-[4-[(2,6-Dichlorophenylacetyl)amino]phenyl]-1H-naphtho[1,2-b][1,4]diazepine-2,4(3H,5H)-dione 2,6-Dichlorophenylacetic acid (62 mg, 0.3 mmol) was treated with thionyl chloride in the same manner as that of Example 13, and then by using the resultant together with 5-(4-aminophenyl)-1H-naphtho[1,2-b][1,4]diazepine-2,4(3H,5H)-dione (63 mg, 0.2 mmol) obtained in Example 1, (3), the title compound (32 mg, yield 32%) was obtained as pale brown crystals in the same manner as that of Example 1, (4).
¹H NMR (DMSO-d₆, 400 MHz) δ: 3.15 (1H, d, J=12 Hz), 3.69 (1H, d, J=12 Hz), 4.07 (2H, s), 7.00 (1H, d, J=9 Hz), 7.17 (2H, d, J=8 Hz), 7.34 (1H, t, J=8 Hz), 7.49 (2H, d, J=8 Hz), 7.5-7.7 (5H, m), 7.92 (1H, d, J=8 Hz), 8.25 (1H, d, J=9 Hz), 10.45 (1H, s), 10.88 (1H, s).

Example 22

5-[4-[(2-Methoxyphenylacetyl)amino]phenyl]-1H-naphtho[1,2-b][1,4]diazepine-2,4(3H,5H)-dione 2-Methoxyphenylacetic acid (75 mg, 0.45 mmol) was treated with thionyl chloride in the same manner as that of Example 13, and then by using the resultant together with 5-(4-aminophenyl)-1H-naphtho[1,2-b][1,4]diazepine-2,4(3H,5H)-dione (95 mg, 0.3 mmol) obtained in Example 1, (3), the title compound (83 mg, yield 60%) was obtained as pale yellow crystals in the same manner as that of Example 1, (4).
¹H NMR (DMSO-d₆, 400 MHz) δ: 3.14 (1H, d, J=12 Hz), 3.64 (2H, s), 3.69 (1H, d, J=12 Hz), 3.77 (3H, s), 6.90 (1H, t, J=7 Hz), 6.9-7.0 (2H, m), 7.15 (2H, d, J=8 Hz), 7.2-7.3

(2H, m), 7.59 (1H, t, J=8 Hz), 7.6-7.7 (4H, m), 7.91 (1H, d, J=8 Hz), 8.25 (1H, d, J=8 Hz), 10.17 (1H, s), 10.86 (1H, s).

Example 23

5-[4-[(2-Hydroxyphenylacetyl)amino]phenyl]-1H-naphtho[1,2-b][1,4]diazepine-2,4(3H,5H)-dione 5-[4-[(2-Methoxyphenylacetyl)amino]phenyl]-1H-naphtho[1,2-b][1,4]diazepine-2,4(3H,5H)-dione (50 mg, 0.11 mmol) obtained in Example 22 was dissolved in dry dichloromethane (20 mL), the solution was added with a 1 M solution of boron tribromide in dichloromethane (0.22 mL), and the mixture was stirred at room temperature for 24 hours. The solvent was evaporated, the residue was added with saturated aqueous sodium hydrogencarbonate, and the mixture was extracted with ethyl acetate. The ethyl acetate layer was washed with saturated brine, and dried over anhydrous sodium sulfate. The solvent was evaporated under reduced pressure, and the residue was washed with ethyl acetate to give the title compound (14 mg, yield 28%) as pale yellow crystals.

$^1$H NMR (DMSO-de, 400 MHz) δ: 3.14 (1H, d, J=12 Hz), 3.61 (2H, s), 3.69 (1H, d, J=12 Hz), 6.7-6.9 (2H, m), 6.9-7.2 (3H m), 7.16 (2H, d, J=7 Hz), 7.4-7.7 (3H, m), 7.67 (2H, d, J=7 Hz), 7.91 (1H, d, J=7 Hz), 8.25 (1H, d, J=8 Hz), 9.48 (1H, s), 10.19 (1H, s), 10.88 (1H, s).

Example 24

1-(2-Chlorophenyl)-3-[4-(2,4-dioxo-1,2,3,4-tetrahydronaphtho[1,2-b][1,4]diazepin-5-yl)phenyl]thiourea By using 5-(4-aminophenyl)-1H-naphtho[1,2-b][1,4]diazepine-2,4(3H,5H)-dione (190 mg, 0.60 mmol) obtained in Example 1, (3), and 2-chlorophenyl isothiocyanate (196 μL, 1.50 mmol), the title compound (127 mg, yield 44%) was obtained in the same manner as that of Example 20.

$^1$H NMR (CDCl$_3$, 400 MHz) δ: 3.61 (2H, s), 7.01 (1H, d, J=9 Hz), 7.19 (1H, t, J=8 Hz), 7.2-7.4 (3H, m), 7.4-7.5 (3H, m), 7.5-7.7 (2H, m), 7.69 (1H, t, J=8 Hz), 7.86 (1H, d, J=8 Hz), 7.9-8.0 (2H, m), 8.08 (1H, br s), 8.12 (1H, d, J=9 Hz), 8.89 (1H, br s).

Example 25

5-[4-[3-(Trifluoromethyl)benzoylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 3-(trifluoromethyl)benzoyl chloride (17 μL, 0.114 mmol), the title compound (6 mg, yield 13%) was obtained in the same manner as that of Example 1, (4).

$^1$H NMR (CDCl$_3$, 400 MHz) δ: 3.58 (1H, d, J=12 Hz), 3.61 (1H, d, J=12 Hz), 7.01 (1H, d, J=9 Hz), 7.13 (2H, d, J=8 Hz), 7.5-7.7 (6H, m), 7.79 (1H, d, J=8 Hz), 7.83 (1H, d, J=8 Hz), 8.10 (2H, t, J=8 Hz), 8.18 (1H, s), 8.40 (1H, br s), 8.86 (1H, br s).

Example 26

5-[4-[2-[(2-Trifluoromethyl)phenyl]acetylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 2-(trifluoromethyl)phenylacetyl chloride (29 μL, 0.143 mmol), the title compound (6 mg, yield 13%) was obtained in the same manner as that of Example 1, (4).

$^1$H NMR (CDCl$_3$, 400 MHz) δ: 3.58 (2H, s), 3.89 (2H, s), 6.99 (1H, d, J=9 Hz), 7.16 (2H, d, J=8 Hz), 7.30 (1H, br s), 7.4-7.6 (7H, m), 7.66 (1H, d, J=8 Hz), 7.71 (1H, d, J=8 Hz), 7.84 (1H, d, J=8 Hz), 8.06 (1H, t, J=8 Hz), 8.54 (1H, br s).

Example 27

1-(2-Chlorophenyl)-3-[4-(2,4-dioxo-1,2,3,4-tetrahydronaphtho[1,2-b][1,4]diazepin-5-yl)phenyl]urea By using 5-(4-aminophenyl)-1H-naphtho[1,2-b][1,4]diazepine-2,4(3H,5H)-dione (32 mg, 0.10 mmol) obtained in Example 1, (3), and 2-chlorophenyl isocyanate (30 μL, 0.25 mmol), the title compound (19 mg, yield 40%) was obtained in the same manner as that of Example 20.

$^1$H NMR (DMSO-d$_6$, 400 MHz) δ: 3.15 (1H, d, J=11 Hz), 3.69 (1H, d, J=12 Hz), 7.0-7.1 (2H, m), 7.16 (2H, d, J=9 Hz), 7.30 (1H, t, J=8 Hz), 7.4-7.8 (6H, m), 7.92 (1H, d, J=8 Hz), 8.16 (1H, d, J=8 Hz), 8.25 (1H, d, J=8 Hz), 8.34 (1H, s), 9.58 (1H, s), 10.89 (1H, s).

Example 28

5-[4-[(2-Phenylpropionyl)amino]phenyl]-1H-naphtho[1,2-b][1,4]diazepine-2,4(3H,5H)-dione 2-Phenylpropionic acid (30 mg, 0.2 mmol) was treated with thionyl chloride in the same manner as that of Example 13, and then by using the resultant together with 5-(4-aminophenyl)-1H-naphtho[1,2-b][1,4]diazepine-2,4(3H,5H)-dione (32 mg, 0.1 mmol) obtained in Example 1, (3), the title compound (10 mg, yield 22%) was obtained as pale brown crystals in the same manner as that of Example 1, (4).

$^1$H NMR (DMSO-d$_6$, 400 MHz) δ: 1.42 (3H, d, J=7 Hz), 3.13 (1H, d, J=12 Hz), 3.68 (1H, d, J=12 Hz), 3.84 (1H, q, J=7 Hz), 6.96 (1H, d, J=9 Hz), 7.14 (2H, d, J=9 Hz), 7.2-7.4 (5H, m), 7.5-7.7 (5H, m), 7.90 (1H, d, J=8 Hz), 8.24 (1H, d, J=8 Hz), 10.19 (1H, s), 10.87 (1H, s).

Example 29

5-[4-(2-Chloro-3-methoxybenzoylamino)phenyl]-1H-naphtho[1,2-b][1,4]diazepine-2,4(3H,5H)-dione By using obtained in 5-(4-aminophenyl)-1H-naphtho[1,2-b][1,4]diazepine-2,4(3H,5H)-dione (150 mg, 0.47 mmol; Example 1, (3), and 2-chloro-3-methoxybenzoyl chloride (0.71 mmol), the title compound (119 mg, yield 52%) was obtained in the same manner as that of Example 1, (4).

$^1$H NMR (DMSO-d$_6$, 400 MHz) δ: 3.15 (1H, d, J=12 Hz), 3.71 (1H, d, J=12 Hz), 3.90 (3H, s), 7.01 (1H, d, J=9 Hz), 7.12 (1H, d, J=8 Hz), 7.20 (2H, d, J=7 Hz), 7.26 (1H, d, J=9 Hz), 7.42 (1H, t, J=7 Hz), 7.59 (1H, t, J=8 Hz), 7.6-7.7 (2H, m), 7.76 (2H, d, J=7 Hz), 7.92 (1H, d, J=8 Hz), 8.25 (1H, d, J=8 Hz), 10.61 (1H, s), 10.89 (1H, s).

Example 30

5-[4-(3-Phenylpropionylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (50 mg, 0.16 mmol) obtained in Example 1, (3), and 3-phenylpropionyl chloride (28 μL, 0.19 mmol), the title compound (21 mg, yield 29%) was obtained in the same manner as that of Example 1, (4).

$^1$H NMR (CDCl$_3$, 400 MHz) δ: 2.64 (2H, t, J=7 Hz), 3.02 (2H, t, J=7 Hz), 3.57 (2H, s), 6.98 (1H, d, J=9 Hz), 7.05 (2H, d, J=8 Hz), 7.1-7.3 (5H, m), 7.38 (2H, d, J=8 Hz), 7.5-7.6 (3H, m), 7.68 (1H, t, J=8 Hz), 7.83 (1H, d, J=8 Hz), 8.13 (1H, d, J=8 Hz), 9.14 (1H, br s).

Example 31

5-[4-[(1H-Indole-3-carbonyl)amino]phenyl]-1H-naphtho[1,2-b][1,4]diazepine-2,4(3H,5H)-dione Indole-3-carboxylic acid (51 mg, 0.316 mmol) was made into acid chloride in a conventional manner. By using 5-(4-aminophenyl)-1H-naphtho[1,2-b][1,4]diazepine-2,4(3H,5H)-dione (50 mg, 0.158 mmol) obtained in Example 1, (3), and indole-3-carboxylic acid chloride mentioned above, the title compound (40 mg, yield 55%) was obtained in the same manner as that of Example 1, (4).

$^1$H NMR (DMSO-d$_6$, 400 MHz) δ: 3.16 (1H, d, J=12 Hz), 3.70 (1H, d, J=12 Hz), 7.05 (1H, d, J=9 Hz), 7.1-7.2 (4H, m), 7.47 (1H, d, J=7 Hz), 7.59 (1H, t, J=8 Hz), 7.6-7.7 (2H, m), 7.85 (2H, d, J=9 Hz), 7.92 (1H, d, J=8 Hz), 8.19 (1H, d, J=8 Hz), 8.2-8.3 (2H, m), 9.84 (1H, s), 10.89 (1H, br s), 11.73 (1H, br s).

Example 32

5-[4-(2-Chloro-3-hydroxybenzoylamino)phenyl]-1H-naphtho[1,2-b][1,4]diazepine-2,4(3H,5H)-dione By using 5-[4-(2-chloro-3-methoxybenzoylamino)phenyl]-1H-naphtho[1,2-b][1,4]diazepine-2,4(3H,5H)-dione obtained in Example 29, the title compound (53 mg, yield 56%) was obtained in the same manner as that of Example 18.

$^1$H NMR (DMSO-d$_6$, 400 MHz) δ: 3.15 (1H, d, J=12 Hz), 3.70 (1H, d, J=12 Hz), 6.96 (1H, d, J=8 Hz), 7.01 (1H, d, J=9 Hz), 7.06 (1H, d, J=8 Hz), 7.1-7.3 (3H, m), 7.59 (1H, t, J=8 Hz), 7.65 (1H, d, J=8 Hz), 7.69 (1H, d, J=8 Hz), 7.77 (2H, d, J=8 Hz), 7.91 (1H, d, J=8 Hz), 8.24 (1H, d, J=9 Hz), 10.42 (1H, s), 10.56 (1H, s), 10.88 (1H, s).

Example 33

5-[4-[(2-Methyl-2-phenylpropionyl)amino]phenyl]-1H-naphtho[1,2-b][1,4]diazepine-2,4(3H,5H)-dione 2-Methyl-2-phenylpropionic acid (33 mg, 0.2 mmol) was treated with thionyl chloride in the same manner as that of Example 13, and then by using the resultant together with 5-(4-aminophenyl)-1H-naphtho[1,2-b][1,4]diazepine-2,4(3H,5H)-dione (32 mg, 0.1 mmol) obtained in Example 1, (3), the title compound (23 mg, yield 50%) was obtained as slightly brown powder in the same manner as that of Example 1, (4).

$^1$H NMR (DMSO-de, 400 MHz) δ: 1.57 (6H, s), 3.14 (1H, d, J=12 Hz), 3.68 (1H, d, J=12 Hz), 6.98 (1H, d, J=9 Hz), 7.13 (2H, d, J=8 Hz), 7.2-7.3 (1H, m), 7.3-7.4 (4H, m), 7.5-7.7 (5H, m), 7.91 (1H, d, J=7 Hz), 8.24 (1H, d, J=8 Hz), 9.23 (1H, s), 10.86 (1H, s).

Example 34

5-[4-(2-Phenoxyacetylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (50 mg, 0.157 mmol) obtained in Example 1, (3), and 2-phenoxyacetyl chloride (27 mg, 0.315 mmol), the title compound (13 mg, yield 18%) was obtained as pale brown crystals in the same manner as that of Example 1, (4).

$^1$H NMR (CDCl$_3$, 400 MHz) δ: 3.60 (2H, s), 4.62 (2H, s), 6.9-7.1 (4H, m), 7.2-7.3 (2H, m), 7.3-7.4 (2H, m), 7.5-7.7 (5H, m), 7.86 (1H, d, J=8 Hz), 8.05 (1H, d, J=8 Hz), 8.25 (1H, br s), 8.33 (1H, s).

Example 35

5-[4-[2-(2-Chloro-4-methoxyphenyl)acetylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (50 mg, 0.158 mmol) obtained in Example 1, (3), and 2-chloro-4-methoxyphenylacetyl chloride (0.237 mmol), the title compound (76 mg, yield 48%) was obtained in the same manner as that of Example 1, (4).

$^1$H NMR (CDCl$_3$, 400 MHz) δ: 3.58 (2H, s), 3.78 (2H, s), 3.81 (3H, s), 6.84 (1H, dd, J=2 Hz, 9 Hz), 6.9-7.0 (2H, m), 7.16 (2H, d, J=8 Hz), 7.29 (1H, d, J=8 Hz), 7.34 (1H, br s), 7.49 (2H, d, J=8 Hz), 7.5-7.6 (2H, m), 7.68 (1H, t, J=8 Hz), 7.84 (1H, d, J=8 Hz), 8.08 (1H, d, J=8 Hz), 8.68 (1H, br s).

Example 36

5-[4-[(1-Methyl-1H-imidazole-2-carbonyl)amino]phenyl]-1H-naphtho[1,2-b][1,4]diazepine-2,4(3H,5H)-dione 1-Methyl-1H-imidazole-2-carboxylic acid (40 mg, 0.317 mmol) was made into acid chloride in a conventional manner. By using 5-(4-aminophenyl)-1H-naphtho[1,2-b][1,4]diazepine-2,4(3H,5H)-dione (50 mg, 0.158 mmol) obtained in Example 1, (3), and 1-methyl-1H-imidazole-2-carboxylic acid chloride mentioned above, the title compound (9 mg, yield 13%) was obtained in the same manner as that of Example 1.

$^1$H NMR (CDCl$_3$, 400 MHz) δ: 3.60 (2H, s), 4.11 (3H, s), 7.0-7.1 (3H, m), 7.2-7.3 (2H, m), 7.5-7.7 (2H, m), 7.6-7.8 (3H, m), 7.86 (1H, d, J=8 Hz), 8.06 (1H, d, J=9 Hz), 8.38 (1H, s), 9.33 (1H, s).

Example 37

5-[4-[2-(2,4-Dichlorophenyl)acetylamino]phenyl]-1H-naphtho[1,2-b][1,4]diazepine-2,4(3H,5H)-dione 2,4-Dichlorophenylacetic acid (65 mg, 0.317 mmol) was made into acid chloride in a conventional manner. By using 5-(4-aminophenyl)-1H-naphtho[1,2-b][1,4]diazepine-2,4(3H,5H)-dione (50 mg, 0.158 mmol) obtained in Example 1, (3), and 2,4-dichlorophenylacetic acid chloride mentioned above, the title compound (27 mg, yield 34%) was obtained in the same manner as that of Example 1.

$^1$H NMR (DMSO-d$_6$, 400 MHz) δ: 3.14 (1H, d, J=12 Hz), 3.69 (1H, d, J=12 Hz), 3.85 (2H, s), 6.99 (1H, d, J=9 Hz), 7.17 (2H, d, J=9 Hz), 7.3-7.5 (2H, m), 7.5-7.7 (6H, m), 7.91 (1H, d, J=8 Hz), 8.25 (1H, d, J=8 Hz), 10.38 (1H, s), 10.88 (1H, s).

Example 38

5-[4-[2-(2-Chloro-4-hydroxyphenyl)acetylamino]phenyl]-1H-naphtho[1,2-b][1,4]diazepine-2,4(3H,5H)-dione By using 5-[4-[2-(2-chloro-4-methoxyphenyl)acetylamino]phenyl]-1H-naphtho[1,2-b][1,4]diazepine-2,4(3H,5H)-dione (40 mg, 0.08 mmol) obtained in Example 35, the title compound (10 mg, yield 26%) was obtained in the same manner as that of Example 18.

$^1$H NMR (DMSO-do, 400 MHz) δ: 3.13 (1H, d, J=12 Hz), 3.6-3.7 (3H, m), 6.70 (1H, d, J=9 Hz), 6.81 (1H, s), 6.98 (1H, d, J=9 Hz), 7.15 (2H, d, J=8 Hz), 7.19 (1H, d, J=8 Hz), 7.5-7.7 (5H, m), 7.90 (1H, d, J=7 Hz), 8.23 (1H, d, J=9 Hz), 9.75 (1H, s), 10.26 (1H, s), 10.87 (1H, s).

Example 39

5-[4-(3-Phenylpropenylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (50 mg, 0.158 mmol) obtained in Example 1, (3), and cinnamoyl chloride (32 mg, 0.19 mmol), the title compound (622 mg, yield 31%) was obtained in the same manner as that of Example 1, (4).

$^1$H NMR (DMSO-$d_6$, 400 MHz) δ: 3.15 (1H, d, J=12 Hz), 3.70 (1H, d, J=12 Hz), 6.83 (1H, d, J=16 Hz), 7.00 (1H, d, J=9 Hz), 7.19 (2H, d, J=9 Hz), 7.3-7.5 (3H, m), 7.5-7.7 (6H, m), 7.76 (2H, d, J=9 Hz), 7.91 (1H, d, J=8 Hz), 8.25 (1H, d, J=9 Hz), 10.35 (1H, s), 10.89 (1H, br s).

Example 40

5-[4-[(3-Pyridylacetyl)amino]phenyl]-1H-naphtho[1,2-b][1,4]diazepine-2,4(3H,5H)-dione hydrochloride (1) 5-[4-[(3-Pyridylacetyl)amino]phenyl]-1H-naphtho[1,2-b][1,4]diazepine-2,4(3H,5H)-dione 3-Pyridylacetic acid (41 mg, 0.3 mmol) was dissolved in dry dichloromethane (1 mL), the solution was added with dimethylformamide (1 drop), and oxalyl chloride (0.03 mL, 0.36 mmol), and the mixture was stirred at room temperature for 1 hour. The solvent was evaporated under reduced pressure to give 3-pyridylacetyl chloride hydrochloride. By using this compound and 5-(4-aminophenyl)-1H-naphtho[1,2-b][1,4]diazepine-2,4(3H,5H)-dione (63 mg, 0.2 mmol) obtained in Example 1, (3), the title compound (6.2 mg, yield 7%) was obtained as yellow amorphous in the same manner as that of Example 1, (4).

$^1$H NMR (CDCl$_3$, 400 MHz) δ: 3.5-3.7 (4H, m), 6.9-7.1 (3H, m), 7.2-7.3 (1H, m), 7.38 (2H, d, J=8 Hz), 7.5-7.6 (2H, m), 7.66 (1H, t, J=7 Hz), 7.73 (1H, d, J=7 Hz), 7.80 (1H, d, J=8 Hz), 8.17 (1H, d, J=9 Hz), 8.47 (1H, s), 8.5-8.7 (2H, m), 9.57 (1H, s).

(2) 5-[4-[(3-Pyridylacetyl)amino]phenyl]-1H-naphtho[1,2-b][1,4]diazepine-2,4(3H,5H)-dione hydrochloride 5-[4-[(3-Pyridylacetyl)amino]phenyl]-1H-naphtho[1,2-b][1,4]diazepine-2,4(3H,5H)-dione (6.2 mg, 0.014 mmol) was dissolved in chloroform (6 mL), the solution was added with a 4 M solution of hydrogen chloride in ethyl acetate (0.01 mL), and the solvent was evaporated under reduced pressure. The residue was concentrated from ethyl acetate under reduced pressure, and then washed with ethyl acetate to obtain the title compound (4.8 mg, yield 71%) ac pale brown powder.

$^1$H NMR (DMSO-de, 400 MHz) δ: 3.14 (1H, d, J=12 Hz), 3.69 (1H, d, J=12 Hz), 3.89 (2H, s), 6.97 (1H, d, J=9 Hz), 7.18 (2H, d, J=9 Hz), 7.5-7.8 (6H, m), 7.91 (1H, d, J=8 Hz), 8.18 (1H, d, J=7 Hz), 8.25 (1H, d, J=9 Hz), 8.67 (1H, d, J=5 Hz), 8.73 (1H, s), 10.47 (1H, s), 10.88 (1H, s).

Example 41

5-[4-(1H-Benzimidazole-2-carbonylamino)phenyl]-1H-naphtho[1,2-b][1,4]diazepine-2,4(3H,5H)-dione 1H-Benzimidazole-2-carboxylic acid monohydrate (14 mg, 0.077 mmol), 5-(4-aminophenyl)-1H-naphtho[1,2-b][1,4]diazepine-2,4(3H,5H)-dione (23 mg, 0.072 mmol) obtained in Example 1, (3), dimethylformamide (1.4 mL), and 1-hydroxybenzotriazole monohydrate (11 mg, 0.08 mmol) were mixed, and the mixture was stirred at room temperature for 3 hours. This reaction mixture was added with water, and the mixture was extracted with ethyl acetate. The ethyl acetate layer was washed with saturated aqueous sodium hydrogencarbonate, and then with saturated brine, and dried over anhydrous sodium sulfate. The solvent was evaporated under reduced pressure, and the residue was purified by silica gel column chromatography (hexane/ethyl acetate=4/1), and then recrystallized from ethyl acetate/hexane to give the title compound (15 mg, yield 43%) as slightly yellow crystals.

1H NMR (DMSO-$d_6$, 400 MHz) δ: 3.16 (1H, d, J=12 Hz), 3.71 (1H, d, J=12 Hz), 7.03 (1H, d, J=9 Hz), 7.24 (2H, d, J=9 Hz), 7.3-7.4 (2H, m), 7.5-7.8 (5H, m), 7.92 (1H, d, J=8 Hz), 7.98 (2H, d, J=9 Hz), 8.26 (1H, d, J=8 Hz), 10.90 (1H, s), 11.04 (1H, s), 13.42 (1H, br s).

Example 42

1-[4-(2,3-Dimethylbenzoylamino)phenyl]-7-methoxy-1H-1,5-benzodiazepine-2,4(3H,5H)-dione (1) tert-Butyl 4-(7-methoxy-2,4-dioxo-2,3,4,5-tetrahydro-1H-benzo[b][1,4]diazepin-1-yl)phenylcarbamate tert-Butyl 4-(2-amino-4-methoxyphenylamino)phenylcarbamate (500 mg, 1.52 mmol) synthesized in the same manner as that of Example 1 by using 4-methoxy-2-nitrophenol as the starting material was dissolved in anhydrous tetrahydrofuran (30 mL), and the solution was added dropwise with malonyl chloride (0.178 mL, 1.82 mmol) on an ice bath. The mixture was stirred at room temperature for 16 hours. After completion of the reaction, the reaction mixture was added with saturated aqueous sodium hydrogencarbonate, the aqueous layer was extracted with chloroform, the organic layer was dried over sodium sulfate, and then the solvent was evaporated under reduced pressure. The obtained residue was purified by silica gel column chromatography (chloroform/methanol=100/1) to give the title compound (230 mg, yield 38%).

$^1$H NMR (CDCl$_3$, 400 MHz) δ: 1.51 (9H, s), 3.53 (2H, s), 3.80 (3H, s), 6.6-6.7 (3H, m), 6.83 (1H, d, J=9 Hz), 7.11 (2H, d, J=9 Hz), 7.37 (2H, d, J=9 Hz), 9.24 (1H, s).

(2) 1-(4-Aminophenyl)-7-methoxy-1H-1,5-benzodiazepine-2,4(3H,5H)-dione

By using tert-butyl 4-(7-methoxy-2,4-dioxo-2,3,4,5-tetrahydro-1H-benzo[b][1,4]diazepin-1-yl)phenylcarbamate (230 mg, 0.58 mmol) obtained above as the starting material, the title compound (125 mg, yield 72%) was obtained in the same manner as that of Example 1.

$^1$H NMR (DMSO-$d_6$, 400 MHz) δ: 3.03 (1H, br s), 3.53 (1H, br s), 3.72 (3H, s), 5.19 (2H, s), 6.53 (2H, d, J=9 Hz), 6.6-6.7 (2H, m), 6.74 (2H, d, J=9 Hz), 6.80 (1H, d, J=8 Hz), 10.4 (1H, s).

(3) 1-[4-(2,3-Dimethylbenzoylamino)phenyl]-7-methoxy-1H-1,5-benzodiazepine-2.4 (3H,5H)-dione By using 1-(4-aminophenyl)-7-methoxy-1H-1,5-benzodiazepine-2,4(3H,5H)-dione (60 mg, 0.4 mmol) obtained above, and 2,3-dimethylbenzoyl chloride (0.6 mmol), the title compound (23 mg, yield 13%) was obtained in the same manner as that of Example 1, (4).

$^1$H NMR (CDCl$_3$, 400 MHz) δ: 2.31 (3H, s), 2.36 (3H, s), 3.53 (2H, s), 3.81 (3H, s), 6.62 (1H, d, J=3 Hz), 6.68 (1H, dd, J=2 Hz, 9 Hz), 6.88 (1H, d, J=9 Hz), 7.1-7.3 (5H, m), 7.55 (1H, s), 7.65 (2H, d, J=9 Hz), 8.17 (1H, s).

Example 43

5-[4-[(Benzoylamino)methyl]phenyl]-1H-naphtha[1,2-b][1,4]diazepine-2,4(3H,5H)-dione

(1) tert-Butyl 4-(1-aminonaphthalen-2-ylamino)benzylcarbamate

By using tert-butyl 4-(1-nitronaphthalen-2-ylamino)benzylcarbamate, the title compound was obtained in the same manner as that of Example 1, (2).

$^1$H NMR (CDCl$_3$, 400 MHz) δ: 1.45 (9H, s), 4.20 (2H, s), 6.74 (2H, d, J=9 Hz), 7.12 (2H, d, J=8 Hz), 7.32 (2H, d, J=8 Hz), 7.4-7.6 (3H, m), 7.81 (1H, d, J=8 Hz), 7.87 (1H, d, J=8 Hz).

(2) tert-Butyl 4-[2,4-dioxo-3,4-dihydro-1H-naphtho[2,1-b][1,4]diazepin-5(2H)-yl]benzylcarbamate By using tert-butyl 4-(1-aminonaphthalen-2-ylamino)benzylcarbamate, the title compound was obtained in the same manner as that of Example 42, (1).

$^1$H NMR (CDCl$_3$, 400 MHz) δ: 1.46 (9H, s), 3.60 (2H, s), 4.34 (2H, s), 4.89 (1H, br s), 7.01 (1H, d, J=9 Hz), 7.22 (2H, d, J=8 Hz), 7.33 (2H, d, J=8 Hz), 7.5-7.7 (2H, m), 7.69 (1H, t, J=8 Hz), 7.84 (1H, d, J=8 Hz), 8.09 (1H, d, J=9 Hz), 8.70 (1H, br s).

(3) 5-[4-(Aminomethyl)phenyl]-1H-naphtho[2,1-b][1,4]diazepine-2,4(3H,5H)-dione By using tert-butyl 4-[2,4-dioxo-3,4-dihydro-1H-naphtho[2,1-b][1,4]diazepin-5(2H)-yl]benzylcarbamate, the title compound was obtained in the same manner as that of Example 1, (3).

$^1$H NMR (CDCl$_3$, 400 MHz) δ: 3.61 (2H, s), 3.91 (2H, s), 7.03 (1H, d, J=9 Hz), 7.2-7.3 (2H, m), 7.38 (2H, d, J=8 Hz), 7.59 (1H, d, J=9 Hz), 7.60 (1H, t, J=7 Hz), 7.69 (1H, t, J=7 Hz), 7.85 (1H, d, J=8 Hz), 8.06 (1H, d, J=9 Hz), 8.32 (1, br s).

(4) 5-[4-[(Benzoylamino)methyl]phenyl]-1H-naphtho[1,2-b][1,4]diazepine-2,4(3H,5H)-dione By using 5-[4-(aminomethyl)phenyl]-1H-naphtho[2,1-b][1,4]diazepine-2,4(3H,5H)-dione, the title compound was obtained in the same manner as that of Example 1, (4).

$^1$H NMR (DMSO-$d_6$, 400 MHz) δ: 3.14 (1H, d, J=12 Hz), 3.70 (1H, d, J=12 Hz), 4.51 (2H, d, J=6 Hz), 6.97 (1H, d, J=9 Hz), 7.18 (2H, d, J=8 Hz), 7.39 (2H, d, J=8 Hz), 7.4-7.7 (6H, m), 7.89 (3H, d, J=8 Hz), 8.24 (1H, d, J=8 Hz), 9.07 (1H, t, J=6 Hz), 10.87 (1H, s).

Example 44

5-[4-[(2-Chlorobenzoylamino)methyl]phenyl]-1H-naphtho[1,2-b][1,4]diazepine-2,4(3H,5H)-dione By using 5-[4-(aminomethyl)phenyl]-1H-naphtho[2,1-b][1,4]diazepine-2,4(3H,5H)-dione obtained in Example 43, (3), and 2-chlorobenzoyl chloride, the title compound was obtained in the same manner as that of Example 43, (5).

$^1$H NMR (DMSO-$d_6$, 400 MHz) δ: 3.14 (1H, d, J=12 Hz), 3.70 (1H, d, J=12 Hz), 4.48 (2H, d, J=6 Hz), 6.97 (1H, d, J=9 Hz), 7.21 (2H, d, J=8 Hz), 7.3-7.7 (9H, m), 7.90 (1H, d, J=8 Hz), 8.25 (1H, d, J=9 Hz), 9.00 (1H, t, J=6 Hz), 10.89 (1H, s).

Example 45

1-[4-(2,3-Dimethylbenzoylamino)phenyl]-7-hydroxy-1H-1,5-benzodiazepine-2,4(3H,5H)-dione By using 1-[4-(2,3-dimethylbenzoylamino)phenyl]-7-methoxy-1-1,5-benzodiazepine-2,4(3H,5H)-dione (20 mg, 0.047 mmol) obtained in Example 42, the title compound (7 mg, yield 36%) was obtained in the same manner as that of Example 18.

$^1$H NMR (DMSO-$d_6$, 400 MHz) δ: 2.24 (3H, s), 2.28 (3H, s), 3.0-3.1 (1H, m), 3.5-3.7 (1H, m), 6.52 (1H, dd, J=3 Hz, 9 Hz), 6.61 (1H, d, J=2 Hz), 6.68 (1H, d, J=9 Hz), 7.09 (2H, d, J=8 Hz), 7.1-7.3 (3H, m), 7.74 (2H, d, J=9 Hz), 9.74 (1H, s), 10.38 (1H, s), 10.42 (1H, s).

Example 46

5-[4-(2-Chlorobenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 2-chlorobenzoyl chloride (14 µL, 0.114 mmol), the title compound (13 mg, yield 30%) was obtained in the same manner as that of Example 1, (4).

$^1$H NMR (CDCl$_3$, 400 MHz) δ: 3.59 (2H, s), 7.06 (1H, d, J=9 Hz), 7.2-7.3 (2H, m), 7.3-7.5 (3H, m), 7.5-7.7 (5H, m), 7.76 (1H, dd, J=2 Hz, 7 Hz), 7.85 (1H, d, J=8 Hz), 7.93 (1H, br s), 8.03 (1H, d, J=8 Hz), 8.07 (1H, s).

Example 47

5-[4-(2-Bromobenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 2-bromobenzoyl chloride (0.143 mmol), the title compound (10 mg, yield 21%) was obtained in the same manner as that of Example 1, (4).

$^1$H NMR (DMSO-d$_6$, 400 MHz) δ: 3.15 (1H, d, J=12 Hz), 3.70 (1H, d, J=12 Hz), 7.02 (1H, d, J=9 Hz), 7.21 (2H, d, J=8 Hz), 7.42 (1H, t, J=7 Hz), 7.50 (1H, t, J=7 Hz), 7.56 (1H, d, J=8 Hz), 7.60 (1H, d, J=8 Hz), 7.6-7.7 (3H, m), 7.77 (2H, d, J=8 Hz), 7.92 (1H, d, J=8 Hz), 8.25 (1H, d, J=9 Hz), 10.63 (1H, s), 10.38 (1H, br s).

Example 48

5-[4-(2-Iodobenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 2-iodobenzoyl chloride (0.143 mmol), the title compound (16 mg, yield 31%) was obtained in the same manner as that of Example 1, (4).

$^1$H NMR (DMSO-d$_6$, 400 MHz) δ: 3.15 (1H, d, J=12 Hz), 3.70 (1H, d, J=12 Hz), 7.02 (1H, d, J=9 Hz), 7.1-7.3 (3H, m), 7.4-7.5 (2B, m), 7.59 (1H, t, J=7 Hz), 7.65 (1H, d, J=8 Hz), 7.70 (1H, d, J=9 Hz), 7.77 (2H, d, J=9 Hz), 7.92 (2H, t, J=7 Hz), 8.25 (1H, d, J=8 Hz), 10.57 (1H, s), 10.89 (1H, s).

Example 49

5-[4-(2,3-Dimethylbenzoylamino)-3-fluorophenyl]-1H-naphtho[1,2-b][1,4]diazepine-2,4(3H,5H)-dione (1) N$^2$-(4-Amino-3-fluorophenyl)naphthalene-1,2-diamine By using 2-fluoro-4-nitroaniline as the starting material, the title compound was obtained in the same manner as that of Example 1.

$^1$H NMR (CDCl$_3$, 400 MHz) δ: 1.51 (9H, s), 4.36 (2H, br s), 5.22 (1H, br s), 6.37 (2H, dd, J=2 Hz, 13 Hz), 6.50 (1H, d, J=9 Hz), 7.23 (1H, d, J=9 Hz), 7.30 (1H, d, J=9 Hz), 7.4-7.5 (2H, m), 7.73 (1H, br s), 7.81 (2H, m).

(2) 5-[4-(2,3-Dimethylbenzoylamino)-3-fluorophenyl]-1H-naphtho[1,2-b][1,4]diazepine-2,4(3H,5H)-dione By using N$^2$-(4-amino-3-fluorophenyl)naphthalene-1,2-diamine obtained above, 5-(4-amino-3-fluorophenyl)-1H-naphtho[1,2-b][1,4]diazepine-2,4(3H,5H)-dione (20 mg, 0.06 mmol) obtained in the same manner as that of Example 42, (1) and (2), and 2,3-dimethylbenzoyl chloride (0.09 mmol), the title compound (18 mg, yield 64%) was obtained in the same manner as that of Example 1, (4).

$^1$H NMR (CDCl$_3$, 400 MHz) δ: 2.33 (3H, s), 2.38 (3H, s), 3.61 (2H, s), 7.06 (2H, d, J=9 Hz), 7.1-7.2 (2H, m), 7.2-7.4 (2H, m), 7.6-7.8 (4H, m), 7.87 (1H, d, J=8 Hz), 8.16 (1H, d, J=9 Hz), 8.55 (1H, t, J=8 Hz), 9.17 (1H, s).

Example 50

5-[4-[2-(2-Methylphenyl)acetylamino]phenyl]-1H-naphtho[1,2-b][1,4]diazepine-2,4(3H,5H)-dione By using o-tolylacetyl chloride, the title compound was obtained in the same manner as that of Example 1, (4).

$^1$H NMR (DMSO-d$_6$, 400 MHz) δ: 2.29 (3H, s), 3.13 (1H, d, J=12 Hz), 3.68 (2H, s), 3.68 (1H, d, J=12 Hz), 6.98 (1H, d, J=9 Hz), 7.1-7.3 (6H, m), 7.5-7.7 (5H, m), 7.90 (1H, d, J=8 Hz), 8.24 (1H, d, J=9 Hz), 10.28 (1H, s), 10.87 (1H, s).

Example 51

5-[4-[(Quinoxalin-2-yl)carbonylamino]phenyl]-1H-naphtho[1,2-b][1,4]diazepine-2,4(3H,5H)-dione 5-(4-Aminophenyl)-1H-naphtho[1,2-b][1,4]diazepine-2,4(3H,5H)-dione (32 mg, 0.101 mmol) obtained in Example 1, (3), quinoxaline-2-carboxylic acid (35 mg, 0.202 mmol), and O-(benzotriazol-1-yl)-N,N,N',N'-tetramethyluronium hexafluorophosphate (42 mg, 0.111 mmol) were dissolved in DMF (2.0 mL), then the solution was added with triethylamine (20 mg, 0.202 mmol), and the mixture was stirred over night. The reaction mixture was treated in a conventional manner to obtain the title compound (10 mg, yield 21%) as yellow crystals.

$^1$H NMR (CDCl$_3$, 400 MHz) δ: 3.63 (2H, s), 7.07 (1H, d, J=9 Hz), 7.33 (2H, d, J=9 Hz), 7.62 (2H, d, J=8 Hz), 7.71 (1H, t, J=8 Hz), 7.8-8.0 (5H, m), 8.09 (1H, d, J=8 Hz), 8.1-8.3 (2H, m), 8.50 (1H, s), 9.75 (1H, s), 9.91 (1H, s).

Example 52

5-[4-[(5-Methylthiophen-2-yl)carbonylamino]phenyl]-1H-naphtho[1,2-b][1,4]diazepine-2,4(3H,5H)-dione 5-(4-Aminophenyl)-1H-naphtho[1,2-b][1,4]diazepine-2,4(3H,5H)-dione (16 mg, 0.050 mmol) obtained in Example 1, (3), 5-methylthiophene-2-carboxylic acid (14 mg, 0.101 mmol), and O-(benzotriazol-1-yl)-N, N, N',N'-tetramethyluronium hexafluorophosphate (21 mg, 0.055 mmol) were dissolved in DMF (2.0 mL), then the solution was added with triethylamine (10 mg, 0.101 mmol), and the mixture was stirred over night. The reaction mixture was treated in a conventional manner to give the title compound (10 mg, yield 45%) as white crystals.

$^1$H NMR (CDCl$_3$, 400 MHz) δ: 2.54 (3H, s), 3.60 (2H, s), 6.79 (1H, d, J=2 Hz), 7.04 (1H, d, J=9 Hz), 7.25 (1H, d, J=9 Hz), 7.45 (1H, d, J=2 Hz), 7.5-7.8 (7H, m), 7.86 (1H, d, J=8 Hz), 8.05 (1H, d, J=8 Hz), 8.26 (1H, s).

Example 53

5-[3-[(2-Chlorophenylacetyl)amino]phenyl]-1H-naphtho[1,2-b][1,4]diazepine-2,4(3H,5H)-dione (1) 5-(3-Aminophenyl)-1H-naphtho[1,2-b][1,4]diazepine-2,4(3H,5H)-dione By using 1-nitro-2-naphthyl trifluoromethanesulfonate (5.94 g, 18.5 mmol), and tert-butyl (3-aminophenyl)carbamate, the title compound (1.02 g, yield 17%) was obtained as brown crystals in the same manner as that of Example 1, (1), (2) and (3).

$^1$H NMR (DMSO-d$_6$, 400 MHz) δ: 3.11 (1H, d, J=12 Hz), 3.66 (1H, d, J=12 Hz), 5.23 (2H, s), 6.35 (1H, s), 6.39 (1H, d, J=8 Hz), 6.52 (1H, d, J=8 Hz), 7.0-7.1 (2H, m), 7.58 (1H, t, J=8 Hz), 7.65 (1H, t, J=8 Hz), 7.70 (1H, d, J=8 Hz), 7.91 (1H, d, J=8 Hz), 8.23 (1H, d, J=8 Hz), 10.86 (1H, s).

(2) 5-[3-[(2-Chlorophenylacetyl)amino]phenyl]-1H-naphtho[1,2-b][1,4]diazepine-2,4(3H,5H)-dione 2-Chlorophenylacetic acid (31 mg, 0.18 mmol) was treated with thionyl chloride in the same manner as that of Example 13, and then by using the resultant together with 5-(3-aminophenyl)-1H-naphtho[1,2b][1,4]diazepine-2,4(3H,5H)-dione (28 mg, 0.088 mmol), the title compound (10 mg, yield 24%) was obtained as yellow crystals in the same manner as that of Example 1, (4).

$^1$H NMR (DMSO-de, 400 MHz) δ: 3.14 (1H, d, J=12 Hz), 3.72 (1H, d, J=12 Hz), 3.79 (2H, s), 7.0-7.1 (2H, m), 7.2-7.3 (2H, m), 7.3-7.5 (3H, m), 7.47 (1H, s), 7.5-7.7 (4H, m), 7.92 (1H, d, J=8 Hz), 8.24 (1H, d, J=8 Hz), 10.33 (1H, s), 10.90 (1H, s).

Example 54

5-[4-[(2,4,6-Trimethylbenzoyl)amino]phenyl]-1H-naphtho[1,2-b][1.4]diazepine-2,4(3H,5H)-dione 2,4,6-Trimethylbenzoic acid (25 mg, 0.15 mmol) was treated with thionyl chloride in the same manner as that of Example 13, and then by using the resultant together with 5-(4-aminophenyl)-1H-naphtho[1,2b][1,4]diazepine-2,4(3H,5H)-dione (32 mg, 0.1 mmol) obtained in Example 1, (3), the title compound (6 mg, yield 13%) was obtained as slightly brown crystals in the same manner as that of Example 1, (4).

$^1$H NMR (DMSO-d$_6$, 400 MHz) δ: 2.25 (6H, s), 2.27 (3H, s), 3.16 (1H, d, J=12 Hz), 3.70 (1H, d, J=12 Hz), 6.93 (2H, s), 7.04 (1H, d, J=9 Hz), 7.20 (2H, d, J=8 Hz), 7.5-7.7 (3H, m), 7.79 (2H, d, J=9 Hz), 7.92 (1H, d, J=7 Hz), 8.26 (1H, d, J=8 Hz), 10.45 (1H, s), 10.87 (1H, s).

Example 55

5-[4-(Cyclohexylcarbonylamino)phenyl]-1,2,3,4,8,9,10,11-octahydronaphtho[1,2-b][1,4]diazepine-2,4(3H,5H)-dione (1) 1-Nitro-5,6,7,8-tetrahydro-2-naphthyl trifluoromethanesulfonate 1-Nitro-5,6,7,8-tetrahydro-2-naphthol (6.95 g, 36 mmol) was dissolved in dichloromethane (70 mL), and the solution was added with triethylamine (5.52 mL, 39.6 mmol). This mixture was added dropwise with trifluoromethanemethanesulfonic anhydride (6.2 mL, 38 mmol) over 15 minutes with stirring under ice cooling, and then the mixture was stirred for 1 hours and 30 minutes under ice cooling. This reaction mixture was added with cold water, and the mixture was stirred for 10 minutes. The dichloromethane layer was washed with saturated brine, and dried over anhydrous sodium sulfate. The solvent was evaporated, and the residue was purified by silica gel column chromatography (hexane/ethyl acetate=5(1) to give the title compound (10.15 g, yield 87%) as yellow oil.

$^1$H NMR (CDCl$_3$, 400 MHz) δ: 1.8-1.9 (4H, m), 2.7-2.9 (4H, m), 7.21 (1H, d, J=9 Hz), 7.29 (1H, d, J=9 Hz).

(2) tert-Butyl [4-[(1-nitro-5,6,7,8-tetrahydro-2-naphthyl)amino]phenyl]carbamate By using 1-nitro-5,6,7,8-tetrahydro-2-naphthyl trifluoromethanesulfonate (2.23 g, 6.86 mmol), and tert-butyl (4-aminophenyl)carbamate (1.43 g, 6.86 mmol), the title compound (2.30 g, yield 87%) was obtained as red crystals in the same manner as that of Example 1, (1).

$^1$H NMR (CDCl$_3$, 400 MHz) δ: 1.52 (9H, s), 1.7-1.9 (4H, m), 2.6-2.9 (4H, m), 6.41 (1H, s), 6.97 (1H, d, J=9 Hz), 7.01 (1H, d, J=9 Hz), 7.04 (2H, d, J=9 Hz), 7.31 (2H, d, J=9 Hz).

(3) tert-Butyl [4-[(1-amino-5,6,7,8-tetrahydro-2-naphthyl)amino]phenyl]carbamate tert-Butyl [4-[(1-nitro-5,6,7,8-tetrahydro-2-naphthyl)amino]phenyl]carbamate (7.66 g, 20 mmol) was dissolved in tetrahydrofuran (77 mL) and methanol (77 mL), the solution was added with 10% palladium-carbon (0.77 g), and the mixture was stirred at room temperature for 42 hours under a hydrogen atmosphere. The catalyst was separated by filtration, then the solvent was evaporated under reduced pressure, and the residue was washed with hexane to obtain the title compound (6.71 g, yield 95%) as pale brown crystals.

$^1$H NMR (CDCl$_3$, 400 MHz) δ: 1.50 (9H, s), 1.7-1.9 (4H, m), 2.4-2.6 (2H, m), 2.7-2.8 (2H, m), 6.24 (1H, s), 6.52 (1H, d, J=8 Hz), 6.63 (2H, d, J=8 Hz), 6.87 (1H, d, J=9 Hz), 7.14 (2H, d, J=8 Hz).

(4) Ethyl 3-[[2-[[4-[(tert-butoxycarbonyl)amino]phenyl]amino]-5,6,7,8-tetrahydro-1-naphthyl]amino]-3-oxopropionate By using tert-butyl [4-[(1-amino-5,6,7,8-tetrahydro-2-naphthyl)amino]phenyl]carbamate (6.01 g, 174 mmol), a crude product (9.7 g) was obtained in the same manner as that of Example 1, (3). The crude product was purified by silica gel column chromatography (hexane/ethyl acetate=1/1) to give the title compound (3.48 g, yield 44%) as pale brown crystals.

$^1$H NMR (CDCl$_3$, 400 MHz) δ: 1.31 (3H, t, J=7 Hz), 1.50 (9H, s), 1.7-1.9 (4H, m), 2.6-2.8 (4H, m), 3.51 (2H, s), 4.25 (2H, q, J=7 Hz), 6.08 (1H, s), 6.31 (1H, s), 6.89 (2H, d, J=9 Hz), 6.92 (1H, d, J=9 Hz), 7.07 (1H, d, J=9 Hz), 7.19 (2H, d, J=9 Hz), 8.66 (1H, s).

(5) 5-[4-(tert-Butoxycarbonyl)aminophenyl]-1,2,3,4,8,9,10,11-octahydronaphtho[1,2-b][1,4]diazepine-2,4(3H,5H)-dione By using ethyl 3-[[2-[[4-[(tertbutoxycarbonyl)amino]phenyl]amino]-5,6,7,8-tetrahydro-1-naphthyl]amino]-3-oxopropionate (3.48 g, 7.44 mmol), a crude product (4.6 g) was obtained in the same manner as that of Example 1, (3). The crude product was purified by silica gel column chromatography (hexane/ethyl acetate=1/2) to give the title compound (2.07 g, yield 66%) as pale brown amorphous.

(6) 5-(4-Aminophenyl)-1,2,3,4,8,9,10,11-octahydronaphtho[1,2-b][1,4]diazepine-2,4(3H,5H)-dione By using 5-[4-(tert-butoxycarbonyl)aminophenyl]-1,2,3,4,8,9,10,11-octahydronaphtho[1,2-b][1,4]diazepine-2,4(3H,5H)-dione (2.07 g, 4.91 mmol), the title compound (1.21 g, yield 77%) was obtained as pale brown crystals in the same manner as that of Example 1, (3).

$^1$H NMR (DMSO-d$_6$, 400 MHz) δ: 1.6-1.9 (4H, m), 2.29 (3H, s), 2.5-2.8 (3H, m), 2.9-3.0 (1H, m), 2.98 (1H, d, J=12 Hz), 3.47 (1H, d, J=12 Hz), 5.20 (2H, s), 6.54 (2H, d, J=9 Hz), 6.66 (1H, d, J=9 Hz), 6.76 (2H, d, J=9 Hz), 6.85 (1H, d, J=9 Hz), 9.79 (1H, s).

(7) 5-[4-(Cyclohexylcarbonylamino)phenyl]-1,2,3,4,8,9,10,11-octahydronaphtho[1,2-b][1,4]diazepine-2,4(3H,5H)-dione By using 5-(4-aminophenyl)-8,9,10,11-tetrahydro-1H-naphtho[2,1-b][1,4]diazepine-2,4(3H,5H)-dione, and cyclohexanecarbonyl chloride, the title compound was obtained in the same manner as that of Example 1, (4).

$^1$H NMR (CDCl$_3$, 400 MHz) δ: 1.2-1.4 (4H, m), 1.4-2.0 (10H, m), 2.2-2.3 (1H, m), 2.6-2.8 (4H, m), 3.46 (1H, d, J=12 Hz), 3.51 (1H, d, J=12 Hz), 6.67 (1H, d, J=9 Hz), 6.81 (1H, d, J=8 Hz), 7.08 (2H, d, J=9 Hz), 7.49 (2H, d, J=9 Hz), 7.59 (1H, s), 8.25 (1H, s).

Example 56

1-[4-(2,3-Dimethylbenzoyl)aminophenyl]-6-methyl-1H-1,5-benzodiazepine-2,4(3H,5H)-dione

(1) tert-Butyl-4-(2-amino-3-methylphenylamino)phenylcarbamate

By using 2-methyl-6-hydroxynitrobenzene, the title compound was obtained in the same manner as that of Example 1.

$^1$H NMR (CDCl$_3$, 400 MHz) δ: 1.50 (9H, s), 2.22 (3H, s), 3.75 (2H, br s), 5.04 (1H, br s), 6.27 (1H, br s), 6.6-6.7 (3H, m), 6.8-7.0 (2H, m), 7.17 (2H, d, J=8 Hz).

(2) 1-(4-tert-Butoxycarbonylaminophenyl)-6-methyl-1H-1,5-benzodiazepine-2,4(3H,5H)-dione tert-Butyl 4-(2-amino-3-methylphenylamino)phenylcarbamate (294 mg, 0.938 m mmol) was dissolved in THF (30 mL), and then the solution was added dropwise with malonyl chloride (91 μL, 0.938 mmol) under ice cooling. After the disappearance of the starting materials was confirmed, the reaction mixture was added with aqueous sodium hydrogencarbonate, and ethyl acetate, and the organic layer was separated. The organic layer was washed with brine and water, and then dried over anhydrous sodium sulfate. The solvent was evaporated under reduced pressure, and the residue was purified by silica gel column chromatography (chloroform to chloroform/methanol=100/1) to obtain the title compound (119 mg, yield 33%).

$^1$H NMR (CDCl$_3$, 400 MHz) δ: 1.51 (9H, s), 2.41 (3H, s), 3.50 (2H, s), 6.53 (1H, br s), 6.80 (1H, d, J=71 Hz), 6.99 (1H, t, J=8 Hz), 7.0-7.2 (3H, m), 7.38 (2H, d, J=9 Hz), 7.63 (1H, br s).

(3) 1-(4-Aminophenyl)-6-methyl-1H-1,5-benzodiazepine-2,4(3H,5H)-dione

In the same manner as that of Example 1, (3), the title compound was obtained.

$^1$H NMR (CDCl$_3$, 400 MHz) δ: 2.40 (3H, s), 3.48 (2H, s), 3.74 (2H, br s), 6.67 (2H, d, J=9 Hz), 6.86 (1H, d, J=8 Hz), 6.9-7.1 (4H, m), 7.74 (1H, br s).

(4) 1-[4-(2,3-Dimethylbenzoyl)aminophenyl]-6-methyl-1H-1,5-benzodiazepine-2,4(3H,5H)-dione 2,3-Dimethylbenzoic acid (21 mg, 0.140 mmol) was made into acid chloride in a conventional manner. By using 1-(4-aminophenyl)-6-methyl-1H-1,5-benzodiazepine-2,4 (3H,5H)-dione (20 mg, 0.071 mmol) mentioned above, and 2,3-dimethylbenzoyl chloride mentioned above, the title compound (27 mg, yield 92%) was obtained in the same manner as that of Example 1.

$^1$H NMR (DMSO-d$_6$, 400 MHz) δ: 2.26 (3H, s), 2.29 (3H, s), 2.38 (3H, s), 3.06 (1H, d, J=12 Hz), 3.57 (1H, d, J=12 Hz), 6.75 (1H, d, J=8 Hz), 7.0-7.3 (7l, m), 7.78 (2H, d, J=8 Hz), 10.01 (1H, s), 10.40 (1H, s).

Example 57

5-[4-[(2-Ethylbenzoyl)amino]phenyl]-1H-naphtho[1,2-b][1,4]diazepine-2,4(3H,5H)-dione 2-Ethylbenzoic acid (23 mg, 0.15 mmol) was treated with thionyl chloride in the same manner as that of Example 13, and then by using the resultant together with 5-(4-aminophenyl)-1H-naphtho[1,2-b][1,4]diazepine-2,4(3H,5H)-dione (32 mg, 0.1 mmol) obtained in Example 1, (3), the title compound (26 mg, yield 58%) was obtained as slightly brown crystals in the same manner as that of Example 1, (4).

$^1$H NMR (DMSO-d$_6$, 400 MHz) δ: 1.18 (3H, t, J=7 Hz), 2.75 (2H, q, J=7 Hz), 3.16 (1H, d, J=11 Hz), 3.71 (1H, d, J=11 Hz), 7.03 (1H, d, J=9 Hz), 7.21 (2H, d, J=8 Hz), 7.3-7.5 (4H, m), 7.6-7.7 (3H, m), 7.81 (2H, d, J=8 Hz), 7.93 (1H, d, J=7 Hz), 8.26 (1H, d, J=8 Hz), 10.49 (1H, s), 10.89 (1H, s).

Example 58

5-[4-[(6-Methylpyridin-2-yl)carbonylamino]phenyl]-1,2,3,4,8,9,10,11-octahydronaphtho[1,2-b][1,4]diazepine-2,4(3H,5H)-dione 6-Methylpyridine-2-carboxylic acid (17 mg, 0.124 mmol) was made into acid chloride in a conventional manner. By using 5-(4-aminophenyl)-1,5,8,9,10,11-hexahydronaphtho[1,2-b][1,4]diazepine-2,4-dione (20 mg, 0.062 mmol) obtained in Example 55, and 6-methylpyridine-2-carboxylic acid chloride mentioned above, the title compound (9 mg, yield 33%) was obtained in the same manner as that of Example 1.

$^1$H NMR (CDCl$_3$, 400 MHz) δ: 1.7-2.1 (4H, m), 2.63 (3H, s), 2.6-2.8 (4H, m), 3.4-3.6 (2H, m), 6.73 (1H, d, J=8 Hz), 6.85 (1H, d, J=9 Hz), 7.22 (2H, d, J=9 Hz), 7.33 (1H, d, J=7 Hz), 7.7-7.9 (4H, m), 8.08 (1H, d, J=8 Hz), 10.11 (1H, s).

Example 59

5-[4-[(2-Methylpyridin-3-yl)carbonylamino]phenyl]-1,2,3,4,8,9,10,11-octahydronaphtho[1,2-b][1,4]diazepine-2,4(3H,5H)-dione 2-Methylpyridine-3-carboxylic acid (17 mg, 0.124 mmol) was made into acid chloride in a conventional manner. By using 5-(4-aminophenyl)-1,5,8,9,10,11-hexahydronaphtho[1,2-b][1,4]diazepine-2,4-dione (20 mg, 0.062 mmol) obtained in Example 55, and 2-methylpyridine-3-carboxylic acid chloride mentioned above, the title compound (20 mg, yield 73%) was obtained in the same manner as that of Example 1.

$^1$H NMR (DMSO-d$_6$, 400 MHz) δ: 1.6-1.9 (4H, m), 2.57 (3H, s), 2.5-2.8 (3H, m), 2.8-3.0 (1H, m), 3.03 (1H, d, J=12 Hz), 3.55 (1H, d, J=12 Hz), 6.65 (1H, d, J=8 Hz), 6.88 (1H, d, J=9 Hz), 7.14 (2H, d, J=9 Hz), 7.3-7.4 (1H, m), 7.76 (2H, d, J=8 Hz), 7.86 (1H, d, J=8 Hz), 8.55 (1H, d, J=5 Hz), 9.87 (1H, s), 10.54 (1H, s).

Example 60

1-[4-(2,4-Dioxo-1,2,3,4-tetrahydronaphtho[1,2-b][1,4]diazepin-5-yl)phenyl]-3-(2-methylphenyl)thiourea By using 5-(4-aminophenyl)-1H-naphtho[1,2-b][1,4]diazepine-2,4(3H,5H)-dione (150 mg, 0.473 mmol), and o-tolyl isothiocyanate (159 μL, 1.183 mmol), the title compound (66 mg, yield 30%) was obtained in the same manner as that of Example 24.

$^1$H NMR (DMSO-d$_6$, 400 MHz) δ: 2.25 (3H, s), 3.15 (1H, d, J=12 Hz), 3.69 (1H, d, J=12 Hz), 7.00 (1H, d, J=9 Hz), 7.1-7.3 (6H, m), 7.5-7.8 (5H, m), 7.92 (1H, d, J=8 Hz), 8.25 (1H, d, J=8 Hz), 9.42 (1H, s), 9.76 (1H, s), 10.89 (1H, s).

Example 61

5-[4-(2-Methoxy-3-methylbenzoyl)aminophenyl]-1,2,3,4,8,9,10,11-octahydronaphtho[1,2-b][1,4]diazepine-2,4(3H,5H)-dione 2-Methoxy-3-methylbenzoic acid (25 mg, 0.15 mmol) was treated with thionyl chloride in the same manner as that of Example 13, and then by using the resultant together with 5-(4-aminophenyl)-1,2,3,4,8,9,10,11-octahydronaphtho[1,2-b][1,4]diazepine-2,4(3H,5H)-dione (39 mg, 0.12 mmol) obtained in Example 55, the title compound (52 mg, yield 92%) was obtained as slightly brown crystals in the same manner as that of Example 1, (4).

$^1$H NMR (DMSO-d$_6$, 400 MHz) δ: 1.6-1.9 (4H, m), 2.29 (3H, s), 2.5-2.8 (2H, m), 2.9-3.0 (1H, m), 3.04 (1H, d, J=12 Hz), 3.56 (1H, d, J=12 Hz), 3.75 (3H, s), 6.66 (1H, d, J=9 Hz), 6.88 (1H, d, J=8 Hz), 7.1-7.2 (3H, m), 7.3-7.4 (2H, m), 7.77 (2H, d, J=9 Hz), 9.86 (1H, s), 10.36 (1H, s).

Example 62

5-[4-(2,3-Dichlorobenzoyl)aminophenyl]-1,2,3,4,8,9,10,11-octahydronaphtho[1,2-b][1,4]diazepine-2,4(3H,5H)-dione By using 5-(4-aminophenyl)-1,5,8,9,10,11l-hexahydronaphtho-1H-naphtho[1,2-b][1,4]diazepine-2,4-dione (40 mg, 0.124 mmol) obtained in Example 55, (6), and 2,3-dichlorobenzoyl chloride (40 mg, 0.187 mmol), the title compound (50 mg, yield 81%) was obtained as white crystals in the same manner as that of Example 1, (4).

$^1$H NMR (DMSO-d$_6$, 400 MHz) δ: 1.6-1.9 (4H, m), 2.5-2.9 (4H, m), 3.01 (1H, d, J=12 Hz), 3.55 (1H, d, J=12 Hz), 6.64 (1H, d, J=8 Hz), 6.87 (1H, d, J=8 Hz), 7.14 (2H, d, J=8 Hz), 7.48 (1H, t, J=8 Hz), 7.56 (1H, d, J=8 Hz), 7.72 (2H, d, J=9 Hz), 7.76 (1H, d, J=8 Hz), 9.86 (1H, s), 10.69 (1H, s).

Example 63

5-[4-(2,3-Dimethylbenzoylamino)-3-hydroxyphenyl]-1H-naphtho[1,2-b][1,4]diazepine-2,4(3H,5H)-dione (1) tert-Butyl 4-(1-aminonaphthalen-2-ylamino)-2-methoxyphenylcarbamate By using tert-butyl 2-methoxy-4-(1-nitronaphthalen-2-ylamino)phenylcarbamate, the title compound was obtained in the same manner as that of Example 1, (2).

$^1$H NMR (CDCl$_3$, 400 MHz) δ: 1.51 (9H, s), 3.72 (3H, s), 4.35 (2H, br s), 5.14 (1H, br s), 6.27 (1H, d, J=2 Hz), 6.34 (1H, dd, J=2 Hz, 8 Hz), 6.77 (1H, br s), 7.27 (1H, d, J=8 Hz), 7.30 (1H, d, J=9 Hz), 7.4-7.5 (2H, m), 7.7-7.9 (2H, m).

(2) tert-Butyl 4-[2,4-dioxo-3,4-dihydro-1H-naphtho[2,1-b][1,4]diazepin-5(2H)-yl]-2-methoxyphenylcarbamate By using tert-butyl 4-(1-aminonaphthalen-2-ylamino)-2-methoxyphenylcarbamate, the title compound was obtained in the same manner as that of Example 42, (1).

$^1$H NMR (CDCl$_3$, 400 MHz) δ: 1.52 (9H, s), 3.5-3.7 (2H, m), 3.83 (3H, s), 6.7-6.8 (2H, m), 7.07 (1H, d, J=9 Hz), 7.10 (1H, br s), 7.5-7.7 (2H, m), 7.69 (1H, t, J=8 Hz), 7.85 (1H, d, J=7 Hz), 8.05 (1H, d, J=9 Hz), 8.11 (1H, d, J=9 Hz), 8.25 (1H, br s).

(3) 5-(4-Amino-3-methoxyphenyl)-1H-naphtho[2,1-b][1,4]diazepine-2,4(3H,5H)-dione By using tert-butyl 4-[2,4-dioxo-3,4-dihydro-1H-naphtho[2,1-b][1,4]diazepin-5(2H)-yl]-2-methoxyphenylcarbamate, the title compound was obtained in the same manner as that of Example 1, (3).

$^1$H NMR (CDCl$_3$, 400 MHz) δ: 3.56 (1H, d, J=12 Hz), 3.60 (1H, d, J=12 Hz), 3.79 (3H, s), 3.90 (2H, br s), 6.6-6.8 (3H, m), 7.12 (1H, d, J=9 Hz), 7.5-7.6 (2H, m), 7.6-7.7 (1H, m), 7.84 (1H, d, J=8 Hz), 8.09 (1H, d, J=9 Hz), 8.68 (1H, br s).

(4) 5-[4-(2,3-Dimethylbenzoylamino)-3-methoxyphenyl]-1H-naphtho[1,2-b][1,4]diazepine-2,4(3H,5H)-dione By using 5-(4-amino-3-methoxyphenyl)-1H-naphtho[2,1-b][1,4]diazepine-2,4(3H,5H)-dione, and 2,3-dimethylbenzoyl chloride, the title compound was obtained in the same manner as that of Example 1, (4).

$^1$H NMR (CDCl$_3$, 400 MHz) δ: 2.33 (3H, s), 2.39 (3H, s), 3.61 (2H, s), 3.82 (3H, s), 6.8-6.9 (2H, m), 7.11 (1H, d, J=9 Hz), 7.18 (1H, t, J=8 Hz), 7.2-7.3 (1H, m), 7.32 (1H, d, J=7 Hz), 7.5-7.7 (2H, m), 7.70 (1H, t, J=7 Hz)), 7.86 (1H, d, J=8 Hz), 8.0-8.1 (2H, m), 8.50 (1H, br s), 8.61 (1H, d, J=9 Hz).

(5) 5-[4-(2,3-Dimethylbenzoylamino)-3-hydroxyphenyl]-1H-naphtho[1,2-b][1,4]diazepine-2,4(3H,5H)-dione By using 5-[4-(2,3-dimethylbenzoylamino)-3-methoxyphenyl]-1H-naphtho[1,2-b][1,4]diazepine-2,4(3H,5H)-dione, the title compound was obtained in the same manner as that of Example 18.

$^1$H NMR (DMSO-d$_6$, 400 MHz) δ: 2.28 (6H, s), 3.14 (1H, d, J=12 Hz), 3.69 (1H, d, J=12 Hz), 6.66 (1H, d, J=8 Hz), 6.77 (1H, s), 7.07 (1H, d, J=9 Hz), 7.17 (1H, t, J=7 Hz), 7.27 (1H, d, J=7 Hz), 7.28 (1H, d, J=7 Hz), 7.59 (1H, t, J=7 Hz), 7.66 (1H, t, J=7 Hz), 7.71 (1H, d, J=9 Hz), 7.80 (1H, d, J=9 Hz), 7.91 (1H, d, J=8 Hz), 8.23 (1H, d, J=8 Hz), 9.34 (1H, br s), 10.88 (1H, s).

Example 64

5-[4-(2-Chloro-3-methoxybenzoylamino)phenyl]-1,3-dihydronaphtho[1,2-e]-1,4-diazepin-2-one (1) 5-(4-Aminophenyl)-1H-naphtho[1,2-e][1,4]diazepin-2(3H)-one 5-(4-Bromophenyl)-1H-naphtho[1,2-e][1,4]diazepin-2(3H)-one (380 mg, 1.04 mmol), benzophenone imine (349 mg, 2.08 mmol), sodium tert-butoxide (200 mg, 2.08 mmol), palladium(II) acetate (23 mg, 0.104 mmol), and 4,5-bis(diphenylphosphino)-9,9-dimethylxanthene (60 mg, 0.208 mmol) were dissolved in anhydrous dioxane (5 mL), and the solution was stirred at 110° C. for 16 hours. The reaction mixture was left to cool, and then poured into water, and the mixture was extracted with chloroform. The organic layer was washed with saturated brine, and dried over anhydrous sodium sulfate. The solvent was evaporated under reduced pressure, and the residue was purified by silica gel column chromatography (chloroform/methanol=100/1) to give the title compound (154 mg, yield 49%).

$^1$H NMR (DMSO-d$_6$, 400 MHz) δ: 3.67 (1H, d, J=10 Hz), 4.42 (1H, d, J=10 Hz), 5.57 (2H, s), 6.54 (2H, d, J=8 Hz), 7.24 (2H, d, J=8 Hz), 7.33 (1H, d, J=9 Hz), 7.6-7.8 (3H, m), 7.9-8.1 (1H, m), 8.3-8.4 (1H, m), 10.67 (1H, br s).

(2) 5-[4-(2-Chloro-3-methoxybenzoylamino)phenyl]-1,3-dihydronaphtho[1,2-e]-1,4-diazepin-2-one By using 5-(4-aminophenyl)-1H-naphtho[1,2-e][1,4]diazepin-2(3H)-one (90 mg, 0.3 mmol) obtained above, and 2-chloro-3-methoxybenzoyl chloride (0.45 mmol), the title compound (78 mg, yield 55%) was obtained in the same manner as that of Example 1, (4).

$^1$H NMR (DMSO-dc, 500 MHz) δ: 3.79 (1H, d, J=10 Hz), 3.91 (3H, s), 4.56 (1H, d, J=10 Hz), 7.15 (1H, d, J=7 Hz), 7.2-7.3 (2H, m), 7.43 (1H, t, J=8 Hz), 7.55 (2H, d, J=8 Hz), 7.7-7.8 (5H, m), 8.03 (1H, d, J=9 Hz), 8.37 (1H, d, J=9 Hz), 10.71 (1H, s), 10.85 (1H, s).

Example 65

5-[4-[(4-Dimethylaminobenzoyl)amino]phenyl]-1H-naphtho[1,2-b][1,4]diazepine-2,4(3H,5H)-dione 4-Dimethylaminobenzoic acid (33 mg, 0.2 mmol) was treated with oxalyl chloride in the same manner as that of Example 40, and then by using the resultant together with 5-(4-aminophenyl)-1H-naphtho[1,2-b][1,4]diazepine-2,4(3H,5H)-dione (32 mg, 0.1 mmol) obtained in Example 1, (3), the title compound (12 mg, yield 26%) was obtained as pale brown crystals in the same manner as that of Example 1, (4). The structure was confirmed by NMR and MS.

MS (FAB) m/z: 465, 929

Example 66

5-[4-[2-(2,4-Dichlorophenoxy)acetylamino]phenyl]-1H-naphtho[1,2-b][1,4]diazepine-2,4(3H,5H)-dione 2,4-Dichlorophenoxyacetic acid (42 mg, 0.190 mmol) was made into acid chloride in a conventional manner. By using 5-(4-aminophenyl)-1H-naphtho[1,2-b][1,4]diazepine-2,4(3H,5H)-dione (30 mg, 0.095 mmol) obtained in Example 1, (3), and 2,4-dichlorophenoxyacetic acid chloride mentioned above, the title compound (11 mg, yield 22%) was obtained in the same manner as that of Example 1.

$^1$H NMR (DMSO-d$_6$, 400 MHz) 0-3.10 (1H, d, J=12 Hz), 3.71 (1H, d, J=12 Hz), 4.88 (2H, s), 6.99 (1H, d, J=9 Hz), 7.11 (1H, d, J=9 Hz), 7.20 (2H, d, J=9 Hz), 7.38 (1H, dd, J=2 Hz, 9 Hz), 7.5-7.7 (6H, m), 7.92 (1H, d, J=9 Hz), 8.25 (1H, d, J=9 Hz), 10.36 (1H, s), 10.92 (1H, s).

Example 67

5-[4-[2-(2-Methylphenoxy)acetylamino]phenyl]-1H-naphtho[1,2-b][1,4]diazepine-2,4(3H,5H)-dione (2-Methylphenoxy)acetic acid (32 mg, 0.193 mmol) was made into acid chloride in a conventional manner. By using 5-(4-aminophenyl)-1H-naphtho[1,2-b][1,4]diazepine-2,4(3H,5H)-dione (30 mg, 0.095 mmol) obtained in Example 1, and (2-methylphenoxy)acetic acid chloride mentioned above, the title compound (21 mg, yield 48%) was obtained in the same manner as that of Example 1.

$^1$H NMR (DMSO-d$_6$, 400 MHz) δ: 2.25 (3H, s), 3.15 (1H, d, J=12 Hz), 3.71 (1H, d, J=12 Hz), 4.74 (2H, s), 6.8-6.9 (2H, m), 6.99 (1H, d, J=9 Hz), 7.1-7.3 (4H, m), 7.60 (1H, t, J=9 Hz), 7.6-7.8 (5H, m), 7.92 (1H, d, J=9 Hz), 8.25 (1H, d, J=9 Hz), 10.23 (1H, s), 10.92 (1H, s).

Example 68

N-[4-(2,4-Dioxo-1,2,3,4-tetrahydronaphtho[1,2-b][1,4]diazepin-5-yl)butyl]-2-chloro-3-methoxybenzamide By using N-(tert-butoxycarbonyl)-1,4-diaminobutane as the starting material, 5-(4-aminobutyl)-1H-naphtho[2,1-b][1,4]diazepine-2,4(3H,5H)-dione was obtained in the same manner as that of Example 42, (1) and (2). By using 5-(4-aminobutyl)-1H-naphtho[2,1-b][1,4]diazepine-2,4(3H,5H)-dione (30 mg, 0.1 mmol), and 2-chloro-3-methoxybenzoyl chloride (0.15 mmol), the title compound (26 mg, yield 56%) was obtained in the same manner as that of Example 1, (4).

$^1$H NMR (DMSO-d$_6$, 500 MHz) δ: 1.4-1.5 (3H, m), 1.5-1.6 (1H, m), 3.08 (1H, d, J=12 Hz), 3.1-3.2 (2H, m), 3.53 (1H, d, J=12 Hz), 3.8-3.9 (1H, m), 3.91 (3H, s), 4.3-4.4 (1H, m), 6.86 (1H, d, J=8 Hz), 7.21 (1H, d, J=8 Hz), 7.2-7.3 (1H, m), 7.6-7.7 (2H, m), 7.78 (1H, d, J=9 Hz), 7.94 (1H, d, J=9 Hz), 8.05 (1H, d, J=8 Hz), 8.25 (1H, d, J=9 Hz), 8.34 (1H, t, J=6 Hz), 10.78 (1H, br s).

Example 69

5-[4-(2-Chloro-3-hydroxybenzoylamino)phenyl]-1,3-dihydronaphtho[1,2-e]-1,4-diazepin-2-one By using 5-[4-(2-chloro-3-methoxybenzoylamino)phenyl]-1,3-dihydronaphtho[1,2-e]-1,4-diazepin-2-one (65 mg, 0.138 mmol) obtained in Example 64, the title compound (18 mg, yield 29%) was obtained in the same manner as that of Example 18.

$^1$H NMR (DMSO-d$_6$, 500 MHz) δ: 3.92 (1H, d, J=10 Hz), 4.69 (1H, d, J=10 Hz), 7.09 (1H, d, J=7 Hz), 7.19 (1H, d, J=8 Hz), 7.36 (1H, t, J=8 Hz), 7.44 (1H, d, J=9 Hz), 7.67 (2H, d, J=9 Hz), 7.8-7.9 (5H, m), 8.16 (1H, d, J=9 Hz), 8.50 (1H, d, J=9 Hz), 10.77 (1H, s), 10.96 (1H, br s).

Example 70

5-[4-(2-Acetylbenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 2-acetylbenzoyl chloride, the title compound (yield 27%) was obtained in the same manner as that of Example 1, (4).

¹H NMR (DMSO-d₆, 400 MHz) δ: 1.65 (3H, s), 3.25 (1H, d, J=12 Hz), 3.82 (1H, d, J=12 Hz), 6.94 (1H, s), 7.1-7.2 (1H, m), 7.40 (2H, d, J=9 Hz), 7.6-7.9 (9H, m), 8.01 (1H, d, J=8 Hz), 8.35 (1H, d, J=9 Hz), 11.02 (1H, br s).

Example 71

5-[4-(2-tert-Butylbenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 2-tert-butylbenzoyl chloride (0.143 mmol), the title compound (20 mg, yield 44%) was obtained in the same manner as that of Example 1, (4).

¹H NMR (DMSO-d₆, 500 MHz) δ: 1.52 (9H, s), 3.28 (1H, d, J=12 Hz), 3.83 (1H, d, J=12 Hz), 7.16 (1H, d, J=9 Hz), 7.33 (2H, d, J=8 Hz), 7.42 (2H, s), 7.54 (1H, br s), 7.66 (1H, d, J=8 Hz), 7.72 (1H, t, J=8 Hz), 7.7-7.8 (2H, m), 7.91 (2H, d, J=8 Hz), 8.05 (1H, d, J=8 Hz), 8.38 (1H, d, J=9 Hz), 10.69 (1H, s), 11.03 (1H, s).

Example 72

5-[2-(2-Iodobenzoyl)aminoethyl]-1H-naphtho[1,2-b][1,4]diazepine-2,4(3H,5H)-dione (1) tert-Butyl [2-[(1-nitro-2-naphthyl)amino]ethyl]carbamate 1-Nitro-2-naphthyl trifluoromethanesulfonate (1.61 g, 5 mmol), N-(tert-butoxycarbonyl)ethylenediamine (0.80 g, 5 mmol), potassium carbonate (0.69 g, 5 mmol), and toluene (20 mL) were mixed, and the mixture was refluxed by heating for 16 hours. This reaction mixture was added with water, the mixture was extracted with ethyl acetate, and the organic layer was washed with saturated brine, and dried over anhydrous sodium sulfate. The solvent was evaporated under reduced pressure to give yellow crystals, and the crystals were washed twice with hexane (20 mL) to obtain the title compound (1.50 g, yield 91%) as yellow crystals.

¹H NMR (CDCl₃, 400 MHz) δ: 1.46 (9H, s), 3.4-3.5 (2H, m), 3.5-3.7 (2H, m), 4.82 (1H, br s), 7.17 (1H, d, J=9 Hz), 7.34 (1H, t, J=7 Hz), 7.60 (1H, ddd, J=1 Hz, 7 Hz, 8 Hz), 7.68 (1H, d, J=8 Hz), 7.82 (1H, d, J=9 Hz), 8.69 (1H, d, J=9 Hz), 8.76 (1H, br s).

(2) tert-Butyl [2-[(1-amino-2-naphthyl)amino]ethyl]carbamate tert-Butyl [2-[(1-nitro-2-naphthyl)amino]ethyl]carbamate (746 mg, 2.25 mmol) was dissolved in tetrahydrofuran (7.5 mL), and methanol (7.5 mL), the solution was added with platinum oxide (7.5 mg), and the mixture was stirred at room temperature for 7 hours under a hydrogen atmosphere. The catalyst was separated by filtration, then the solvent was evaporated under reduced pressure, and the residue was washed with hexane to give the title compound (646 mg, yield 95%) as brown crystals.

¹H NMR (CDCl₃, 400 MHz) δ: 1.46 (9H, s), 3.1-3.6 (5H, m), 3.80 (2H, br s), 4.88 (1H, br s), 7.11 (1H, d, J=9 Hz), 7.2-7.3 (1H, m), 7.41 (2H, t, J=8 Hz), 7.73 (2H, d, J=8 Hz).

(3) 5-[2-(tert-Butoxycarbonyl)aminoethyl]-1H-naphtho[1,2-b][1,4]diazepine-2,4(3H,5H)-dione tert-Butyl [2-[(1-amino-2-naphthyl)amino]ethyl]carbamate (646 mg, 2.14 mmol) was dissolved in dry tetrahydrofuran (65 mL), the solution was added with malonyl chloride (0.23 mL, 2.3 mmol) with stirring under ice cooling, and then the mixture was stirred under ice cooling for 1 hour and then at room temperature for 2 hours. This reaction mixture was added with saturated aqueous sodium hydrogencarbonate and water, the mixture was extracted with ethyl acetate, and the organic layer was washed with saturated brine, and dried over anhydrous sodium sulfate. The solvent was evaporated under reduced pressure to give brown oil (1.1 g), and the oil was purified by silica gel column chromatography (methanol/chloroform=1/20) to obtain brown oil (0.5 g). The oil was further purified by silica gel column chromatography (hexane/ethyl acetate=1/1) to give the title compound (16 mg, yield 2%) as white powder.

¹H NMR (CDCl₃, 400 MHz) δ: 1.21 (9H, s), 3.3-3.5 (4H, m), 3.9-4.1 (1H, m), 4.3-4.4 (1H, m), 4.96 (1H, br s), 7.51 (1H, d, J=9 Hz), 7.59 (1H, t, J=7 Hz), 7.67 (1H, t, J=7 Hz), 7.79 (1H, d, J=9 Hz), 7.88 (1H, d, J=8 Hz), 8.07 (1H, d, J=7 Hz), 8.79 (1H, br s).

(4) 5-[2-(2-Iodobenzoyl)aminoethyl]-1H-naphtho[1,2-b][1,4]diazepine-2,4(3H,5H)-dione 5-[2-(tert-Butoxycarbonyl)aminoethyl]-1H-naphtho[1,2-b][1,4]diazepine-2,4(3H,5H)-dione (16 mg, 0.043 mmol) was dissolved in dichloromethane (4 mL), the solution was added with trifluoroacetic acid (0.1 mL), and the mixture was stirred at room temperature for 19 hours. This reaction mixture was added with saturated aqueous sodium hydrogencarbonate (8 mL) with stirring under ice cooling, and the mixture was stirred for 5 minutes. Further, the mixture was added with 2-iodobenzoyl chloride (0.22 mmol) dissolved in dichloromethane (4 mL) with stirring under ice cooling. This reaction mixture was stirred under ice cooling for 30 minutes, and then at room temperature for 30 minutes. The dichloromethane layer was washed with saturated brine, and dried over anhydrous sodium sulfate. The solvent was evaporated, and the residue was purified by silica gel column chromatography (methanol/chloroform=1150), and then recrystallized from ethyl acetate/hexane to give the title compound (9 mg, yield 42%) as white crystals. The structure was confirmed by NMR and MS.

MS (FAB) m/z: 500, 999

Example 73

5-[3-[(2-Iodobenzoyl)amino]phenyl]-1H-naphtho[1,2-b][1,4]diazepine-2,4(3H,5H)-dione 2-Iodobenzoic acid (50 mg, 0.2 mmol) was treated with thionyl chloride in the same manner as that of Example 13, and then by using the resultant together with 5-(3-aminophenyl)-1H-naphtho[1,2-b][1,4]diazepine-2,4(3H,5H)-dione (32 mg, 0.1 mmol) obtained in Example 53, (1), the title compound (21 mg, yield 38%) was obtained as pale brown crystals in the same manner as that of Example 1, (4). The structure was confirmed by NMR and MS.

MS (FAB) m/z: 548, 1095

Example 74

6,7-Dimethyl-1-[4-(2-iodobenzoyl)aminophenyl]-1H-1,5-benzodiazepine-2,4(3H,5H)-dione 2-Iodobenzoic acid (34 mg, 0.137 mmol) was made into acid chloride in a conventional manner. By using 1-(4-aminophenyl)-6,7-dimethyl-1H-1,5-benzodiazepine-2,4

(3H,5H)-dione (20 mg, 0.068 mmol) obtained in Example 56, and 2-iodobenzoyl chloride mentioned above, the title compound (31 mg, yield 87%) was obtained in the same manner as that of Example 1.

$^1$H NMR (DMSO-$d_6$, 400 MHz) δ: 2.24 (3H, s), 2.25 (3H, s), 3.03 (1H, d, J=12 Hz), 3.56 (1H, d, J=12 Hz), 6.66 (1H, d, J=9 Hz), 6.98 (1H, d, J=9 Hz), 7.13 (2H, d, J=9 Hz), 7.2-7.3 (1H, m), 7.4-7.6 (2H, m), 7.7-7.8 (2H, m), 7.94 (1H, d, J=9 Hz), 10.07 (1H, s), 10.56 (1H, s).

Example 75

5-[4-[(1-Methylpiperidin-4-yl)carbonylamino]phenyl]-1H-naphtho[1,2-b][1,4]diazepine-2,4(3H,5H)-dione hydrochloride (1) 5-[4-[(1-Methylpiperidin-4-yl)carbonylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 1-methylpiperidine-4-carbonyl chloride, the title compound (yield 100%) was obtained in the same manner as that of Example 1, (4).

(2) 5-[4-[(1-Methylpiperidin-4-yl)carbonylamino]phenyl]-1H-naphtho[1,2-b][1,4]diazepine-2,4(3H,5H)-dione hydrochloride By using 5-[4-[(1-methylpiperidin-4-yl)carbonylamino]phenyl]-1H-naphtho[1,2-b][1,4]diazepine-2,4(3H,5H)-dione, the title compound was obtained in the same manner as that of Example 40, (2).

$^1$H NMR (DMSO-$d_6$, 400 MHz) δ: 1.8-2.1 (4H, m), 2.5-2.7 (1H, m), 2.75 (3H, s), 2.95 (2H, t, J=11 Hz), 3.14 (1H, dd, J=1 Hz, 12 Hz), 3.4-3.5 (2H, m), 3.70 (1H, d, J=12 Hz), 6.97 (1H, d, J=9 Hz), 7.17 (2H, d, J=9 Hz), 7.5-7.8 (5H, m), 7.92 (1H, d, J=8 Hz), 8.24 (1H, d, J=8 Hz), 10.31 (1H, br s), 10.91 (1H, br s).

Example 76

5-[4-[(Benzofuran-2-yl)carbonylamino]phenyl]-1H-naphtho[1,2-b][1,4]diazepine-2,4(3H,5H)-dione Benzofuran-2-carboxylic acid (31 mg, 0.189 mmol) was made into acid chloride in a conventional manner. By using 5-(4-aminophenyl)-1H-naphtho[1,2-b][1,4]diazepine-2,4(3H,5H)-dione (40 mg, 0.126 mmol) obtained in Example 1, and benzofuran-2-carboxylic acid chloride mentioned above, the title compound (59 mg, yield 100%) was obtained in the same manner as that of Example 1.

$^1$H NMR (DMSO-$d_6$, 400 MHz) δ: 3.16 (1H, d, J=12 Hz), 3.72 (1H, d, J=12 Hz), 7.01 (1H, d, J=9 Hz), 7.23 (2H, d, J=9 Hz), 7.36 (1H, t, J=8 Hz), 7.50 (1H, t, J=8 Hz), 7.5-7.8 (4H, m), 7.8-8.0 (5H, m), 8.25 (1H, d, J=8 Hz), 10.69 (1H, s), 10.93 (1H, s).

Example 77

5-[4-[(1-Methyl-1H-indol-3-yl)carbonylamino]phenyl]-1H-naphtho[1,2-b][1,4]diazepine-2,4(3H,5H)-dione 1-Methyl-1H-indole-3-carboxylic acid (55 mg, 0.314 mmol) was made into acid chloride in a conventional manner. By using 5-(4-aminophenyl)-1H-naphtho[1,2-b][1,4]diazepine-2,4(3H,5H)-dione (50 mg, 0.158 mmol) obtained in Example 1, and 1-methyl-1H-indole-3-carboxylic acid chloride mentioned above, the title compound (11 mg, yield 15%) was obtained in the same manner as that of Example 1.

$^1$H NMR (DMSO-$d_6$, 400 MHz) δ: 3.16 (1H, d, J=12 Hz), 3.71 (1H, d, J=12 Hz), 3.89 (3H, s), 7.04 (1H, d, J=9 Hz), 7.1-7.3 (4H, m), 7.5-7.8 (4H, m), 7.8-7.9 (2H, m), 7.93 (1H, d, J=8 Hz), 8.20 (1H, d, J=7 Hz), 8.2-8.3 (2H, m), 9.90 (1H, s), 10.93 (1H, s).

Example 78

5-[4-(2-Propenylbenzoylamino)phenyl]-1H-naphtho[1,2-b][1,4]diazepine-2,4(3H,5H)-dione 5-[4-(2-Iodobenzoylamino)phenyl]-1H-naphtho[1,2-b][1,4]diazepine-2,4(3H,5H)-dione (70 mg, 0.128 mmol), allyltributyltin (98 mg, 0.32 mmol), and tetrakistriphenylphosphine palladium(0) (15 mg, 12.8 mmol) were dissolved in anhydrous toluene (0.6 mL), and the solution was stirred at 110° C. for 16 hours. The reaction mixture was left to cool, and then added with acetonitrile, the mixture was washed with petroleum ether, and the solvent of the acetonitrile layer was evaporated under reduced pressure. The obtained residue was purified by silica gel column chromatography (chloroform/methanol=100/1) to obtain the title compound (40 mg, yield 68%).

$^1$H NMR (DMSO-$d_6$, 400 MHz) δ: 3.15 (1H, d, J=12 Hz), 3.54 (2H, d, J=6 Hz), 3.70 (1H, d, J=12 Hz), 4.9-5.1 (2H, m), 5.8-6.0 (1H, m), 7.02 (1H, d, J=9 Hz), 7.19 (2H, d, J=9 Hz), 7.3-7.4 (2H, m), 7.4-7.5 (2H, m), 7.59 (1H, t, J=8 Hz), 7.6-7.7 (2H, m), 7.79 (2H, d, J=9 Hz), 7.92 (1H, d, J=7 Hz), 8.25 (1H, d, J=9 Hz), 10.47 (1H, s), 10.86 (1H, br s).

Example 79

5-[4-(2-Propylbenzoylamino)phenyl]-1H-naphtho[1,2-b][1,4]diazepine-2,4(3H,5H)-dione 5-[4-(2-Propenylbenzoylamino)phenyl]-1H-naphtho[1,2-b][1,4]diazepine-2,4(3H,5H)-dione (30 mg, 0.065 mmol) was dissolved in a mixture of methanol (0.3 mL) and tetrahydrofuran (0.3 mL), the atmosphere was substituted with argon, then the solution was added with 10% palladiumcarbon (3 mg), and the mixture was stirred for 16 hours under a hydrogen atmosphere. After completion of the reaction, the reaction mixture was filtered through Celite, and the solvent was evaporated under reduced pressure. The obtained residue was purified by silica gel column chromatography (chloroform/methanol=100/1) to give the title compound (14 mg, yield 46%).

$^1$H NMR (DMSO-$d_6$, 400 MHz) δ: 0.86 (3H, t, J=7 Hz), 1.58 (2H, q, J=7 Hz), 2.71 (2H, t, J=7 Hz), 3.15 (1H, d, J=12 Hz), 3.70 (1H, d, J=12 Hz), 7.02 (1H, d, J=9 Hz), 7.20 (2H, d, J=9 Hz), 7.31 (2H, d, J=8 Hz), 7.3-7.5 (2H, m), 7.59 (1H, t, J=8 Hz), 7.6-7.7 (2H, m), 7.79 (2H, d, J=9 Hz), 7.92 (1H, d, J=8 Hz), 8.25 (1H, d, J=8 Hz), 10.46 (1H, s), 10.88 (1H, br s).

Example 80

5-[3-Fluoro-4-(2-iodobenzoylamino)phenyl]-1H-naphtho[1,2-b][1,4]diazepine-2,4(3H,5H)-dione By using 5-(4-amino-3-fluorophenyl)-1H-naphtho[1,2-b][1,4]diazepine-2,4(3H,5H)-dione (30 mg, 0.09 mmol) synthesized in the same manner as that of Example 1, (3), and 2-iodobenzoyl chloride (0.134 mmol), the title compound (19 mg, yield 38%) was obtained in the same manner as that of Example 1, (4).

$^1$H NMR (DMSO-d$_6$, 400 MHz) δ: 3.17 (1H, d, J=12 Hz), 3.71 (1H, d, J=12 Hz), 7.00 (1H, d, J=9 Hz), 7.07 (1H, d, J=9 Hz), 7.2-7.3 (1H, m), 7.37 (1H, d, J=11 Hz), 7.49 (2H, s), 7.6-7.8 (3H, m), 7.8-8.0 (3H, m), 8.27 (1H, d, J=8 Hz), 10.40 (1H, s), 10.90 (1H, s).

Example 81

5-[4-(2-Hydroxy-3-methylbenzoyl)aminophenyl]-1,2,3,4,8,9,10,11-octahydronaphtho[1,2-b][1,4]diazepine-2,4(3H,5H)-dione 5-[4-(2-Methoxy-3-methylbenzoyl)aminophenyl]-1,2,3,4,8,9,10,11-octahydronaphtho[1,2-b][1,4]diazepine-2,4(3H,5H)-dione (24 mg, 0.051 mmol) obtained in Example 61 was treated with a 1 M solution of boron tribromide in dichloromethane in the same manner as that of Example 23 to give the title compound (10 mg, yield 43%) as white crystals.

$^1$H NMR (DMSO-d$_6$, 400 MHz) δ: 1.6-1.9 (4H, m), 2.19 (3H, s), 2.5-2.8 (3H, m), 2.9-3.0 (1H, m), 3.04 (1H, d, J=12 Hz), 3.57 (1H, d, J=12 Hz), 6.66 (1H, d, J=8 Hz), 6.8-6.9 (2H, m), 7.17 (2H, d, J=9 Hz), 7.37 (1H, d, J=7 Hz), 7.74 (2H, d, J=9 Hz), 7.90 (1H, d, J=8 Hz), 9.89 (1H, s), 10.53 (1H, br s), 12.44 (1H, s).

Example 82

5-[4-[(2-Isopropoxybenzoyl)amino]phenyl]-1H-naphtho[1,2-b][1,4]diazepine-2,4(3H,5H)-dione 2-Isopropoxybenzoic acid (36 mg, 0.2 mmol) was treated with thionyl chloride in the same manner as that of Example 13, and then by using the resultant together with 5-(4-aminophenyl)-1H-naphtho[1,2-b][1,4]diazepine-2,4(3H,5H)-dione (32 mg, 0.1 mmol), the title compound (36 mg, yield 75%) was obtained as white crystals in the same manner as that of Example 1, (4).

$^1$H NMR (DMSO-d$_6$, 400 MHz) δ: 1.37 (6H, d, J=6 Hz), 3.16 (1H, d, J=12 Hz), 3.71 (1H, d, J=12 Hz), 4.7-4.8 (1H, m), 7.0-7.1 (2H, m), 7.2-7.3 (3H, m), 7.50 (1H, t, J=7 Hz), 7.60 (1H, t, J=7 Hz), 7.6-7.8 (2H, m), 7.78 (2H, d, J=9 Hz), 7.93 (1H, d, J=8 Hz), 8.26 (1H, d, J=8 Hz), 10.27 (1H, s), 10.91 (1H, s).

Example 83

5-[4-[(3-Methylthiophen-2-yl)carbonylamino]phenyl]-1H-naphtho[1,2-b][1,4]diazepine-2,4(3H,5H)-dione 3-Methyl-2-thiophenecarboxylic acid (28 mg, 0.2 mmol) was treated with thionyl chloride in the same manner as that of Example 13, and then by using the resultant together with 5-(4-aminophenyl)-1H-naphtho[1,2-b][1,4]diazepine-2,4(3H,5H)-dione (32 mg, 0.1 mmol) obtained in Example 1, (3), the title compound (42 mg, yield 95%) was obtained as white crystals in the same manner as that of Example 1, (4).

$^1$H NMR (DMSO-d$_6$, 400 MHz) δ: 2.46 (3H, s), 3.16 (1H, d, J=12 Hz), 3.70 (1H, d, J=12 Hz), 7.0-7.1 (2H, m), 7.20 (2H, d, J=9 Hz), 7.60 (1H, t, J=7 Hz), 7.6-7.8 (3H, m), 7.75 (2H, d, J=9 Hz), 7.92 (1H, d, J=8 Hz), 8.26 (1H, d, J=8 Hz), 10.11 (1H, s), 10.90 (1H, s).

Example 84

5-[4-(2-Phenoxypropionylamino)phenyl]-1H-naphtho[1,2-b][1,4]diazepine-2,4(3H,5H)-dione 2-Phenoxypropionic acid (32 mg, 0.193 mmol) was made into acid chloride in a conventional manner. By using 5-(4-aminophenyl)-1H-naphtho[1,2-b][1,4]diazepine-2,4(3H,5H)-dione (30 mg, 0.095 mmol) obtained in Example 1, (3), and 2-phenoxypropionic acid chloride mentioned above, the title compound (39 mg, yield 88%) was obtained in the same manner as that of Example 1.

$^1$H NMR (DMSO-d$_6$, 400 MHz) δ: 1.56 (3H, d, J=7 Hz), 3.14 (1H, d, J=12 Hz), 3.68 (1H, d, J=12 Hz), 4.87 (1H, q, J=7 Hz), 6.9-7.0 (4H, m), 7.17 (2H, d, J=9 Hz), 7.2-7.4 (2H, m), 7.5-7.7 (5H, m), 7.91 (1H, d, J=8 Hz), 8.25 (1H, d, J=9 Hz), 10.27 (1H, s), 10.88 (1H, br s).

Example 85

5-[4-[2-(4-Chloro-2-methylphenoxy)acetylamino]phenyl]-1H-naphtho[1,2-b][1,4]diazepine-2,4(3H,5H)-dione (4-Chloro-2-methylphenoxy)acetic acid (38 mg, 0.189 mmol) was made into acid chloride in a conventional manner. By using 5-(4-aminophenyl)-1H-naphtho[1,2-b][1,4]diazepine-2,4(3H,5H)-dione (30 mg, 0.095 mmol) obtained in Example 1, and (4-chloro-2-methylphenoxy)acetic acid chloride mentioned above, the title compound (47 mg, yield 99%) was obtained in the same manner as that of Example 1.

$^1$H NMR (DMSO-d$_6$, 400 MHz) δ: 2.24 (3H, s), 3.15 (1H, d, J=12 Hz), 3.69 (1H, d, J=12 Hz), 4.74 (2H, s), 6.89 (1H, d, J=9 Hz), 6.99 (1H, d, J=9 Hz), 7.1-7.3 (4H, m), 7.59 (1H, t, J=8 Hz), 7.5-7.7 (5H, m), 7.91 (1H, d, J=8 Hz), 8.25 (1H, d, J=8 Hz), 10.22 (1H, s), 10.88 (1H, br s).

Example 86

5-[4-(4-Fluoro-2-trifluoromethylbenzoyl)aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 4-fluoro-2-(trifluoromethyl)benzoyl chloride, the title compound (yield 52%) was obtained in the same manner as that of Example 1, (4).

$^1$H NMR (DMSO-d$_6$, 400 MHz) δ: 3.15 (1H, d, J=12 Hz), 3.70 (1H, d, J=12 Hz), 7.01 (1H, d, J=9 Hz), 7.22 (2H, d, J=9 Hz), 7.5-7.9 (8H, m), 7.91 (1H, d, J=8 Hz), 8.24 (1H, d, J=8 Hz), 10.72 (1H, s), 10.88 (1H, br s).

Example 87

5-[4-(4-Fluoro-2-methoxybenzoyl)aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 4-fluoro-2-methoxybenzoyl chloride, the title compound (yield 62%) was obtained in the same manner as that of Example 1, (4).

$^1$H NMR (DMSO-d$_6$, 400 MHz) δ: 3.15 (1H, d, J=12 Hz), 3.69 (1H, d, J=12 Hz), 3.90 (3H, s), 6.89 (1H, dt, J=2 Hz, 9 Hz), 7.01 (1H, d, J=9 Hz), 7.09 (1H, dd, J=2 Hz, 9 Hz), 7.19

(2H, d, J=8 Hz), 7.5-7.7 (3H, m), 7.77 (2H, d, J=9 Hz), 7.91 (1H, d, J=8 Hz), 8.24 (1H, d, J=9 Hz), 10.18 (1H, s), 10.88 (1H, br s).

Example 88

5-[4-(4-Fluoro-2-hydrooxybenzoyl)aminophenyl]-1H-naphtho[1,2-b][1,4]diazepine-2,4(3H,5H)-dione By using 5-[4-(4-fluoro-2-methoxybenzoyl)aminophenyl]-1H-naphtho[1,2-b][1,4]diazepine-2,4(3H,5H)-dione obtained in Example 87, the title compound (yield 49%) was obtained in the same manner as that of Example 18.

$^1$H NMR (DMSO-$d_6$, 400 MHz) δ: 3.15 (1H, d, J=12 Hz), 3.71 (1H, d, J=12 Hz), 6.7-6.9 (2H, m), 7.01 (1H, d, J=9 Hz), 7.23 (2H, d, J=9 Hz), 7.59 (1H, t, J=7 Hz), 7.65 (1H, d, J=7 Hz), 7.69 (1H, d, J=9 Hz), 7.76 (1H, d, J=9 Hz), 7.91 (1H, d, J=8 Hz), 8.01 (1H, t, J=8 Hz), 8.25 (1H, d, J=9 Hz), 10.50 (1H, br s), 10.89 (1H, s).

Example 89

5-[3-[(2-Iodophenylacetyl)amino]phenyl]-1H-naphtho[1,2-b][1,4]diazepine-2,4(3H,5H)-dione 2-Iodophenylacetic acid (39 mg, 0.15 mmol) was treated with thionyl chloride in the same manner as that of Example 13, and then by using the resultant together with 5-(3-aminophenyl)-1H-naphtho[1,2-b][1,4]diazepine-2,4(3H,5H)-dione (32 mg, 0.1 mmol) obtained in Example 53, (1), the title compound (13 mg, yield 23%) was obtained as pale brown powder in the same manner as that of Example 1, (4).

$^1$H NMR (DMSO-$d_6$, 400 MHz) δ: 3.14 (1H, d, J=12 Hz), 3.72 (1H, d, J=12 Hz), 3.79 (2H, s), 7.0-7.1 (3H, m), 7.3-7.5 (3H, m), 7.47 (1H, s), 7.5-7.7 (4H, m), 7.82 (1H, d, J=8 Hz), 7.92 (1H, d, J=9 Hz), 8.24 (1H, d, J=9 Hz), 10.33 (1H, s), 10.90 (1H, s).

Example 90

5-[4-(2-Methyl-2-phenoxypropionylamino)phenyl]-1H-naphtho[1,2-b][1,4]diazepine-2,4(3H,5H)-dione 2-Methyl-2-phenoxypropionic acid (34 mg, 0.189 mmol) was made into acid chloride in a conventional manner. By using 5-(4-aminophenyl)-1H-naphtho[1,2-b][1,4]diazepine-2,4(3H,5H)-dione (30 mg, 0.095 mmol) obtained in Example 1, (3), and 2-methyl-2-phenoxypropionic acid chloride mentioned above, the title compound (46 mg, yield 100%) was obtained in the same manner as that of Example 1.

$^1$H NMR (DMSO-$d_6$, 400 MHz) δ: 1.54 (6H, s), 3.15 (1H, d, J=12 Hz), 3.69 (1H, d, J=12 Hz), 6.93 (2H, d, J=9 Hz), 6.9-7.1 (2H, m), 7.16 (2H, d, J=9 Hz), 7.2-7.4 (2H, m), 7.59 (1H, t, J=8 Hz), 7.5-7.7 (3H, m), 7.76 (2H, d, J=9 Hz), 7.91 (1H, d, J=8 Hz), 8.25 (1H, d, J=8 Hz), 10.16 (1H, s), 10.88 (1H, br s)

Example 91

5-[4-(2-tert-Butylbenzoylamino)phenyl]1,3-dihydronaphtho[1,2-e]-1,4-diazepin-2-one 2-tert-Butylbenzoic acid (24 mg, 0.135 mmol) was made into acid chloride in a conventional manner. By using 5-(4-aminophenyl)-1,3-dihydronaphtho[1,2-e]-1,4-diazepin-2-one (20 mg, 0.066 mmol) obtained in Example 64, and 2-tert-butylbenzoyl chloride (24 mg, 0.135 mmol) mentioned above, the title compound (30 mg, yield 99%) was obtained in the same manner as that of Example 1.

$^1$H NMR (DMSO-$d_6$, 400 MHz) δ: 1.39 (9H, s), 3.78 (1H, d, J=10 Hz), 4.56 (1H, d, J=10 Hz), 7.2-7.4 (3H, m), 7.3-7.5 (1H, m), 7.54 (3H, d, J=9 Hz), 7.6-7.8 (5H, m), 8.0-8.1 (1H, m), 8.3-8.4 (1H, m), 10.61 (1H, s), 10.81 (1H, s).

Example 92

5-[4-[(3-Dimethylaminobenzoyl)amino]phenyl]-1H-naphtho[1,2-b][1,4]diazepine-2,4(3H,5H)-dione 3-Dimethylaminobenzoic acid (50 mg, 0.3 mmol) was treated oxalyl chloride with in the same manner as that of Example 40, and then by using the resultant together with 5-(4-aminophenyl)-1H-naphtho[1,2-b][1,4]diazepine-2,4(3H,5H)-dione (32 mg, 0.1 mmol) obtained in Example 1, (3), the title compound (17 mg, yield 37%) was obtained as pale brown crystals in the same manner as that of Example 1, (4).

$^1$H NMR (DMSO-$d_6$, 400 MHz) δ: 2.97 (6H, s), 3.16 (1H, d, J=12 Hz), 3.70 (1H, d, J=12 Hz), 6.93 (1H, d, J=9 Hz), 7.02 (1H, d, J=9 Hz), 7.1-7.3 (4H, m), 7.32 (1H, t, J=8 Hz), 7.60 (1H, t, J=7 Hz), 7.66 (1H, d, J=7 Hz), 7.70 (1H, d, J=9 Hz), 7.84 (2H, d, J=9 Hz), 7.92 (1H, d, J=8 Hz), 8.26 (1H, d, J=8 Hz), 10.25 (1H, s), 10.89 (1H, s).

Example 93

5-[4-(4-Iodo-2-methoxybenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 4-iodo-2-methoxybenzoyl chloride, the title compound (yield 93%) was obtained in the same manner as that of Example 1, (4).

$^1$H NMR (DMSO-$d_6$, 400 MHz) δ: 3.15 (1H, d, J=12 Hz), 3.69 (1H, d, J=12 Hz), 3.89 (3H, s), 7.00 (1H, d, J=9 Hz), 7.19 (2H, d, J=9 Hz), 7.35 (1H, d, J=8 Hz), 7.44 (1H, d, J=8 Hz), 7.51 (1H, s), 7.58 (1H, t, J=7 Hz), 7.6-7.7 (2H, m), 7.76 (2H, d, J=9 Hz), 7.91 (1H, d, J=8 Hz), 8.24 (1H, d, J=8 Hz), 10.22 (1H, br s), 10.88 (1H, br s).

Example 94

5-[4-(6-Fluoro-2-methoxybenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 2-fluoro-6-methoxybenzoyl chloride, the title compound (yield 78%) was obtained in the same manner as that of Example 1, (4).

$^1$H NMR (DMSO-$d_6$, 400 MHz) δ: 3.15 (1H, d, J=12 Hz), 3.70 (1H, d, J=12 Hz), 3.82 (3H, s), 6.90 (1H, t, J=8 Hz), 6.98 (1H, d, J=8 Hz), 7.01 (1H, d, J=9 Hz), 7.20 (2H, d, J=9 Hz), 7.4-7.5 (1H, m), 7.59 (1H, t, J=7 Hz), 7.6-7.7 (2H, m), 7.75 (2H, d, J=9 Hz), 7.92 (1H, d, J=8 Hz), 8.24 (1H, J=8H), 10.64 (1H, s), 10.88 (1H, br s).

Example 95

5-[4-(2-Hydroxy-4-iodobenzoylamino)phenyl]-1H-naphtho[1,2-b][1,4]diazepine-2,4(3H,5H)-dione By using 5-[4-(4-iodo-2-methoxybenzoylamino)phenyl]-1H-naphtho[1,2-b][1,4]diazepine-2,4(3H,5H)-dione obtained in Example 93, the title compound (yield 26%) was obtained in the same manner as that of Example 18.

$^1$H NMR (DMSO-d$_6$, 400 MHz) δ: 3.15 (1H, d, J=12 Hz), 3.70 (1H, d, J=12 Hz), 7.00 (1H, d, J=9 Hz), 7.22 (2H, d, J=9 Hz), 7.33 (1H, dd, J=2 Hz, 8 Hz), 7.37 (1H, d, J=2 Hz), 7.5-7.7 (4H, m), 7.76 (2H, d, J=9 Hz), 7.91 (1H, d, J=8 Hz), 8.25 (1H, d, J=8 Hz), 10.43 (1H, s), 10.89 (1H, s), 11.82 (1H, br s).

Example 96

5-[4-(6-Fluoro-2-hydroxyamino)phenyl]-1H-naphtho[1,2-b][1,4]diazepine-2,4(3H,5H)-dione By using 5-[4-(6-fluoro-2-methoxybenzoylamino)phenyl]-1H-naphtho[1,2-b][1,4]diazepine-2,4(3H,5H)-dione obtained in Example 94, the title compound (yield 98%) was obtained in the same manner as that of Example 18.

$^1$H NMR (DMSO-d$_6$, 400 MHz) δ: 3.15 (1H, d, J=12 Hz), 3.70 (1H, d, J=12 Hz), 6.70 (1H, t, J=9 Hz), 6.75 (1H, d, J=8 Hz), 7.01 (1H, d, J=9 Hz), 7.19 (2H, d, J=9 Hz), 7.2-7.3 (1H, m), 7.58 (1H, t, J=7 Hz), 7.6-7.7 (2H, m), 7.76 (2H, d, J=9 Hz), 7.91 (1H, d, J=8 Hz), 8.25 (1H, d, J=9 Hz), 10.34 (1H, br s), 10.57 (1H, s), 10.88 (1H, s).

Example 97

5-[4-(2-Fluorobenzoyl)aminophenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (32 mg, 0.101 mmol) obtained in Example 1, (3), and 2-fluorobenzoyl chloride (32 mg, 0.202 mmol), the title compound (30 mg, yield 67%) was obtained as white crystals in the same manner as that of Example 1, (4).

$^1$H NMR (DMSO-d$_6$, 400 MHz) δ: 3.15 (1H, d, J=12 Hz), 3.72 (1H, d, J=12 Hz), 7.03 (1H, d, J=9 Hz), 7.2-7.4 (4H, m), 7.5-7.7 (5H, m), 7.79 (2H, d, J=9 Hz), 7.93 (1H, d, J=8 Hz), 8.25 (1H, d, J=8 Hz), 10.59 (1H, s), 10.93 (1H, s).

Example 98

5-[4-[(2-Dimethylaminobenzoyl)amino]phenyl]-1H-naphtho[1,2-b][1,4]diazepine-2,4(3H,5H)-dione 2-Dimethylaminobenzoic acid (50 mg, 0.3 mmol) was treated with oxalyl chloride in the same manner as that of Example 40, and then by using the resultant together with 5-(4-aminophenyl)-1H-naphtho[1,2-b][1,4]diazepine-2,4(3H,5H)-dione (32 mg, 0.1 mmol) obtained in Example 1, (3), the title compound (38 mg, yield 82%) was obtained as pale yellow crystals in the same manner as that of Example 1, (4).

$^1$H NMR (DMSO-d$_6$, 400 MHz) δ: 2.79 (6H, s), 3.16 (1H, d, J=12 Hz), 3.71 (1H, d, J=12 Hz), 7.04 (1H, d, J=9 Hz), 7.09 (1H, t, J=8 Hz), 7.2-7.3 (3H, m), 7.46 (1H, dt, J=2 Hz, 8 Hz), 7.60 (1H, t, J=7 Hz), 7.6-7.8 (3H, m), 7.80 (2H, d, J=8 Hz), 7.93 (1H, d, J=8 Hz), 8.26 (1H, d, J=9 Hz), 10.89 (1H, s), 11.37 (1H, s).

Example 99

5-[4-(2-Methoxy-6-methylbenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 2-methoxy-6-methylbenzoyl chloride, the title compound (yield 61%) was obtained in the same manner as that of Example 1, (4).

$^1$H NMR (DMSO-d$_6$, 400 MHz) δ: 2.23 (3H, s), 3.15 (1H, d, J=12 Hz), 3.70 (1H, d, J=12 Hz), 3.76 (3H, s), 6.87 (1H, d, J=8 Hz), 6.94 (1H, d, J=9 Hz), 7.03 (1H, d, J=9 Hz), 7.18 (2H, d, J=8 Hz), 7.29 (1H, t, J=8 Hz), 7.5-7.7 (3H, m), 7.78 (2H, d, J=8 Hz), 7.92 (1H, d, J=8 Hz), 8.25 (1H, d, J=9 Hz), 10.43 (1H, br s), 10.87 (1H, br s).

Example 100

5-[4-(2-Hydroxy-6-methylbenzoylamino)phenyl]-1H-naphtho[1,2-b][1,4]diazepine-2,4(3H,5H)-dione By using 5-[4-(2-methoxy-6-methylbenzoylamino)phenyl]-1H-naphtho[1,2-b][1,4]diazepine-2,4(3H,5H)-dione, the title compound (yield 67%) was obtained in the same manner as that of Example 18.

$^1$H NMR (DMSO-d$_6$, 400 MHz) δ: 2.22 (3H, s), 3.15 (1H, d, J=12 Hz), 3.69 (1H, d, J=12 Hz), 6.68 (1H, d, J=7 Hz), 6.73 (1H, d, J=8 Hz), 7.02 (1H, d, J=9 Hz), 7.10 (1H, t, J=8 Hz), 7.17 (2H, d, J=9 Hz), 7.58 (1H, t, J=8 Hz), 7.66 (1H, t, J=7 Hz), 7.69 (1H, d, J=9 Hz), 7.79 (2H, d, J=9H), 7.91 (1H, d, J=8 Hz), 3.25 (1H, d, J=9 Hz), 9.65 (1H, br s), 10.37 (1H, br s), 10.87 (1H, br s).

Example 101

5-[4-[3-(2-Methylphenyl)propionylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 3-(2-methylphenyl)propionic acid chloride (0.114 mmol), the title compound (28 mg, yield 64%) was obtained as white crystals in the same manner as that of Example 1, (4).

$^1$H NMR (DMSO-d$_6$, 400 MHz) δ: 2.29 (3H, s), 2.58 (2H, t, J=8 Hz), 2.88 (2H, t, J=8 Hz), 3.12 (1H, d, J=12 Hz), 3.67 (1H, d, J=12 Hz), 6.97 (1H, d, J=9 Hz), 7.0-7.2 (6H, m), 7.5-7.7 (5H, m), 7.90 (1H, d, J=8 Hz), 8.23 (1H, d, J=8 Hz), 10.07 (1H, br s), 10.89 (1H, br s).

Example 102

5-(4-Phenylcarbamoylphenyl)-1H-naphtho[1,2-b][1,4]diazepine-2,4(3H,5H)-dione (1) Ethyl 4-(1-aminonaphthalen-2-ylamino)benzoate By using ethyl 4-(1-nitronaphthalen-2-ylamino)benzoate, the title compound was obtained in the same manner as that of Example 1, (2).

$^1$H NMR (CDCl$_3$, 400 MHz) δ: 1.35 (3H, t, J=7 Hz), 4.32 (2H, q, J=7 Hz), 4.36 (2H, br s), 5.62 (1H, br s), 6.66 (2H, d, J=9 Hz), 7.2-7.4 (2H, m), 7.4-7.6 (2H, m), 7.8-7.9 (4H, m).

(2) Ethyl 4-[1-(3-ethoxy-3-oxopropanamido)naphthalen-2-ylamino]benzoate

By using ethyl 4-(1-aminonaphthalen-2-ylamino)benzoate, the title compound was obtained in the same manner as that of Example 1, (3).

$^1$H NMR (CDCl$_3$, 400 MHz) δ: 1.36 (3H, t, J=7 Hz), 1.37 (3H, t, J=7 Hz), 3.66 (2H, s), 4.33 (2H, q, J=7 Hz), 4.33 (2H, q, J=7 Hz), 6.9-7.0 (2H, m), 7.06 (1H, s), 7.45 (1H, t, J=7 Hz), 7.56 (1H, dt, J=1 Hz, 8 Hz), 7.63 (1H, d, J=9 Hz), 7.78 (1H, d, J=9 Hz), 7.84 (1H, d, J=8 Hz), 7.91 (2H, d, J=8 Hz), 7.96 (1H, d, J=8 Hz), 9.62 (1H, s).

(3) Ethyl 4-[2,4-dioxo-3,4-dihydro-1H-naphtho[2,1-b][1,4]diazepin-5(2H)-yl]benzoate By using ethyl 4-[1-(3-ethoxy-3-oxopropanamido)naphthalen-2-ylamino]benzoate, the title compound was obtained in the same manner as that of Example 1, (3).
$^1$H NMR (CDCl$_3$, 400 MHz) δ: 1.39 (3H, t, J=7 Hz), 3.63 (2H, s), 4.39 (2H, q, J=7 Hz), 6.96 (1H, d, J=9 Hz), 7.3-7.4 (2H, m), 7.5-7.8 (3H, m), 7.87 (1H, d, J=8 Hz), 8.0-8.2 (3H, m), 8.68 (1H, s).

(4) 4-[2,4-Dioxo-3,4-dihydro-1H-naphtho[2,1-b][1,4]diazepin-5(2H)-yl]benzoic acid Ethyl 4-[2,4-Dioxo-3,4-dihydro-1H-naphtho[2,1-b][1,4]diazepin-5(2H)-yl]benzoate (1.19 g, 3.18 mmol) obtained in Example 102, (3), and 8 N aqueous sodium hydroxide (1.00 mL, 8.00 mmol) were stirred at room temperature in ethanol (10 mL) and water (5 mL). After the disappearance of the starting materials was confirmed, a post-treatment was performed in a conventional manner to obtain the title compound (905 mg, yield 82%).
$^1$H NMR (DMSO-d$_6$, 400 MHz) δ: 3.17 (1H, d, J=12 Hz), 3.75 (1H, d, J=12 Hz), 6.95 (1H, d, J=9 Hz), 7.35 (2H, d, J=9 Hz), 7.5-7.8 (3H, m), 7.93 (1H, d, J=8 Hz), 7.99 (2H, d, J=9 Hz), 8.27 (1H, d, J=8 Hz), 10.93 (1H, s).

(5) 5-(4-Phenylcarbamoylphenyl)-1H-naphtho[1,2-b][1,4]diazepine-2,4(3H,5H)-dione 4-[2,4-Dioxo-3,4-dihydro-1H-naphtho[2,1-b][1,4]diazepin-5(2H)-yl]benzoic acid (50 mg, 0.144 mmol) obtained in Example 102, (4), WSC.HCl (39 mg, 0.202 mmol), HOBt (31 mg, 0.202 mmol), N-methylmorpholine (47 μL, 0.432 mmol), and aniline (14 L, 0.158 mmol) were stirred at room temperature for 16 hours in anhydrous DMF (1.5 mL). The reaction mixture was post-treated in a conventional manner to give the title compound (30 mg, yield 49%).
$^1$H NMR (DMSO-d$_6$, 400 MHz) δ: 3.18 (1H, d, J=12 Hz), 3.75 (1H, d, J=12 Hz), 6.98 (1H, d, J=9 Hz), 7.10 (1H, t, J=7 Hz), 7.3-7.4 (4H, m), 7.5-7.8 (5H, m), 7.93 (1H, d, J=8 Hz), 8.01 (2H, d, J=8 Hz), 8.27 (1H, d, J=8 Hz), 10.30 (1H, br s), 10.93 (1H, br s).

Example 103

5-(4-Benzylcarbamoylphenyl)-1H-naphtho[1,2-b][1,4]diazepine-2,4(3H,5H)-dione By using 4-[2,4-dioxo-3,4-dihydro-1H-naphtho[2,1-b][1,4]diazepin-5(2H)-yl]benzoic acid obtained in Example 102, (4), and benzylamine, the title compound (yield 56%) was obtained in the same manner as that of Example 102, (5).
$^1$H NMR (DMSO-d$_6$, 400 MHz) δ: 3.16 (1H, d, J=12 Hz), 3.74 (1H, d, J=12 Hz), 4.48 (2H, d, J=6 Hz), 6.95 (1H, d, J=9 Hz), 7.2-7.4 (7H, m), 7.5-7.7 (3H, m), 7.9-8.0 (31H, m), 8.27 (1H, d, J=8 Hz), 9.09 (1H, t, J=6 Hz), 10.91 (1H, br s).

Example 104

5-[4-[3-(2-Methylphenyl)propenoylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 2-methylcinnamic acid chloride (0.114 mmol), the title compound (18 mg, yield 41%) was obtained as white crystals in the same manner as that of Example 1, (4).
$^1$H NMR (DMSO-d$_6$, 400 MHz) δ: 2.42 (3H, s), 3.17 (1H, d, J=12 Hz), 3.71 (1H, d, J=12 Hz), 6.80 (1H, d, J=16 Hz), 7.02 (1H, d, J=9 Hz), 7.20 (2H, d, J=8 Hz), 7.2-7.3 (3H, m), 7.6-7.7 (4H, m), 7.7-7.9 (3H, m), 7.92 (1H, d, J=8 Hz), 8.26 (1H, d, J=8 Hz), 10.50 (1H, br s), 10.93 (1H, br s).

Example 105

5 [4-[3-(2-Chlorophenyl)propionylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3) (35 mg, 0.110 mmol), and 3-(2-chlorophenyl)propionic acid chloride (0.132 mmol), the title compound (30 mg, yield 56%) was obtained as white crystals in the same manner as that of Example 1, (4).
$^1$H NMR (DMSO-d$_6$, 400 MHz) δ: 2.67 (2H, t, J=8 Hz), 3.03 (2H, t, J=8 Hz), 3.14 (1H, d, J=12 Hz), 3.70 (1H, d, J=12 Hz), 6.98 (1H, d, J=9 Hz), 7.16 (2H, d, J=9 Hz), 7.2-7.3 (2H, m), 7.3-7.4 (1H, m), 7.4-7.5 (1H, m), 7.5-7.7 (5H, m), 7.92 (1H, d, J=8 Hz), 8.22 (1H, d, J=8 Hz), 10.16 (1H, br s), 10.92 (1H, br s).

Example 106

5-[4-(2-Iodobenzoyl)aminophenyl]-1,2,3,4,8,9,10,11-octahydronaphtho[1,2-b][1,4]diazepine-2,4(3H,5H)-dione 2-Iodobenzoic acid (74 mg, 0.3 mmol) was treated with thionyl chloride in the same manner as that of Example 13, and then by using the resultant together with 5-(4-aminophenyl)-1,2,3,4,8,9,10,11-octahydronaphtho[1,2-b][1,4]diazepine-2,4(3H,5H)-dione (64 mg, 0.2 mmol) obtained in Example 55, (6), the title compound (45 mg, yield 41%) was obtained as off-white crystals in the same manner as that of Example 1, (4).
$^1$H NMR (DMSO-d$_6$, 400 MHz) δ: 1.6-1.9 (4H, m), 2.5-2.8 (3H, m), 2.8-3.0 (1H, m), 3.04 (1H, d, J=12 Hz), 3.56 (1H, d, J=12 Hz), 6.66 (1H, d, J=8H), 6.88 (1H, d, J=8 Hz), 7.14 (2H, d, J=9 Hz), 7.23 (1H, ddd, J=2 Hz, 7 Hz, 8 Hz), 7.4-7.6 (2H, m), 7.54 (2H, d, J=9 Hz), 7.93 (1H, d, J=8 Hz), 9.86 (1H, s), 10.52 (1H, s).

Example 107

5-[4-[(1-Methyl-1H-pyrrol-2-ylacetyl)amino]phenyl]-1,2,3,4,8,9,10,11-octahydronaphtho[1,2-b][1,4]diazepine-2,4(3H,5H)-dione 1-Methylpyrrole-2-acetic acid (14 mg, 0.1 mmol), 5-(4-aminophenyl)-1,2,3,4,8,9,10,11-octahydronaphtho[1,2-b][1,4]diazepine-2,4(3H,5H)-dione (16 mg, 0.05 mmol) obtained in Example 55, (6), dimethylformamide (1 mL), 1-hydroxybenzotriazole monohydrate (14 mg, 0.1 mmol), and 1-ethyl-3-(3-dimethylaminopropyl)carbodiimide hydrochloride (19 mg, 0.1 mmol) were mixed, and the mixture was stirred at room temperature for 24 hours. This reaction mixture was added with water, and the mixture was extracted with ethyl acetate. The ethyl acetate layer was washed with saturated aqueous sodium hydrogencarbonate, then washed with saturated brine, and dried over anhydrous sodium sulfate. The solvent was evaporated under reduced pressure, and the residue was purified by silica gel column chromatography (methanol/chloroform=1/50), and then washed with ethyl acetate to give the title compound (6 mg, yield 28%) as slightly brown crystals.

$^1$H NMR (DMSO-d$_6$, 400 MHz) δ: 1.6-1.9 (4H, m), 2.5-2.8 (3H, m), 2.8-3.0 (1H, m), 3.02 (1H, d, J=12 Hz), 3.54 (1H, d, J=12 Hz), 3.56 (3H, s), 3.64 (2H, s), 5.8-6.0 (2H, m), 6.6-6.7 (2H, m), 6.86 (1H, d, J=8 Hz), 7.08 (2H, d, J=9 Hz), 7.61 (2H, d, J=9 Hz), 9.85 (1H, s), 10.16 (1H, s).

Example 108

5-[4-(2-Chlorobenzyl)carbamoylphenyl]-1H-naphtho[1,2-b][1,4]diazepine-2,4(3H,5H)-dione By using 4-[2,4-dioxo-3,4-dihydro-1H-naphtho[2,1-b][1,4]diazepin-5(2H)-yl]benzoic acid obtained in Example 102, (4), and 2-chlorobenzylamine, the title compound (yield 15%) was obtained in the same manner as that of Example 102, (5).

$^1$H NMR (DMSO-d$_6$, 400 MHz) δ: 3.17 (1H, d, J=12 Hz), 3.74 (1H, d, J=12 Hz), 4.54 (2H, d, J=6 Hz), 6.96 (1H, d, J=9 Hz), 7.2-7.7 (9H, m), 7.92 (1H, d, J=7 Hz), 7.97 (2H, d, J=9 Hz), 8.27 (1H, d, J=8 Hz), 9.09 (1H, t, J=6 Hz), 10.91 (1H, br s).

Example 109

5-[4-[3-(2-Chlorophenyl)propenoylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3) (40 mg, 0.126 mmol), and 2-chlorocinnamic acid chloride (0.151 mmol), the title compound (30 mg, yield 50%) was obtained as white crystals in the same manner as that of Example 1, (4).

$^1$NMR (DMSO-d$_6$, 400 MHz) δ: 3.17 (1H, d, J=12 Hz), 3.71 (11H, d, J=12 Hz), 6.9-7.1 (2H, m), 7.21 (2H, d, J=9 Hz), 7.4-7.5 (2H, m), 7.5-7.6 (2H, m), 7.6-7.7 (2H, m), 7.80 (3H, t, J=9 Hz), 7.8-7.9 (2H, m), 8.26 (1H, d, J=8 Hz), 10.72 (1H, br s), 10.94 (1H, br s).

Example 110

5-[4-(2-Chlorophenyl)carbamoylphenyl]-1H-naphtho[1,2-b][1,4]diazepine-2,4(3H,5H)-dione By using 4-[2,4-dioxo-3,4-dihydro-1H-naphtho[2,1-b][1,4]diazepin-5(2H)-yl]benzoic acid obtained in Example 102, (4), and 2-chloroaniline, the title compound (yield 15%) was obtained in the same manner as that of Example 102, (5).

$^1$H NMR (DMSO-d$_6$, 400 MHz) δ: 3.18 (1H, d, J=12 Hz), 3.76 (1H, d, J=12 Hz), 6.99 (1H, d, J=9 Hz), 7.30 (1H, t, J=8 Hz), 7.3-7.8 (8H, m), 7.93 (1H, d, J=8 Hz), 8.05 (2H, d, J=8 Hz), 8.28 (1H, d, J=8 Hz), 10.13 (1H, br s), 10.93 (1H, br s).

Example 111

5-[4-(6-Bromo-2,3-methylenedioxybenzolamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 5-bromo-1,3-benzodioxol-4-carbonyl chloride, the title compound (yield 64%) was obtained in the same manner as that of Example 1, (4).

$^1$H NMR (DMSO-d$_6$, 400 MHz) δ: 3.15 (1H, d, J=12 Hz), 3.70 (1H, d, J=12 Hz), 6.13 (21, s), 6.98 (1H, d, J=8 Hz), 7.01 (1H, d, J=9 Hz), 7.16 (1H, d, J=8 Hz), 7.22 (2H, d, J=9 Hz), 7.5-7.8 (5H, m), 7.92 (1H, d, J=8 Hz), 8.25 (1H, d, J=9 Hz), 10.77 (1H, br s), 10.87 (1H, br s).

Example 112

5-[4-(6-Bromo-2-methoxybenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 2-bromo-6-methoxybenzoyl chloride, the title compound (yield 76%) was obtained in the same manner as that of Example 1, (4).

$^1$H NMR (DMSO-d$_6$, 400 MHz) δ: 3.15 (1H, d, J=12 Hz), 3.70 (1H, d, J=12 Hz), 3.81 (3H, s), 7.03 (1H, d, J=9 Hz), 7.15 (1H, d, J=8 Hz), 7.19 (2H, d, J=8 Hz), 7.25 (1H, d, J=8 Hz), 7.36 (1H, t, J=9 Hz), 7.59 (1H, t, J=7 Hz), 7.6-7.8 (4H, m), 7.92 (1H, d, J=8 Hz), 8.25 (1H, d, J=9 Hz), 10.60 (1H, br s), 10.88 (1H, br s).

Example 113

5-[4-[(2-tert-Butylbenzoyl)amino]phenyl]-1,2,3,4,8,9,10,11-octahydronaphtho[1,2-b][1,4]diazepine-2,4(3H,5H)-dione 2-tert-Butyl benzoate (43 mg, 0.24 mmol) was treated with thionyl chloride in the same manner as that of Example 13, and then by using the resultant together with 5-(4-aminophenyl)-1,2,3,4,8,9,10,11-octahydronaphtho[1,2-b][1,4]diazepine-2,4(3H,5H)-dione (64 mg, 0.2 mmol) obtained in Example 55, (6), the title compound (81 mg, yield 85%) was obtained as slightly brown crystals in the same manner as that of Example 1, (4).

$^1$H NMR (DMSO-d$_6$, 400 MHz) δ: 1.39 (9H, s), 1.6-1.9 (4H, m), 2.5-2.8 (3H, m), 2.8-3.0 (1H, m), 3.04 (1H, d, J=12 Hz), 3.55 (1H, d, J=12 Hz), 6.66 (1H, d, J=8 Hz), 6.88 (1H, d, J=9 Hz), 7.12 (2H, d, J=9 Hz), 7.2-7.4 (2H, m), 7.40 (1H, dt, J=2 Hz, 8 Hz), 7.53 (1H, d, J=8 Hz), 7.74 (2H, d, J=9 Hz), 9.85 (1H, s), 10.50 (1H, s).

Example 114

5-[2-(2-Iodobenzoyl)aminopyridin-5-yl]-1H-naphtho[1,2-b][1,4]diazepine-2,4(3H,5H)-dione (1) tert-Butyl 5-(2,4-dioxo-3,4-dihydro-1H-naphtho[2,1-b][1,4]diazepin-5(2H)-yl)pyridin-2-ylcarbamate By using 2-amino-5-nitropyridine as the starting material, the title compound was obtained in the same manner as that of Example 42, (1).

$^1$H NMR (CDCl$_3$, 400 MHz) δ: 1.49 (9H, s), 3.62 (2H, s), 6.99 (1H, d, J=9 Hz), 7.5-7.8 (4H, m), 7.8-8.0 (1H, m), 8.03 (1H, d, J=9 Hz), 8.1-8.2 (2H, m), 9.06 (1H, br s).

(2) 5-[2-(2-Iodobenzoyl)aminopyridin-5-yl]-1H-naphtho[1,2-b][1,4]diazepine-2,4(3H,5H)-dione By using tert-butyl 5-(2,4-dioxo-3,4-dihydro-1H-naphtho[2,1-b][1,4]diazepin-5(2H)-yl)pyridin-2-ylcarbamate obtained above, 5-(6-aminopyridin-3-yl)-1H-naphtho[2,1-b][1,4]diazepine-2,4(3H,5H)-dione (15 mg, 0.047 mmol) obtained in the same manner as that of Example 42, (2), and 2-iodobenzoyl chloride (0.07 mmol), the title compound (3 mg, yield 38%) was obtained in the same manner as that of Example 1, (4).

$^1$H NMR (CDCl$_3$, 400 MHz) δ: 3.63 (2H, s), 7.01 (1H, d, J=9 Hz), 7.13 (1H, t, J=8 Hz), 7.42 (1H, t, J=8 Hz), 7.52 (1H, d, J=8 Hz), 7.6-7.7 (2H, m), 7.7-7.8 (2H, m), 7.8-8.0 (2H, m), 8.10 (2H, d, J=8 Hz), 8.46 (1H, d, J=9 Hz), 8.5-8.7 (2H, m).

Example 115

5-[4-(6-Bromo-2-hydroxybenzoylamino)phenyl]-1H-naphtho[1,2-b][1,4]diazepine-2,4(3H,5H)-dione By using 5-[4-(6-bromo-2-methoxybenzoylamino)phenyl]-1H-naphtho[1,2-b][1,4]diazepine-2,4(3H,5H)-dione obtained in Example 112, the title compound (yield 32%) was obtained in the same manner as that of Example 18.

$^1$H NMR (DMSO-d$_6$, 400 MHz) δ: 3.15 (1H, d, J=12 Hz), 3.69 (1H, d, J=12 Hz), 6.91 (1H, d, J=8 Hz), 7.1-7.2 (2H, m), 7.15 (1H, d, J=8 Hz), 7.19 (2H, d, J=9 Hz), 7.58 (1H, t, J=8 Hz), 7.6-7.7 (2H, m), 7.91 (1H, d, J=8 Hz), 7.76 (2H, d, J=9 Hz), 8.25 (1H, d, J=9 Hz), 10.24 (1H, br s), 10.60 (1H, br s), 10.86 (1H, br s).

Example 116

5-[4-(6-Chloro-2-methoxybenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 2-chloro-6-methoxybenzoyl chloride, the title compound (yield 76%) was obtained in the same manner as that of Example 1, (4).

$^1$H NMR (DMSO-d$_6$, 400 MHz) δ: 3.15 (1H, d, J=12 Hz), 3.70 (1H, d, J=12 Hz), 3.81 (3H, s), 7.03 (1H, d, J=9 Hz), 7.11 (1H, d, J=8 Hz), 7.12 (1H, d, J=8 Hz), 7.20 (2H, d, J=9 Hz), 7.43 (1H, t, J=8 Hz), 7.59 (1H, t, J=7 Hz), 7.66 (1H, t, J=8 Hz), 7.69 (1H, d, J=9 Hz), 7.69 (1H, d, J=9 Hz), 7.75 (2H, d, J=9 Hz), 7.92 (1H, d, J=8 Hz), 8.25 (1H, d, J=8 Hz), 10.61 (1H, br s), 10.86 (1H, br s).

Example 117

5-[4-(2-Iodobenzoylamino)phenyl]-1H-[1,4]diazepino[2,3-h]quinoline-2,4(3H,5H)-dione (1) 5-(4-Aminophenyl)-1H-[1,4]diazepino[2,3-h]quinoline-2,4(3H,5H)-dione By using 7-hydroxy-8-nitroquinoline as the starting material, the title compound was obtained in the same manner as that of Example 42, (1) and (2).

$^1$H NMR (CDCl$_3$, 400 MHz) δ: 3.61 (2H, s), 3.81 (2H, br s), 6.69 (2H, d, J=9 Hz), 6.99 (2H, d, J=9 Hz), 7.13 (1H, d, J=9 Hz), 7.45 (2H, d, J=9 Hz), 7.50 (1H, dd, J=4 Hz, 8 Hz), 8.12 (1H, dd, J=1 Hz, 8 Hz), 8.91 (1H, dd, J=1 Hz, 4 Hz), 9.51 (1H, br s).

(2) 5-[4-(2-Iodobenzoylamino)phenyl]-1H-[1,4]diazepino[2,3-h]quinoline-2,4(3H,5H)-dione By using 5-(4-aminophenyl)-1H-[1,4]diazepino[2,3-h]quinolone-2,4(3H,5H)-dione (30 mg, 0.097 mmol) obtained above, and 2-iodobenzoyl chloride (0.14 mmol), the title compound (10 mg, yield 19%) was obtained in the same manner as that of Example 1, (4).

$^1$H NMR (DMSO-d$_6$, 400 MHz) δ: 3.2-3.5 (2H, m), 7.11 (1H, d, J=9 Hz), 7.2-7.4 (3H, m), 7.4-7.6 (2H, m), 7.6-7.7 (1H, m), 7.71 (1H, d, J=9 Hz), 7.78 (2H, d, J=8 Hz), 7.93 (1H, d, J=8 Hz), 8.39 (1H, d, J=8 Hz), 9.00 (1H, d, J=5 Hz), 10.25 (1H, s), 10.56 (1H, s).

Example 118

5-[4-(6-Chloro-2-hydroxybenzoylamino)phenyl]-1H-naphtho[1,2-b][1,4]diazepine-2,4(3H,5H)-dione By using 5-[4-(6-chloro-2-methoxybenzoylamino)phenyl]-1H-naphtho[1,2-b][1,4]diazepine-2,4(3H,5H)-dione obtained in Example 116, the title compound (yield 80%) was obtained in the same manner as that of Example 18.

$^1$H NMR (DMSO-d$_6$, 400 MHz) δ: 3.15 (1H, d, J=12 Hz), 3.69 (1H, d, J=12 Hz), 6.88 (1H, d, J=8 Hz), 6.92 (1H, d, J=8 Hz), 7.02 (1H, d, J=9 Hz), 7.19 (2H, d, J=9 Hz), 7.23 (1H, t, J=8 Hz), 7.59 (1H, t, J=7 Hz), 7.6-7.7 (2H, m), 7.76 (2H, d, J=9 Hz), 7.92 (1H, d, J=8 Hz), 8.25 (1H, d, J=9 Hz), 10.25 (1H, br s), 10.62 (1H, br s), 10.87 (1H, br s).

Example 119

5-[4-(2-Hydroxy-6-methoxybenzoylamino)phenyl]-1H-naphtho[1,2-b][1,4]diazepine-2,4(3H,5H)-dione (1) 5-[4-(2,6-Dimethoxybenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 2,6-dimethoxybenzoyl chloride, the title compound (yield 71%) was obtained in the same manner as that of Example 1, (4).

$^1$H NMR (DMSO-d$_6$, 400 MHz) δ: 3.15 (1H, d, J=12 Hz), 3.69 (1H, d, J=12 Hz), 3.76 (3H, s), 3.76 (3H, s), 6.73 (2H, d, J=8 Hz), 7.02 (1H, d, J=9 Hz), 7.16 (2H, d, J=9 Hz), 7.35 (1H, t, J=8 Hz), 7.5-7.7 (3H, m), 7.76 (2H, d, J=9 Hz), 7.92 (1H, d, J=8 Hz), 8.25 (1H, d, J=8 Hz), 10.34 (1H, br s), 10.86 (1H, br s).

(2) 5-[4-(2-Hydroxy-6-methoxybenzoylamino)phenyl]-1H-naphtho[1,2-b][1,4]diazepine-2,4(3H,5H)-dione By using 5-[4-(2,6-dimethoxybenzoylamino)phenyl]-1H-naphtho[1,2-b][1,4]diazepine-2,4(3H,5H)-dione, the title compound was obtained in the same manner as that of Example 18.

$^1$H NMR (DMSO-dc, 400 MHz) δ: 3.15 (1H, d, J=12 Hz), 3.69 (1H, d, J=12 Hz), 3.80 (3H, s), 6.53 (1H, d, J=8 Hz), 6.55 (1H, d, J=9 Hz), 7.01 (1H, d, J=9 Hz), 7.18 (2H, d, J=9 Hz), 7.22 (1H, t, J=8 Hz), 7.59 (1H, t, J=7 Hz), 7.66 (1H, t, J=7 Hz), 7.69 (1H, d, J=9 Hz), 7.76 (2H, d, J=9 Hz), 7.91 (1H, d, J=8 Hz), 8.25 (1H, d, J=8 Hz), 10.36 (1H, br s), 10.65 (1H, br s), 10.87 (1H, br s).

Example 120

5-[4-[2-Methoxy-6-(trifluoromethyl)benzoylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 2-methoxy-6-(trifluoromethyl)benzoyl chloride, the title compound (yield 74%) was obtained in the same manner as that of Example 1, (4).

¹H NMR (DMSO-d₆, 400 MHz) δ: 3.15 (1H, d, J=12 Hz), 3.69 (1H, d, J=12 Hz), 3.86 (3H, s), 7.03 (1H, d, J=8 Hz), 7.19 (2H, d, J=9 Hz), 7.36 (1H, d, J=8 Hz), 7.47 (1H, d, J=9 Hz), 7.5-7.8 (6H, m), 7.91 (1H, d, J=9 Hz), 8.24 (1H, d, J=3 Hz), 10.61 (1H, br s), 10.87 (1H, br s).

Example 121

5-[4-[2-Hydroxy-6-(trifluoromethyl)benzoylamino] phenyl]-1H-naphtho[1,2-b][1,4]diazepine-2,4(3H,5H)-dione By using 5 [4-[2-methoxy-6-(trifluoromethyl)benzoylamino]phenyl]-1H-naphtho[1,2-b][1,4]diazepine-2,4(3H,5H)-dione, the title compound was obtained in the same manner as that of Example 18.

¹H NMR (DMSO-d₆, 400 MHz) δ: 3.15 (1H, d, J=12 Hz), 3.70 (1H, d, J=12 Hz), 7.03 (1H, d, J=9 Hz), 7.1-7.3 (4H, m), 7.45 (1H, t, J=8 Hz), 7.59 (1H, t, J=7 Hz), 7.6-7.8 (4H, m), 7.92 (1H, d, J=7 Hz), 8.25 (1H, d, J=8 Hz), 10.43 (1H, br s), 10.56 (1H, br s), 10.87 (1H, br s).

Example 122

5-[4-[(2-Isopropenylbenzoyl)amino]phenyl]-1,2,3,4, 8,9,10,11-octahydronaphtho[1,2-b][1,4]diazepine-2, 4(3H,5H)-dione 5-[4-(2-Iodobenzoyl)aminophenyl]-1,2,3,4,8,9,10,11-octahydronaphtho[1,2-b][1,4]diazepine-2,4(3H,5H)-dione (55 mg, 0.1 mmol) obtained in Example 106, isopropenylboronic acid pinacol ester (20 mg, 0.12 mmol), [1,1'-bis (diphenylphosphino)ferrocene]palladium (II) dichloride-dichloromethane complex (1:1, 0.8 mg, 1 μmol), cesium carbonate (65 mg, 02 mmol), and dry dimethylformamide (1 mL) were mixed, and the mixture was stirred at 90° C. for 16 hours under a nitrogen atmosphere. This reaction mixture was added with water, the mixture was extracted with ethyl acetate, and the organic layer was washed with saturated brine, and dried over anhydrous sodium sulfate. The solvent was evaporated under reduced pressure, and the residue was purified by silica gel column chromatography (methanol/chloroform=1/50), and then recrystallized from ethyl acetate/hexane to obtain the title compound (5 mg, yield 11%) as pale yellow powder.

¹H NMR (DMSO-d₆, 400 MHz) δ: 1.6-1.9 (4H, m), 2.07 (3H, s), 2.5-2.8 (3H, m), 2.8-3.0 (1H, m), 3.03 (1H, d, J=12 Hz), 3.55 (1H, d, J=12 Hz), 4.97 (1H, s), 5.09 (1H, s), 6.65 (1H, d, J=9 Hz), 6.88 (1H, d, J=9 Hz), 7.10 (2H, d, J=9 Hz), 7.3-7.5 (4H, m), 7.70 (2H, d, J=9 Hz), 9.85 (1H, s), 10.34 (1H, s).

Example 123

5-[4-[(2-Isopropylbenzoyl)amino]phenyl]-1,2,3,4,8, 9,10,11-octahydronaphtho[1,2-b][1,4]diazepine-2,4 (3H,5H)-dione 5-[4-[(2-Isopropenylbenzoyl)amino]phenyl]-1,2,3,4,8,9, 10,11-octahydronaphtho[1,2-b][1,4]diazepine-2,4(3H,5H)-dione (2.0 mg, 43 μmol) obtained in Example 122 was dissolved in tetrahydrofuran (1 mL) and methanol (0.5 mL), the solution was added with platinum oxide (0.1 mg), and the mixture was stirred at room temperature for 24 hours under a hydrogen atmosphere. The solvent was evaporated under reduced pressure, and the residue was purified by silica gel column chromatography (methanol/chloroform=1/100) to give the title compound (1.5 mg, yield 74%) as pale brown powder.

¹H NMR (CDCl₃, 400 MHz) δ: 1.28 (6H, d, J=7 Hz), 1.7-2.1 (4H, m), 2.5-2.9 (4H, m), 3.39 (1H, m), 3.50 (2H, s), 6.73 (1H, d, J=8 Hz), 6.85 (1H, d, J=9 Hz), 7.1-7.3 (4H, m), 7.3-7.6 (5H, m), 7.65 (1H, d, J=8 Hz).

Example 124

5-[4-[2-Chloro-5-(methylthio)benzoylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (50 mg, 0.16 mmol) obtained in Example 1, (3), and 2-chloro-5-methylthiobenzoyl chloride (0.24 mmol), the title compound (39 mg, yield 49%) was obtained in the same manner as that of Example 1, (4).

¹H NMR (DMSO-d₆, 400 MHz) δ: 2.52 (3H, s), 3.15 (1H, d, J=12 Hz), 3.70 (1H, d, J=12 Hz), 7.01 (1H, d, J=9 Hz), 7.21 (2H, d, J=9 Hz), 7.3-7.4 (1H, m), 7.4-7.5 (2H, m), 7.59 (1H, t, J=8 Hz), 7.6-7.7 (2H, m), 7.77 (2H, d, J=9 Hz), 7.92 (1H, d, J=8 Hz), 8.25 (1H, d, J=8 Hz), 10.64 (1H, s), 10.87 (1H, s).

Example 125

5-[4-[2-(Methylthio)benzoylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 2-methylthiobenzoyl chloride (0.24 mmol), the title compound (22 mg, yield 20%) was obtained in the same manner as that of Example 1, (4).

¹H NMR (DMSO-d₆, 400 MHz) δ: 2.49 (3H, s), 3.15 (1H, d, J=12 Hz), 3.70 (1H, d, J=12 Hz), 7.02 (1H, d, J=9 Hz), 7.20 (2H, d, J=9 Hz), 7.26 (1H, t, J=7 Hz), 7.42 (1H, d, J=7 Hz), 7.4-7.6 (2H, m), 7.59 (1H, t, J=7 Hz), 7.6-7.7 (2H, m), 7.78 (2H, d, J=8 Hz), 7.92 (1H, d, J=8 Hz), 8.25 (1H, d, J=8 Hz), 10.45 (1H, s), 10.87 (1H, s).

Example 126

5-[4-[3-(Methylthio)benzoylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (30 mg, 0.095 mmol) obtained in Example 1, (3), and 3-methylthiobenzoyl chloride (0.24 mmol), the title compound (69 mg, yield 92%) was obtained in the same manner as that of Example 1, (4).

¹H NMR (DMSO-d₆, 400 MHz) δ: 2.54 (3H, s), 3.15 (1H, d, J=12 Hz), 3.70 (1H, d, J=12 Hz), 7.01 (1H, d, J=9 Hz), 7.22 (2H, d, J=9 Hz), 7.4-7.5 (2H, m), 7.59 (1H, t, J=8 Hz), 7.6-7.7 (3H, m), 7.7-7.9 (3H, m), 7.91 (1H, d, J=8 Hz), 8.25 (1H, d, J=8 Hz), 10.39 (1H, s), 10.88 (1H, s).

Example 127

5-[4-[2-Ethyl-6-methoxybenzoylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (50 mg, 0.16 mmol) obtained in Example 1, (3), and 2-ethyl-5-methoxybenzoyl chloride (0.24 mmol), the title compound (69 mg, yield 90%) was obtained in the same manner as that of Example 1, (4).

$^1$H NMR (DMSO-d6, 400 MHz) δ: 1.16 (3H, t, J=8 Hz), 2.57 (2H, q, J=8 Hz), 3.15 (1H, d, J=12 Hz), 3.70 (1H, d, J=12 Hz), 3.77 (3H, s), 6.9-7.0 (2H, m), 7.03 (1H, d, J=9 Hz), 7.18 (2H, d, J=9 Hz), 7.33 (1H, t, J=8 Hz), 7.59 (1H, t, J=8 Hz), 7.6-7.7 (2H, m), 7.78 (2H, d, J=9 Hz), 7.92 (1H, d, J=8 Hz), 8.25 (1H, d, J=9 Hz), 10.43 (1H, s), 10.86 (1H, s).

Example 128

5-[4-(3-Methanesulfonylbenzoylamino)phenyl]-1H-naphtho[1,2-b][1,4]diazepine-2,4(3H,5H)-dione 5-[4-[3-(Methylthio)benzoylamino]phenyl]-1H-naphtho[1,2-b][1,4]diazepine-2,4(3H,5H)-dione (20 mg, 0.043 mmol) obtained in Example 126 was dissolved in dimethylformamide (0.4 mL, the solution was added with n-chloroperbenzoic acid (16 mg, 0.065 mmol), and the mixture was stirred at room temperature for 5 minutes. After completion of the reaction, the reaction mixture was added with ethyl acetate, the organic layer was washed with saturated aqueous sodium hydrogencarbonate, water, and saturated brine. The solvent of the organic layer was evaporated under reduced pressure, and the obtained residue was purified by silica gel column chromatography (chloroform/methanol=100/1) to give the title compound (13 mg, yield 61%).

$^1$H NMR (CDCl$_3$, 400 MHz) δ: 3.10 (3H, s), 3.5-3.6 (2H, m), 6.9-7.1 (3H, m), 7.4-7.6 (4H, m), 7.6-7.7 (2H, m), 7.79 (1H, d, J=8 Hz), 8.06 (1H, d, J=7 Hz), 8.16 (1H, d, J=8 Hz), 8.21 (1H, d, J=7 Hz), 8.51 (1H, s), 9.02 (1H, br s), 9.44 (1H, br s).

Example 129

6-Ethyl-1-[4-(2-iodobenzoyl)aminophenyl]-1H-1,5-benzodiazepine-2,4(3H,5H)-dione (1) tert-Butyl 4-(2-amino-3-ethylphenylamino)phenylcarbamate By using tert-butyl 4-(3-ethyl-2-nitrophenylamino)phenylcarbamate, the title compound was obtained in the same manner as that of Example 1, (2).

$^1$H NMR (CDCl$_3$, 400 MHz) δ: 1.28 (3H, t, J=7 Hz), 1.50 (9H, s), 2.57 (2H, q, J=7 Hz), 3.75 (2H, br s), 5.04 (1H, br s), 6.26 (1H, br s), 6.6-6.8 (3H, m), 6.9-7.0 (2H, m), 7.17 (2H, d, J=8 Hz).

(2) Ethyl 3-[2-[4-(tert-butoxycarbonylamino)phenylamino]-6-ethylphenylamino]-3-oxopropionate By using tert-butyl 4-(2-amino-3-ethylphenylamino)phenylcarbamate, the title compound was obtained in the same manner as that of Example 1, (3).

$^1$H NMR (CDCl$_3$, 400 MHz) δ: 1.22 (3H, t, J=7 Hz), 1.32 (3H, t, J=7 Hz), 1.51 (9H, s), 2.64 (2H, q, J=7 Hz), 3.53 (2H, s), 4.26 (2H, q, J=7 Hz), 6.21 (1H, s), 6.33 (1H, br s), 6.8-6.9 (1H, m), 6.96 (2H, d, J=9 Hz), 7.0-7.3 (4H, m), 8.73 (1H, s).

(3) tert-Butyl 4-(6-ethyl-2,4-dioxo-2,3,4,5-tetrahydro-1H-benzo[b][1,4]diazepin-1-yl)phenylcarbamate By using ethyl 3-[2-[4-(tert-butoxycarbonylamino)phenylamino]-6-ethylphenylamino]-3-oxopropionate, the title compound was obtained in the same manner as that of Example 1, (3).

$^1$H NMR (CDCl$_3$, 400 MHz) δ: 1.30 (3H, t, J=7 Hz), 1.51 (9H, s), 2.7-2.8 (2H, m), 3.49 (2H, s), 6.51 (1H, s), 6.82 (1H, d, J=7 Hz), 7.0-7.2 (4H, m), 7.38 (2H, d, J=9 Hz), 7.48 (1H, (4) 1-(4-Aminophenyl)-6-ethyl-1H-benzo[b][1,4]diazepine-2,4(3H,5H)-dione By using tert-butyl 4-(6-ethyl-2,4-dioxo-2,3,4,5-tetrahydro-1H-benzo[b][1,4]diazepin-1-yl)phenylcarbamate, the title compound was obtained in the same manner as that of Example 1, (3).

$^1$H NMR (DMSO-d$_6$, 400 MHz) δ: 1.14 (3H, t, J=7 Hz), 2.64 (1H, dq, J=8 Hz, 7 Hz), 2.89 (1H, dq, J=8 Hz, 7 Hz), 3.00 (1H, d, J=12 Hz), 3.46 (1H, d, J=12 Hz), 5.20 (2H, br s), 6.54 (2H, d, J=8 Hz), 6.77 (3H, d, J=8 Hz), 7.3-7.1 (2H, m), 9.93 (1H, s).

(5) 6-Ethyl-1-[4-(2-iodobenzoyl)aminophenyl]-1H-1,5-benzodiazepine-2,4(3H,5H)-dione By using 1-(4-aminophenyl)-6-ethyl-1H-benzo[b][1,4]diazepine-2,4(3H,5H)-dione, and 2-iodobenzoyl chloride, the title compound was obtained in the same manner as that of Example 1, (4).

$^1$H NMR (DMSO-d$_6$, 400 MHz) δ: 1.16 (3H, t, J=7 Hz), 2.6-3.0 (2H, m), 3.06 (1H, d, J=12 Hz), 3.55 (1H, d, J=12 Hz), 6.77 (1H, d, J=7 Hz), 7.0-7.3 (5H, m), 7.4-7.6 (2H, m), 7.75 (2H, d, J=9 Hz), 7.93 (1H, d, J=8 Hz), 10.02 (1H, s), 10.53 (1H, s).

Example 130

5-[4-[2-Ethyl-6-hydroxybenzoylamino]phenyl]-1H-naphtho[1,2-b][1,4]diazepine-2,4(3H,5H)-dione By using 5-[4-[2-ethyl-6-methoxybenzoylamino]phenyl]-1H-naphtho[1,2-b][1,4]diazepine-2,4(3H,5H)-dione (20 mg, 0.042 mmol) obtained in Example 127, the title compound (12 mg, yield 61%) was obtained in the same manner as that of Example 18.

$^1$H NMR (DMSO-d$_6$, 400 MHz) δ: 1.15 (3H, t, J=8 Hz), 2.55 (2H, q, J=8 Hz), 3.15 (1H, d, J=12 Hz), 3.69 (1H, d, J=12 Hz), 6.73 (2H, t, J=8 Hz), 7.03 (1H, d, J=9 Hz), 7.1-7.2 (3H, m), 7.59 (1H, t, J=8 Hz), 7.6-7.7 (2H, m), 7.79 (2H, d, J=9 Hz), 7.92 (1H, d, J=8 Hz), 8.24 (1H, d, J=9 Hz), 9.58 (1H, br s), 10.37 (1H, s), 10.86 (1H, br s).

Example 131

5-[4-(3-Methanesulfinylbenzoylamino)phenyl]-1H-naphtho[1,2-b][1,4]diazepine-2,4(3H,5H)-dione 5-[4-[3-(Methylthio)benzoylamino]phenyl]-1H-naphtho[1,2-b][1,4]diazepine-2,4(3H,5H)-dione (20 mg, 0.043 mmol) obtained in Example 126 was dissolved in dimethylformamide (0.4 mL), the solution was added with m-chloroperbenzoic acid (11 mg, 0.03 mmol) at −20° C., and the mixture was stirred for 30 minutes. After completion of the reaction, the reaction mixture was added with ethyl acetate at −20° C., the organic layer was washed with saturated aqueous sodium hydrogencarbonate, water, and saturated brine. The solvent of the organic layer was evaporated under reduced pressure, and the obtained residue was purified by silica gel column chromatography (chloroform/methanol=100/1) to obtain the title compound (8 mg, yield 38%).

$^1$H NMR (CDCl$_3$, 400 MHz) δ: 2.77 (3H, s), 3.57 (2H, s), 7.00 (1H, d, J=9 Hz), 7.1-7.2 (2H, m), 7.5-7.8 (7H, m), 7.82

Example 132

5-[4-(2-Chloro-5-methanesulfinylbenzoylamino)phenyl]-1H-naphtho[1,2-b][1,4]diazepine-2,4(3H,5H)-dione By using 5-[4-[2-chloro-5-(methylthio)benzoylamino]phenyl]-1H-naphtho[1,2-b][1,4]diazepine-2,4(3H,5H)-dione (20 mg, 0.04 mmol) obtained in Example 124, the title compound (7 mg, yield 34%) was obtained in the same manner as that of Example 131.

$^1$H NMR (CDCl$_3$, 400 MHz) δ: 2.75 (3H, s), 3.55 (1H, d, J=11 Hz), 3.59 (1H, d, J=11 Hz), 7.04 (1H, d, J=9 Hz), 7.23 (2H, d, J=8 Hz), 7.5-7.8 (7H, m), 7.86 (1H, d, J=8 Hz), 7.89 (1H, d, J=2 Hz), 8.11 (1H, d, J=8 Hz), 8.46 (1H, s), 8.69 (1H, s).

Example 133

5-[4-(2-Methanesulfinylbenzoylamino)phenyl]-1H-naphtho[1,2-b][1,4]diazepine-2,4(3H,5H)-dione By using 5-[4-[2-(methylthio)benzoylamino]phenyl]-1H-naphtho[1,2-b][1,4]diazepine-2,4(3H,5H)-dione (20 mg, 0.043 mmol) obtained in Example 125, the title compound (9 mg, yield 43%) was obtained in the same manner as that of Example 131.

$^1$H NMR (CDCl$_3$, 400 MHz) δ: 2.92 (3H, s), 3.59 (2H, s), 6.99 (1H, dd, J=3, 9 Hz), 7.15 (2H, t, J=8 Hz), 7.5-7.7 (5H, m), 7.71 (2H, q, J=8 Hz), 7.84 (2H, dd, J=8 Hz), 8.12 (1H, dd, J=4, 9 Hz), 8.22 (1H, dd, J=4 Hz, 8 Hz), 8.7-8.9 (1H, m), 9.0-9.1 (1H, m).

Example 134

5-[4-[[2-(4-Morpholinyl)acetyl]amino]phenyl]-1,2,3,4,8,9,10,11-octahydronaphtho[1,2-b][1,4]diazepine-2,4(3H,5H)-dione hydrochloride (1) 5-[4-[(2-Chloroacetyl)amino]phenyl]-1,2,3,4,8,9,10,11-octahydronaphtho[1,2-b][1,4]diazepine-2,4(3H,5H)-dione 5-(4-Aminophenyl)-1,2,3,4,8,9,10,11-octahydronaphtho[1,2-b][1,4]diazepine-2,4(3H,5H)-dione (64 mg, 0.2 mmol) obtained in Example 55, (6), and sodium hydrogencarbonate (50 mg, 0.6 mmol) were suspended in chloroform (6.4 mL), the suspension was added with chloroacetyl chloride (38 μL, 0.48 mmol), and the mixture was stirred at room temperature for 7 hours. This reaction mixture was added with water, the mixture was stirred for 10 minutes, and then the chloroform layer was washed with saturated brine, and dried over anhydrous sodium sulfate. The solvent was evaporated under reduced pressure, and the residue was washed with ethyl acetate and then with hexane to give the title compound (74 mg, yield 41%) as off-white crystals.

$^1$H NMR (DMSO-d$_6$, 400 MHz) δ: 1.6-1.9 (4H, m), 2.5-2.8 (3H, m), 2.8-3.0 (1H, m), 3.03 (1H, d, J=12 Hz), 3.55 (1H, d, J=12 Hz), 4.25 (2H, s), 6.62 (1H, d, J=8 Hz), 6.87 (1H, d, J=8 Hz), 7.12 (2H, d, J=8 Hz), 7.62 (2H, d, J=9 Hz), 9.86 (1H, s), 10.39 (1H, s).

(2) 5-[4-[[2-(4-Morpholinyl)acetyl]amino]phenyl]-1,2,3,4,8,9,10,11-octahydronaphtho[1,2-b][1,4]diazepine-2,4(3H,5H)-dione hydrochloride 5-[4-[(2-Chloroacetyl)amino]phenyl]-1,2,3,4,8,9,10,11-octahydronaphtho[1,2-b][1,4]diazepine-2,4(3H,5H)-dione (27 mg, 0.068 mmol), morpholine (30 mg, 0.34 mmol), and ethanol (6.8 mL) were mixed, and the mixture was refluxed by heating for 8 hours. The solvent was evaporated under reduced pressure, and the residue was washed several times with water to give 5-[4-[[2-(4-morpholinyl)acetyl]amino]phenyl]-1,2,3,4,8,9,10,11-octahydronaphtho[1,2-b][1,4]diazepine-2,4(3H,5H)-dione (28 mg, 0.062 mmol).

This compound was dissolved in chloroform (3 mL) and methanol (1 mL), and the solution was added with a 4 M solution of hydrogen chloride in ethyl acetate (0.03 mL). The solvent was evaporated under reduced pressure, and the residue was concentrated twice from ethyl acetate under reduced pressure, and then washed with ethyl acetate to obtain the title compound (30 mg yield 91%) as gray amorphous.

$^1$H NMR (DMSO-d$_6$, 400 Hz) δ: 1.6-1.9 (4, m), 2.5-2.8 (3H, m), 2.8-3.0 (1H, m), 3.03 (1H, d, J=12 Hz), 3.2-3.6 (4H, m), 3.55 (1H, d, J=12 Hz), 3.7-4.1 (4H, m), 4.21 (2H, s), 6.61 (1H, d, J=8 Hz), 6.87 (1H, d, J=8 Hz), 7.15 (2H, d, J=9 Hz), 7.65 (2H, d, J=9 Hz), 9.88 (1H, s), 10.67 (1H, br s), 11.01 (1H, s).

Example 135

5-[4-(2-Chloro-6-methoxybenzoylamino)phenyl]-1,3-dihydronaphtho[1,2-e]-1,4-diazepin-2-one By using 5-(4-aminophenyl)-1,3-dihydronaphtho[1,2-e]-1,4-diazepin-2-one (40 mg, 0.13 mmol) obtained in Example 64, and 2-chloro-6-methoxybenzoyl chloride (0.2 mmol), the title compound (51 mg, yield 54%) was obtained in the same manner as that of Example 1, (4).

$^1$H NMR (DMSO-d$_6$, 400 MHz) δ: 3.78 (1H, d, J=10 Hz), 3.81 (3H, s), 4.55 (1H, d, J=10 Hz), 7.1-7.2 (2H, m), 7.31 (1H, d, J=9 Hz), 7.43 (1H, t, J=8 Hz), 7.53 (2H, d, J=8 Hz), 7.6-7.8 (5H, m), 8.0-8.1 (1H, m), 8.36 (1H, d, J=9 Hz), 10.69 (1H, s), 10.80 (1H, s).

Example 136

5-[4-[[(3-Chloropyridin-2-yl)carbonyl]amino]phenyl]-1H-naphtho[1,2-b][1,4]diazepine-2,4(3H,5H)-dione 3-Chloropyridine-2-carboxylic acid (47 mg, 0.3 mmol) was treated with thionyl chloride in dichloroethane, and then by using the resultant together with 5-(4-aminophenyl)-1H-naphtho[1,2-b][1,4]diazepine-2,4(3H,5H)-dione (63 mg, 0.2 mmol) obtained in Example 1, (3), the title compound (41 mg, yield 45%) was obtained as pale brown crystals in the same manner as that of Example 1, (4).

$^1$H NMR (CDCl$_3$, 400 MHz) δ: 3.61 (2H, s), 7.03 (1H, d, J=9 Hz), 7.25 (2H, d, J=9 Hz), 7.41 (1H, dd, J=4 Hz, 8 Hz), 7.5-7.6 (2H, m), 7.68 (1H, t, J=8 Hz), 7.77 (2H, d, J=9 Hz), 7.8-7.9 (2H, m), 8.24 (1H, d, J=8 Hz), 8.51 (1H, dd, J=1 Hz, 4 Hz), 9.94 (1H, s), 9.99 (1H, s).

Example 137

5-[4-(2-Chloro-6-hydroxybenzoylamino)phenyl]-1,3-dihydronaphtho[1,2-e]-1,4-diazepin-2-one By using 5-[4-(2-chloro-6-methoxybenzoylamino)phenyl]-1,3-dihydronaphtho[1,2-e]-1,4-diazepin-2-one (46 mg, 0.098 mmol) obtained in Example 135, the title compound (36 mg, yield 81%) was obtained in the same manner as that of Example 18.

$^1$H NMR (DMSO-$d_6$, 400 MHz) δ: 3.78 (1H, d, J=10 Hz), 4.55 (1H, d, J=10 Hz), 6.89 (1H, d, J=8 Hz), 6.94 (1H, d, J=8 Hz), 7.24 (1H, t, J=8 Hz), 7.31 (1H, d, J=9 Hz), 7.52 (2H, d, J=9 Hz), 7.6-7.8 (5H, m), 8.0-8.1 (1H, m), 8.36 (1H, d, J=10 Hz), 10.27 (1H, s), 10.60 (1H, s), 10.80 (1H, s).

Example 138

5-[4-(3-Chloro-2-methoxybenzoylamino)phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 3-chloro-2-methoxybenzoyl chloride, the title compound (yield 9%) was obtained in the same manner as that of Example 1, (4).

$^1$H NMR (DMSO-$d_6$, 400 MHz) δ: 3.15 (1H, d, J=12 Hz), 3.70 (1H, d, J=12 Hz), 3.84 (3H, s), 7.02 (1H, d, J=9 Hz), 7.21 (2H, d, J=8 Hz), 7.26 (1H, t, J=8 Hz), 7.4-7.7 (5H, m), 7.78 (2H, d, J=9 Hz), 7.92 (1H, d, J=8 Hz), 8.25 (1H, d, J=8 Hz), 10.54 (1H, s), 10.88 (1H, br s).

Example 139

5-[4-[(3-Methylpyridin-2-yl)carbonylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 3-methylpicolinic acid chloride, the title compound (yield 87%) was obtained in the same manner as that of Example 1, (4).

$^1$H NMR (DMSO-$d_6$, 400 MHz) δ: 2.57 (3H, s), 3.15 (1H, d, J=12 Hz), 3.70 (1H, d, J=12 Hz), 7.02 (1H, d, J=9 Hz), 7.21 (2H, d, J=9 Hz), 7.51 (1H, dd, J=4 Hz, 7 Hz), 7.59 (1H, t, J=8 Hz), 7.6-7.7 (3H, m), 7.81 (1H, d, J=8 Hz), 7.8-8.0 (3H, m), 8.25 (1H, d, J=8 Hz), 8.54 (1H, d, J=4 Hz), 10.68 (1H, s), 10.89 (1H, s).

Example 140

5-[4-[[(3-Chloropyridin-2-yl)carbonyl]amino]phenyl]-1,2,3,4,8,9,10,11-octahydronaphtho[1,2-b][1,4]diazepine-2,4(3H,5H)-dione 3-Chloropyridine-2-carboxylic acid (47 mg, 0.3 mmol) was treated with thionyl chloride in dichloroethane, and then by using the resultant together with 5-(4-aminophenyl)-1,2,3,4,8,9,10,11-octahydronaphtho[1,2-b][1,4]diazepine-2,4(3H,5H)-dione (64 mg, 0.2 mmol) obtained in Example 55, (6), the title compound (72 mg, yield 53%) was obtained as pale brown powder in the same manner as that of Example 1, (4).

$^1$H NMR (DMSO-$d_6$, 400 MHz) δ: 1.6-1.9 (4H, m), 2.5-2.8 (3H, m), 2.8-3.0 (1H, m), 3.04 (1H, d, J=12 Hz), 3.57 (1H, d, J=12 Hz), 6.66 (1H, d, J=8 Hz), 6.89 (1H, d, J=9 Hz), 7.16 (2H, d, J=9 Hz), 7.61 (1H, dd, J=4 Hz, 8 Hz), 7.78 (2H, d, J=9 Hz), 8.11 (1H, dd, J=1 Hz, 8 Hz), 8.63 (1H, dd, J=1 Hz, 4 Hz), 9.89 (1H, s), 10.78 (1H, s).

Example 141

5-[4-(3-Chloro-2-hydroxybenzoylamino)phenyl]-1H-naphtho[1,2-b][1,4]diazepine-2,4(3H,5H)-dione By using 5-[4-(3-chloro-2-methoxybenzoylamino)phenyl]-1H-naphtho[1,2-b][1,4]diazepine-2,4(3H,5H)-dione obtained in Example 138, the title compound (yield 77%) was obtained in the same manner as that of Example 18.

$^1$H NMR (DMSO-$d_6$, 400 MHz) δ: 3.16 (1H, d, J=12 Hz), 3.72 (1H, d, J=12 Hz), 7.01 (2H, d, J=9 Hz), 7.26 (2H, d, J=9 Hz), 7.59 (1H, t, J=7 Hz), 7.6-7.7 (3H, m), 7.77 (2H, d, J=9 Hz), 7.92 (1H, d, J=7 Hz), 8.00 (1H, dd, J=1 Hz, 8 Hz), 8.26 (1H, d, J=8 Hz), 10.68 (1H, br s), 10.90 (1H, s).

Example 142

5-[4-f[[(3-Hydroxypyridin-2-yl)carbonyl]amino] phenyl]-1H-naphtho[1,2-b][1,4]diazepine-2,4(3H,5H)-dione 5-(4-Aminophenyl)-1H-naphtho[1,2-b][1,4]diazepine-2,4(3H,5H)-dione (63 mg, 0.2 mmol), 3-hydroxypyridine-2-carboxylic acid (33 mg, 0.24 mmol), dry dimethylacetamide (6 mL), triethylamine (0.07 mL, 0.5 mmol), and O-(7-azabenzotriazol-1-yl)-N,N,N',N'-tetramethyluronium hexafluorophosphate (95 mg, 0.25 mmol) were mixed, and the mixture was stirred at room temperature for 24 hours. This reaction mixture was added with water, the mixture was extracted with ethyl acetate, and the organic layer was washed with saturated brine, and dried over anhydrous sodium sulfate. The solvent was evaporated under reduced pressure, and the residue was purified by silica gel column chromatography (methanol/chloroform=1/100), and then washed several times with ethyl acetate to give the title compound (37 mg, yield 42%) as white crystals.

$^1$H NMR (DMSO-$d_6$, 400 MHz) δ: 3.18 (1H, d, J=12 Hz), 3.72 (1H, d, J=12 Hz), 7.03 (1H, d, J=9 Hz), 7.26 (2H, d, J=8 Hz), 7.50 (1H, d, J=8 Hz), 7.5-7.7 (2H, m), 7.67 (1H, d, J=8 Hz), 7.72 (1H, d, J=9 Hz), 7.9-8.0 (31H, m), 8.2-8.3 (2H, m), 10.91 (1H, s), 11.03 (1H, s), 12.03 (1H, s).

Example 143

5-[4. [(3-Vinylpyridin-2-yl)carbonylamino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione obtained in Example 1, (3), and 3-vinylpicolinic acid chloride, the title compound (yield 35%) was obtained in the same manner as that of Example 1, (4).

$^1$H NMR (DMSO-$d_6$, 400 MHz) δ: 3.15 (1H, d, J=12 Hz), 3.70 (1H, d, J=12 Hz), 5.46 (1H, d, J=11 Hz), 5.91 (1H, d, J=17 Hz), 7.01 (1H, d, J=9 Hz), 7.22 (2H, d, J=9 Hz), 7.39 (1H, dd, J=11 Hz, 17 Hz), 7.5-7.8 (4H, m), 7.87 (2H, d, J=9 Hz), 7.92 (1H, d, J=8 Hz), 8.20 (1H, d, J=8 Hz), 8.25 (1H, d, J=8 Hz), 8.61 (1H, dd, J=1 Hz, 5 Hz), 10.74 (1H, s), 10.89 (1H, s).

Example 144

5-[4-[(3-Ethylpyridin-2-yl)carbonylamino]phenyl]-1H-naphtho[1,2-b][1,4]diazepine-2,4(3H,5H)-dione 5-(4-Aminophenyl)-1H-naphtho[1,2-b][1,4]diazepine-2,4(3H,5H)-dione (100 mg, 0.315 mmol) obtained in Example 1, (3), HATU (180 mg, 0.473 mmol), triethylamine (132 μL, 0.945 mmol), and 3-ethylpicolinic acid (71 mg, 0.473 mmol) were stirred at room temperature for 2 hours in anhydrous dimethylacetamide (10 mL). The reaction mixture was post-treated in a conventional manner to give the title compound (98 mg, yield 69%).

¹H NMR (DMSO-d₆, 400 MHz) δ: 1.20 (3H, t, J=7 Hz), 2.94 (2H, q, J=7 Hz), 3.15 (1H, d, J=12 Hz), 3.70 (1H, d, J=12 Hz), 7.02 (1H, d, J=9 Hz), 7.21 (2H, d, J=9 Hz), 7.53 (1H, dd, J=4 Hz, 8 Hz), 7.59 (1H, t, J=7 Hz), 7.6-7.8 (2H, m), 7.8-8.0 (4H, m), 8.25 (1H, d, J=8 Hz), 8.53 (1H, dd, J=1 Hz, 4 Hz), 10.67 (1H, s), 10.89 (1H, br s).

Example 145

N-[4-(2,4-Dioxo-1,2,3,4-tetrahydronaphtho[1,2-b][1,4]diazepin-5-yl)phenyl]-2-nitrobenzenesulfonamide 5-(4-Aminophenyl)-1H-naphtho[1,2-b][1,4]diazepine-2,4(3H,5H)-dione (40 mg, 0.13 mmol) obtained in Example 1, (3), and 2-nitrobenzenesulfonyl chloride (42 mg, 0.19 mmol) were stirred at 80° C. in anhydrous pyridine (1 mL). After the disappearance of the starting materials was confirmed, a post-treatment was performed in a conventional manner to obtain the title compound (45 mg, yield 71%).

¹H NMR (CDCl₃, 400 MHz) δ: 3.57 (2H, s), 6.93 (1H, d, J=9 Hz), 7.1-7.2 (4H, m), 7.45 (1H, s), 7.5-7.8 (5H, m), 7.86 (1H, d, J=8 Hz), 7.87 (1H, dd, J=1 Hz, 8 Hz), 7.93 (1H, dd, J=1 Hz, 8 Hz), 8.65 (1H, br s).

Example 146

N-[4-(2,4-Dioxo-1,2,3,4-tetrahydronaphtho[1,2-b][1,4]diazepin-5-yl)phenyl]benzenesulfonamide 5-(4-Aminophenyl)-1H-naphtho[1,2-b][1,4]diazepine-2,4(3H,5H)-dione (10 mg, 0.0315 mmol) obtained in Example 1, (3), and benzenesulfonyl chloride (8.3 mg, 0.0473 mmol) were treated by heating in pyridine (1.0 mL). After the disappearance of the starting materials was confirmed, the same treatment as that of Example 145 was performed to give the title compound (14 mg, yield 97%) as slightly brown amorphous.

¹H NMR (CDCl₃, 400 MHz) δ: 3.57 (2H, s), 6.78 (1H, br s), 6.93 (1H, d, J=9 Hz), 7.09 (2H, d, J=9 Hz), 7.14 (2H, d, J=9 Hz), 7.47 (2H, t, J=8 Hz), 7.5-7.8 (3H, m), 7.69 (1H, t, J=8 Hz), 7.81 (2H, d, J=8 Hz), 7.86 (1H, d, J=8 Hz), 8.05 (1H, d, J=9 Hz), 8.34 (1H, br s).

Example 147

3-Bromo-N-[4-(2,4-dioxo-1,2,3,4-tetrahydronaphtho[1,2-b][1,4]diazepin-5-yl)phenyl]benzenesulfonamide 5-(4-Aminophenyl)-1H-naphtho[1,2-b][1,4]diazepine-2,4(3H,5H)-dione obtained in Example 1, (3) (15 mg, 0.047 mmol), and 3-bromobenzenesulfonyl chloride (24 mg, 0.095 mmol) were treated by heating in pyridine (1.0 mL). After the disappearance of the starting materials was confirmed, the same treatment as that of Example 145 was performed to give the title compound (15 mg, yield 60%) as slightly brown amorphous.

¹H NMR (CDCl₃, 400 MHz) δ: 3.58 (2H, s), 6.81 (1H, br s), 6.94 (1H, d, J=9 Hz), 7.10 (2H, d, J=9 Hz), 7.17 (2H, d, J=9 Hz), 7.35 (1H, t, J=8 Hz), 7.5-7.8 (5H, m), 7.86 (1H, d, J=8 Hz), 7.92 (1H, t, J=2 Hz), 8.05 (1H, d, J=8 Hz), 8.32 (1H, br s).

Example 148

N-[4-(2,4-Dioxo-1,2,3,4-tetrahydronaphtho[1,2-b][1,4]diazepin-5-yl)phenyl]-3-methoxybenzenesulfonamide 5-(4-Aminophenyl)-1H-naphtho[1,2-b][1,4]diazepine-2,4(3H,5H)-dione (10 mg, 0.032 mmol) obtained in Example 1, (3), and 3-methoxybenzenesulfonyl chloride (13 mg, 0.063 mmol) were treated by heating in pyridine (1.0 mL). After the disappearance of the starting materials was confirmed, the same treatment as that of Example 145 was performed to obtain the title compound (9 mg, yield 59%) as slightly brown amorphous.

¹H NMR (CDCl₃, 400 MHz) δ: 3.57 (2H, s), 3.77 (3H, s), 6.59 (1H, s), 6.94 (1H, d, J=9 Hz), 7.0-7.2 (5H, m), 7.3-7.4 (2H, m), 7.5-7.7 (3H, m), 7.86 (1H, d, J=8 Hz), 8.03 (1H, d, J=8 Hz), 8.14 (1H, s).

Example 149

N-[3-(2-Oxo-2,3-dihydro-1H-naphtho[1,2-e][1,4]diazepin-5-yl)phenyl]benzenesulfonamide (1) 5-(3-Bromophenyl)-1,3-dihydronaphtho[1,2-e]-1,4-diazepin-2-one By using 1-nitro-2-naphthoaldehyde and 1-bromo-3-iodobenzene, the title compound was obtained in the same manner as that of the method described in WO2008/023847.

¹H NMR (CDCl₃, 400 MHz) δ: 3.2-5.6 (2H, m), 7.2-7.4 (2H, m), 7.49 (1H, d, J=8 Hz), 7.60 (1H, d, J=8 Hz), 7.6-7.8 (3H, m), 7.78 (1H, s), 7.95 (1H, m), 8.13 (1H, m), 8.44 (1H, s).

(2) 5-(3-Aminophenyl)-1,3-dihydronaphtho[1,2-e]-1,4-diazepin-2-one 5-(3-Bromophenyl)-1,3-dihydronaphtho[1,2-e]-1,4-diazepin-2-one (50 mg, 0.14 mmol) was dissolved in tetrahydrofuran (5 mL), the solution was added with sodium tert-butoxide (26 mg, 0.27 mmol), benzophenone imine (46 μL, 0.27 mmol), 2,2'-bis(diphenylphosphino)-1,1'-binaphthyl (5 mg, 8 mmol), and tris(dibenzylideneacetone)dipalladium (8 mg, 8 μmol), and the mixture was refluxed by heating for 5 hours under a nitrogen atmosphere. The solvent was evaporated under reduced pressure, the residue was added with methanol (1 mL) and 2 M hydrochloric acid (3 mL), and the mixture was stirred at room temperature for 10 minutes. The mixture was added with saturated aqueous sodium hydrogencarbonate, and extracted with chloroform, and the organic layer was dried over anhydrous sodium sulfate. The solvent was evaporated under reduced pressure, and the residue was purified by silica gel column chromatography (ethyl acetate) to give the title compound (30 mg, yield 71%) as yellow amorphous.

¹H NMR (CDCl₃, 400 MHz) δ: 3.49 (2H, s), 3.72 (2H, s), 6.78 (1H, dd, J=2 Hz, 8 Hz), 6.85 (1H, d, J=8 Hz), 6.99 (1H, t, J=2 Hz), 7.16 (1H, t, J=8 Hz), 7.37 (1H, d, J=9 Hz), 7.62 (1H, d, J=9 Hz), 7.6-7.7 (2H, m), 7.92 (1H, m), 8.15 (1H, m), 8.63 (1H, s).

(3) N-[3-(2-Oxo-2,3-dihydro-1H-naphtho[1,2-e]-1,4-diazepin-5-yl)-phenyl]benzenesulfonamide 5-(3-Aminophenyl)-1,3-dihydronaphtho[1,2-e]-1,4-diazepin-2-one (10 mg, 0.033 mmol), and benzenesulfonyl chloride (13 μL, 0.1 mmol) were treated by heating in pyridine (1.0 mL). A post-treatment was performed in a conventional manner to give the title compound (14 mg, yield 95%) as white amorphous.

$^1$H NMR (CDCl$_3$, 400 MHz) δ: 6.56 (1H, s), 7.1-7.2 (2H, m), 7.2-7.5 (51, m), 7.54 (1H, t, J=7 Hz), 7.60 (1H, d, J=9 Hz), 7.6-7.8 (4H, m), 7.9-8.0 (1H, m), 8.0-8.1 (1H, m), 8.18 (1H, s).

Example 150

N-[3-(2,4-Dioxo-1,2,3,4-tetrahydronaphtho[1,2-b][1,4]diazepin-5-yl)phenyl]-2-nitrobenzenesulfonamide By using 5-(3-aminophenyl)-1H-naphtho[1,2-b][1,4]diazepine-2,4(3H,5H)-dione obtained in Example 53, (1), and 2-nitrobenzenesulfonyl chloride, the title compound was obtained in the same manner as that of Example 145.

$^1$H NMR (DMSO-d$_6$, 400 MHz) δ: 3.12 (1H, d, J=12 Hz), 3.69 (1H, d, 12 Hz), 6.75 (1H, d, J=9 Hz), 6.94 (1H, s), 6.98 (1H, d, J=8 Hz), 7.0-7.1 (1H, m), 7.34 (1H, t, J=8 Hz), 7.6-7.7 (4H, m), 7.77 (1H, dt, J=1 Hz, 8 Hz), 7.8-8.0 (3H, in), 8.24 (1H, d, J=8 Hz), 10.76 (1H, br s), 10.90 (1H, s).

Example 151

N-[4-(2,4-Dioxo-1,2,3,4,8,9,10,11-octahydro-naphtho[1,2-b][1,4]diazepin-5-yl)phenyl]-2-nitro-benzenesulfonamide By using 5-(4-aminophenyl)-1,2,3,4,8,9,13,11-octahydronaphtho[1,2-b][1,4]diazepine-2,4(3H,5H)-dione obtained in Example 55, (6), the title compound was obtained in the same manner as that of Example 145.

$^1$H NMR (CDCl$_3$, 400 MHz) δ: 1.7-2.1 (4H, m), 2.6-2.8 (4H, m), 3.44 (1H, d, J=12 Hz), 3.49 (1H, d, J=12 Hz), 6.60 (1H, d, J=8 Hz), 6.83 (1H, d, J=8 Hz), 7.12 (2H, d, J=9H), 7.22 (2H, d, J=9 Hz), 7.47 (1H, s), 7.62 (1H, dt, J=2 Hz, 8 Hz), 7.71 (1-1, dt, J=2 Hz, 8 Hz), 7.80 (1H, br s), 7.86 (1H, dd, J=2 Hz, 8 Hz), 7.91 (1H, dd, J=2 Hz, 8 Hz).

Example 152

N-[4-(2,4-Dioxo-1,2,3,4,8,9,10,11-octahydro-naphtho[1,2-b][1,4]diazepin-5-yl)phenyl]-N-methyl-2-nitrobenzenesulfonamide N-[4-(2,4-Dioxo-1,2,3,4,8,9,10,11-octahydro-naphtho[1,2-b][1,4]diazepin-5-yl)phenyl]-2-nitro-benzenesulfonamide (150 mg, 0.30 mmol) obtained in Example 151, iodomethane (22 μL, 0.36 mmol), and potassium carbonate (45 mg, 0.33 mmol) were stirred in anhydrous DMF (3 mL) for 16 hours. After the disappearance of the starting materials was confirmed, a post-treatment was performed in a conventional manner to obtain the title compound (112 mg, yield 73%).

$^1$H NMR (DMSO-de, 400 MHz) δ: 1.6-1.9 (4H, m), 2.4-3.0 (4H, m), 3.04 (1H, d, J=12 Hz), 3.2-3.4 (3H, m), 3.57 (1H, d, J=12 Hz), 6.62 (1H, d, J=8 Hz), 6.90 (1H, d, J=9 Hz), 7.16 (2H, d, J=9H), 7.27 (2H, d, J=9 Hz), 7.72 (1H, dd, J=1 Hz, 8 Hz), 7.80 (1H, dt, J=1 Hz, 8 Hz), 7.91 (1H, dt, J=1 Hz, 8 Hz), 7.97 (1H, d, J=8 Hz), 9.90 (1H, br s).

Example 153

N-[3-(2,4-Dioxo-1,2,3,4-tetrahydronaphtho[1,2-b][1,4]diazepin-5-yl)phenyl]-N-methyl-2-nitrobenzenesulfonamide By using N-[3-(2,4-dioxo-1,2,3,4-tetrahydronaphtho[1,2-b][1,4]diazepin-5-yl)phenyl]-2-nitrobenzenesulfonamide obtained in Example 150, the title compound was obtained in the same manner as that of Example 152.

$^1$H NMR (CDCl$_3$, 400 MHz) δ: 3.39 (3H, s), 3.58 (2H, s), 7.00 (1H, d, J=9 Hz), 7.1-7.2 (1H, m), 7.19 (1H, d, J=2 Hz), 7.2-7.3 (2H, in), 7.38 (1H, t, J=8 Hz), 7.4-7.7 (6H, m), 7.87 (1H, d, J=8 Hz), 8.0-8.1 (1H, m), 8.61 (1H, br s).

Example 154

4-(2,4-Dioxo-1,2,3,4,8,9,10,11-octahydronaphtho[1,2-b][1,4]diazepin-5-yl)-N-phenylbenzenesulfonamide By using 4-amino-N-phenylbenzenesulfonamide, the title compound was obtained with referring to Examples 42 and 55.

$^1$H NMR (DMSO-d$_6$, 400 MHz) δ: 1.6-1.9 (4H, m), 2.6-3.0 (4H, m), 3.03 (1H, d, J=12 Hz), 3.57 (1H, d, J=12 Hz), 6.32 (1H, d, J=8 Hz), 6.83 (1H, d, J=8 Hz), 6.9-7.1 (3H, m), 7.1-7.2 (2H, m), 7.41 (1H, d, J=8 Hz), 7.45 (1H, s), 7.56 (1H, t, J=8 Hz), 7.64 (1H, d, J=8 Hz), 9.92 (1H, s), 10.24 (1H, br s).

Example 155

N-[3-(2,4-Dioxo-1,2,3,4-tetrahydronaphtho[1,2-b][1,4]diazepin-5-yl)phenyl]-2-naphthalenesulfonamide By using 5-(3-aminophenyl)-1H-naphtho[1,2-b][1,4]diazepine-2,4(3H,5H)-dione obtained in Example 53, (1), and naphthalene-2-sulfonyl chloride, the title compound (yield 100%) was obtained in the same manner as that of Example 150.

$^1$H NMR (CDCl$_3$, 400 MHz) δ: 3.50 (2H, s), 6.34 (1H, s), 6.63 (1H, d, J=9 Hz), 7.09 (1H, d, J=8 Hz), 7.18 (2H, d, J=9 Hz), 7.30 (1H, t, J=8 Hz), 7.39 (1H, br s), 7.5-7.9 (9H, m), 8.12 (1H, d, J=8 Hz), 8.26 (1H, s), 9.20 (1H, br s).

Example 156

N-[3-(2,4-Dioxo-1,2,3,4-tetrahydronaphtho[1,2-b][1,4]diazepin-5-yl)phenyl]-1-naphthalenesulfonamide By using 5-(3-aminophenyl)-1H-naphtho[1,2-b][1,4]diazepine-2,4(3H,5H)-dione obtained in Example 53, (1), and naphthalene-1-sulfonyl chloride, the title compound (yield 100%) was obtained in the same manner as that of Example 150.

$^1$H NMR (CDCl$_3$, 400 MHz) δ: 3.48 (2H, s), 5.82 (1H, br s), 6.47 (1H, d, J=9 Hz), 7.0-7.1 (3H, m), 7.17 (1H, t, J=8 Hz), 7.29 (1H, t, J=8 Hz), 7.35 (1H, d, J=9 Hz), 7.48 (2H, t, J=8 Hz), 7.6-7.8 (3H, m), 7.81 (1H, d, J=8 Hz), 7.89 (1H, d, J=8 Hz), 8.01 (1H, dd, J=1 Hz, 8 Hz), 8.15 (1H, d, J=8 Hz), 8.56 (1H, d, J=9 Hz), 9.45 (1H, br s).

Example 157

N-[4-(2,4-Dioxo-1,2,3,4-tetrahydronaphtho[1,2-b][1,4]diazepin-5-yl)phenyl]cyclohexanesulfonamide 5-(4-Aminophenyl)-1H-naphtho[1,2-b][1,4]diazepine-2,4(3H,5H)-dione (30 mg, 0.095 mmol) obtained in Example 1, (3), and cyclohexanesulfonyl chloride (69 µL, 0.47 mmol) were treated by heating in pyridine (3 mL). A post-treatment was performed in a conventional manner to give the title compound (15 mg, yield 34%) as brown amorphous.

$^1$H NMR (CDCl$_3$, 400 MHz) δ: 1.1-1.4 (4H, m), 1.5-1.8 (2H, m), 1.8-2.0 (2H, m), 2.1-2.3 (2H, m), 3.0-3.1 (1H, m), 3.60 (2H, s), 7.01 (1H, d, J=9 Hz), 7.2-7.4 (5H, m), 7.5-7.7 (2H, m), 7.70 (1H, t, J=7 Hz), 7.85 (1H, d, J=8 Hz), 8.17 (1H, d, J=9 Hz), 9.25 (1H, br s).

Example 158

N-[4-(2,4-Dioxo-1,2,3,4-tetrahydronaphtho[1,2-b][1,4]diazepin-5-yl)phenyl]-3-pyridinesulfonamide hydrochloride 5-(4-Aminophenyl)-1H-naphtho[1,2-b][1,4]diazepine-2,4(3H,5H)-dione (30 mg, 0.095 mmol) obtained in Example 1, (3), and 3-pyridinesulfonyl chloride (20 mg, 0.11 mmol) were treated by heating in pyridine (3 mL). A post-treatment was performed in a conventional manner to give N-[4-(2,4-dioxo-1,2,3,4-tetrahydronaphtho[1,2-b][1,4]diazepin-5-yl)phenyl]-3-pyridinesulfonamide (40 mg).

This compound was dissolved in chloroform (1 mL) and methanol (1 mL), and the solution was added with a 4 M solution of hydrogen chloride in ethyl acetate (1 mL). The solvent was evaporated under reduced pressure to obtain the title compound (43 mg, yield 87%) as white amorphous.

$^1$H NMR (CD$_3$OD, 400 MHz) δ: 3.3-3.4 (1H, m), 3.68 (1H, d, J=12 Hz), 6.96 (1H, d, J=9 Hz), 7.1-7.3 (4H, m), 7.5-7.7 (3H, m), 7.8-7.9 (2H, m), 7.5-7.6 (4H, m), 8.20 (1H, d, J=8 Hz), 8.49 (1H, d, J=8 Hz), 8.87 (1H, dd, J=1 Hz, 5 Hz), 9.04 (1H, d, J=2 Hz).

Example 159

N-[4-(2,4-Dioxo-1,2,3,4-tetrahydronaphtho[1,2-b][1,4]diazepin-5-yl)phenyl]-4-isopropylbenzenesulfonamide 5-(4-Aminophenyl)-1H-naphtho[1,2-b][1,4]diazepine-2,4(3H,5H)-dione (32 mg, 0.102 mmol) obtained in Example 1, (3), and 4-isopropylbenzenesulfonyl chloride (33 mg, 0.150 mmol) were treated by heating in pyridine (2.0 mL). After the disappearance of the starting materials was confirmed, the same treatment as that of Example 145 was performed to give the title compound (29 mg, yield 58%) as white crystals.

$^1$H NMR (CDCl$_3$, 400 MHz) δ: 1.24 (6H, d, J=7 Hz), 2.95 (1H, m), 3.57 (2H, s), 6.75 (1H, br s), 6.94 (1H, d, J=9 Hz), 7.10 (2H, d, J=9 Hz), 7.14 (2H, d, J=9 Hz), 7.32 (2H, d, J=8 Hz), 7.5-7.7 (3H, m), 7.74 (2H, d, J=8 Hz), 7.86 (1H, d, J=8 Hz), 8.05 (1H, d, J=8 Hz), 8.32 (1H, br s).

Example 160

N-[4-(2,4-Dioxo-1,2,3,4-tetrahydronaphtho[1,2-b][1,4]diazepin-5-yl)phenyl]phenylmethanesulfonamide 5-(4-Aminophenyl)-1H-naphtho[1,2-b][1,4]diazepine-2,4(3H,5H)-dione (32 mg, 0.102 mmol) obtained in Example 1, (3), and phenylmethanesulfonyl chloride (29 mg, 0.150 mmol) were treated by heating in pyridine (2.0 mL). After the disappearance of the starting materials was confirmed, the same treatment as that of Example 145 was performed to give the title compound (13 mg, yield 27%) as slightly brown amorphous.

$^1$H NMR (CDCl$_3$, 400 MHz) δ: 3.60 (2H, s), 4.29 (2H, s), 6.32 (1H, s), 7.01 (1H, d, J=9 Hz), 7.14 (2H, d, J=9 Hz), 7.2-7.3 (4H, m), 7.3-7.4 (3H, m), 7.6-7.8 (3H, m), 7.87 (1H, d, J=9 Hz), 8.04 (1H, d, J=9 Hz), 8.11 (1H, br s).

Example 161

N-[4-(2,4-Dioxo-1,2,3,4-tetrahydronaphtho[1,2-b][1,4]diazepin-5-yl)phenyl]-3-pyridinesulfonamide 5-(4-Aminophenyl)-1H-naphtho[1,2-b][1,4]diazepine-2,4(3H,5H)-dione (30 mg, 0.095 mmol) obtained in Example 1, (3), and 2-thiophenesulfonyl chloride (26 mg, 0.14 mmol) were treated by heating in pyridine (3 mL). A post-treatment was performed in a conventional manner to obtain the title compound (27 mg, yield 61%) as white amorphous.

$^1$H NMR (CDCl$_3$, 400 MHz) δ: 3.59 (2H, s), 6.95 (1H, d, J=9 Hz), 7.01 (1H, dd, J=1 Hz, 5 Hz), 7.16 (4H, s), 7.38 (1H, s), 7.5-7.6 (4H, m), 7.69 (1H, t, J=7 Hz), 7.85 (1H, d, J=8 Hz), 8.14 (1H, d, J=8 Hz), 9.03 (1H, s).

Example 162

N-[4-(2,4-Dioxo-1,2,3,4-tetrahydronaphtho[1,2-b][1,4]diazepin-5-yl)phenyl]-2-naphthalenesulfonamide 5-(4-Aminophenyl)-1H-naphtho[1,2-b][1,4]diazepine-2,4(3H,5H)-dione (30 mg, 0.095 mmol) obtained in Example 1, (3), and 2-naphthalenesulfonyl chloride (32 mg, 0.14 mmol) were treated by heating in pyridine (3 mL). A post-treatment was performed in a conventional manner to give the title compound (31 mg, yield 64%) as white amorphous.

$^1$H NMR (CDCl$_3$, 400 MHz) δ: 3.56 (2H, s), 6.86 (1H, d, J=9 Hz), 7.0-7.2 (4H, m), 7.24 (1H, s), 7.5-7.7 (5H, m), 7.7-8.0 (5H, m), 8.08 (1H, d, J=9 Hz), 8.38 (1H, d, J=1 Hz), 8.76 (1H, s).

Example 163

4-(2,4-Dioxo-1,2,3,4,8,9,10,11-octahydronaphtho-[1,2-b][1,4]diazepin-5-yl)phenyl 3-bromobenzenesulfonate (1) N$^2$-(4-Methoxyphenyl)-5,6,7,8-tetrahydronapthalene-1,2-diamine By using N-(4-methoxyphenyl)-1-nitro-5,6,7,8-tetrahydronaphthalene-2-amine, the title compound was obtained in the same manner as that of Example 55, (3).

$^1$H NMR (CDCl$_3$, 400 MHz) δ: 1.7-1.8 (2H, m), 1.8-2.0 (2H, m), 2.51 (2H, t, J=6 Hz), 2.7-2.8 (2H, m), 3.75 (3H, s), 3.7-3.8 (2H, m), 4.86 (1H, br s), 6.51 (1H, d, J=8 Hz), 6.66 (2H, d, J=9 Hz), 6.7-6.8 (2H, m), 6.85 (1H, d, J=8 Hz).

(2) 5-(4-Methoxyphenyl)-8,9,10,11-tetrahydro-1H-naphtho[2,1-b][1,4]diazepine-2,4(3H,5H)-dione By using N$^2$-(4-methoxyphenyl)-5,6,7,8-tetrahydronaphthalene-1,2-diamine, the title compound was obtained in the same manner as that of Example 42, (1).

$^1$H NMR (CDCl$_3$, 400 MHz) δ: 1.7-2.1 (4H, m), 2.5-2.8 (4H, m), 3.49 (2H, s), 3.81 (3H, s), 6.72 (1H, d, J=8 Hz), 6.84 (1H, d, J=8 Hz), 6.90 (2H, dt, J=2 Hz, 9 Hz), 7.12 (2H, dt, J=2 Hz, 9 Hz), 7.44 (1H, br s).

(3) 5-(4-Hydroxyphenyl)-8,9,10,11-tetrahydro-1H-naphtho[2,1-b][1,4]diazepine-2,4(3H,5H)-dione By using 5-(4-methoxyphenyl)-8,9,10,11-tetrahydro-1H-naphtho[2,1-b][1,4]diazepine-2,4(3H,5H)-dione, the title compound was obtained in the same manner as that of Example 18.

$^1$H NMR (CDCl$_3$, 400 MHz) δ: 1.6-1.9 (4H, m), 2.5-3.0 (4H, m), 3.00 (1H, d, J=12 Hz), 3.50 (1H, d, J=12 Hz), 6.63 (1H, d, J=9 Hz), 6.76 (2H, d, J=8 Hz), 6.85 (1H, d, J=9 Hz), 6.93 (2H, d, J=9 Hz), 9.60 (1H, br s), 9.82 (1H, br s).

(4) 4-(2,4-Dioxo-1,2,3,4,8,9,10,11-octahydronaphtho-[1,2-b][1,4]diazepin-5-yl)phenyl 3-bromobenzene-sulfonate By using 5-(4-hydroxyphenyl)-8,9,10,11-tetrahydro-1H-naphtho[2,1-b][1,4]diazepine-2,4(3H,5H)-dione, the title compound was obtained in the same manner as that of Example 145.

$^1$H NMR (CDCl$_3$, 400 MHz) δ: 1.7-2.1 (4H, m), 2.6-2.8 (4H, m), 3.46 (1H, d, J=12 Hz), 3.51 (1H, d, J=12 Hz), 6.63 (1H, d, J=8 Hz), 6.87 (1H, d, J=8 Hz), 7.02 (1H, dt, J=2 Hz, 5 Hz), 7.17 (1H, dt, J=2 Hz, 5 Hz), 7.42 (1H, t, J=8 Hz), 7.62 (1H, br s), 7.7-7.9 (1H, m), 7.99 (1H, t, J=2 Hz).

Example 164

N-Benzyl-N-[4-(1-benzyl-2,4-dioxo-1,2,3,4-tetrahydronaphtho[1,2-b][1,4]diazepin-5-yl)phenyl]-2-nitrobenzenesulfonamide N-[4-(2,4-Dioxo-1,2,3,4-tetrahydronaphtho[1,2-b][1,4]diazepin-5-yl)phenyl]-2-nitrobenzenesulfonamide (110 mg, 0.22 mmol) obtained in Example 145, dimethylformamide (1 mL), potassium carbonate (91 mg, 0.66 mmol), and benzyl bromide (31 μL, 0.26 mmol) were mixed, and the mixture was stirred at room temperature for 2 hours and 30 minutes. This reaction mixture was added with water, and the mixture was extracted with ethyl acetate. The ethyl acetate layer was washed with water, and then with saturated brine, and dried over anhydrous sodium sulfate. The solvent was evaporated under reduced pressure, and the residue was purified by silica gel column chromatography (hexane/ethyl acetate=3/1 to 3/2) to give N-benzyl-N-[4-(1-benzyl-2,4-dioxo-1,2,3,4-tetrahydronaphtho[1,2-b][1,4]diazepin-5-yl)phenyl]-2-nitrobenzenesulfonamide (47 mg, yield 31%) as white amorphous, and N-benzyl-N-[4-(2,4-dioxo-1,2,3,4-tetrahydronaphtho[1,2-b][1,4]diazepin-5-yl)phenyl]-2-nitrobenzenesulfonamide (54 mg, yield 41%) as white amorphous.

$^1$H NMR (CDCl$_3$, 400 MHz) δ: 3.50 (1H, d, J=12 Hz), 3.58 (1H, d, J=12 Hz), 4.52 (1H, d, J=14 Hz), 4.82 (1H, d, J=15 Hz), 5.02 (1H, d, J=15 Hz), 6.10 (1H, d, J=14 Hz), 6.20 (2H, d, J=9 Hz), 6.66 (1H, d, J=9 Hz), 6.8-7.0 (7H, m), 7.2-7.4 (4H, m), 7.5-7.8 (7H, m), 7.89 (1H, d, J=8 Hz), 8.05 (1H, d, J=8 Hz).

Example 165

N-Benzyl-N-[4-(2,4-dioxo-1,2,3,4-tetrahydronaphtho[1,2-b][1,4]diazepin-5-yl)phenyl]-2-nitrobenzenesulfonamide 1H NMR (CDCl$_3$, 400 MHz) δ: 3.56 (2H, s), 4.96 (2H, s), 6.85 (1H, d, J=9 Hz), 7.12 (4H, s), 7.2-7.3 (5H, m), 7.5-7.7, m), 7.86 (1H, d, J=8 Hz), 8.07 (1H, d, J=8 Hz), 8.60 (1H, s).

Example 166

3-Bromo-N-[4-(2,4-dioxo-1,2,3,4-tetrahydronaphtho[1,2-b][1,4]diazepin-5-yl)phenyl]-N-methylbenzenesulfonamide By using 3-bromo-N-[4-(2,4-dioxo-1,2,3,4-tetrahydronaphtho[1,2-b][1,4]diazepin-5-yl)phenyl]benzenesulfonamide (78 mg, 0.145 mmol) obtained in Example 147, potassium carbonate (22 mg, 0.159 mmol), and methyl iodide (11 μL, 0.177 mmol), the title compound (58 mg, yield 73%) was obtained in the same manner as that of Example 152.

$^1$H NMR (CDCl$_3$, 400 MHz) δ: 3.20 (3H, s), 3.61 (2H, s), 7.01 (1H, d, J=9 Hz), 7.15 (2H, d, J=9 Hz), 7.24 (2H, d, J=9 Hz), 7.36 (1H, t, J=8 Hz), 7.52 (1H, d, J=8 Hz), 7.6-7.8 (5H, m), 7.88 (1H, d, J=8 Hz), 8.09 (1H, d, J=8 Hz), 8.58 (1H, s).

Example 167

N-[4-(2,4-Dioxo-1,2,3,4-tetrahydronaphtho[1,2-b][1,4]diazepin-5-yl)phenyl]-N-methyl-2-nitrobenzenesulfonamide By using N-[4-(2,4-dioxo-1,2,3,4-tetrahydronaphtho[1,2-b][1,4]diazepin-5-yl)phenyl]-2-nitrobenzenesulfonamide obtained in Example 145, the title compound was obtained in the same manner as that of Example 152.

$^1$H NMR (CDCl$_3$, 400 MHz) δ: 3.40 (3H, s), 3.61 (2H, s), 7.03 (1H, d, J=9 Hz), 7.2-7.3 (4H, m), 7.5-7.8 (7H, m), 7.88 (1H, d, J=8 Hz), 8.10 (1H, d, J=8 Hz), 8.65 (1H, br s).

Example 168

N-[4-(2,4-Dioxo-1,2,3,4-tetrahydronaphtho[1,2-b][1,4]diazepin-5-yl)phenyl]-N-(2-hydroxyethyl)-2-nitrobenzene sulfonamide By using N-[4-(2,4-dioxo-1,2,3,4-tetrahydronaphtho[1,2-b][1,4]diazepin-5-yl)phenyl]-2-nitrobenzenesulfonamide obtained in Example 145, and 2-iodoethanol, the title compound was obtained in the same manner as that of Example 152.

$^1$H NMR (DMSO-d$_6$, 400 MHz) δ: 3.15 (1H, d, J=12 Hz), 3.4-3.5 (2H, m), 3.70 (1H, d, J=12 Hz), 3.78 (2H, t, J=6 Hz), 4.8-4.9 (1H, m), 6.93 (1H, d, J=9 Hz), 7.22 (2H, d, J=9 Hz), 7.27 (2H, d, J=9 Hz), 7.60 (1H, t, J=7 Hz), 7.66 (1H, t, J=7 Hz), 7.7-7.8 (3H, m), 7.8-8.0 (31, m), 8.25 (1H, d, J=8 Hz), 10.90 (1H, br s).

Example 169

N-[4-(7-Chloro-2,4-dioxo-2,3,4,5-tetrahydro-1H-benzo[b][1,4]diazepin-1-yl)phenyl]benzenesulfonamide

(1) N-[4-(2-Amino-4-chlorophenylamino)phenyl]benzenesulfonamide

By using 4-chloro-2-nitrophenol and 4-amino-N-phenylbenzenesulfonamide, the title compound was obtained in the same manner as that of Example 1.

$^1$H NMR (CDCl$_3$, 400 MHz) δ: 3.81 (2H, br s), 5.06 (1H, br s), 6.14 (1H, br s), 6.56 (2H, d, J=9 Hz), 6.69 (1H, dd, J=2 Hz, 8 Hz), 6.77 (1H, d, J=2 Hz), 6.86 (2H, d, J=9 Hz), 6.96 (1H, d, J=9 Hz), 7.44 (2H, d, J=8 Hz), 7.55 (1H, d, J=8 Hz), 7.7-7.8 (2H, m).

(2) N-[4-(7-Chloro-2,4-dioxo-2,3,4,5-tetrahydro-1H-benzo[b][1,4]diazepin-1-yl)phenyl]benzenesulfonamide By using N-[4-(2-amino-4-chlorophenylamino)phenyl]benzenesulfonamide obtained above, the title compound was obtained in the same manner as that of Example 42.

$^1$H NMR (CDCl$_3$, 400 MHz) δ: 6.73 (1H, d, J=9 Hz), 7.02 (2H, d, J=9 Hz), 7.09 (2H, d, J=9 Hz), 7.13 (1H, dd, J=2 Hz, 9 Hz), 7.23 (1H, d, J=2 Hz), 7.5-7.7 (3H, m), 7.77 (2H, d, J=7 Hz), 10.47 (1H, br s), 10.60 (1H, br s).

Example 170

N-[4-(7-Bromo-2,4-dioxo-2,3,4,5-tetrahydro-1H-benzo[b][1,4]diazepin-1-yl)phenyl]benzenesulfonamide

(1) N-[4-(2-Amino-4-chlorophenylamino)phenyl]benzenesulfonamide

By using 4-bromo-2-nitrophenol and 4-amino-N-phenylbenzenesulfonamide, the title compound was obtained in the same manner as that of Example 1.

$^1$H NMR (CDCl$_3$, 400 MHz) δ: 3.73 (2H, br s), 5.12 (1H, br s), 5.92 (1H, br s), 6.54 (2H, d, J=9 Hz), 6.7-7.0 (5H, m), 7.3-7.5 (2H, m), 7.5-7.6 (1H, m), 7.6-7.8 (2H, m).

(2) N-[4-(7-Bromo-2,4-dioxo-2,3,4,5-tetrahydro-1H-benzo[b][1,4]diazepin-1-yl)phenyl]benzenesulfonamide By using N-[4-(2-amino-4-bromophenylamino)phenyl]benzenesulfonamide obtained above, the title compound was obtained in the same manner as that of Example 42.

$^1$H NMR (CD$_3$ OD, 400 MHz) δ: 3.2-3.7 (2H, m), 6.76 (1H, d, J=9 Hz), 7.06 (2H, d, J=9 Hz), 7.17 (2H, d, J=9 Hz), 7.24 (1H, dd, J=2 Hz, 9 Hz), 7.41 (1H, d, J=2 Hz), 7.4-7.6 (3H, m), 7.7-7.9 (2H, m).

Example 171

N-[4-[(2,4-Dioxo-7-(trifluoromethyl)-2,3,4,5-tetrahydro-1H-benzo[b][1,4]diazepin-1-yl)]phenyl]benzenesulfonamide

(1) N-[4-[2-Amino-4-(trifluoromethyl)phenylamino]phenyl]benzenesulfonamide

By using 2-nitro-4-trifluorophenol and 4-amino-N-phenylbenzenesulfonamide, the title compound was obtained in the same manner as that of Example 1.

$^1$H NMR (CDCl$_3$, 400 MHz) δ: 3.80 (2H, br s), 5.38 (1H, br s), 6.69 (2H, d, J=9 Hz), 6.9-7.0 (4H, m), 7.09 (1H, d, J=8 Hz), 7.42 (2H, t, J=8 Hz), 7.53 (1H, t, J=8 Hz), 7.73 (2H, d, J=8 Hz).

(2) N-[4-[2,4-Dioxo-7-(trifluoromethyl)-2,3,4,5-tetrahydro-1H-benzo[b][1,4]diazepin-1-yl]phenyl]benzenesulfonamide By using N-[4-[2-amino-4-(trifluoromethyl)phenylamino]phenyl]benzenesulfonamide obtained above, the title compound was obtained in the same manner as that of Example 42.

$^1$H NMR (DMSO-d$_6$, 400 MHz) δ: 6.91 (1H, d, J=8 Hz), 7.08 (2H, d, J=9 Hz), 7.13 (2H, d, J=9 Hz), 7.42 (1H, dd, J=2 Hz, 9 Hz), 7.5-7.7 (4H, m), 7.7-7.8 (2H, in), 10.50 (1H, br s), 10.71 (1H, s).

Example 172

N-[4-(2,4-Dioxo-2,3,4,5-tetrahydro-1H-benzo[b][1,4]diazepin-1-yl)phenyl]benzenesulfonamide N-[4-(7-Chloro-2,4-dioxo-2,3,4,5-tetrahydro-1H-benzo[b][1,4]diazepin-1-yl)phenyl]benzenesulfonamide (28 mg, 0.06 mmol) obtained in Example 169 was dissolved in methanol (0.6 mL), tetrahydrofuran (0.6 mL), and water (0.6 mL), the solution was added with ammonium formate (38 mg, 0.6 mmol), and the mixture was stirred at room temperature for 16 hours. After completion of the reaction, the reaction mixture was filtered through Cerite, and the solvent was evaporated under reduced pressure. The obtained residue was added with water, the mixture was extracted with chloroform, and the organic layer was dried over anhydrous sodium sulfate. The solvent was evaporated under reduced pressure, and the residue was purified by silica gel column chromatography (chloroform/methanol=100/1) to obtain the title compound (19 mg, yield 77%).

$^1$H NMR (CD$_3$ OD, 400 MHz) δ: 3.2-3.7 (2H, m), 6.84 (1H, d, J=7 Hz), 7.0-7.3 (7H, m), 7.4-7.6 (3H, m), 7.79 (2H, dd, J=2 Hz, 7 Hz), 7.8-79 (1H, m).

Example 173

1-(2-Chlorophenyl)-N-[4-(2,4-dioxo-1,2,3,4-tetrahydronaphtho[1,2-b][1,4]diazepin-5-yl)phenyl]methanesulfonamide By using 5-(4-aminophenyl)-1H-naphtho[1,2-b][1,4]diazepine-2,4(3H,5H)-dione obtained in Example 1, (3), and (2-chlorophenyl)methanesulfonyl chloride, the title compound (yield 72%) was obtained in the same manner as that of Example 145.

$^1$H NMR (CDCl$_3$, 400 MHz) δ: 3.56 (2H, s), 4.63 (2H, s), 6.96 (1H, d, J=9 Hz), 7.1-7.3 (6H, m), 7.42 (1H, t, J=4 Hz), 7.5-7.7 (4H, m), 7.83 (1H, d, J=8 Hz), 8.17 (1H, d, J=9 Hz), 9.39 (1H, br s).

Example 174

1-(3-Bromophenyl)-N-[4-(2,4-dioxo-1,2,3,4-tetrahydronaphtho[1,2-b][1,4]diazepin-5-yl)phenyl]methanesulfonamide By using 5-(4-aminophenyl)-1H-naphtho[1,2-b][1,4]diazepine-2,4(3H,5H)-dione obtained in Example 1, (3), and (3-bromophenyl)methanesulfonyl chloride, the title compound (yield 92%) was obtained in the same manner as that of Example 145.

$^1$H NMR (CDCl$_3$, 400 MHz) δ: 3.57 (2H, s), 4.30 (2H, s), 6.99 (1H, d, J=9 Hz), 7.1-7.2 (5H, m), 7.42 (2H, s), 7.52 (1H, s), 7.5-7.7 (2H, m), 7.70 (1H, t, J=8 Hz), 7.83 (1H, d, J=8 Hz), 8.17 (1H, d, J=8 Hz), 9.33 (1H, br s).

Example 175

N-[4-(2,4-Dioxo-1,2,3,4-tetrahydronaphtho[1,2-b][1,4]diazepin-5-yl)phenyl]-2-trifluoromethylbenzenesulfonamide By using 5-(4-aminophenyl)-1H-naphtho[1,2-b][1,4]diazepine-2,4(3H,5H)-dione obtained in Example 1, (3), and 2-(trifluoromethyl)benzene-1-sulfonyl chloride, the title compound (yield 94%) was obtained in the same manner as that of Example 145.

$^1$H NMR (CDCl$_3$, 400 MHz) δ: 3.56 (2H, s), 6.89 (1H, d, J=9 Hz), 7.1-7.2 (4H, m), 7.29 (1H, br s), 7.5-7.7 (5H, m), 7.84 (1H, d, J=8 Hz), 7.38 (1H, d, J=8 Hz), 8.11 (1H, d, J=8 Hz), 8.13 (1H, d, J=8 Hz), 9.15 (1H, br s).

Example 176

N-[4-(7-Bromo-6-methyl-2,4-dioxo-2,3,4,5-tetrahydro-1H-benzo[b][1,4]diazepin-1-yl)phenyl]benzenesulfonamide N-[4-(2-Amino-4-bromo-3-methylphenylamino)phenyl]benzenesulfonamide (100 mg, 0.231 mmol) synthesized by using 4-bromo-3-methyl-2-nitrophenol was treated with malonyl chloride (22 µL, 0.226 mmol) in THF to give the title compound (12 mg, yield 10%).

$^1$H NMR (CDCl$_3$, 400 MHz) δ: 2.52 (3H, s), 3.48 (2H, s), 6.60 (1H, d, J=9 Hz), 6.95 (1H, s), 7.0-7.1 (4H, m), 7.30 (1H, d, J=9 Hz), 7.46 (2H, t, J=8 Hz), 7.56 (1H, t, J=7 Hz), 7.80 (2H, d, J=8 Hz), 7.96 (1H, s).

Example 177

1-(2-Chlorophenyl)-N-[4-(2,4-dioxo-1,2,3,4,8,9,10,11-octahydronaphtho[1,2-b][1,4]diazepin-5-yl)phenyl]methanesulfonamide 5-(4-Aminophenyl)-1,2,3,4,8,9,10,11-octahydronaphtho[1,2-b][1,4]diazepine-2,4(3H,5H)-dione (64 mg, 0.2 mmol) obtained in Example 55, (6), and 2-chlorophenylmethanesulfonyl chloride (50 mg, 0.22 mmol) were treated by heating in pyridine (0.4 mL). A post-treatment was performed in a conventional manner to give the title compound (80 mg, yield 80%) as pale brown powder.

$^1$H NMR (DMSO-d$_6$, 400 MHz) δ: 1.6-1.9 (4H, m), 2.5-2.8 (3H, m), 2.8-3.0 (1H, m), 3.02 (1H, d, J=12 Hz), 3.54 (1H, d, J=12 Hz), 4.65 (2H, e), 6.59 (1H, d, J=9 Hz), 6.90 (1H, d, J=8 Hz), 7.06 (2H, d, J=8 Hz), 7.19 (2H, d, J=8 Hz), 7.3-7.4 (2H, m), 7.4-7.5 (2H, m), 9.99 (1H, s), 10.17 (1H, br s).

Example 178

3-Bromo-N-[4-(2,4-dioxo-1,2,3,4,8,9,10,11-octahydronaphtho[1,2-b][1,4]diazepin-5-yl)phenyl]benzenesulfonamide 5-(4-Aminophenyl)-1,5,8,9,10,11-hexahydronaphtho[1,2-b][1,4]diazepine-2,4-dione (65 mg, 202 mmol) obtained in Example 55, and 3-bromobenzenesulfonyl chloride (78 mg, 0.305 mmol) were treated by heating in pyridine (2.0 mL). After the disappearance of the starting materials was confirmed, the same treatment as that of Example 145 was performed to obtain the title compound (47 mg, yield 43%) as white crystals.

$^1$H NMR (CDCl$_3$, 400 MHz) δ: 1.6-2.1 (4H, m), 2.5-2.9 (4H, m), 3.4-3.5 (2H, br), 6.61 (1H, d, J=8 Hz), 6.84 (1H, d, J=8 Hz), 7.01 (2H, d, J=9 Hz), 7.09 (2H, d, J=9 Hz), 7.33 (1H, t, J=8 Hz), 7.6-7.8 (2H, m), 7.89 (1H, s).

Example 179

N-[4-(2,4-Dioxo-1,2,3,4,8,9,10,11-octahydronaphtho[1,2-b][1,4]diazepin-5-yl)phenyl]-3-methoxybenzenesulfonamide 5-(4-Aminophenyl)-1,5,8,9,10,11-hexahydronaphtho[1,2-b][1,4]diazepine-2,4-dione (65 mg, 0.202 mmol) obtained in Example 55, and 3-methoxybenzenesulfonyl chloride (63 mg, 0.305 mmol) were treated by heating in pyridine (2.0 mL). After the disappearance of the starting materials was confirmed, the same treatment as that of Example 145 was performed to give the title compound (48 mg, yield 48%) as white crystals.

$^1$H NMR (CDCl$_3$, 400 MHz) δ: 1.8-2.1 (4H, m), 2.5-2.8 (4H, m), 3.47 (1H, d, J=11 Hz), 3.49 (1H, d, J=11 Hz), 3.76 (3H, s), 6.60 (1H, d, J=8 Hz), 6.77 (1H, s), 6.83 (1H, d, J=8 Hz), 7.0-7.2 (5H, m), 7.22 (1H, t, J=1 Hz), 7.3-7.4 (2H, m), 7.58 (1H, s).

Example 180

1-(2-Bromophenyl)-N-[4-(2,4-dioxo-1,2,3,4-tetrahydronaphtho[1,2-b][1,4]diazepin-5-yl)phenyl]methanesulfonamide By using 5-(4-aminophenyl)-1H-naphtho[1,2-b][1,4]diazepine-2,4(3H,5H)-dione obtained in Example 1, (3), and (2-bromophenyl)methanesulfonyl chloride, the title compound (yield 46%) was obtained in the same manner as that of Example 145.

$^1$H NMR (CDCl$_3$, 400 MHz) δ: 3.59 (2H, s), 4.69 (2H, s), 6.69 (1H, s), 6.97 (1H, d, J=9 Hz), 7.1-7.2 (5H, m), 7.30 (1H, t, J=8 Hz), 7.49 (1H, d, J=8 Hz), 7.53 (1H, d, J=8 Hz), 7.5-7.8 (3H, m), 7.87 (1H, d, J=8 Hz), 8.07 (1H, d, J=8 Hz), 8.43 (1H, br s).

Example 181

N-[4-(2,4-Dioxo-1,2,3,4-tetrahydronaphtho[1,2-b][1,4]diazepin-5-yl)phenyl]-1-(2-methylphenyl)methanesulfonamide By using 5-(4-aminophenyl)-1H-naphtho[1,2-b][1,4]diazepine-2,4(3H,5H)-dione obtained in Example 1, (3), and o-tolyl-methanesulfonyl chloride, the title compound (yield 37%) was obtained in the same manner as that of Example 145.

$^1$H NMR (CDCl$_3$, 400 MHz) δ: 2.37 (3H, s), 3.60 (2H, s), 4.47 (2H, s), 6.45 (1H, br s), 7.00 (1H, d, J=9 Hz), 7.1-7.3 (8H, m), 7.5-7.7 (2H, m), 7.71 (1H, t, J=8 Hz), 7.87 (1H, d, J=8 Hz), 8.05 (1H, d, J=8 Hz), 8.24 (1H, br s).

Example 182

N-[4-(2,4-Dioxo-1,2,3,4-tetrahydronaphtho[1,2-b][1,4]diazepin-5-yl)phenyl]-1-(2-nitrophenyl) methanesulfonamide By using 5-(4-aminophenyl)-1H-naphtho[1,2-b][1,4]diazepine-2,4(3H,5H)-dione obtained in Example 1, (3), and (2-nitrophenyl)methanesulfonyl chloride, the title compound (yield 41%) was obtained in the same manner as that of Example 145.

$^1$H NMR (CDCl$_3$, 400 MHz) δ: 3.59 (2H, s), 5.00 (2H, s), 6.89 (1H, s), 7.00 (1H, d, J=9 Hz), 7.13 (2H, d, J=9 Hz), 7.18 (2H, d, J=9 Hz), 7.48 (1H, d, J=8 Hz), 7.55 (1H, d, J=8 Hz), 7.5-7.7 (3H, m), 7.71 (1H, t, J=8 Hz), 7.86 (1H, d, J=8 Hz), 7.99 (1H, d, J=8 Hz), 8.07 (1H, d, J=8 Hz), 8.44 (1H, s).

Example 183

N-[4-(2,4-Dioxo-1,2,3,4-tetrahydronaphtho[1,2-b][1,4]diazepin-5-yl)phenyl]-2-phenylethanesulfonamide By using 5-(4-aminophenyl)-1H-naphtho[1,2-b][1,4]diazepine-2,4(3H,5H)-dione obtained in Example 1, (3), and 2-phenylethanesulfonyl chloride, the title compound (yield 22%) was obtained in the same manner as that of Example 145.
$^1$H NMR (CDCl$_3$, 400 MHz) δ: 3.16 (2H, t, J=8 Hz), 3.41 (2H, t, J=8 Hz), 3.60 (2H, s), 6.20 (1H, s), 6.98 (1H, d, J=9 Hz), 7.02 (2H, d, J=9 Hz), 7.1-7.4 (7H, m), 7.5-7.7 (2H, m), 7.70 (1H, t, J=8 Hz), 7.86 (1H, d, J=8 Hz), 8.05 (1H, d, J=8 Hz), 8.24 (1H, s).

Example 184

1-(2,3-Dichlorophenyl)-N-[4-(2,4-dioxo-1,2,3,4,8,9,10,11-octahydronaphtho[1,2-b][1,4]diazepin-5-yl)phenyl]methanesulfonamide By using 5-(4-aminophenyl)-1,5,8,9,10,11-hexahydronaphtho[1,2-b][1,4]diazepine-2,4-dione (32 mg, 0.100 mmol) obtained in Example 55, and (2,3-dichlorophenyl)methanesulfonyl chloride (31 mg, 0.119 mmol), the title compound (50 mg, yield 92%) was obtained in the same manner as that of Example 145.
$^1$H NMR (DMSO-d$_6$, 400 MHz) δ: 1.6-1.9 (4H, m), 2.4-2.8 (3H, m), 2.8-3.0 (1H, m), 3.02 (1H, d, J=12 Hz), 3.54 (1H, d, J=12 Hz), 4.74 (2H, s), 6.60 (1H, d, J=8 Hz), 6.90 (1H, d, J=8 Hz), 7.07 (2H, d, J=9 Hz), 7.19 (2H, d, J=9 Hz), 7.36 (1H, t, J=8 Hz), 7.43 (1H, dd, J=1 Hz, J=8 Hz), 7.62 (1H, d, J=8 Hz), 9.87 (1H, s), 10.21 (1H, br s).

Example 185

1-(2-Chlorophenyl)-N-[4-(2,4-dioxo-7-methoxy-1H-benzo[1,2-b][1,4]diazepin-1-yl)phenyl]methanesulfonamide By using 1-(4-aminophenyl)-7-methoxy-1H-1,5-benzodiazepine-2,4(3H,5H)-dione (65 mg, 0.22 mmol), and 2-chlorobenzylsulfonyl chloride (74 μL, 0.33 mmol), the title compound (23 mg, yield 13%) was obtained in the same manner as that of Example 145.
$^1$H NMR (CDCl$_3$, 400 MHz) δ: 3.51 (2H, s), 3.82 (3H, s), 4.64 (2H, s), 6.62 (1H, d, J=2 Hz), 6.68 (1H, dd, J=2 Hz, 9 Hz), 6.80 (1H, d, J=9 Hz), 6.94 (1H, br s), 7.09 (2H, d, J=9 Hz), 7.12 (2H, d, J=9 Hz), 7.2-7.5 (4H, m), 8.37 (1H, br s).

Example 186

1-(2-Chlorophenyl)-N-[4-(2,4-dioxo-7-hydroxy-1H-benzo[1,2-b][1,4]diazepin-1-yl)phenyl]methanesulfonamide By using 1-(2-chlorophenyl)-N-[4-(2,4-dioxo-7-methoxy-1H-benzo[1,2-b][1,4]diazepin-1-yl)phenyl]methanesulfonamide (83 mg, 0.17 mmol), the title compound (14 mg, yield 17%) was obtained in the same manner as that of Example 18.
$^1$H NMR (DMSO-d$_6$, 400 MHz) δ: 3.0-3.1 (1H, m), 3.5-3.6 (1H, m), 4.64 (2H, s), 6.5-6.7 (3H, m), 7.03 (2H, d, J=9 Hz), 7.17 (2H, d, J=9 Hz), 7.3-7.5 (4H, m), 9.73 (1H, s), 10.12 (1H, br s), 10.40 (1H, s).

Example 187

1-(4-Chlorophenyl)-N-[4-(2,4-dioxo-1,2,3,4-tetrahydronaphtho[1,2-b][1,4]diazepin-5-yl)phenyl]methanesulfonamide By using 5-(4-aminophenyl)-1H-naphtho[1,2-b][1,4]diazepine-2,4(3H,5H)-dione obtained in Example 1, (3), and 4-chlorobenzylsulfonyl chloride, the title compound (yield 56%) was obtained in the same manner as that of Example 145.
$^1$H NMR (CDCl$_3$, 400 MHz) δ: 3.60 (2H, s), 4.35 (2H, s), 6.50 (1H, br s), 7.00 (1H, d, J=9 Hz), 7.15 (2H, d, J=9 Hz), 7.2-7.3 (4H, m), 7.33 (2H, d, J=8 Hz), 7.6-7.7 (2H, m), 7.71 (1H, t, J=8 Hz), 7.87 (1H, d, J=8 Hz), 8.07 (1H, d, J=8 Hz), 8.39 (1H, s).

Example 188

1-(2-Chlorophenyl)-N-[4-(2,4-dioxo-1,2,3,4-tetrahydronaphtho[1,2-b][1,4]diazepin-5-yl)benzyl]methanesulfonamide By using 5-[4-(aminomethyl)phenyl]-1H-naphtho[2,1-b][1,4]diazepine-2,4(3H,5H)-dione obtained in Example 45, (4), and 2-chlorobenzylsulfonyl chloride, the title compound was obtained in the same manner as that of Example 145.
$^1$H NMR (DMSO-d$_6$, 400 MHz) δ: 3.14 (1H, d, J=12 Hz), 3.70 (1H, d, J=12 Hz), 4.18 (2H, s), 4.50 (2H, s), 6.95 (1H, d, J=9 Hz), 7.20 (2H, d, J=8 Hz), 7.3-7.4 (4H, m), 7.4-7.5 (2H, m), 7.58 (1H, t, J=7 Hz), 7.6-7.7 (2H, m), 7.8-8.0 (2H, m), 8.25 (1H, d, J=8 Hz), 10.85 (1H, br s).

Example 189

1-(2-Chlorophenyl)-N-[4-(2,4-dioxo-1,2,3,4-tetrahydronaphtho[1,2-b][1,4]diazepin-5-yl)-2-methoxyphenyl]methanesulfonamide By using 5-(4-amino-3-methoxyphenyl)-1H-naphtho[2,1-b][1,4]diazepine-2,4(3H,5H)-dione obtained in Example 63, (3), and 2-chlorobenzylsulfonyl chloride, the title compound was obtained in the same manner as that of Example 145.
$^1$H NMR (CDCl$_3$, 400 MHz) δ: 3.60 (2H, s), 3.77 (3H, s), 4.62 (2H, s), 6.74 (1H, dd, J=2 Hz, 9 Hz), 6.83 (1H, d, J=2 Hz), 6.90 (1H, s), 7.03 (1H, d, J=9 Hz), 7.2-7.4 (3H, m), 7.46 (1H, dd, J=2 Hz, 7 Hz), 7.49 (1H, d, J=9 Hz), 7.5-7.7 (2H, m), 7.6-7.8 (1H, m), 7.87 (1H, d, J=8 Hz), 8.10 (1H, d, J=8 Hz), 8.60 (1H, s).

Example 190

1-(2-Chlorophenyl)-N-[4-(2,4-dioxo-1,2,34-tetrahydronaphtho[1,2-b][1,4]diazepin-5-yl)-2-hydroxyphenyl]methanesulfonamide By using 1-(2-chlorophenyl)-N-[4-(2,4-dioxo-1,2,3,4-tetrahydronaphtho[1,2-b][1,4]diazepin-5-yl)-2-methoxyphenyl]methanesulfonamide obtained in Example 189, the title compound was obtained in the same manner as that of Example 18.
$^1$H NMR (DMSO-d$_6$, 400 MHz) δ: 3.13 (1H, d, J=12 Hz), 3.69 (1H, d, J=12 Hz), 4.64 (2H, s), 6.61 (1H, d, J=8 Hz), 6.77 (1H, s), 7.02 (1H, d, J=9 Hz), 7.19 (1H, d, J=9 Hz), 7.2-7.4 (2H, m), 7.4-7.8 (5H, m), 7.93 (1H, d, J=8 Hz), 8.24 (1H, d, J=8 Hz), 9.09 (1H, br s), 10.22 (1H, br s), 10.90 (1H, s).

Example 191

1-(2,6-Dichlorophenyl)-N-[4-(2,4-dioxo 1,2,3,4,8,9,10,11-octahydronaphtho[1,2-b][1,4]diazepin-5-yl)phenyl]methanesulfonamide By using 5-(4-aminophenyl)-1,5,8,9,10,11-hexahydronaphtho[1,2-b][1,4]diazepine-2,4-dione (50 mg, 0.156 mmol) obtained in Example 55, and 2,6-dichlorobenzylsulfonyl chloride (81 mg, 0.312 mmol), the title compound (25 mg, yield 29%) was obtained in the same manner as that of Example 145.

$^1$H NMR (DMSO-$d_6$, 400 MHz) δ: 1.6-1.9 (4H, m), 2.5-2.8 (3H, m), 2.8-3.0 (1H, m), 3.02 (1H, d, J=12 Hz), 3.54 (1H, d, J=12 Hz), 4.80 (2H, s), 6.57 (1H, d, J=8 Hz), 6.89 (1H, d, J=8 Hz), 7.07 (2H, d, J=9 Hz), 7.22 (2H, d, J=9 Hz), 7.38 (1H, dd, J=1 Hz, J=8 Hz), 7.49 (2H, d, J=8 Hz), 9.87 (1H, s), 10.35 (1H, s).

Example 192

1-(2-Chlorophenyl)-N-[4-(2,4-dioxo-6-methyl-1H-benzo[1,2-b][1,4]diazepin-1-yl)phenyl]methanesulfonamide By using 1-(4-aminophenyl)-6-methyl-1H-1,5-benzodiazepine-2,4(3H,5H)-dione (20 mg, 0.071 mmol), and 2-chlorobenzylsulfonyl chloride (19 mg, 0.084 mmol), the title compound (32 mg, yield 96%) was obtained in the same manner as that of Example 145.

$^1$H NMR (DMSO-$d_6$, 400 MHz) δ: 2.38 (3H, s), 3.04 (1H, d, J=12 Hz), 3.55 (1H, d, J=12 Hz), 4.66 (2H, s), 6.68 (1H, d, J=8 Hz), 7.0-7.1 (3H, m), 7.14 (1H, d, J=7 Hz), 7.20 (2H, d, J=9 Hz), 7.3-7.4 (2H, m), 7.4-7.5 (2H, m), 10.01 (1H, s), 10.18 (1H, br s).

Example 193

1-(2-Chlorophenyl)-N-[4-(2,4-dioxy-1,2,3,4-tetrahydronaphtho[1,2-b][1,4]diazepin-5-yl)propyl]methanesulfonamide (1) 5-(4-Aminopropyl)-1H-naphtho[1,2-b][1,4]diazepine-2,4(3H,5H)-dione By using N-(tert-butoxycarbonyl)-1,4-diaminopropane, the title compound was obtained with referring to Examples 1 and 42.

$^1$H NMR (CDCl$_3$+CD$_3$OD, 400 MHz) δ: 1.5-1.8 (2H, m), 2.5-9.27 (2H, m, 3.38 (1H, J=12 Hz), 3.45 (1H, d, J=12 Hz), 3.7-3.9 (1H, m), 4.5-4.7 (1H, m), 7.50 (1H, d, J=9 Hz), 7.60 (1H, t, J=8 Hz), 7.68 (1H, t, J=8 Hz), 7.79 (1H, d, J=9 Hz), 7.90 (1H, d, J=8 Hz), 8.01 (1H, d, J=8 Hz).

(2) 1-(2-Chlorophenyl)-N-[4-(2,4-dioxy-1,2,3,4-tetrahydronaphtho[1,2-b][1,4]diazepin-5-yl)propyl]methanesulfonamide By using 5-(4-aminopropyl)-1H-naphtho[1,2-b][1,4]diazepine-2,4(3H,5H)-dione (20 mg, 0.063 mmol) obtained above, and 2-chlorobenzylsulfonyl chloride (17 mg, 0.076 mmol), the title compound (10 mg, yield 35%) was obtained in the same manner as that of Example 145.

$^1$H NMR (CDCl$_3$, 400 MHz) δ: 1.5-1.6 (1H, m), 1.7-1.8 (1H, m), 2.7-3.0 (2H, m), 3.37 (1H, d, J=12 Hz), 3.42 (1H, d, J=12 Hz), 3.7-3.8 (1H, m), 4.43 (2H, s), 4.4-4.6 (1H, m), 4.98 (1H, t, J=7 Hz), 7.2-7.3 (2H, m), 7.3-7.4 (1H, m), 7.4-7.5 (2H, m), 7.61 (1H, t, J=7 Hz), 7.69 (1H, t, J=7 Hz), 7.79 (1H, d, J=9 Hz), 7.90 (1H, d, J=8 Hz), 8.06 (1H, d, J=8 Hz), 8.56 (1H, br s).

Example 194

1-(2-Chlorophenyl)-N-[2-(2,4-dioxo-1,2,3,4-tetrahydronaphtho[1,2-b][1,4]diazepin-5-yl)ethyl]methanesulfonamide 5-[2-(tert-Butoxycarbonyl)aminoethyl]-1H-naphtho[1,2-b][1,4]diazepine-2,4(3H,5H)-dione (10 mg, 0.027 mol) obtained in Example 72, (3) was treated with trifluoroacetic acid in the same manner as that of Example 72, (4) to give a solution of 5-(2-aminoethyl)-1H-naphtho[1,2-b][1,4]diazepine-2,4(3H,5H)-dione in saturated aqueous sodium hydrogencarbonate and dichloromethane. This solution was added with 2-chlorobenzylsulfonyl chloride (7 mg, 0.03 mol) with stirring under ice cooling, and the mixture was stirred for 1 hour under ice cooling, and then at room temperature for 2 hours. This reaction mixture was added with water, and the dichloromethane layer was washed with saturated brine, and dried over anhydrous sodium sulfate. The solvent was evaporated, and the residue was recrystallized from ethyl acetate/hexane to obtain the title compound (7 mg, yield 56%) as pale brown crystals.

$^1$H NMR (DMSO-$d_6$, 400 MHz) δ: 3.02 (1H, d, J=12 Hz), 3.0-3.2 (2H, m), 3.46 (1H, d, J=12 Hz), 3.8-3.9 (1H, m), 4.1-4.2 (1H, m), 4.4-4.5 (2H, m), 7.3-7.4 (2H, m), 7.4-7.6 (3H, m), 7.6-7.7 (3H, m), 7.88 (1H, d, J=9 Hz), 7.99 (1H, d, J=7 Hz), 8.20 (1H, d, J=8 Hz), 10.67 (1H, s).

Example 195

N-[4-(2,4-Dioxo-1,2,3,4,8,9,10,11-octahydronaphtho[1,2-b][1,4]diazepin-5-yl)phenyl]-1-(2-iodophenyl)methanesulfonamide By using 5-(4-aminophenyl)-1,2,3,4,8,9,10,11-octahydronaphtho[1,2-b][1,4]diazepine-2,4(3H,5H)-dione obtained in Example 55, (6), and 2-iodobenzylsulfonyl chloride, the title compound was obtained in the same manner as that of Example 145.

$^1$H NMR (CDCl$_3$, 400 MHz) δ: 1.7-2.1 (4H, m), 2.5-2.8 (4H, m), 3.48 (1H, s), 3.48 (1H, s), 4.67 (2H, s), 6.6-6.7 (1H, m), 6.65 (1H, d, J=8 Hz), 6.85 (1H, d, J=8 Hz), 7.02 (1H, t, J=8 Hz), 7.11 (4H, s), 7.33 (1H, t, J=7 Hz), 7.47 (1H, d, J=8 Hz), 7.59 (1H, br s), 7.81 (1H, d, J=8 Hz).

Example 196

1-(2-Chlorophenyl)-N-[4-(2,4-dioxo-1,2,3,4,8,9,10,11-octahydronaphtho[1,2-b][1,4]diazepin-5-yl)phenyl]-N-methylmethanesulfonamide (1) 5-[4-(Methylamino)phenyl]-8,9,10,11-tetrahydro-1H-naphtho[1,2-b][1,4]diazepine-2,4(3H,5H)-dione N-[4-(2,4-Dioxo-1,2,3,4,8,9,10,11-octahydro-naphtho[1,2-b][1,4]diazepin-5-yl)phenyl]-N-methyl-2-nitrobenzenesulfonamide (99 mg, 0.190 mmol) obtained in Example 152, thiophenol (23 μL, 0.228 mmol), potassium carbonate (79 mg, 0.570 mmol), and anhydrous DMF were mixed, and the mixture was stirred at room temperature for 16 hours. After the disappearance of the starting materials was confirmed, a post-treatment was performed in a conventional manner to give the title compound (35 mg, yield 55%).

$^1$H NMR (CDCl$_3$, 400 MHz) δ: 1.6-2.1 (4H, m), 2.5-2.8 (4H, m), 2.83 (3H, s), 3.47 (2H, s), 3.81 (1H, br s), 6.58 (2H, d, J=9 Hz), 6.77 (1H, d, J=9 Hz), 6.83 (1H, d, J=9 Hz), 6.99 (2H, d, J=8 Hz), 7.43 (1H, br s).

(2) 1-(2-Chlorophenyl)-N-[4-(2,4-dioxo-1,2,3,4,8,9,10,11-octahydronaphtho[1,2-b][1,4]diazepin-5-yl)phenyl]-N-methylmethanesulfonamide By using 5-[4-(methylamino)phenyl]-8,9,10,11-tetrahydro-1H-naphtho[1,2-b][1,4]diazepine-2,4(3H,5H)-dione mentioned above, the title compound was obtained in the same manner as that of E ample 145.

$^1$H NMR (CDCl$_3$, 400 MHz) δ: 1.7-2.1 (4H, m), 2.5-2.8 (4H, m), 3.48 (1H, s), 3.48 (1H, s), 4.56 (2H, s), 6.64 (1H, d, J=8 Hz), 6.86 (1H, d, J=8 Hz), 7.11 (2H, d, J=9 Hz), 7.19 (2H, d, J=9 Hz), 7.2-7.3 (2H, m), 7.41 (1H, dd, J=1 Hz, 8 Hz), 7.48 (1H, s), 7.53 (1H, dd, J=2 Hz, 7 Hz).

Example 197

1-(2-Chlorophenyl)-N-[4-(2-oxo-2,3-dihydro-1H-naphtho[1,2-e][1,4]diazepin-5-yl)phenyl]methanesulfonamide By using 5-(4-aminophenyl)-H-naphtho[1,2-e][1,4]diazepin-2(3H)-one (30 mg, 0.1 mmol) obtained in Example 64, (1), and (2-chlorophenyl)methanesulfonyl chloride (34 mg, 0.15 mmol), the title compound (20 mg, yield 27%) was obtained in the same manner as that of Example 145.

$^1$H NMR (DMSO-d$_6$, 500 MHz) δ: 3.84 (1H, d, J=10 Hz), 4.61 (1H, d, J=10 Hz), 4.74 (2H, s), 7.26 (2H, d, J=8 Hz), 7.35 (1H, d, J=9 Hz), 7.4-7.5 (2H, m), 7.5-7.6 (4H, m), 7.7-7.8 (2H, m), 7.83 (1H, d, J=9 Hz), 8.10 (1H, d, J=9 Hz), 8.43 (1H, d, J=9 Hz), 10.48 (1H, br s), 10.89 (1H, s).

Example 198

1-[(2-Trifluoromethyl)phenyl]-N-[4-(2,4-dioxo-1,2,3,4-tetrahydronaphtho[1,2-b][1,4]diazepin-5-yl)phenyl]phenyl-N-methylmethanesulfonamide (1) 5-[4-(Methylamino)phenyl]-1H-naphtho[1,2-b][1,4]diazepine-2,4(3H,5H)-dione By using N-[4-(2,4-dioxo-1,2,3,4-tetrahydronaphtho[1,2-b][1,4]diazepin-5-yl)phenyl]-2-nitrobenzenesulfonamide obtained in Example 145, the title compound was obtained with referring to Examples 151 and 152.

$^1$H NMR (CDCl$_3$, 400 MHz) δ: 2.85 (3H, s), 3.55 (1H, d, J=12 Hz), 3.60 (1H, d, J=12 Hz), 3.87 (1H, br s), 6.61 (2H, d, J=9 Hz), 7.05 (2H, d, J=9 Hz), 7.11 (1H, d, J=9 Hz), 7.5-7.7 (3H, m), 7.84 (1H, d, J=8 Hz), 8.04 (1H, d, J=8 Hz), 8.31 (1H, s).

(2) 1-[(2-Trifluoromethyl)phenyl]-N-[4-(2,4-dioxo-1,2,3,4-tetrahydronaphtho[1,2-b][1,4]diazepin-5-yl)phenyl]phenyl-N-methylmethanesulfonamide 5-[4-(Methylamino)phenyl]-1H-naphtho[1,2-b][1,4]diazepine-2,4(3H,5H)-dione (30 mg, 0.091 mmol) mentioned above, and 2-(trifluoromethyl)benzylsulfonyl chloride (35 mg, 0.137 mmol) were treated by heating in pyridine (2.0 mL). After the disappearance of the starting materials was confirmed, the same treatment as that of Example 145 was performed to give the title compound (25 mg, yield 50%) as white crystals.

$^1$H NMR (DMSO-d$_6$, 400 MHz) δ: 3.17 (1H, d, J=12 Hz), 3.73 (1H, d, J=12 Hz), 4.69 (2H, s), 6.96 (1H, d, J=9 Hz), 7.27 (2H, d, J=8 Hz), 7.49 (2H, d, J=8 Hz), 7.6-7.8 (6H, m), 7.79 (1H, d, J=8 Hz), 7.95 (1H, d, J=8 Hz), 8.27 (1H, d, J=9 Hz), 10.95 (1H, br s).

Example 199

1-(2-Ethylphenyl)-N-[4-(2,4-dioxo-1,2,3,4-tetrahydronaphtho[1,2-b][1,4]diazepin-5-yl)phenyl]phenyl-N-methylmethanesulfonamide 5-[4-(Methylamino)phenyl]-1H-naphtho[1,2-b][1,4]diazepine-2,4(3H,5H)-dione (40 mg, 0.121 mmol) obtained in Example 198, (1), and 2-ethylbenzylsulfonyl chloride (132 mg, 0.605 mmol) were treated by heating in pyridine (1.0 mL). After the disappearance of the starting materials was confirmed, the same treatment as that of Example 145 was performed to obtain the title compound (10 mg, yield 16%) as white crystals.

$^1$H NMR (CD$_3$OD, 400 MHz) δ: 1.16 (3H, t, J=8 Hz), 2.69 (2H, q, J=8 Hz), 3.3-3.4 (4H, m), 3.72 (1H, d, J=12 Hz), 4.50 (2H, s), 7.05 (1H, d, J=9 Hz), 7.1-7.2 (1H, m), 7.2-7.3 (4H, m), 7.3-7.4 (1H, m), 7.4-7.5 (2H, m), 7.5-7.6 (1H, m), 7.6-7.7 (2H, m), 7.90 (1H, d, J=8 Hz), 8.22 (1H, d, J=8 Hz).

Example 200

1-(2,3-Dimethylphenyl)-N-[4-(2,4-dioxo-1,2,3,4-tetrahydronaphtho[1,2-b][1,4]diazepin-5-yl)phenyl]phenyl-N-methylmethanesulfonamide 5-[4-(Methylamino)phenyl]-1H-naphtho[1,2-b][1,4]diazepine-2,4(3H,5H)-dione (40 mg, 0.121 mmol) obtained in Example 198, (1), and 2,3-dimethylbenzylsulfonyl chloride (132 mg, 0.605 mmol) were treated by heating in pyridine (1.0 mL). After the disappearance of the starting materials was confirmed, the same treatment as that of Example 145 was performed to give the title compound (20 mg, yield 32%) as pale yellow crystals.

$^1$H NMR (DMSO-d$_6$, 400 MHz) δ: 2.17 (3H, s), 2.24 (3H, s), 3.15 (1H, d, J=12 Hz), 3.29 (3H, s), 3.71 (1H, d, J=12 Hz), 4.59 (2H, s), 6.96 (1H, d, J=9 Hz), 7.0-7.1 (1H, m), 7.1-7.2 (2H, m), 7.2-7.3 (2H, m), 7.3-7.4 (2H, m), 7.60 (1H, t, J=7 Hz), 7.67 (1H, t, J=7 Hz), 7.72 (1H, d, J=9 Hz), 7.92 (1H, t, J=8 Hz), 8.25 (1H, d, J=8 Hz), 10.93 (1H, br s).

Example 201

2-(2-Chlorophenyl)-N-[4-(2,4-dioxo-1,2,3,4-tetrahydronaphtho[1,2-b][1,4]diazepin-5-yl)phenyl]phenyl-N-methylethanesulfonamide 5-[4-(Methylamino)phenyl]-1H-naphtho[1,2-b][1,4]diazepine-2,4(3H,5H)-dione (40 mg, 0.121 mmol) obtained in Example 198, (1), and (2-chlorophenyl)ethanesulfonyl chloride (132 mg, 0.605 mmol) were treated by heating in pyridine (1.0 mL). After the disappearance of the starting materials was confirmed, the same treatment as that of Example 145 was performed to give the title compound (13 mg, yield 20%) as white crystals.

¹H NMR (DMSO-d₆, 400 MHz) δ: 3.15 (1H, d, J=12 Hz), 3.3-3.5 (2H, m), 3.71 (1H, d, J=12 Hz), 6.96 (1H, d, J=9 Hz), 7.2-7.3 (4H, m), 7.4-7.5 (2H, m), 7.51 (2H, d, J=9 Hz), 7.5-7.6 (1H, m), 7.6-7.7 (2H, m), 7.91 (1H, d, J=7 Hz), 824 (1H, d, J=9 Hz), 10.92 (1H, br s).

Example 202

1-(2-Nitrophenyl)-N-[4-(2,4-dioxo-1,2,3,4-tetrahydronaphtho[1,2-b][1,4]diazepin-5-yl)phenyl]phenyl-N-methylmethanesulfonamide 5-[4-(Methylamino)phenyl]-1H-naphtho[1,2-b][1,4]diazepine-2,4(3H,5H)-dione (80 mg, 0.240 mmol) obtained in Example 198, (1), and 2-nitrobenzylsulfonyl chloride (112 mg, 0.480 mmol) were treated by heating in pyridine (3.0 mL). After the disappearance of the starting materials was confirmed, the same treatment as that of Example 145 was performed to obtain the title compound (40 mg, yield 31%) as white crystals.

¹H NMR (CD₃OD, 400 MHz) δ: 3.33 (3H, s), 3.36 (1H, d, J=12 Hz), 3.72 (1H, d, J=12 Hz), 5.00 (2H, s), 7.06 (1H, d, J=8 Hz), 7.26 (2H, d, J=9 Hz), 7.41 (2H, d, J=9 Hz), 7.5-7.6 (3H, m), 7.6-7.7 (3H, m), 7.90 (1H, d, J=8 Hz), 8.02 (1H, d, J=8 Hz), 8.21 (1H, d, J=8 Hz).

Example 203

1-(2-Aminophenyl)-N-[4-(2,4-dioxo-1,2,3,4-tetrahydronaphtho[1,2-b][1.4]diazepin-5-yl)phenyl]phenyl-N-methylmethanesulfonamide 1-(2-Nitrophenyl)-N-[4-(2,4-dioxo-1,2,3,4-tetrahydronaphtho[1,2-b][1,4]diazepin-5-yl)phenyl]phenyl-N-methylmethanesulfonamide (33 mg, 0.062 mmol) mentioned above was dissolved in a mixed solvent of dichloromethane (0.5 mL) and ethyl acetate (1.5 mL), then the solution was added with tin(II) chloride dihydrate (70 mg, 0.310 mmol), and the mixture was stirred at 30° C. for 16 hours. After the disappearance of the starting materials was confirmed, the reaction mixture was treated in a conventional manner to give the title compound (26 mg, yield 31%) as white crystals.

¹H NMR (CD₃OD, 400 MHz) δ: 3.27 (3H, s), 3.29 (1H, d, J=12 Hz), 3.65 (1H, d, J=12 Hz), 4.39 (2H, s), 6.66 (1H, d, J=7 Hz), 6.73 (1H, d, J=7 Hz), 6.97 (1H, d, J=9 Hz), 7.0-7.1 (2H, m), 7.17 (1H, dd, J=2 Hz, 7 Hz), 7.35 (2H, dd, J=2 Hz, 7 Hz), 7.55 (1H, t, J=7 Hz), 7.5-7.7 (2H, m), 7.84 (1H, d, J=8 Hz), 8.16 (1H, d, J=8 Hz).

Example 204

1-(2-Dimethylaminophenyl)-N-[4-(2,4-dioxo-1,2,3,4-tetrahydronaphtho[1,2-b][1,4]diazepin-5-yl)phenyl]phenyl-N-methylmethanesulfonamide 1-(2-Aminophenyl)-N-[4-(2,4-dioxo-1,2,3,4-tetrahydronaphtho[1,2-b][1,4]diazepin-5-yl)phenyl]phenyl-N-methylmethanesulfonamide (18 mg, 0.036 mmol) mentioned above, zinc chloride (12 mg, 0.090 mmol), formalin (2.7 mg, 0.090 mmol), and sodium cyanoborohydride (5.7 mg, 0.090 mmol) were dissolved in methanol, and the solution was refluxed by heating for 5 hours under a nitrogen atmosphere. After the disappearance of the starting materials was confirmed, the reaction mixture was treated in a conventional manner to give the title compound (8 mg, yield 42%) as white crystals.

¹H NMR (CD₃OD, 400 MHz) δ: 2.54 (6H, s), 3.20 (3H, s), 3.28 (1H, d, J=12 Hz), 3.65 (1H, d, J=12 Hz), 4.61 (2H, s), 6.9-7.0 (2H, m), 7.1-7.2 (3H, m), 7.2-7.3 (3H, m), 7.45 (1H, dd, J=1 Hz, 8 Hz), 7.5-7.6 (1H, m), 7.6-7.7 (2H, m), 7.84 (1H, d, J=8 Hz), 8.15 (1H, d, J=8 Hz).

Example 205

5-[4-[(Pyridin-4-yl)carbonylamino]phenyl]-1H-naphtho[1,2-b][1,4]diazepine-2,4(3H,5H)-dione hydrochloride By using 5-(4-aminophenyl)-1H-naphtho[1,2-b][1,4]diazepine-2,4(3H,5H)-dione (63 mg, 0.2 mmol) obtained in Example 1, (3), and isonicotinoyl chloride hydrochloride (71 mg, 0.4 mmol), 5-[4-[(pyridin-4-yl)carbonylamino]phenyl]-1H-naphtho[1,2-b][1,4]diazepine-2,4(3H,5H)-dione (43 mg, yield 50%) was obtained as pale green crystals in the same manner as that of Example 1, (4).

This compound was dissolved in chloroform (3 mL) and methanol (1 mL), the solution was added with 4 M hydrogen chloride in ethyl acetate (0.05 mL), and the solvent was evaporated under reduced pressure. The residue was washed with ethyl acetate to obtain the title compound (43 mg, yield 94%) as yellow crystals.

¹H NMR (DMSO-d₆, 400 MHz) δ: 3.17 (1H, d, J=12 Hz), 3.72 (1H, d, J=12 Hz), 7.02 (1H, d, J=9 Hz), 7.26 (2H, d, J=9 Hz), 7.60 (1H, t, J=8 Hz), 7.68 (1H, t, J=8 Hz), 7.71 (1H, d, J=9 Hz), 7.86 (2H, d, J=9 Hz), 7.93 (1H, d, J=8 Hz), 7.97 (2H, d, J=6 Hz), 8.27 (1H, d, J=8 Hz), 8.85 (2H, d, J=6 Hz), 10.72 (1H, s), 10.91 (1H, s).

Example 206

5-[4-[2-[(Pyridin-3-yl)oxy]acetylamino]phenyl]-1H-naphtho[1,2-b][1,4]diazepine-2,4(3H,5H)-dione hydrochloride 5-(4-Aminophenyl)-1H-naphtho[1,2-b][1,4]diazepine-2,4(3H,5H)-dione (32 mg, 0.1 mmol) obtained in Example 1, (3), pyridin-3-yloxyacetic acid hydrochloride (23 mg, 0.12 mmol), WSC.HCl (23 mg, 0.12 mmol), and dry pyridine (1 mL) were mixed, and the mixture was stirred at room temperature for 4 hours. This reaction mixture was added with water, and the mixture was extracted with ethyl acetate. The ethyl acetate layer was washed with saturated brine, and dried over anhydrous sodium sulfate. The solvent was evaporated under reduced pressure, and the residue was washed with ethyl acetate and hexane to give 5-[4-[2-[(pyridin-3-yl)oxy]acetylamino]phenyl]-1H-naphtho[1,2-b][1,4]diazepine-2,4(3H,5H)-dione (41 mg, yield 91%) as yellow crystals.

This compound was dissolved in chloroform (3 mL) and methanol (1 mL), and the solution was added with 4 M hydrogen chloride in ethyl acetate (0.05 mL). The solvent was evaporated under reduced pressure, and the residue was washed with ethyl acetate to give the title compound (30 mg, yield 67%) as red crystals.

¹H NMR (DMSO-d₆, 400 MHz) δ: 3.15 (1H, d, J=12 Hz), 3.70 (1H, d, J=12 Hz), 4.98 (2H, s), 6.98 (1H, d, J=9 Hz), 7.20 (2H, d, J=8 Hz), 7.6-7.8 (6H, m), 7.92 (2H, d, J=8 Hz), 7.93 (1H, d, J=8 Hz), 8.26 (1H, d, J=8 Hz), 8.42 (1H, d, J=5 Hz), 8.63 (1H, s), 10.43 (1H, s), 10.89 (1H, s).

Example 207

5-[4-[(Pyridin-3-yl)carbonylamino]phenyl]-1H-naphtho[1,2-b][1,4]diazepine-2,4(3H,5H)-dione hydrochloride By using 5-(4-aminophenyl)-1H-naphtho[1,2-b][1,4]diazepine-2,4(3H,5H)-dione (95 mg, 0.3 mmol) obtained in Example 1, (3), and nicotinoyl chloride hydrochloride (64 mg, 0.36 mmol), 5-[4-[(pyridin-3-yl)carbonylamino]phenyl]-1H-naphtho[1,2-b][1,4]diazepine-2,4(3H,5H)-dione (116 mg, yield 92%) was obtained as white crystals in the same manner as that of Example 1, (4).

This compound was dissolved in chloroform (6 mL) and methanol (6 mL), the solution was added with 4 M hydrogen chloride in ethyl acetate (0.1 mL), and the solvent was evaporated under reduced pressure to obtain the title compound (129 mg) as pale yellow powder.

$^1$H NMR (DMSO-$d_6$, 400 MHz) δ: 3.17 (11H, d, J=12 Hz), 3.72 (1H, d, J=12 Hz), 7.02 (1H, d, J=9 Hz), 7.26 (2H, d, J=9 Hz), 7.60 (1H, t, J=7 Hz), 7.6-7.8 (31H, m), 7.87 (2H, d, J=9 Hz), 7.93 (1H, d, J=8 Hz), 8.27 (1H, d, J=8 Hz), 8.50 (1H, d, J=8 Hz), 8.85 (1H, d, J=4 Hz), 9.21 (1H, d, J=1 Hz), 10.72 (1H, s), 10.91 (1H, s).

Example 208

5-[4-[(2-Methylpyridin-3-yl)carbonylamino]phenyl]-1H-naphtho[1,2-b][1,4]diazepine-2,4(3H,5H)-dione hydrochloride 2-Methylnicotinic acid (55 mg, 0.4 mmol) was suspended in dry dichloromethane (4 mL), the suspension was added with DMF (0.08 mL) and oxalyl dichloride (0.05 mL, 0.6 mmol), and the mixture was stirred at room temperature for 21 hours. The solvent was evaporated under reduced pressure, and the residue was concentrated twice from dry dichloromethane (1 mL) under reduced pressure. The resultant was added with 5-(4-aminophenyl)-1H-naphtho[1,2-b][1,4]diazepine-2,4(3H,5H)-dione (63 mg, 0.2 mmol) obtained in Example 1, (3), dry tetrahydrofuran (4 mL), and triethylamine (0.11 mL), and the mixture was stirred at room temperature for 24 hours. This reaction mixture was added with saturated aqueous sodium hydrogencarbonate, and the mixture was extracted with ethyl acetate. The ethyl acetate layer was washed with saturated brine, and dried over anhydrous sodium sulfate. The solvent was evaporated under reduced pressure, and the residue was purified by silica gel column chromatography (methanol/chloroform=1/20) to give 5-[4-[(2-methylpyridin-3-yl)carbonylamino]phenyl]-1H-naphtho[1,2-b][1,4]diazepine-2,4(3H,5H)-dione (68 mg, yield 80%) as white crystals.

This compound was dissolved in chloroform (7 mL) and methanol (7 mL), the solution was added with 4 M hydrogen chloride in ethyl acetate (0.08 mL), and the solvent was evaporated under reduced pressure. The residue was washed with ethyl acetate to give the title compound (60 mg, yield 81%) as pale brown crystals.

$^1$H NMR (DMSO-$d_6$, 400 MHz) δ: 2.69 (3H, s), 3.16 (1H, d, J=12 Hz), 3.72 (1H, d, J=12 Hz), 7.02 (1H, d, J=9 Hz), 7.25 (2H, d, J=9 Hz), 7.5-7.7 (3H, m), 7.71 (1H, d, J=9 Hz), 7.80 (2H, d, J=9 Hz), 7.93 (1H, d, J=8 Hz), 8.2-8.3 (2H, m), 8.71 (1H, d, J=5 Hz), 10.77 (1H, s), 10.90 (1H, s).

Example 209

5-[4-[(2-Chloropyridin-3-yl)carbonylamino]phenyl]-1H-naphtho[1,2-b][1,4]diazepine-2,4(3H,5H)-dione 2-Chloronicotinic acid (63 mg, 0.4 mmol) was suspended in dry dichloromethane (2 mL), the suspension was added with DMF (0.08 mL) and oxalyl dichloride (0.05 mL, 0.6 mmol), and the mixture was stirred at room temperature for 20 hours. The solvent was evaporated under reduced pressure, and the residue was concentrated twice from dry dichloromethane (1 mL) under reduced pressure. The resultant was added with 5-(4-aminophenyl)-1H-naphtho[1,2-b][1,4]diazepine-2,4(3H,5H)-dione (63 mg, 0.2 mmol) obtained in Example 1, (3), dry tetrahydrofuran (4 mL) and triethylamine (0.11 mL), and the mixture was stirred at room temperature for 22 hours, and then refluxed by heating for 4 hours. This reaction mixture was added with saturated aqueous sodium hydrogencarbonate, and the mixture was extracted with ethyl acetate. The ethyl acetate layer was washed with saturated brine, and dried over anhydrous sodium sulfate. The solvent was evaporated under reduced pressure, and the residue was recrystallized from chloroform to obtain the title compound (56 mg, yield 60%) as pale yellow crystals.

1H NMR (DMSO-$d_6$, 400 MHz) δ: 3.16 (1H, d, J=12 Hz), 3.72 (1H, d, J=12 Hz), 7.02 (1H, d, J=9 Hz), 7.24 (2H, d, J=9 Hz), 7.58 (1H, dd, J=5 Hz, 8 Hz), 7.60 (1H, t, J=7 Hz), 7.67 (1H, t, J=7 Hz), 7.71 (1H, d, J=9 Hz), 7.77 (2H, d, J=9 Hz), 7.93 (1H, d, J=7 Hz), 8.09 (1H, dd, J=2 Hz, 8 Hz), 8.26 (1H, d, J=8 Hz), 8.54 (1H, dd, J=2 Hz, 5 Hz), 10.80 (1H, s), 10.90 (1H, s).

Example 210

5-[4-[2-[(Pyridin-2-yl)oxy]acetylamino]phenyl]-1H-naphtho[1,2-b][1,4]diazepine-2,4(3H,5H)-dione 5-(4-Aminophenyl)-1H-naphtho[1,2-b][1,4]diazepine-2,4(3H,5H)-dione (32 mg, 0.1 mmol) obtained in Example 1, (3), 2-(pyridin-2-yloxy)acetic acid (23 mg, 0.15 mmol), HATU (23 mg, 0.15 mmol), triethylamine (0.04 mL), and dry dimethylformamide (1 mL) were mixed, and the mixture was stirred at room temperature for 2 hours. This reaction mixture was added with water, and the mixture was extracted with ethyl acetate. The ethyl acetate layer was washed with saturated brine, and dried over anhydrous sodium sulfate. The solvent was evaporated under reduced pressure, and the residue was purified by silica gel column chromatography (methanol/chloroform=1/50) to give the title compound (22 mg, yield 49%) as pale yellow crystals.

$^1$H NMR (DMSO-$d_6$, 400 MHz) δ: 3.14 (1H, d, J=12 Hz), 3.69 (1H, d, J=12 Hz), 4.92 (2H, s), 6.9-7.1 (3H, m), 7.17 (2H, d, J=9 Hz), 7.59 (1H, t, J=7 Hz), 7.6-7.8 (5H, m), 7.91 (1H, d, J=8 Hz), 8.13 (1H, dd, J=2 Hz, 5 Hz), 8.25 (1H, d, J=9 Hz), 10.24 (1H, s), 10.88 (1H, s).

Example 211

5-[4-[[4-(Trifluoromethyl)pyridin-3-yl]carbonylamino]phenyl]-1H-naphtho[1,2-b][1,4]diazepine-2,4(3H,5H)-dione By using 4-(trifluoromethyl)nicotinic acid (76 mg, 0.4 mmol) and 5-(4-aminophenyl)-1H-naphtho[1,2-b][1,4]diazepine-2,4(3H,5H)-dione (63 mg, 0.2 mmol) obtained in Example 1, (3), the title compound was obtained in the same manner as that of Example 149 (59 mg, yield 60%) as white crystals.

$^1$H NMR (DMSO-d$_6$, 400 MHz) δ: 3.17 (1H, d, J=12 Hz), 3.72 (1H, d, J=12 Hz), 7.03 (1H, d, J=9 Hz), 7.25 (2H, d, J=9 Hz), 7.60 (1H, t, J=7 Hz), 7.67 (1H, t, J=7 Hz), 7.71 (1H, d, J=9 Hz), 7.76 (2H, d, J=9 Hz), 7.91 (1H, d, J=5 Hz), 7.93 (1H, d, J=8 Hz), 8.26 (1H, d, J=8 Hz), 8.99 (1H, d, J=5 Hz), 9.03 (1H, s), 10.91 (1H, s), 10.92 (1H, s).

Example 212

5-[4-[(2-Chloropyridin-3-yl)carbonylamino]phenyl]-1H-[1,4]diazepino[2,3-f]isoquinoline-2,4(3H,5H)-dione (1) 5-Nitroisoquinolin-6-yl trifluoromethanesulfonate 6-Methoxy-5-nitroisoquinoline [WO2007-109182] (1.02 g, 5 mmol), and 48% hydrobromic acid (20 mL) were mixed, an mixture was refluxed by heating for 16 hours. The reaction mixture was cooled to room temperature, and then the precipitated crystals were collected by filtration, washed with water, combined with secondary crystals, and dried under reduced pressure to give yellow crystals (0.64 g).

This crude 5-nitro-6-isoquinolinol hydrobromide (0.64 g) was dissolved in dry dichloromethane (6.4 mL) and triethylamine (1 mL), the solution was added with trifluoromethanemethanesulfonic anhydride (0.58 mL, 3.54 mmol), and the mixture was stirred at room temperature for 15 hours. This reaction mixture was added with water, and the dichloromethane layer was washed with saturated brine, and dried over anhydrous sodium sulfate. The solvent was evaporated, and the residue was purified by silica gel column chromatography (ethyl acetate/hexane=1/2) to obtain the title compound (0.26 g, yield 14%) as pale yellow crystals.

$^1$H NMR (CDCl$_3$, 400 MHz) δ: 7.71 (1H, d, J=9 Hz), 7.80 (1H, d, J=6 Hz), 8.32 (1H, d, J=9 Hz), 8.82 (1H, d, J=6 Hz), 9.44 (1H, s).

(2) tert-Butyl [4-[(5-nitroisoquinolin-6-yl)amino]phenyl]carbamate

By using 5-nitroisoquinolin-6-yl trifluoromethanesulfonate (258 mg, 0.8 mmol), and tert-butyl 4-aminophenylcarbamate (250 mg, 1.2 mmol), the title compound (80 mg, yield 26%) was obtained as red crystals in the same manner as that of Example 1, (1).

$^1$H NMR (DMSO-d$_6$, 400 MHz) δ: 1.49 (9H, s), 7.2-7.3 (3H, m), 7.54 (2H, d, J=9 Hz), 8.07 (1H, d, J=9 Hz), 8.14 (1H, d, J=6 Hz), 8.55 (1H, d, J=6 Hz), 9.08 (1H, s), 9.48 (1H, s), 9.98 (1H, s).

(3) Ethyl 3-[[6-[[4-[(tert-butoxycarbonyl)amino]phenyl]amino]isoquinolin-5-yl]amino]-3-oxopropionate By using tert-butyl [4-[(5-nitroisoquinolin-6-yl)amino]phenyl]carbamate (80 mg, 0.21 mmol), a crude product of tert-butyl [4-[(5-aminoisoquinolin-6-yl)amino]phenyl]carbamate was obtained as dark brown oil in the same manner as that of Example 1, (2).

By using this crude product, the title compound (60 mg, yield 61%) was obtained as yellow powder in the same manner as that of Example 1, (3).

$^1$H NMR (CDCl$_3$, 400 MHz) δ: 1.30 (3H, t, J=7 Hz), 1.51 (9H, s), 3.63 (2H, s), 4.26 (2H, q, J=7 Hz), 6.84 (1H, s), 6.95 (1H, s), 7.02 (2H, d, J=9 Hz), 7.28 (2H, d, J=9 Hz), 7.42 (1H, d, J=9 Hz), 7.51 (1H, d, J=6 Hz), 7.64 (1H, d, J=9 Hz), 8.34 (1H, d, J=6 Hz), 8.93 (1H, s), 9.28 (1H, s).

(4) 5-(4-Aminophenyl)-1H-[1,4]diazepino[2,3-f]isoquinoline-2,4(3H,5H)-dione

By using ethyl 3-[[6-[[4-[(tert-butoxycarbonyl)amino]phenyl]amino]isoquinolin-5-yl]amino]-3-oxopropionate (59 mg, 0.13 mmol), the title compound (7 mg, yield 17%) was obtained as pale brown powder in the same manner as that of Example 1, (3).

$^1$H NMR (CDCl$_3$, 400 MHz) δ: 3.53 (1H, d, J=11 Hz), 3.64 (1H, d, J=11 Hz), 3.80 (2H, s), 6.71 (2H, d, J=9 Hz), 7.01 (2H, d, J=9 Hz), 7.23 (1H, d, J=9 Hz), 7.71 (1H, d, J=9 Hz), 7.82 (1H, d, J=6 Hz), 8.19 (1H, s), 8.71 (1H, d, J=6 Hz), 9.22 (1H, s).

(5) 5-[4-[(2-Chloropyridin-3-yl)carbonylamino]phenyl]-1H-[1,4]diazepino[2,3-f]isoquinoline-2,4(3H,5H)-dione By using 2-chloronicotinic acid (32 mg, 0.2 mmol), and 5-(4-aminophenyl)-1H-[1,4]diazepino[2,3-f]isoquinoline-2,4(3H,5H)-dione (6 mg, 0.02 mmol), the title compound (8 mg, yield 85%) was obtained as pale brown powder in the same manner as that of Example 149.

$^1$H NMR (DMSO-d$_6$, 400 MHz) δ: 3.19 (1H, d, J=12 Hz), 3.75 (1H, d, J=12 Hz), 7.16 (1H, d, J=9 Hz), 7.26 (2H, d, J=8 Hz), 7.58 (1H, dd, J=5 Hz, 7 Hz), 7.78 (2H, d, J=8 Hz), 7.88 (1H, d, J=9 Hz), 8.09 (1H, d, J=8 Hz), 8.13 (1H, d, J=6 Hz), 8.54 (1H, d, J=5 Hz), 8.64 (1H, d, J=6 Hz), 9.27 (1H, s), 10.80 (1H, s), 11.01 (1H, bs).

Example 213

5-[4-[(2-Chloropyridin-3-yl)carbonylamino]phenyl]-8,9,10,11-tetrahydro-1H-[1,4]diazepino[2,3-f]isoquinoline-2,4(3H,5H)-dione 5-[4-[(2-Chloropyridin-3-yl)carbonylamino]phenyl]-1H-[1,4]diazepino[2,3-f]isoquinoline-2,4(3H,5H)-dione (10 mg, 0.022 mmol) was dissolved in acetic acid (0.4 mL), the solution was added with sodium borohydride (64 mg, 0.11 mmol), the mixture was stirred at room temperature for 2 hours, and then further added with sodium borohydride (64 mg, 0.11 mmol), and the mixture was stirred at room temperature for 2 hours. This reaction mixture was added with water, made basic with sodium carbonate, and extracted three times with chloroform, and the organic layer was dried over anhydrous sodium sulfate. The solvent was evaporated under reduced pressure, and the residue was washed with ethyl acetate to give the title compound (7 mg, yield 68%) as pale brown crystals.

$^1$H NMR (DMSO-d$_6$, 400 MHz) δ: 2.8-3.0 (2H, m), 3.0-3.1 (2H, m), 3.05 (1H, d, J=11 Hz), 3.56 (1H, d, J=11 Hz), 3.79 (1H, s), 6.67 (1H, d, J=8 Hz), 6.84 (1H, d, J=8 Hz), 7.16 (2H, d, J=9 Hz), 7.57 (1H, dd, J=5 Hz, 8 Hz), 7.73 (2H, d, J=9 Hz), 7.78 (2H, d, J=8 Hz), 8.08 (1H, dd, J=2 Hz, 8 Hz), 8.54 (1H, dd, J=2 Hz, 5 Hz), 8.64 (1H, d, J=6 Hz), 9.93 (1H, s), 10.75 (1H, s).

Example 214

5-[4-[(2-Isopropylbenzoyl)amino]phenyl]-1H-naphtho[1,2-b][1,4]diazepine-2,4(3H,5H)-dione By using 5-(4-aminophenyl)-1H-naphtho[1,2-b][1,4]diazepine-2,4(3H,5H)-dione (32 mg, 0.10 mmol) obtained in Example 1, (3), and 2-isopropylbenzoyl chloride (0.20 mmol), the title compound (16 mg, yield 35%) was obtained in the same manner as that of Example 1, (4).

$^1$H NMR (CDCl$_3$, 400 MHz) δ: 1.23 (6H, d, J=6 Hz), 3.16 (1H, d, J=12 Hz), 3.2-3.3 (1H, m), 3.70 (1H, d, J=12 Hz), 7.03 (1H, d, J=9 Hz), 7.20 (2H, d, J=9 Hz), 7.2-7.5 (4H, m), 7.5-7.8 (3H, m), 7.81 (2H, d, J=8 Hz), 7.92 (1H, d, J=8 Hz), 8.26 (1H, d, J=8 Hz), 10.51 (1H, s), 10.88 (1H, s).

Example 215

(P2X4 Receptor Antagonist Activity)
(Test Method)

The P2X4 receptor antagonist activity of the compounds of the present invention was measured as follows. The 1321N1 cells stably expressing human P2X4 receptor were inoculated on a 96-well plate, cultured under the conditions of 37° C. and 5% CO$_2$ for 24 hours, and then used for intracellular calcium measurement. Fura-2 AM, which is a calcium fluorescent indicator, was used for the intracellular calcium measurement. Fura-2 AM dissolved in an assay buffer was added to the cells, the cells were left standing at room temperature for 45 minutes so that Fura-2 AM was incorporated into the cells, and then the plate was subjected to the fluorescence measurement. The treatment of the cells with each test substance was performed 15 minutes before the addition of ATP, and inflow of calcium into the cells as a response induced by the addition of ATP was measured over time by using a microplate reader. The ratio of fluorescence values obtained with excitation lights of 340 nm and 380 nm was used as an index of the change of intracellular calcium level, and the inhibition activity of the test substance was calculated on the basis of the comparison with the value obtained in the absence of the test substance (control).

(Test Results)

TABLE 22

| Test compound | Inhibitory activity IC$_{50}$ (μM) |
| --- | --- |
| Example 13 | 0.54 |
| Example 20 | 1.2 |
| Example 48 | 0.43 |
| Example 106 | 1.8 |
| Example 173 | 0.064 |
| Example 196 | 0.97 |
| Example 197 | 0.44 |
| Paroxetine | 4.0 |

As clearly seen from the results shown in Table 22, it was found that the compounds of the present invention have superior P2X4 receptor antagonist activity.

Example 216

In the same manner as that of Example 215, the compounds of Examples 118, and 208 to 210 were tested for the P2X4 receptor antagonist activity, and the results shown in Table 23 were obtained.

TABLE 23

| Test compound | Inhibitory activity IC$_{50}$ (μM) |
| --- | --- |
| Example 118 | 1.1 |
| Example 208 | 1.3 |
| Example 209 | 0.94 |
| Example 210 | 1.4 |

As clearly seen from the results shown in Table 23, it was found that the compounds of the present invention described in the examples have superior P2X4 receptor antagonist activity.

Example 217

(Analgesic Activity)

The analgesic activity of the compounds of the present invention was measured by the following method.

Preparation of Neuropathic, Pain Model (Modified Chung Model)

Neurogenic pain model (modified Chung model) was prepared according to the description of Non-patent document 9. More specifically, under isoflurane anesthesia, back hair of rats was extensively shaved, the shaved parts were wiped with rubbing alcohol, the rats were fixed on an incubator in the abdominal position, and the skins were cut and opened along the dorsal median line on the upper and lower sides of the sacroiliac bone. The left lateral paravertebral muscle was separated in the sacral region, and then the ligament was separated. The sacroiliae rim and the upper part thereof were cut and opened along the pyramid, the L5 nerve was ligated, and the nerve was cut on the peripheral side. The operative wound was sutured, and infection was prevented by intraperitoneal injection of Luinesin after the operation.

The pain threshold value (paw withdrawal threshold (g)) was calculated according to the up down method by stimulating the sole with a von Frey filament (Stoelting Co., TOUCH-TEST SENSORY EVALUATOR) and determining presence or absence of withdrawal response. The rats that showed a 50% pain threshold value of 5 g or lower in the von Frey filament test were determined to have allodynia.

EVALUATION METHOD AND RESULTS

The efficacy was evaluated by orally administering the compounds of Examples 48 and 118 using an oral feeding needle to rats on the day 9 after the modified Chung operation, and observing the influence on the pain threshold value determined by the von Frey filament test. As a result, oral administration of 50 mg/kg of the compounds of Examples 48 and 118 raised the pain threshold value of the diseased limb, and it was observed that there was a significant difference compared with the result for the vehicle group.

The invention claimed is:

1. A method of treating pain which comprising administrating a therapeutically an effective amount of a compound having the following formula (I), or a pharmacologically acceptable salt thereof to a subject in need thereof:

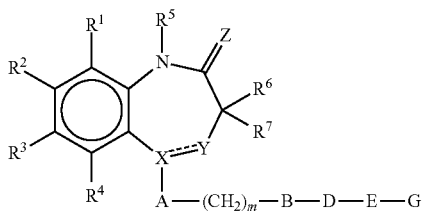

(I)

wherein, $R^1$ and $R^2$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, a carboxamido group having 2 to 8 carbon atoms, carboxyl group, an alkanoyl group having 2 to 8 carbon atoms, an alkoxycarbonyl group which has 1 to 8 carbon atoms in the alkoxy moiety, a phenyl group which may be substituted, a pyridyl group which may be substituted, or an aralkyl group which has 6 to 10 carbon atoms in the aryl moiety and 1 to 8 carbon atoms in the alkylene moiety, wherein the phenyl group and the pyridyl group may be substituted with a halogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms, or $R^1$ and $R^2$ may bind together to form a condensed ring selected from naphthalene ring, quinoline ring, isoquinoline ring, tetrahydronaphthalene ring, indane ring, tetrahydroquinoline ring, and tetrahydroisoquinoline ring together with the benzene ring to which they bind, and the ring constituted by $R^1$ and $R^2$, bound to each other, together with the carbon atoms to which $R^1$ and $R^2$ bind may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, a carboxamido group having 2 to 8 carbon atoms, carboxyl group, an alkanoyl group having 2 to 8 carbon atoms, an alkoxycarbonyl group which has 1 to 8 carbon atoms in the alkoxy moiety, and an aralkyl group which has 6 to 10 carbon atoms in the aryl moiety and 1 to 8 carbon atoms in the alkylene moiety, $R^3$ and $R^4$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, a carboxamido group having 2 to 8 carbon atoms, carboxyl group, an alkanoyl group having 2 to 8 carbon atoms, an alkoxycarbonyl group which has 1 to 8 carbon atoms in the alkoxy moiety, or an aralkyl group which has 6 to 10 carbon atoms in the aryl moiety and 1 to 8 carbon atoms in the alkylene moiety, $R^5$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group which has 6 to 10 carbon atoms in the aryl moiety and 1 to 8 carbon atoms in the alkylene moiety, $R^6$ and $R^7$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group, X represents N, Y represents C(=O), the double line consisting of the solid line and the broken line represents a single bond, Z represents oxygen atom, A represents benzene ring, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group which has 6 to 10 carbon atoms in the aryl moiety and 1 to 8 carbon atoms in the alkylene moiety, phenyl group, or pyridyl group, B represents $N(R^8)C(=O)$, wherein $R^8$ represents hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group which has 6 to 10 carbon atoms in the aryl moiety and 1 to 8 carbon atoms in the alkylene moiety, D and E represents atomic bond, G represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an alkanoyl group having 2 to 8 carbon atoms, methylenedioxy group, carboxyl group, an alkylsulfinyl group having 1 to 6 carbon atoms, an alkylthio group having 1 to 6 carbon atoms, an alkylsulfonyl group having 1 to 6 carbon atoms, an aralkyl group which has 6 to 10 carbon atoms in the aryl moiety and 1 to 8 carbon atoms in the alkylene moiety, a phenyl group which may be substituted, a pyridyl group which may be substituted, an imidazolyl group which may be substituted, an oxazolyl group which may be substituted, and a thiazolyl group which may be substituted, wherein the substituents on the phenyl group, the pyridyl group, the imidazolyl group, the oxazolyl group, and the thiazolyl group are chosen from a halogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms, and m represents an integer of 0.

2. The method according to claim 1, wherein $R^1$ and $R^2$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, a phenyl group which may be substituted, a pyridyl group which may be substituted, or an aralkyl group which has 6 to 10 carbon atoms in the aryl moiety and 1 to 8 carbon atoms in the alkylene moiety, wherein the phenyl group and the pyridyl group may be substituted with a halogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms.

3. The method according to claim 1, wherein $R^1$ and $R^2$ bind together to form naphthalene ring, or tetrahydronaphthalene ring together with the benzene ring to which they bind, and the benzene ring or cyclohexene ring formed by $R^1$, $R^2$, bound to each other, together with the carbon atoms to which $R^1$ and $R^2$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, a carboxamido group having 2 to 8 carbon atoms, carboxyl group, an alkanoyl group having 2 to 8 carbon atoms, an alkoxycarbonyl group which has 1 to 8 carbon atoms in the alkoxy moiety, and an aralkyl group which has 6 to 10 carbon atoms in the aryl moiety and 1 to 8 carbon atoms in the alkylene moiety.

4. The method according to claim 1, wherein $R^1$ and $R^2$ bind together to form naphthalene ring together with the benzene ring to which they bind, and the benzene ring formed by $R^1$ and $R^2$, bound to each other, together with the carbon atoms to which $R^1$ and $R^2$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, and amino group.

5. The method according to claim 1, wherein $R^3$ and $R^4$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, or an aralkyl group which has 6 to 10 carbon atoms in the aryl moiety and 1 to 8 carbon atoms in the alkylene moiety.

6. The method according to claim 1, wherein $R^5$ is hydrogen atom, an alkyl group having 1 to 8 carbon atoms, or an aralkyl group which has 6 to 10 carbon atoms in the aryl moiety and 1 to 8 carbon atoms in the alkylene moiety.

7. The method according to claim 1, wherein $R^5$ is hydrogen atom.

8. The method according to claim 1, wherein $R^6$ and $R^7$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms.

9. The method according to claim 1, wherein both $R^6$ and $R^7$ are hydrogen atoms.

10. The method according to claim 1, wherein A is phenyl group, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group which has 6 to 10 carbon atoms in the aryl moiety and 1 to 8 carbon atoms in the alkylene moiety, phenyl group, and pyridyl group.

11. The method according to claim 1, wherein A is phenyl group, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, and amino group.

12. The method according to claim 1, wherein B is NHC(=O).

13. The method according to claim 1, wherein G is piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine or pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an alkanoyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms.

14. The method according to claim 1, wherein G is benzene, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an alkanoyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms.

15. The method according to claim 1, wherein the compound is selected from the group consisting of the following (1) to (8), (11), (12), (14) to (19), (25), (29), (31), (32), (36), (41), (42), (45) to (49), (51), (52), (54) to (59), (61) to (63), (65), (70), (71), (73) to (83), (86) to (88), (92) to (95), (97) to (100), (106), (111) to (113), (115) to (133), (136), (138) to (144), (205), (207) to (209) and (211), to (214):

(1) 5-(4-benzoylaminophenyl)-1H-naphtho[1,2-b][1,4]diazepine-2,4(3H,5H)-dione;
(2) 5-[4-[2-(trifluoromethyl)benzoyl]aminophenyl]-1H-naphtho[1,2-b][1,4]diazepine-2,4(3H,5H)-dione;
(3) 5-[4-(3-bromobenzoyl)aminophenyl]-1H-naphtho[1,2-b][1,4]diazepine-2,4(3H,5H)-dione;
(4) 5-[4-[4-(trifluoromethyl)benzoyl]aminophenyl]-1H-naphtho[1,2-b][1,4]diazepine-2,4(3H,5H)-dione;
(5) 5-[4-(2-methylbenzoyl)aminophenyl]-1H-naphtho[1,2-b][1,4]diazepine-2,4(3H,5H)-dione;
(6) 5-[4-(2,6-dDimethylbenzoylamino)phenyl]-1H-naphtho[1,2-b][1,4]diazepine-2,4(3H,5H)-dione;
(7) 5-[4-(2,6-dichlorobenzoyl)aminophenyl]-1H-naphtho[1,2-b][1,4]diazepine-2,4(3H,5H)-dione;
(8) 5-[4-(3-chlorobenzoyl)aminophenyl]-1H-naphtho[1,2-b][1,4]diazepine-2,4(3H,5H)-dione;
(11) 5-[4-(2,3-dimethoxybenzoylamino)phenyl]-1H-naphtho[1,2-b][1,4]diazepine-2,4(3H,5H)-dione;
(12) 5-[4-(2-methoxybenzoylamino)phenyl]-1H-naphtho[1,2-b][1,4]diazepine-2,4(3H,5H)-dione;
(14) 5-[4-(2,3-dimethylbenzoylamino)phenyl]-1H-naphtho[1,2-b][1,4]diazepine-2,4(3H,5H)-dione;
(15) 5-[4-(2,5-dimethylbenzoylamino)phenyl]-1H-naphtho[1,2-b][1,4]diazepine-2,4(3H,5H)-dione;
(16) 5-[4-(5-bromo-2-chlorobenzoylamino)phenyl]-1H-naphtho[1,2-b][1,4]diazepine-2,4(3H,5H)-dione;
(17) 5-[4-(2,4-dichlorobenzoylamino)phenyl]-1H-naphtho[1,2-b][1,4]diazepine-2,4(3H,5H)-dione;
(18) 5-[4-(2-hydroxybenzoylamino)phenyl]-1H-naphtho[1,2-b][1,4]diazepine-2,4(3H,5H)-dione;
(19) 5-[4-(2,3-dihydroxybenzoylamino)phenyl]-1H-naphtho[1,2-b][1,4]diazepine-2,4(3H,5H)-dione;
(25) 5-[4-[3-(trifluoromethyl)benzoylamino]phenyl]-1H-naphtho[1,2-b][1,4]diazepine-2,4(3H,5H)-dione;
(29) 5-[4-(2-chloro-3-methoxybenzoylamino)phenyl]-1H-naphtho[1,2-b][1,4]diazepine-2,4(3H,5H)-dione;
(31) 5-[4-[(1H-indole-3-carbonyl)amino]phenyl]-1H-naphtho[1,2-b][1,4]diazepine-2,4(3H,5H)-dione;
(32) 5-[4-(2-chloro-3-hydroxybenzoylamino)phenyl]-1H-naphtho[1,2-b][1,4]diazepine-2,4(3H,5H)-dione;
(36) 5-[4-[4-[(1-methyl-1H-imidazole-2-carbonyl)amino]phenyl]-1H-naphtho[1,2-b][1,4]diazepine-2,4(3H,5H)-dione;
(41) 5-[4-(1H-benzimidazole-2-carbonylamino)phenyl]-1H-naphtho[1,2-b][1,4]diazepine-2,4(3H,5H)-dione;
(42) 1-[4-(2,3-dimethylbenzoylamino)phenyl]-7-methoxy-1H-1,5-benzodiazepine-2,4(3H,5H)-dione;
(45) 1-[4-(2,3-dimethylbenzoylamino)phenyl]-7-hydroxy-1H-1,5-benzodiazepine-2,4(3H,5H)-dione;
(46) 5-[4-(2-chlorobenzoylamino)phenyl]-1H-naphtho[1,2-b][1,4]diazepine-2,4(3H,5H)-dione;
(47) 5-[4-(2-bromobenzoylamino)phenyl]-1H-naphtho[1,2-b][1,4]diazepine-2,4(3H,5H)-dione;
(48) 5-[4-(2-iodobenzoylamino)phenyl]-1H-naphtho[1,2-b][1,4]diazepine-2,4(3H,5H)-dione;
(49) 5-[4-(2,3-dimethylbenzoylamino)-3-fluorophenyl]-1H-naphtho[1,2-b][1,4]diazepine-2,4(3H,5H)-dione;
(51) 5-[4-[(quinoxalin-2-yl)carbonylamino]phenyl]-1H-naphtho[1,2-b][1,4]diazepine-2,4(3H,5H)-dione;
(52) 5-[4-[(5-methylthiophen-2-yl)carbonylamino]phenyl]-1H-naphtho[1,2-b][1,4]diazepine-2,4(3H,5H)-dione;
(54) 5-[4-[(2,4,6-trimethylbenzoyl)amino]phenyl]-1H-naphtho[1,2-b][1,4]diazepine-2,4(3H,5H)-dione;
(55) 5-[4-(cyclohexylcarbonylamino)phenyl]-1,2,3,4,8,9,10,11-octahydronaphtho[1,2-b][1,4]diazepine-2,4(3H,5H)-dione;
(56) 1-[4-(2,3-dimethylbenzoyl)aminophenyl]-6-methyl-1H-1,5-benzodiazepine-2,4(3H,5H)-dione;
(57) 5-[4-[(2-ethylbenzoyl)amino]phenyl]-1H-naphtho[1,2-b][1,4]diazepine-2,4(3H,5H)-dione;
(58) 5-[4-[(6-methylpyridin-2-yl)carbonylamino]phenyl]-1,2,3,4,8,9,10,11-octahydronaphtho[1,2-b][1,4]diazepine-2,4(3H,5H)-dione;
(59) 5-[4-[(2-methylpyridin-3-yl)carbonylamino]phenyl]-1,2,3,4,8,9,10,11-octahydronaphtho[1,2-b][1,4]diazepine-2,4(3H,5H)-dione;
(61) 5-[4-(2-methoxy-3-methylbenzoyl)aminophenyl]-1,2,3,4,8,9,10,11-octahydronaphtho[1,2-b][1,4]diazepine-2,4(3H,5H)-dione;
(62) 5-[4-(2,3-dichlorobenzoyl)aminophenyl]-1,2,3,4,8,9,10,11-octahydronaphtho[1,2-b][1,4]diazepine-2,4(3H,5H)-dione;
(63) 5-[4-(2,3-dimethylbenzoylamino)-3-hydroxyphenyl]-1H-naphtho[1,2-b][1,4]diazepine-2,4(3H,5H)-dione;
(65) 5-[4-[(4-dimethylaminobenzoyl)amino]phenyl]-1H-naphtho[1,2-b][1,4]diazepine-2,4(3H,5H)-dione;
(70) 5-[4-(2-acetylbenzoylamino)phenyl]-1H-naphtho[1,2-b][1,4]diazepine-2,4(3H,5H)-dione;
(71) 5-[4-(2-tert-butylbenzoylamino)phenyl]-1H-naphtho[1,2-b][1,4]diazepine-2,4(3H,5H)-dione;
(73) 5-[3-[(2-iodobenzoyl)amino]phenyl]-1H-naphtho[1,2-b][1,4]diazepine-2,4(3H,5H)-dione;

(74) 6,7-dimethyl-1-[4-(2-iodobenzoyl)aminophenyl]-1H-1,5-benzodiazepine-2,4(3H,5H)-dione;
(75) 5-[4-[(1-methylpiperidin-4-yl)carbonylamino]phenyl]-1H-naphtho[1,2-b][1,4]diazepine-2,4(3H,5H)-dione hydrochloride;
(76) 5-[4-[(benzofuran-2-yl)carbonylamino]phenyl]-1H-naphtho[1,2-b][1,4]diazepine-2,4(3H,5H)-dione;
(77) 5-[4-[(1-methyl-1H-indol-3-yl)carbonylamino]phenyl]-1H-naphtho[1,2-b][1,4]diazepine-2,4(3H,5H)-dione;
(78) 5-[4-(2-propenylbenzoylamino)phenyl]-1H-naphtho[1,2-b][1,4]diazepine-2,4(3H,5H)-dione;
(79) 5-[4-(2-propylbenzoylamino)phenyl]-1H-naphtho[1,2-b][1,4]diazepine-2,4(3H,5H)-dione;
(80) 5-[3-fluoro-4-(2-iodobenzoylamino)phenyl]-1H-naphtho[1,2-b][1,4]diazepine-2,4(3H,5H)-dione;
(81) 5-[4-(2-hydroxy-3-methylbenzoyl)aminophenyl]-1,2,3,4,8,9,10,11-octahydronaphtho[1,2-b][1,4]diazepine-2,4(3H,5H)-dione;
(82) 5-[4-[(2-isopropoxybenzoyl)amino]phenyl]-1H-naphtho[1,2-b][1,4]diazepine-2,4(3H,5H)-dione;
(83) 5-[4-[(3-methylthiophen-2-yl)carbonylamino]phenyl]-1H-naphtho[1,2-b][1,4]diazepine-2,4(3H,5H)-dione;
(86) 5-[4-(4-fluoro-2-trifluoromethylbenzoyl)aminophenyl]-1H-naphtho[1,2-b][1,4]diazepine-2,4(3H,5H)-dione;
(87) 5-[4-(4-fluoro-2-methoxybenzoyl)aminophenyl]-1H-naphtho[1,2-b][1,4]diazepine-2,4(3H,5H)-dione;
(88) 5-[4-(4-fluoro-2-hydroxybenzoyl)aminophenyl]-1H-naphtho[1,2-b][1,4]diazepine-2,4(3H,5H)-dione;
(92) 5-[4-[(3-dimethylaminobenzoyl)amino]phenyl]-1H-naphtho[1,2-b][1,4]diazepine-2,4(3H,5H)-dione;
(93) 5-[4-(4-iodo-2-methoxybenzoylamino)phenyl]-1H-naphtho[1,2-b][1,4]diazepine-2,4(3H,5H)-dione;
(94) 5-[4-(6-fluoro-2-methoxybenzoylamino)phenyl]-1H-naphtho[1,2-b][1,4]diazepine-2,4(3H,5H)-dione;
(95) 5-[4-(2-hydroxy-4-iodobenzoylamino)phenyl]-1H-naphtho[1,2-b][1,4]diazepine-2,4(3H,5H)-dione;
(97) 5-[4-(2-fluorobenzoyl)aminophenyl]-1H-naphtho[1,2-b][1,4]diazepine-2,4(3H,5H)-dione;
(98) 5-[4-[(2-dimethylaminobenzoyl)amino]phenyl]-1H-naphtho[1,2-b][1,4]diazepine-2,4(3H,5H)-dione;
(99) 5-[4-(2-methoxy-6-methylbenzoylamino)phenyl]-1H-naphtho[1,2-b][1,4]diazepine-2,4(3H,5H)-dione;
(100) 5-[4-(2-hydroxy-6-methylbenzoylamino)phenyl]-1H-naphtho[1,2-b][1,4]diazepine-2,4(3H,5H)-dione;
(106) 5-[4-(2-iodobenzoyl)aminophenyl]-1,2,3,4,8,9,10,11-octahydronaphtho[1,2-b][1,4]diazepine-2,4(3H,5H)-dione;
(111) 5-[4-(6-bromo-2,3-methylenedioxybenzoylamino)phenyl]-1H-naphtho[1,2-b][1,4]diazepine-2,4(3H,5H)-dione;
(112) 5-[4-(6-bromo-2-methoxybenzoylamino)phenyl]-1H-naphtho[1,2-b][1,4]diazepine-2,4(3H,5H)-dione;
(113) 5-[4-[(2-tert-butylbenzoyl)amino]phenyl]-1,2,3,4,8,9,10,11-octahydronaphtho[1,2-b][1,4]diazepine-2,4(3H,5H)-dione;
(115) 5-[4-(6-bromo-2-hydroxybenzoylamino)phenyl]-1H-naphtho[1,2-b][1,4]diazepine-2,4(3H,5H)-dione;
(116) 5-[4-(6-chloro-2-methoxybenzoylamino)phenyl]-1H-naphtho[1,2-b][1,4]diazepine-2,4(3H,5H)-dione;
(117) 5-[4-(2-iodobenzoylamino)phenyl]-1H-[1,4]diazepino[2,3-h]quinoline-2,4(3H,5H)-dione;
(118) 5-[4-(6-chloro-2-hydroxybenzoylamino)phenyl]-1H-naphtho[1,2-b][1,4]diazepine-2,4(3H,5H)-dione;
(119) 5-[4-(2-hydroxy-6-methoxybenzoylamino)phenyl]-1H-naphtho[1,2-b][1,4]diazepine-2,4(3H,5H)-dione;
(120) 5-[4-[2-methoxy-6-(trifluoromethyl)benzoylamino]phenyl]-1H-naphtho[1,2-b][1,4]diazepine-2,4(3H,5H)-dione;
(121) 5-[4-[2-hydroxy-6-(trifluoromethyl)benzoylamino]phenyl]-1H-naphtho[1,2-b][1,4]diazepine-2,4(3H,5H)-dione;
(122) 5-[4-[(2-isopropenylbenzoyl)amino]phenyl]-1,2,3,4,8,9,10,11-octahydronaphtho[1,2-b][1,4]diazepine-2,4(3H,5H)-dione;
(123) 5-[4-[(2-isopropylbenzoyl)amino]phenyl]-1,2,3,4,8,9,10,11-octahydronaphtho[1,2-b][1,4]diazepine-2,4(3H,5H)-dione;
(124) 5-[4-[2-chloro-5-(methylthio)benzoylamino]phenyl]-1H-naphtho[1,2-b][1,4]diazepine-2,4(3H,5H)-dione;
(125) 5-[4-[2-(methylthio)benzoylamino]phenyl]-1H-naphtho[1,2-b][1,4]diazepine-2,4(3H,5H)-dione;
(126) 5-[4-[3-(methylthio)benzoylamino]phenyl]-1H-naphtho[1,2-b][1,4]diazepine-2,4(3H,5H)-dione;
(127) 5-[4-[2-ethyl-6-methoxybenzoylamino]phenyl]-1H-naphtho[1,2-b][1,4]diazepine-2,4(3H,5H)-dione;
(128) 5-[4-(3-methanesulfonybenzoylamino)phenyl]-1H-naphtho[1,2-b][1,4]diazepine-2,4(3H,5H)-dione;
(129) 6-ethyl-1-[4-(2-iodobenzoyl)aminophenyl]-1H-1,5-benzodiazepine-2,4(3H,5H)-dione;
(130) 5-[4-[2-ethyl-6-hydroxybenzoylamino]phenyl]-1H-naphtho[1,2-b][1,4]diazepine-2,4(3H,5H)-dione;
(131) 5-[4-(3-methanesulfinylbenzoylamino)phenyl]-1H-naphtho[1,2-b][1,4]diazepine-2,4(3H,5H)-dione;
(132) 5-[4-(2-chloro-5-methanesulfinylbenzoylamino)phenyl]-1H-naphtho[1,2-b][1,4]diazepine-2,4(3H,5H)-dione;
(133) 5-[4-(2-methanesulfinylbenzoylamino)phenyl]-1H-naphtho[1,2-b][1,4]diazepine-2,4(3H,5H)-dione;
(136) 5-[4-[[(3-chloropyridin-2-yl)carbonyl]amino]phenyl]-1H-naphtho[1,2-b][1,4]diazepine-2,4(3H,5H)-dione;
(138) 5-[4-(3-chloro-2-methoxybenzoylamino)phenyl]-1H-naphtho[1,2-b][1,4]diazepine-2,4(3H,5H)-dione;
(139) 5-[4-[(3-methylpyridin-2-yl)carbonylamino]phenyl]-1H-naphtho[1,2-b][1,4]diazepine-2,4(3H,5H)-dione;
(140) 5-[4-[[(3-chloropyridin-2-yl)carbonyl]amino]phenyl]-1,2,3,4,8,9,10,11-octahydronaphtho[1,2-b][1,4]diazepine-2,4(3H,5H)-dione;
(141) 5-[4-(3-chloro-2-hydroxybenzoylamino)phenyl]-1H-naphtho[1,2-b][1,4]diazepine-2,4(3H,5H)-dione;
(142) 5-[4-[[(3-hydroxypyridin-2-yl)carbonyl]amino]phenyl]-1H-naphtho[1,2-b][1,4]diazepine-2,4(3H,5H)-dione;
(143) 5-[4-[(3-vinylpyridin-2-yl)carbonylamino]phenyl]-1H-naphtho[1,2-b][1,4]diazepine-2,4(3H,5H)-dione;
(144) 5-[4-[(3-ethylpyridin-2-yl)carbonylamino]phenyl]-1H-naphtho[1,2-b][1,4]diazepine-2,4(3H,5H)-dione;
(205) 5-[4-[(pyridin-4-yl)carbonylamino]phenyl]-1H-naphtho[1,2-b][1,4]diazepine-2,4(3H,5H)-dione hydrochloride;
(207) 5-[4-[(pyridin-3-yl)carbonylamino]phenyl]-1H-naphtho[1,2-b][1,4]diazepine-2,4(3H,5H)-dione hydrochloride;
(208) 5-[4-[(2-methylpyridin-3-yl)carbonylamino]phenyl]-1H-naphtho[1,2-b][1,4]diazepine-2,4(3H,5H)-dione hydrochloride;

(209) 5-[4-[(2-chloropyridin-3-yl)carbonylamino]phenyl]-1H-naphtho[1,2-b][1,4]diazepine-2,4(3H,5H)-dione;
(211) 5-[4-[[4-(trifluoromethyl)pyridin-3-yl]carbonylamino]phenyl]-1H-naphtho [1,2-b][1,4]diazepine-2,4(3H,5H)-dione;
(212) 5-[4-[(2-chloropyridin-3-yl)carbonylamino]phenyl]-1H-[1,4]diazepino[2,3-f]isoquinoline-2,4(3H,5H)-dione;
(213) 5-[4-[(2-chloropyridin-3-yl)carbonylamino]phenyl]-8,9,10,11-tetrahydro-1H-[1,4]diazepino[2,3-f]isoquinoline-2,4(3H,5H)-dione; and
(214) 5-[4-[(2-isopropylbenzoyl)amino]phenyl]-1H-naphtho[1,2-b][1,4]diazepine-2,4(3H,5H)-dione.

16. The method according to claim 1, wherein the compound is 5-[4-[2-(trifluoromethyl)benzoyl]aminophenyl]-1H-naphtho[1,2-b][1,4]diazepine-2,4(3H,5H)-dione.

17. The method according to claim 1, wherein the compound is 5-[4-(2-iodobenzoylamino)phenyl]-1H-naphtho[1,2-b][1,4]diazepine-2,4(3H,5H)-dione.

18. The method according to claim 1, wherein the compound is 5-[4-[(2-ethylbenzoyl)amino]phenyl]-1H-naphtho[1,2-b][1,4]diazepine-2,4(3H,5H)-dione.

19. The method according to claim 1, wherein the compound is 5-[4-(2-tert-butylbenzoylamino)phenyl]-1H-naphtho[1,2-b][1,4]diazepine-2,4(3H,5H)-dione.

20. The method according to claim 1, wherein the compound is 5-[4-(6-chloro-2-hydroxybenzoylamino)phenyl]-1H-naphtho[1,2-b][1,4]diazepine-2,4(3H,5H)-dione.

21. The method according to claim 1, wherein the compound is 5-[4-[(2-isopropylbenzoyl)amino]phenyl]-1H-naphtho[1,2-b][1,4]diazepine-2,4(3H,5H)-dione.

22. The method according to claim 1, wherein the compound is 5-[4-(2-iodobenzoyl)aminophenyl]-1,2,3,4,8,9,10,11-octahydronaphtho-[1,2-b][1,4]diazepine-2,4(3H,5H)-dione.

23. The method according to claim 1, wherein the compound is 5-[4-[(2-methylpyridin-3-yl)carbonylamino]phenyl]-1H-naphtho[1,2-b][1,4]diazepine-2,4(3H,5H)-dione hydrochloride.

24. The method according to claim 1, wherein the compound is 5-[4-[(2-chloropyridin-3-yl)carbonylamino]phenyl]-1H-naphtho[1,2-b][1,4]diazepine-2,4(3H,5H)-dione.

25. The method according to claim 1, wherein the pain is nociceptive pain.

26. The method according to claim 1, wherein the pain is inflammatory pain.

27. The method according to claim 1, wherein the pain is neuropathic pain.

28. The method according to claim 1, wherein the subject is a human.

29. A method of treating pain which comprising administrating a therapeutically an effective amount of a compound having the following formula (III), or a pharmacologically acceptable salt thereof to a subject in need thereof:

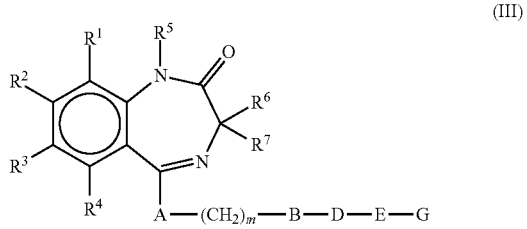

(III)

wherein,
$R^1$ and $R^2$ bind together to form a condensed ring selected from naphthalene ring, quinoline ring, isoquinoline ring, tetrahydronaphthalene ring, indane ring, tetrahydroquinoline ring, and tetrahydroisoquinoline ring together with the benzene ring to which they bind, and the ring constituted by $R^1$ and $R^2$, bound to each other, together with the carbon atoms to which $R^1$ and $R^2$ bind may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carboxamido group having 2 to 8 carbon atoms, a carboxyl group, an alkanoyl group having 2 to 8 carbon atoms, an alkoxycarbonyl group which has 1 to 8 carbon atoms in the alkoxy moiety, and an aralkyl group which has 6 to 10 carbon atoms in the aryl moiety and 1 to 8 carbon atoms in the alkylene moiety, $R^3$ and $R^4$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carboxamido group having 2 to 8 carbon atoms, a carboxyl group, an alkanoyl group having 2 to 8 carbon atoms, an alkoxycarbonyl group which has 1 to 8 carbon atoms in the alkoxy moiety, or an aralkyl group which has 6 to 10 carbon atoms in the aryl moiety and 1 to 8 carbon atoms in the alkylene moiety, $R^5$ represents a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group which has 6 to 10 carbon atoms in the aryl moiety and 1 to 8 carbon atoms in the alkylene moiety, $R^6$ and $R^7$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, or an amino group, A represents a benzene ring, a pyridine ring, a thiophene ring, a pyrimidine ring, a naphthalene ring, a quinoline ring, or an indole ring, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an aralkyl group which has 6 to 10 carbon atoms in the aryl moiety and 1 to 8 carbon atoms in the alkylene moiety, a phenyl group, and a pyridyl group, as a substituent, or represents an atomic bond, B represents $N(R^8)C(=O)$, NHCONH, $CON(R^9)$, NHC($=S$)NH, $N(R^{10})SO_2$, $SO_2N(R^{11})$, or $OSO_2$, wherein $R^8$, $R^9$, $R^{10}$, and $R^{11}$ independently represents a hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group which has 6 to 10 carbon atoms in the aryl moiety and 1 to 8 carbon atoms in the alkylene moiety, D represents an alkylene chain having 1 to 6 carbon atoms, which may have 1 to 4 of the same or different substituents selected from an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, and an aralkyl group in which the aryl moiety has 6 to 10 carbon atoms and the alkylene moiety has 1 to 8 carbon atoms, as a substituent, and may further have a double bond, or represents an atomic bond, E represents O, S, $NR^{12}$, or an atomic bond, wherein $R^{12}$ represents a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group in which the aryl moiety has 6 to 10 carbon atoms and the alkylene moiety has 1 to 8 carbon atoms, G represents a piperazine, a piperidine, a morpholine, a cyclohexane, a benzene, a naphthalene, a quinoline, a quinoxaline, a benzimidazole, a thiophene, an imidazole, a thiazole, an oxazole, an indole, a benzofuran, a pyrrole, a pyridine, or a pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an alkanoyl group having 2 to 8 carbon atoms, a methylenedioxy group, a carboxyl group, an alkylsulfinyl group having 1 to 6 carbon atoms, an alkylthio group having 1 to 6 carbon atoms, an alkylsulfonyl group having 1 to 6 carbon atoms, an aralkyl group which has 6 to 10 carbon atoms in the aryl moiety and 1 to 8 carbon atoms in the alkylene moiety, a phenyl group which may be substituted, a pyridyl group which may be substituted, an imidazolyl group which may be substituted, an oxazolyl group which may be substituted, and a thiazolyl group which may be substituted, wherein the substituents on the phenyl group, the pyridyl group, the imidazolyl group, the oxazolyl group, and the thiazolyl group are chosen from a halogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms, and m represents an integer of 0 to 5.

30. The method according to claim 29, wherein A is a benzene ring.

31. The method according to claim 29, wherein A is a pyridine ring.

32. The method according to claim 29, wherein B is NHC($=O$).

33. The method according to claim 29, wherein B is $NHSO_2$.

34. The method according to claim 29, wherein D represents an alkylene chain having 1 to 6 carbon atoms, which may have 1 to 4 of the same or different substituents selected from an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, and an aralkyl group in which the aryl moiety has 6 to 10 carbon atoms and the alkylene moiety has 1 to 8 carbon atoms, as a substituent, and may further have a double bond.

35. The method according to claim 29, wherein D is an atomic bond.

36. The method according to claim 29, wherein E is an atomic bond.

37. The method according to claim 29, wherein m is 0.

38. The method according to claim 29, wherein the compound is selected from the group consisting of the following compounds: (64), (69), (91), (135), (137), (149), and (197):

(64) 5-[4-(2-chloro-3-methoxybenzoylamino)phenyl]-1,3-dihydronaphtho[1,2-e]-1,4-diazepin-2-one;

(69) 5-[4-(2-chloro-3-hydroxybenzoylamino)phenyl]-1,3-dihydronaphtho[1,2-e]-1,4-diazepin-2-one;

(91) 5-[4-(2-tert-butylbenzoylamino)phenyl]-1,3-dihydronaphtho[1,2-e]-1,4-diazepin-2-one;

(135) 5-[4-(2-chloro-6-methoxybenzoylamino)phenyl]-1,3-dihydronaphtho[1,2-e]-1,4-diazepin-2-one;

(137) 5-[4-(2-chloro-6-hydroxybenzoylamino)phenyl]-1,3-dihydronaphtho[1,2-e]-1,4-diazepin-2-one;

(149) N-[3-(2-oxo-2,3-dihydro-1H-naphtho[1,2-e][1,4]diazepin-5-yl)phenyl]benzenesulfonamide; and (197) 1-(2-chlorophenyl)-N-[4-(2-oxo-2,3-dihydro-1H-naphtho[1,2-e][1,4]diazepin-5-yl)phenyl]methanesulfonamide.

39. The method according to claim 29, wherein the compound is 1-(2-chlorophenyl)-N-[4-(2-oxo-2,3-dihydro-1H-naphtho[1,2-e][1,4]diazepin-5-yl)phenyl]methanesulfonamide.

40. The method according to claim 29, wherein the pain is nociceptive pain.

41. The method according to claim 29, wherein the pain is inflammatory pain.

42. The method according to claim 29, wherein the pain is neuropathic pain.

43. The method according to claim 29, wherein the subject is a human.

* * * * *

UNITED STATES PATENT AND TRADEMARK OFFICE
CERTIFICATE OF CORRECTION

| | |
|---|---|
| PATENT NO. | : 11,434,207 B2 |
| APPLICATION NO. | : 16/826877 |
| DATED | : September 6, 2022 |
| INVENTOR(S) | : M. Ushioda et al. |

It is certified that error appears in the above-identified patent and that said Letters Patent is hereby corrected as shown below:

In the Claims

At Column 114, Line 65 (Claim 1), please change "an effective" to -- effective --.
At Column 120, Line 13 (Claim 15), please change "[4-[4-[" to -- [4-[ --.
At Column 123, Line 52 (Claim 29), please change "an effective" to -- effective --.

Signed and Sealed this
Fourteenth Day of March, 2023

Katherine Kelly Vidal
*Director of the United States Patent and Trademark Office*